(12) United States Patent
Uehara et al.

(10) Patent No.: US 7,572,793 B2
(45) Date of Patent: Aug. 11, 2009

(54) 3-SUBSTITUTED-4-PYRIMIDONE DERIVATIVES

(75) Inventors: Fumiaki Uehara, Tokyo (JP); Keiichi Aritomo, Tokyo (JP); Aya Shoda, Tokyo (JP); Shinsuke Hiki, Tokyo (JP); Masahiro Okuyama, Tokyo (JP); Yoshihiro Usui, Tokyo (JP); Mitsuru Ooizumi, Tokyo (JP); Kazutoshi Watanabe, Tokyo (JP)

(73) Assignees: Mitsubishi Tanabe Pharma Corporation, Osaka-shi (JP); Sanofi-Aventis, Paris (FR)

( * ) Notice: Subject to any disclaimer, the term of this patent is extended or adjusted under 35 U.S.C. 154(b) by 752 days.

(21) Appl. No.: 10/489,607

(22) PCT Filed: Sep. 20, 2002

(86) PCT No.: PCT/JP02/09684

§ 371 (c)(1),
(2), (4) Date: Feb. 8, 2005

(87) PCT Pub. No.: WO03/027080

PCT Pub. Date: Apr. 3, 2003

(65) Prior Publication Data

US 2005/0130967 A1 Jun. 16, 2005

(30) Foreign Application Priority Data

| Sep. 21, 2001 | (JP) | ............................ 2001-331674 |
| Sep. 21, 2001 | (JP) | ............................ 2001-331675 |
| Sep. 21, 2001 | (JP) | ............................ 2001-331676 |
| Sep. 21, 2001 | (JP) | ............................ 2001-331678 |

(51) Int. Cl.
| A61K 31/535 | (2006.01) |
| A61K 31/54 | (2006.01) |
| C07D 403/00 | (2006.01) |
| C07D 237/02 | (2006.01) |
| C07D 265/30 | (2006.01) |
| C07D 295/00 | (2006.01) |
| C07D 413/00 | (2006.01) |

(52) U.S. Cl. ................... 514/235.8; 514/247; 514/256; 514/228.8; 514/231.5; 514/235.5; 544/63; 544/98; 544/106; 544/111; 544/149; 544/224; 544/242; 544/295; 544/296

(58) Field of Classification Search ................... 544/63, 544/98, 106, 111, 149, 224, 242, 295, 296; 514/228.8, 231.2, 231.5, 235.8, 247, 256, 514/235.5
See application file for complete search history.

(56) References Cited

U.S. PATENT DOCUMENTS 4,166,180 A 8/1979 Kato et al.
4,507,302 A 3/1985 Fast et al.

(Continued)

FOREIGN PATENT DOCUMENTS

| EP | 0168262 | 1/1986 |
| EP | 0354179 | 7/1989 |
| EP | 1136482 | 9/2001 |
| HU | 218974 | 1/2001 |
| HU | P 0001698 | 4/2001 |
| JP | 49-035631 | 4/1974 |
| JP | 49-35632 | 4/1974 |

(Continued)

OTHER PUBLICATIONS

Taguchi, Chemistry Letters, pp. 273-274, 1978 (3).*

(Continued)

*Primary Examiner*—Kamal A Saeed
*Assistant Examiner*—Samantha L Shterengarts
(74) *Attorney, Agent, or Firm*—Greenblum & Bernstein, P.L.C.

(57) ABSTRACT

A pyrimidone derivative represented by formula (I) or a salt thereof, or a solvate thereof or a hydrate thereof having inhibitory activity against tau protein kinase 1:

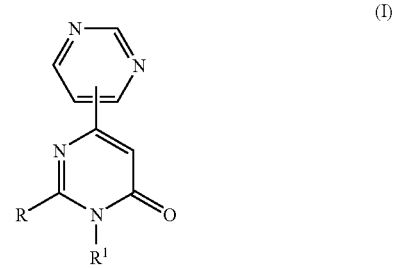

wherein $R^1$ represents a $C_1$-$C_{12}$ alkyl group which may be substituted;
R represents, for example, a group represented by the following formula (II):

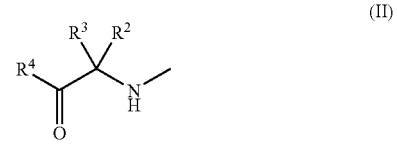

wherein $R^2$ and $R^3$ independently represent a hydrogen atom or a $C_1$-$C_8$ alkyl group;
$R^4$ represents a benzene ring which may be substituted, a naphthalene ring which may be substituted, an indan ring which may be substituted, a tetrahydronaphthalene ring which may be substituted, or an optionally substituted heterocyclic ring having 1 to 4 hetero atoms selected from the group consisting of oxygen atom, sulfur atom and nitrogen atom, and having 5 to 10 ring-constituting atoms in total.

23 Claims, No Drawings

U.S. PATENT DOCUMENTS

| | | | |
|---|---|---|---|
| 4,619,933 | A | 10/1986 | Stringfellow et al. |
| 4,725,600 | A | 2/1988 | Takaya et al. |
| 5,612,286 | A | 3/1997 | Mayer et al. |
| 6,096,753 | A | 8/2000 | Spohr et al. |
| 6,107,301 | A | 8/2000 | Aldrich et al. |
| 6,410,729 | B1 | 6/2002 | Spohr et al. |
| 6,420,385 | B1 | 7/2002 | Spohr et al. |
| 6,586,441 | B2 | 7/2003 | Borroni et al. |
| 6,844,335 | B2 | 1/2005 | Almario Garcia et al. |
| 2003/0187004 | A1 | 10/2003 | Almario Garcia et al. |
| 2005/0090490 | A1 | 4/2005 | Uehara et al. |
| 2005/0130998 | A1 | 6/2005 | Almario Garcia et al. |
| 2006/0252768 | A1 | 11/2006 | Watanabe et al. |

FOREIGN PATENT DOCUMENTS

| | | |
|---|---|---|
| JP | 49-035633 | 4/1974 |
| JP | 49-35634 | 4/1974 |
| JP | 49-35631 | 9/1974 |
| JP | 49-35632 | 9/1974 |
| JP | 49-35633 | 9/1974 |
| JP | 49-35634 | 9/1974 |
| JP | 52-071481 | 6/1977 |
| JP | 52 139085 | 11/1977 |
| JP | 6 239893 | 8/1994 |
| JP | 6-329551 | 11/1994 |
| WO | 93/11231 | 6/1998 |
| WO | 98/24780 | 6/1998 |
| WO | 98 24782 | 6/1998 |
| WO | 98/24782 | 6/1998 |
| WO | 00-18758 | 4/2000 |
| WO | 00/18758 | 4/2000 |
| WO | 01/70728 | 9/2001 |
| WO | 01/70729 | 9/2001 |
| WO | 03/037888 | 5/2003 |
| WO | 2004/055007 | 7/2004 |
| WO | 2004/085408 | 10/2004 |

OTHER PUBLICATIONS

Morissette et al. Advanced Drug Delivery Reviews 2004, 56, 275-300.*
U.S. Appl. No. 10/538,766, filed Dec. 12, 2003 to Usui et al.
Anthony R. West, Solid State Chemistry and Its Applications, Wiley, New York, 1988 pp. 358 and 365.
Sudha R. Vippagunta et al., "Crystalline Solids", Advance Drug Delivery Reviews, vol. 48, pp. 3-26 (2001).
Tani et al., CAPLUS Abstract 84:44112 (1976).
Joachim Ulrich, Chapter 4: Crystallization, Krik-Othmer Encyclopedia of Chemical Technology (Aug. 2002).
G. Glenner et al., Biochemical and Biophysical Research Communications, vol. 120, No. 3, 1984, pp. 885-890.
C.L. Masters et al., The EMBO Journal, vol. 4, No. 11, 1985, pp. 2757-2763.
C.L. Masters et al., Proc. Natl. Acad. Sci. USA, vol. 82, Jun. 1985, pp. 4245-4249.
C.M. Wischik et al., Proc. Natl. Acad. Sci. USA, vol. 85, Jun. 1988, pp. 4506-4510.
J. Kondo et al., Neuron, vol. 1, Nov. 1988, pp. 827-834.
R. Sherrington et al., Nature, vol. 375, Jun. 29, 1995, pp. 754-760.
E. Levy-Lahad et al., Science, vol. 269, Aug. 18, 1995, pp. 973-977.
E.I. Rogaev et al., Nature, vol. 376, Aug. 31, 1995, pp. 775-778.
D.R. Borchelt et al., Neuron, vol. 17, Nov. 1996, pp. 1005-1013.
T. Tomita et al., Proc. Natl. Acad. Sci. USA, vol. 94, Mar. 1997, pp. 2025-2030.
Y. Ihara et al., J. Biochem., vol. 99, 1986, pp. 1807-1810.
I. Grundke-Iqbal et al., Proc. Natl. Acad. Sci. USA, vol. 83, Jul. 1986, pp. 4913-4917.
K. Ishiguro et al., J. Biol. Chem., vol. 267, No. 15, May 25, 1992, pp. 10897-10901.
K. Ishiguro et al., FEBS Lett., vol. 325, Jul. 1993, pp. 167-172.
English Language Abstract of JP 6-239893, Date Publication Aug. 30, 1994.
B.A. Yankner et al., Science, vol. 250, 1990, pp. 279-283.
A. Takashima et al., Proc. Natl. Acad. Sci. USA, vol. 90, Aug. 1993, pp. 7789-7793.
H. Yinglin, Tetrahedron Letters, vol. 30, No. 39, 1989, pp. 5285-5286.
English language Abstract of JP 6-329551 Date Publication Nov. 29, 1994.
H. Yinglin, Synthesis, pp. 122-124, Feb. 1990.
R.L. Duncan Jr. et al., J. Med. Chem., vol. 13, No. 1, Jan. 1970, pp. 1-6.
D.L. Thai et al., J. Med. Chem., vol. 41, 1998, pp. 591-601.
Chemical Abstracts, vol. 100, No. 28, 1984, Columbus, Ohio, US, Abstract No. 174768e, M.F. Brana et al., "Reaction of N-(1-Oxido-4-Pyridylmethyl)-3,5-Dimethylbenzamide with Malononitrile in Acetic Anhydride", p. 627; XP002127059.
Chemical Abstracts, vol. 84, No. 7, 1976, Columbus, Ohio, US, Abstract No. 44112b, Tani et al., "4-Hydroxy-Pyridylpyrimidine Derivatives", p. 502, XP002127060.
Chemical Abstracts, vol. 82, No. 28, 1975, Columbus, Ohio, US, Abstract No. 171028n, Tani et al., "2,4,5-Trisubstituted-6-Pyridylpyrimidine Derivatives", p. 555, XP002127061.
Chemical Abstracts, vol. 83, No. 28, 1975, Columbus, Ohio, US, Abstract No. 10127z, Tani et al., "5-Nitro-6-Pyridylpyrimidine Derivatives", p. 853, XP002127062.
Chemical Abstract 1992, vol. 116, Abstract #59167.
Chemical Abstract 1966, vol. 65, Abstact #90645.
Von Hans-Joachim Kabbe, "Substituierte 4-Hydroxy- und 4-Amino-Pyrimidine", Liebigs. Ann. Chem., vol. 701, pp. 144-149 (1967).
Harvey I. Skulnick et al., "Pyrimidinones. 1. 2-Amino-5-Halo-6-Arly-4(3H)-Pyrimidinones. Interferon-Inducing Antiviral Agents", J. Med. Chem., vol. 28, pp. 1864-1869 (1985).
U.S. Appl. No. 09/787,426, filed Jul. 2, 2001 to Watanabe et al.
English language Abstract of JP 52-071481, Date Publication Jun. 14, 1977.
G. Glenner et al., Biochemical and Biophysical Research Communications, vol. 120, No. 3, 1984, pp. 885-890.
C.L. Masters et al., The EMBO Journal, vol. 4, No. 11, 1985, pp. 2757-2763.
C.L. Masters et al., Proc. Natl. Acad. Sci. USA, vol. 82, Jun. 1985, pp. 4245-4249.
C.M. Wischik et al., Proc. Natl. Acad. Sci. USA, vol. 85, Jun. 1988, pp. 4506-4510.
T. Tomita et al., Proc. Natl. Acad. Sci. USA, vol. 94, Mar. 1997, pp. 2025-2030.
Sai-Shin Igaku, vol. 49, No. 9, 1994, pp. 1506-1512.
D.W. Dickson et al., Society for Neuroscience Abstracts, vol. 17, 1991, pp. 1445.
R. Siman et al., The Journal of Neuroscience, vol. 10, No. 7, Jul. 1990, pp. 2400-2411.
Shin-kei Shinpo, vol. 34, 1990, pp. 343-349.
Tanpaku-shitu Kaku-san Koso, vol. 41, 1996, pp. 1476-1483.
Tanpaku-shitu Kaku-san Koso, vol. 36, 1991, pp. 2-11.
Igaku no Ayumi, vol. 158, No. 9, Aug. 31, 1991, pp. 511-514.
I Grundke-Iqbal et al., Proc. Natl. Acad. Sci. USA, vol. 83, Jul. 1986, pp. 4913-4917.
Seikagaku, vol. 64, No. 5, pp. 308-312.
K. Ishiguro et al., J. Biol. Chem., vol. 267, No. 15, May 25, 1992, pp. 10897-10901.
A. Takashima et al., Proc. Natl. Acad. Sci. USA, vol. 90, Aug. 1993, pp. 7789-7793.
Chemical Abstracts, vol. 100, No. 28, 1984, Columbus, Ohio, US, Abstract No. 174768e, M.F. Brana et al., "Reaction of N-(1-Oxido-4-Pyridylmethyl)-3,5-Dimethylbenzamide with Malononitrile in Acetic Anhydride", p. 627; XP002127059.
Chemical Abstracts, vol. 84, No. 7, 1976, Columbus, Ohio, US, Abstract No. 44112b, Tani et al., "4-Hydroxy-Pyridylpyrimidine Derivatives", p. 502, XP002127060.
Chemical Abstracts, vol. 82, No. 28, 1975, Columbus, Ohio, US, Abstract No. 171028n, Tani et al., "2,4,5-Trisubstituted-6-Pyridylpyrimidine Derivatives", p. 555, XP002127061.

Chemical Abstracts, vol. 83, No. 28, 1975, Columbus, Ohio, US, Abstract No. 10127z, Tani et al., "5-Nitro-6-Pyridylpyrimidine Derivatives", p. 853, XP002127062.

Von Hans-Joachim Kabbe, "Substituierte 4-Hydroxy- und 4-Amino-Pyrimidine", Liebigs. Ann. Chem., vol. 701, pp. 144-149 (1967).

Harvey I. Skulnick et al., "Pyrimidinones. 1. 2-Amino-5-Halo-6-Arly-4-(3H)-Pyrimidinones. Interferon-Inducing Antiviral Agents", J. Med. Chem., vol. 28, pp. 1864-1869 (1985).

D.W. Dickson et al., Society for Neuroscience Abstracts, vol. 17, 1991, pp. 1445.

R. Siman et al., The Journal of Neuroscience, vol. 10, No. 7, Jul. 1990, pp. 2400-2411.

Chemical Abstract No. 83:10129 of JP 49-35634 (1974).

* cited by examiner

3-SUBSTITUTED-4-PYRIMIDONE DERIVATIVES

TECHNICAL FIELD

The present invention relates to compounds that are useful as an active ingredient of a medicament for preventive and/or therapeutic treatment of diseases mainly caused by abnormal activity of tau protein kinase 1, such as neurodegenerative diseases (e.g. Alzheimer disease).

BACKGROUND ART

Alzheimer disease is progressive senile dementia, in which marked cerebral cortical atrophy is observed due to degeneration of nerve cells and decrease of nerve cell number. Pathologically, numerous senile plaques and neurofibrillary tangles are observed in brain. The number of patients has been increased with the increment of aged population, and the disease arises a serious social problem. Although various theories have been proposed, a cause of the disease has not yet been elucidated. Early resolution of the cause has been desired.

It has been known that the degree of appearance of two characteristic pathological changes of Alzheimer disease well correlates to the degree of intellectual dysfunction. Therefore, researches have been conducted from early 1980's to reveal the cause of the disease through molecular level investigations of components of the two pathological changes. Senile plaques accumulate extracellularly, and β amyloid protein has been elucidated as their main component (abbreviated as "Aβ" hereinafter in the specification: Biochem. Biophys. Res. Commun., 120, 855 (1984); EMBO J., 4, 2757 (1985); Proc. Natl. Acad. Sci. USA, 82, 4245 (1985)). In the other pathological change, i.e., the neurofibrillary tangles, a double-helical filamentous substance called paired helical filament (abbreviated as "PHF" hereinafter in the specification) accumulate intracellularly, and tau protein, which is a kind of microtubule-associated protein specific for brain, has been revealed as its main component (Proc. Natl. Acad. Sci. USA, 85, 4506 (1988); Neuron, 1, 827 (1988)).

Furthermore, on the basis of genetic investigations, presenilins 1 and 2 were found as causative genes of familial Alzheimer disease (Nature, 375, 754 (1995); Science, 269, 973 (1995); Nature. 376, 775 (1995)), and it has been revealed that presence of mutants of presenilins 1 and 2 promotes the secretion of Aβ (Neuron, 17, 1005 (1996); Proc. Natl. Acad. Sci. USA, 94, 2025 (1997)). From these results, it is considered that, in Alzheimer disease, Aβ abnormally accumulates and agglomerates due to a certain reason, which engages with the formation of PHF to cause death of nerve cells. It is also expected that extracellular outflow of glutamic acid and activation of glutamate receptor responding to the outflow may possibly be important factors in an early process of the nerve cell death caused by ischemic cerebrovascular accidents (Saishin.Igaku [Latest Medicine], 49, 1506 (1994)).

It has been reported that kainic acid treatment that stimulates the AMPA receptor, one of glutamate receptor, increases mRNA of the amyloid precursor protein (abbreviated as "APP" hereinafter in the specification) as a precursor of Aβ (Society for Neuroscience Abstracts, 17, 1445 (1991)), and also promotes metabolism of APP (The Journal of Neuroscience, 10, 2400 (1990)). Therefore, it has been strongly suggested that the accumulation of Aβ is involved in cellular death due to ischemic cerebrovascular disorders. Other diseases in which abnormal accumulation and agglomeration of Aβ are observed include, for example, Down syndrome, cerebral bleeding due to solitary cerebral amyloid angiopathy, Lewy body disease (Shin-kei Shinpo [Nerve Advance], 34, 343 (1990); Tanpaku-shitu Kaku-san Koso [Protein, Nucleic Acid, Enzyme], 41, 1476 (1996)) and the like. Furthermore, as diseases showing neurofibrillary tangles due to the PHF accumulation, examples include progressive supranuclear palsy, subacute sclerosing panencephalitic parkinsonism, postencephalitic parkinsonism, pugilistic encephalitis, Guam parkinsonism-dementia complex, Lewy body disease and the like (Tanpakushitu Kakusan Koso [Protein, Nucleic Acid, Enzyme], 36, 2 (1991); Igaku no Ayumi [Progress of Medicine], 158, 511 (1991); Tanpakushitu Kakusan Koso [Protein, Nucleic Acid, Enzyme], 41, 1476 (1996)).

The tau protein is generally composed of a group of related proteins that forms several bands at molecular weights of 48-65 kDa in SDS-polyacrylamide gel electrophoresis, and it promotes the formation of microtubules. It has been verified that tau protein incorporated in the PHF in the brain suffering from Alzheimer disease is abnormally phosphorylated compared with usual tau protein (J. Biochem., 99, 1807 (1986); Proc. Natl. Acad. Sci. USA, 83, 4913 (1986)). An enzyme catalyzing the abnormal phosphorylation has been isolated. The protein was named as tau protein kinase 1 (abbreviated as "TPK1" hereinafter in the specification), and its physicochemical properties have been elucidated (Seikagaku [Biochemistry], 64, 308 (1992); J. Biol. Chem., 267, 10897 (1992)). Moreover, cDNA of rat TPK1 was cloned from a rat cerebral cortex cDNA library based on a partial amino acid sequence of TPK1, and its nucleotide sequence was determined and an amino acid sequence was deduced (Japanese Patent Un-examined Publication [Kokai] No. 6-239893/1994). As a result, it has been revealed that the primary structure of the rat TPK1 corresponds to that of the enzyme known as rat GSK-3β (glycogen synthase kinase 3β, FEBS Lett., 325, 167 (1993)).

It has been reported that Aβ, the main component of senile plaques, is neurotoxic (Science, 250, 279 (1990)). However, various theories have been proposed as for the reason why Aβ causes the cell death, and any authentic theory has not yet been established. Takashima et al. observed that the cell death was caused by Aβ treatment of fetal rat hippocampus primary culture system, and then found that the TPK1 activity was increased by Aβ treatment and the cell death by Aβ was inhibited by antisense of TPK1 (Proc. Natl. Acad. Sci. USA, 90, 7789 (1993); Japanese Patent Un-examined Publication [Kokai] No. 6-329551/1994).

In view of the foregoing, compounds which inhibit the TPK1 activity may possibly suppress the neurotoxicity of Aβ and. the formation of PHF and inhibit the nerve cell death in the Alzheimer disease, thereby cease or defer the progress of the disease. The compounds may also be possibly used as a medicament for therapeutic treatment of ischemic cerebrovascular disorder, Down syndrome, cerebral amyloid angiopathy, cerebral bleeding due to Lewy body disease and the like by suppressing the cytotoxicity of Aβ. Furthermore, the compounds may possibly be used as a medicament for therapeutic treatment of neurodegenerative diseases such as progressive supranuclear palsy, subacute sclerosing panencephalitic parkinsonism, postencephalitic parkinsonism, pugilistic encephalitis, Guam parkinsonism-dementia complex, Lewy body disease, Pick's disease, corticobasal degeneration, frontotemporal dementia, vascular dementia, traumatic injuries, brain and spinal cord trauma, peripheral neuropathies, retinopathies and glaucoma, as well as other diseases such as non-insulin dependent diabetes, obesity, manic depressive illness, schizophrenia, alopecia, breast cancer, non-small cell lung carcinoma, thyroid cancer, T or B-cell leukemia, and several virus-induced tumors.

As structurally similar compounds to the compounds of the present invention represented by formula (I) described later, compounds represented by the following formula (A) are known:

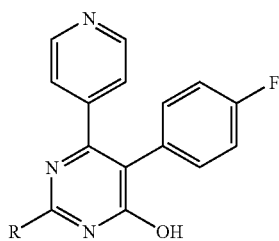

wherein R represents 2,6-dichlorobenzyl group, 2-(2-chlorophenyl)ethylamino group, 3-phenylpropylamino group, or 1-methyl-3-phenylpropylamino group (WO98/24782). The compounds represented by formula (A) are characterized to have 4-fluorophenyl group at the 5-position of the pyrimidine ring and a hydroxy group at the 4-position, and not falling within the scope of the present invention. Moreover, main pharmacological activity of the compounds represented by formula (A) is anti-inflammatory effect, whereas the compounds of the present invention represented by formula (I) are useful as a TPK1 inhibitor or a medicament for therapeutic treatment of neutodegenerative diseases, and therefore, their pharmacological activities are totally different to each other.

OBJECT TO BE ACHIEVED BY THE INVENTION

An object of the present invention is to provide compounds useful as an active ingredient of a medicament for preventive and/or therapeutic treatment of diseases such as Alzheimer disease. More specifically, the object is to provide novel compounds useful as an active ingredient of a medicament that enables radical prevention and/or treatment of the neurodegenerative diseases such as Alzheimer disease by inhibiting the TPK1 activity to suppress the neurotoxicity of Aβ and the formation of the PHF and by inhibiting the death of nerve cells.

MEANS TO ACHIEVE THE OBJECT

In order to achieve the foregoing object, the inventors of the present invention conducted screenings of various compounds having inhibitory activity against the phosphorylation of TPK1. As a result, they found that compounds represented by the following formula (I) had the desired activity and were useful as an active ingredient of a medicament for preventive and/or therapeutic treatment of the aforementioned diseases. The present invention was achieved on the basis of these findings.

The present invention thus provide a pyrimidone derivative represented by formula (I) or a salt thereof, or a solvate thereof or a hydrate thereof:

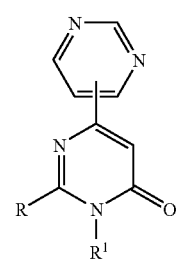

wherein $R^1$ represents a $C_1$-$C_{12}$ alkyl group which may be substituted;

R represents any one of groups represented by the following formulas (II) to (V):

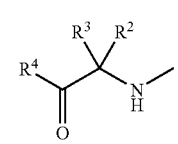

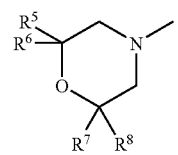

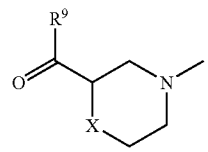

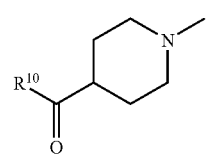

wherein $R^2$ and $R^3$ independently represent a hydrogen atom or a $C_1$-$C_8$ alkyl group;

$R^4$ represents a benzene ring which may be substituted, a naphthalene ring which may be substituted, an indan ring which may be substituted, a tetrahydronaphthalene ring which may be substituted, or an optionally substituted heterocyclic ring having 1 to 4 hetero atoms selected from the group consisting of oxygen atom, sulfur atom and nitrogen atom, and having 5 to 10 ring-constituting atoms in total;

$R^5$ represents a $C_1$-$C_8$ alkyl group which may be substituted, a $C_3$-$C_8$ cycloalkyl group which may be substituted, a benzene ring which may be substituted, a naphthalene ring which may be substituted, an indan ring which may be substituted, a tetrahydronaphthalene ring which may be substituted, or an optionally substituted heterocyclic ring having 1 to 4 hetero atoms selected from the group consisting of oxygen atom, sulfur atom, and nitrogen atom, and having 5 to 10 ring-constituting atoms in total;

R$^6$ represents a hydrogen atom, a C$_1$-C$_8$ alkyl group which may be substituted, a benzene ring which may be substituted;

or R$^5$ and R$^6$ may bind to each other to form together with the carbon to which R$^5$ and R$^6$ are attached an optionally substituted spiro carbocyclic ring having 3 to 11 ring-constituting atoms in total;

R$^7$ and R$^8$ independently represent a hydrogen atom or a C$_1$-C$_8$ alkyl group, or R$^7$ and R$^8$ may combine to each other to form a C$_2$-C$_6$ alkylene group;

R$^9$ and R$^{10}$ represent a C$_1$-C$_8$ alkyl group which may be substituted, a C$_3$-C$_8$ cycloalkyl group which may be substituted, a benzene ring which may be substituted, a naphthalene ring which may be substituted, an optionally substituted heterocyclic ring having 1 to 4 hetero atoms selected from the group consisting of oxygen atom, sulfur atom, and nitrogen atom, and having 5 to 10 ring-constituting atoms in total, or R$^9$ and R$^{10}$ represent —N(R$^{11}$)(R$^{12}$) wherein R$^{11}$ represents a hydrogen atom, a C$_1$-C$_8$ alkyl group; and R$^{12}$ represents a C$_1$-C$_8$ alkyl group, a benzene ring which may be substituted, a naphthalene ring which may be substituted, or an optionally substituted heterocyclic ring having 1 to 4 hetero atoms selected from the group consisting of oxygen atom, sulfur atom, and nitrogen atom, and having 5 to 10 ring-constituting atoms in total;

and X represents CH$_2$, O or NR$^{13}$ wherein R$^{13}$ represents a hydrogen atom or a C$_1$-C$_8$ alkyl group.

According to preferred embodiments of the present invention, provided are:

the aforementioned pyrimidone derivative or the salt thereof, or the solvate thereof or the hydrate thereof, wherein R$^1$ is methyl group;

the aforementioned pyrimidone derivative or the salt thereof, or the solvate thereof or the hydrate thereof, wherein R is the group represented by formula (II);

the aforementioned pyrimidone derivative or the salt thereof, or the solvate thereof or the hydrate thereof, wherein each of R$^2$ and R$^3$ is hydrogen atom;

the aforementioned pyrimidone derivative or the salt thereof, or the solvate thereof or the hydrate thereof, wherein R is the group represented by formula (III);

the aforementioned pyrimidone derivative or the salts thereof, or the solvate thereof or the hydrate thereof, wherein R$^6$ is hydrogen atom;

the aforementioned pyrimidone derivative or the salts thereof, or the solvate thereof or the hydrate thereof, wherein each of R$^7$ and R$^8$ is hydrogen atom;

the aforementioned pyrimidone derivative or the salts thereof, or the solvate thereof or the hydrate thereof, wherein each of R$^7$ and R$^8$ is methyl group;

the aforementioned pyrimidone derivative or the salt thereof, or the solvate thereof or the hydrate thereof, wherein R is the group represented by formula (IV);

the aforementioned pyrimidone derivative or the salts thereof, or the solvate thereof or the hydrate thereof, wherein R$^9$ is a benzene ring which may be substituted;

the aforementioned pyrimidone derivative or the salts thereof, or the solvate thereof or the hydrate thereof, wherein X is CH$_2$;

the aforementioned pyrimidone derivative or the salts thereof, or the solvate thereof or the hydrate thereof, wherein X is O;

the aforementioned pyrimidone derivative or the salt thereof, or the solvate thereof or the hydrate thereof, wherein R is the group represented by formula (V);

the aforementioned pyrimidone derivative or the salts thereof, or the solvate thereof or the hydrate thereof, wherein R$^{10}$ is a benzene ring which may be substituted; and the aforementioned pyrimidone derivative or the salts thereof, or the solvate thereof or the hydrate thereof, wherein R$^{10}$ is a heterocyclic ring having 1 to 4 hetero atoms selected from the group consisting of oxygen atom, sulfur atom, and nitrogen atom, and having total ring-constituting atoms of 5 to 10 which may be substituted.

From another aspect, the present invention provides a medicament comprising as an active ingredient a substance selected from the group consisting of the pyrimidone derivative represented by the aforementioned formula (I) and a salt thereof, and a solvate thereof and a hydrate thereof, and a tau protein kinase 1 inhibitor selected from the group consisting of the pyrimidone derivative represented by the aforementioned formula (I) and a salt thereof, and a solvate thereof and a hydrate thereof.

According to preferred embodiments of the aforementioned medicament, provided are the aforementioned medicament which is used for preventive and/or therapeutic treatment of a disease caused by tau protein kinase 1 hyperactivity;

the aforementioned medicament which is used for preventive and/or therapeutic treatment of a neurodegenerative disease;

the aforementioned medicament, wherein the disease is selected from the group consisting of Alzheimer disease, ischemic cerebrovascular accidents, Down syndrome, cerebral bleeding due to cerebral amyloid angiopathy, progressive supranuclear palsy, subacute sclerosing panencephalitic parkinsonism, postencephalitic parkinsonism, pugilistic encephalitis, Guam parkinsonism-dementia complex, Lewy body disease, Pick's disease, corticobasal degeneration, frontotemporal dementia, vascular dementia, traumatic injuries, brain and spinal cord trauma, peripheral neuropathies, retinopathies and glaucoma; and the aforementioned medicament, wherein the disease is selected from the group consisting of non-insulin dependent diabetes, obesity, manic depressive illness, schizophrenia, alopecia, breast cancer, non-small cell lung carcinoma, thyroid cancer, T or B-cell leukemia, and a virus-induced tumor.

According to further aspects of the present invention, there are provided a method for preventive and/or therapeutic treatment of a disease caused by tau protein kinase 1 hyperactivity, which comprises the step of administering to a patient a preventively and/or therapeutically effective amount of a substance selected from the group consisting of the 3-substituted-4-pyrimidone derivative of formula (I) and the physiologically acceptable salt thereof, and the solvate thereof and the hydrate thereof; and a use of a substance selected from the group consisting of the 3-substituted-4-pyrimidone derivative of formula (I) and the physiologically acceptable salt thereof, and the solvate thereof and the hydrate thereof for the manufacture of the aforementioned medicament.

From further aspect of the present invention, provided are a pyrimidone derivative represented by formula (VI) or a salt thereof, or a solvate thereof or a hydrate thereof:

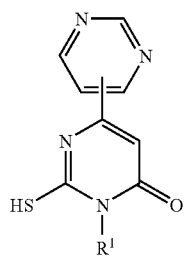

(VI)

wherein R¹ represents a $C_1$-$C_{12}$ alkyl group which may be substituted, and a pyrimidone derivative represented by formula (VII) or a salt thereof, or a solvate thereof or a hydrate thereof:

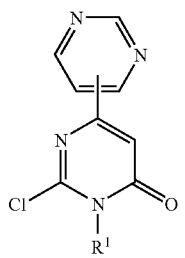

(VII)

wherein R¹ represents a $C_1$-$C_{12}$ alkyl group which may be substituted.

BEST MODE FOR CARRYING OUT THE INVENTION

The alkyl group used herein may be either linear or branched. The $C_1$-$C_{12}$ alkyl group represented by R¹ may be, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, or a linear or branched heptyl group, octyl group, nonyl group, decyl group, undecyl group or dodecyl group. In the specification, when a functional group is defined as "which may be substituted" or "optionally substituted", the number of substituents as well as their types and substituting positions are not particularly limited, and when two or more substituents are present, they may be the same or different.

When the $C_1$-$C_{12}$ alkyl group represented by R¹ has one or more substituents, the alkyl group may have one or more substituents selected from the group consisting of a $C_1$-$C_5$ alkoxyl group such as methoxy group, ethoxy group, propoxy group, isopropoxy group, butoxy group, isobutoxy group, tert-butoxy group; amino group, $C_1$-$C_3$ alkylamino group or $C_2$-$C_6$ dialkylamino group: a $C_6$-$C_{10}$ aryl group such as phenyl group, 1-naphthyl group, and 2-naphthyl group;

The $C_1$-$C_8$ alkyl group represented by R² or R³ may be, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, or a linear or branched heptyl group or octyl group.

When the benzene ring, the naphthalene ring, the indan ring, the tetrahydronaphthalene ring, or the heterocyclic ring represented by R⁴ or R⁵ has one or more substituents, the rings may have one or more substituents selected from the groups consisting of a $C_1$-$C_5$ alkyl group such as methyl group, ethyl group, propyl group, isopropyl group, butyl group, isobutyl group, sec-butyl group, tert-butyl group, pentyl group, isopentyl group, neopentyl group, 1,1-dimethylpropyl group; $C_3$-$C_6$ cycloalkyl group such as cyclopropyl group, cyclobutyl group, cyclopentyl group, cyclohexyl group; a $C_3$-$C_6$ cycloalkyloxy group such as cyclopropyloxy group, cyclobutyloxy group, cyclopentyloxy group, cyclohexyloxy group; a $C_1$-$C_5$ alkoxyl group such as methoxy group, ethoxy group, propoxy group, isopropoxy group, butoxy group, isobutoxy group, tert-butoxy group, pentyloxy group, and isopentyloxy group; a $C_4$-$C_7$ cycloalkylalkoxy group such as cyclopropylmethoxy group, cyclopentylmethoxy group; a $C_1$-$C_5$ alkylthio group such as methylthio group, ethylthio group, propylthio group, butylthio group, and pentylthio group; a $C_1$-$C_5$ alkylsulfonyl group such as methanesulfonyl group, ethanesulfonyl group, propanesulfonyl group, butanesulfonyl group, and pentanesulfonyl group; a halogen atom such as fluorine atom, chlorine atom, bromine atom, and iodine atom; a $C_1$-$C_5$ halogenated alkyl group such as trifluoromethyl group; a $C_1$-$C_5$ halogenated alkoxy group such as trifluoromethoxy group, 2,2,2-trifluoroethoxy group; hydroxyl group; cyano group; nitro group; formyl group; a $C_2$-$C_6$ alkylcarbonyl group such as acetyl group, propionyl group, butyryl group, and valeryl group; benzene ring which may be substituted, naphthalene ring which may be substituted, an optionally substituted heterocyclic ring having 1 to 4 hetero atoms selected from the group consisting of oxygen atom, sulfur atom and nitrogen atom, and having 5 to 10 ring-constituting atoms, phenoxy group which may be substituted or phenylamino group which may be substituted; amino group; a $C_1$-$C_5$ monoalkylamino group such as methylamino group, ethylamino group, propylamino group, isopropylamino group, butylamino group, isobutylamino group, tert-butylamino group, pentylamino group, and isopentylamino group; a $C_2$-$C_{10}$ dialkylamino group such as dimethylamino group, ethylmethylamino group, diethylamino group, methylpropylamino group, and diisopropylamino group; a $C_2$-$C_{10}$ monoalkylaminomethyl group such as methylaminomethyl group, ethylaminomethyl group, propylaminomethyl group, isopropylaminomethyl group, butylaminomethyl group, isobutylaminomethyl group, tert-butylaminomethyl group, pentylaminomethyl group, isopentylaminomethyl group; a $C_3$-$C_{11}$ dialkylaminomethyl group such as dimethylaminomethyl group, diethylaminomethyl group, ethylmethylaminomethyl group, methylpropylaminomethyl group; pyrrolidinylmethyl group; piperidinylmethyl group; morpholinomethyl group; piperazinylmethyl group; pyrrolylmethyl group; imidazolylmethyl group; pyrazolylmethyl group; and triazolylmethyl group.

When the benzene ring, the naphthalene ring, the indan ring, the tetrahydronaphthalene ring or the heterocyclic ring has one or more substituents, the substituent may further have one or more substituents selected from the group consisting of a $C_1$-$C_5$ alkyl group such as methyl group, ethyl group, propyl group, isopropyl group, butyl group, isobutyl group, sec-butyl group, tert-butyl group, pentyl group, isopentyl group, neopentyl group, 1,1-dimethylpropyl group; $C_3$-$C_6$ cycloalkyl group such as cyclopropyl group, cyclobutyl group, cyclopentyl group, cyclohexyl group; a $C_3$-$C_6$ cycloalkyloxy group such as cyclopropyloxy group, cyclobutyloxy group, cyclopentyloxy group, cyclohexyloxy group; a $C_1$-$C_5$ alkoxy group such as methoxy group, ethoxy group, propoxy group, isopropoxy group, butoxy group, isobutoxy group, tert-butoxy group, pentyloxy group, and isopentyloxy group; a $C_4$-$C_7$ cycloalkylalkoxy group such as cyclopropylmethoxy group, cyclopentylmethoxy group; a $C_1$-$C_5$ alkylthio group such as methylthio group, ethylthio group, propylthio group, butylthio group, and pentylthio group; a $C_1$-$C_5$ alkylsulfonyl group such as methanesulfonyl group, ethanesulfonyl group, propanesulfonyl group, butanesulfonyl group, and penitanesulfonyl group; a halogen atom such as fluorine atom, chlorine atom, bromine atom, and iodine atom; a $C_1$-$C_5$ halogenated alkyl group such as trifluoromethyl group; a $C_1$-$C_5$ halogenated alkoxy group such as trifluoromethoxy group, 2,2,2-trifluoroethoxy group; hydroxyl group; cyano group; nitro group; formyl group; a $C_2$-$C_6$ alkylcarbonyl group such as acetyl group, propionyl group, butyryl group, and valeryl group; amino group; a $C_1$-$C_5$ monoalkylamino group such as methylamino group, ethylamino group, propylamino group, isopropylamino group, butylamino group, isobutylamino group, tert-butylamino group, pentylamino group, and isopentylamino group; a $C_2$-$C_{10}$ dialkylamino group such as dimethylamino group, ethylmethylamino group, diethylamino group, methylpropylamino group, and diisopropylamino group; a $C_2$-$C_{10}$ monoalkylaminomethyl group such as methylaminomethyl group, ethyiaminomethyl group, propylaminomethyl group, isoproylaminomethyl group, butylaminomethyl group, isobutylaminomethyl group, tert-butylaminomethyl group, pentylaminomethyl group, isopentylaminomethyl group; a $C_3$-$C_{11}$ dialkylaminomethyl group such as dimethylaminomethyl group, diethylaminomethyl group, ethylmethylaminomethyl group, methylpropylaminomethyl group and the like.

The heterocyclic ring having 1 to 4 hetero atoms selected from the group consisting of oxygen atom, sulfur atom, and nitrogen atom, and having 5 to 10 ring-constituting atoms represented by $R^4$ or $R^5$ may be, for example, furan ring, dihydrofuran ring, tetrahydrofuran ring, pyran ring, dihydropyran ring, tetrahydropyran ring, benzofuran ring, dihydrobenzofuran, isobenzofuran ring, benzodioxole ring, chromene ring, chroman ring, isochroman ring, thiophene ring, benzothiophene ring, pyrrole ring, pyrroline ring, pyrrolidine ring, imidazole ring, imidazoline ring, imidazolidine ring, pyrazole ring, pyrazoline ring, pyrazolidine ring, triazole ring, tetrazole ring, pyridine ring, pyridine oxide ring, piperidine ring, pyrazine ring, piperazine ring, pyrimidine ring, pyridazine ring, indole ring, indoline ring, isoindole ring, isoindoline ring, indazole ring, benzimidazole ring, benzotriazole ring, tetrahydroisoquinoline ring, benzothiazolinone ring, benzoxazolinone ring, purine ring, quinolizine ring, quinoline ring, phthalazine ring, naphthyridine ring, quinoxaline ring, quinazoline ring, cinnoline ring, pteridine ring, oxazole ring, oxazolidine ring, isoxazole ring, isoxazolidine ring, oxadiazole ring, thiazole ring, benzothiazole ring, thiazylidine ring, isothiazole ring, isothiazolidine ring, benzodioxole ring, dioxane ring, benzodioxane ring, dithian ring, morpholine ring, thiomorpholine ring, and phthalimide ring.

The $C_1$-$C_8$ alkyl group represented by $R^5$, $R^6$, $R^7$ or $R^8$ may be, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, or a linear or branched heptyl group or octyl group.

The $C_3$-$C_8$ cycloalkyl group represented by $R^5$ may be, for example, cyclopropyl group, cyclobutyl group, cyclopentyl group, cyclohexyl group, cycloheptyl group or cyclooctyl group.

When the $C_1$-$C_8$ alkyl group or $C_3$-$C_8$ cycloalkyl group represented by $R^5$ or the $C_1$-$C_8$ alkyl group represented by $R^6$ has one or more substituents, the group may have one or more substituents selected from the groups consisting of a halogen atom, a $C_1$-$C_6$ alkoxyl group, a $C_3$-$C_8$ cycloalkyl group, a benzene ring which may be substituted, a naphthalene ring which may be substituted, phenoxy group which may be substituted or phenylamino group which may be substituted; amino group, a $C_1$-$C_6$ alkylamino group, a $C_2$-$C_{12}$ dialkylamino group, 1-pyrrolidinyl group, 1-pyperidinyl group, 1-morpholinyl group, 1-(tetrahydro-1,2,3,4-quinolinyl) group, or 1-(tetrahydro-1,2,3,4-isoquinolinyl) group.

When the benzene ring represented by $R^6$ has one or more substituents, the ring may have one or more substituents selected from the group consisting of a $C_1$-$C_5$ alkyl group such as methyl group, ethyl group, propyl group, isopropyl group, butyl group, isobutyl group, sec-butyl group, tert-butyl group, pentyl group, isopentyl group, neopentyl group, 1,1-dimethylpropyl group; a $C_3$-$C_6$ cycloalkyl group such as cyclopropyl group, cyclobutyl group, cyclopentyl group, cyclohexyl group; a $C_3$-$C_6$ cycloalkyloxy group such as cyclopropyloxy group, cyclobutyloxy group, cyclopentyloxy group, cyclohexyloxy group; a $C_1$-$C_5$ alkoxyl group such as methoxy group, ethoxy group, propoxy group, isopropoxy group, butoxy group, isobutoxy group, tert-butoxy group, pentyloxy group, and isopentyloxy group; a $C_4$-$C_7$ cycloalkylalkoxyl group such as cyclopropylmethoxy group, cyclopentylmethoxy group; a $C_1$-$C_5$ alkylthio group such as methylthio group, ethylthio group, propylthio group, butylthio group, and pentylthio group; a $C_1$-$C_5$ alkylsulfonyl group such as methanesulfonyl group, ethanesulfonyl group, propanesulfonyl group, butanesulfonyl group, and pentanesulfonyl group; a halogen atom such as fluorine atom, chlorine atom, bromine atom, and iodine atom; a $C_1$-$C_5$ halogenated, alkyl group such as trifluoromethyl group; a $C_1$-$C_5$ halogenated alkoxyl group such as trifluoromethoxy group, 2,2,2-trifluoroethoxy group; hydroxyl group; cyano group; nitro group; formyl group; a $C_2$-$C_6$ alkylcarbonyl group such as acetyl group, propionyl group, butyryl group, and valeryl group; a benzene ring which may be substituted, a naphthalene ring which may be substituted, an optionally substituted heterocyclic ring having 1 to 4 hetero atoms selected from the group consisting of oxygen atom, sulfur atom and nitrogen atom, and having 5 to 10 ring-constituting atoms, phenoxy group which may be substituted or phenylamino group which may be substituted; amino group; a $C_1$-$C_5$ monoalkylamino group such as methylamino group, ethylamino group, propylamino group, isopropylamino group, butylamino group, isobutylamino group, tert-butylamino group, pentylamino group, and isopentylamino group; a $C_2$-$C_{10}$ dialkylamino group such as dimethylamino group, ethylmethylamino group, diethylamino group, methylpropylamino group, and diisopropylamino group; a $C_2$-$C_{10}$ monoalkylaminomethyl group such as methylaminomethyl group, ethylaminomethyl group, propylaminomethyl group, isopropylaminomethyl group, butylaminomethyl group, isobutylaminomethyl group, tert-butylaminomethyl group, pentylaminomethyl group, isopentylaminomethyl group; a $C_3$-$C_{11}$ dialkylaminomethyl group such as dimethylaminomethyl group, diethylaminomethyl group, ethylmethylaminomethyl group, methylpropylaminomethyl group; pyrrolidinylmethyl group; pipelidinylmethyl group; morpholinomethyl group; piperazinylmethyl group; pyrrolylmethyl group; imidazolylmethyl group; pyrazolylmethyl group; triazolylmethyl group.

When the benzene ring represented by $R^6$ has one or more substituents, the substituent may further have one or more substituents selected from the groups consisting of a $C_1$-$C_5$ alkyl group such as methyl group, ethyl group, propyl group, isopropyl group, butyl group, isobutyl group, sec-butyl group, tert-butyl group, pentyl group, isopentyl group, neopentyl group, 1,1-dimethylpropyl group; $C_3$-$C_6$ cycloalkyl group such as cyclopropyl group, cyclobutyl group, cyclopentyl group, cyclohexyl group; a $C_3$-$C_6$ cycloalkyloxy group such as cyclopropyloxy group, cyclobutyloxy group, cyclopentyloxy group, cyclohexyloxy group; a $C_1$-$C_5$ alkoxyl group such as methoxy group, ethoxy group, propoxy group, isopropoxy group, butoxy group, isobutoxy group, tert-butoxy group, pentyloxy group, and isopentyloxy group; a $C_4$-$C_7$ cycloalkylalkoxyl group such as cyclopropylmethoxy group, cyclopentylmethoxy group; a $C_1$-$C_5$ alkylthio group such as methylthio group, ethylthio group, propylthio group, butylthio group, and pentylthio group; a $C_1$-$C_5$ alkylsulfonyl group such as methanesulfonyl group, ethanesulfonyl group, propanesulfonyl group, butanesulfonyl group, and pentanesulfonyl group; a halogen atom such as fluorine atom, chlorine atom, bromine atom, and iodine atom; a $C_1$-$C_5$ halogenated alkyl group such as trifluoromethyl group; a $C_1$-$C_5$ halogenated alkoxyl group such as trifluoromethoxy.group, 2,2,2-trifluoroethoxy group; hydroxyl group; cyano group; nitro group; formyl group; a $C_2$-$C_6$ alkylcarbonyl group such as acetyl group, propionyl group, butyryl group, and valeryl group; amino group; a $C_1$-$C_5$ monoalkylamino group such as methylamino group, ethylamino group, propylamino group, isopropylamino group, butylamino group, isobutylamino group, tert-butylamino group, pentylamino group, and isopentylamino group; a $C_2$-$C_{10}$ dialkylamino group such as dimethylamino group, ethylmethylamino group, diethylamino group, methylpropylamino group, and diisopropylamino group; a $C_2$-$C_{10}$ monoalkylaminomethyl group such as methylaminomethyl group, ethylaminomethyl group, propylaminomethyl group, isopropylaminomethyl group, butylaminomethyl group, isobutylaminomethyl group, tert-butylaminomethyl group, pentylaminomethyl group, isopentylaminomethyl group; a $C_3$-$C_{11}$ dialkylaminomethyl group such as dimethylaminomethyl group, diethylaminomethyl group, ethylmethylaminomethyl group, methylpropylamino-methyl group.

When $R^5$ and $R^6$ combine to each other to form a spiro carbocyclic ring, together with the carbon atom to which $R^5$ and $R^6$ bind, the carbocyclic ring may be, for example, cyclopropyl ring, cyclobutyl ring, cyclopentyl ring, cyclohexyl ring, cycloheptyl ring, tetrahydrobenzocycloheptene ring, tetrahydronaphthalene ring, indane ring, bicyclo[4,2,0]octa-1,3,5-triene ring.

The $C_1$-$C_8$ alkyl group represented by $R^9$, $R^{10}$, $R^{11}$, $R^{12}$ or $R^{13}$ may be, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, or a linear or branched heptyl group or octyl group.

The $C_3$-$C_8$ cycloalkyl group represented by $R^9$ or $R^{10}$ may be, for example, cyclopropyl group, cyclobutyl group, cyclopentyl group, cyclohexyl group, cycloheptyl group or cyclooctyl group.

When the $C_1$-$C_8$ alkyl group or $C_3$-$C_8$ cycloalkyl group represented by $R^9$ or $R^{10}$ has one or more substituents, the group may have one or more substituents selected from, for example, the groups consisting of a halogen atom, $C_3$-$C_8$ cycloalkyl group, a benzene ring which may be substituted, a naphthalene ring which may be substituted, an optionally substituted heterocyclic ring having 1 to 4 hetero atoms selected from the group consisting of oxygen atom, sulfur atom and nitrogen atom, and having 5 to 10 ring-constituting atoms in total.

When the benzene ring, the naphthalene ring or the heterocyclic ring represented by $R^9$ or RiO has one or more substituents, the ring may have one or more substituents selected form the group consisting of a $C_1$-$C_5$ alkyl group such as methyl group, ethyl group, propyl group, isopropyl group, butyl group, isobutyl group, sec-butyl group, tert-butyl group, pentyl group, isopentyl group, neopentyl group, 1,1-dimethylpropyl group; $C_3$-$C_6$ cycloalkyl group such as cyclopropyl group, cyclobutyl group, cyclopentyl group, cyclohexyl group; a $C_3$-$C_6$ cycloalkyloxy group such as cyclopropyloxy group, cyclobutyloxy group, cyclopentyloxy group, cyclohexyloxy group; a $C_1$-$C_5$ alkoxy group such as methoxy group, ethoxy group, propoxy group, isopropoxy group, butoxy group, isobutoxy group, tert-butoxy group, pentyloxy group, and isopentyloxy group; a $C_4$-$C_7$ cycloalkylalkoxyl group such as cyclopropylmethoxy group, cyclopentylmethoxy group; a $C_1$-$C_5$ alkylthio group such as methylthio group, ethylthio group, propylthio group, butylthio group, and pentylthio group; a $C_1$-$C_5$ alkylsulfonyl group such as methanesulfonyl group, ethanesulfonyl group, propanesulfonyl group,.butanesulfonyl group, and pentanesulfonyl group; a halogen atom such as fluorine atom, chlorine atom, bromine atom, and iodine atom; a $C_1$-$C_5$ halogenated alkyl group such as trifluoromethyl group; a $C_1$-$C_5$ halogenated alkoxyl group such as trifluoromethoxy group, 2,2,2-trifluoroethoxy group; hydroxyl group; cyano group; nitro group; formyl group; a $C_2$-$C_6$ alkylcarbonyl group such as acetyl group, propionyl group, butyryl group, and valeryl group; a benzene ring which may be substituted, a naphthalene ring which may be substituted, an optionally substituted heterocyclic ring having 1 to 4 hetero atoms selected from the group consisting of oxygen atom, sulfur atom and nitrogen atom, and having 5 to 10 ring-constituting atoms in total; a phenoxy group which may be substituted; a phenylamino group which may be substituted; an amino group; a $C_1$-$C_5$ monoalkylamino group such as methylamino group, ethylamino group, propylamino group, isopropylamino group, butylamino group, isobutylamino group, tert-butylamino group, pentylamino group, and isopentylamino group; a $C_2$-$C_{10}$ dialkylamino group such as dimethylamino group, ethylmethylamino group, diethylamino group, methylpropylamino group, and diisopropylamino group; a $C_1$-$C_5$ monoalkylaminomethyl group such as methylaminomethyl group, ethylaminomethyl group, propylaminomethyl group, isopropylaminomethyl group, butylaminomethyl group, isobutylaminomethyl group, tert-butylaminomethyl group, pentylaminomethyl group, isopentylaminomethyl group; a $C_2$-$C_{10}$ dialkylaminomethyl group such as dimethylaminomethyl group, diethylaminomethyl group, ethylmethylaminomethyl group, methylpropylaminomethyl group; pyrrolidinylmethyl group; piperidinylmethyl group; morpholinomethyl group; piperazinylmethyl group; pyrrolylmethyl group; imidazolylmethyl group; pyrazolylmethyl group; and triazolylmethyl group.

The heterocyclic ring having 1 to 4 hetero atoms selected from the group consisting of oxygen atom, sulfur atom, and nitrogen atom, and having 5 to 10 ring-constituting atoms in total represented by $R^9$ or $R^{10}$ may be, for example, furan ring, dihydrofuran ring, tetrahydrofuran ring, pyran ring, dihydropyran ring, tetrahydropyran ring, benzofuran ring, dihydrobenzofuran, isobenzofuran ring, benzodioxol ring, chromene ring, chroman ring, isochroman ring, thiophene ring, benzothiophene ring, pyrrole ring, pyrroline ring, pyrrolidine ring, imidazole ring, imidazoline ring, imidazolidine ring, pyrazole ring, pyrazoline ring, pyrazolidine ring, triazole ring, tetrazole ring, pyridine ring, pyridine oxide ring, piperidine ring, pyrazine ring, piperazine ring, pyrimidine ring, pyridazine ring, indole ring, indoline ring, isoindole ring, isoindoline ring, indazole ring, benzimidazole ring, benzotriazole ring, tetrahydroisoquinoline ring, benzothiazolinone ring, benzoxazolinone ring, purine ring, quinolizine ring, quinoline ring, phthalazine ring, naphthyridine ring, quinoxaline ring, quinazoline ring, cinnoline ring, pteridine ring, oxazole ring, oxazolidine ring, isoxazole ring, isoxazolidine ring, oxadiazole ring, thiazole ring, benzothiazole ring, thiazylidine ring, isothiazole ring, isothiazolidine ring, benzodioxole ring, dioxane ring, benzodioxane ring, dithian ring, morpholine ring, thiomorpholine ring, or phthalimide ring.

When the benzene ring, the naphthalene ring, or the heterocyclic ring represented by $R^{12}$ has one or more substituents, the ring may be substituted by one or more substituents selected from the groups consisting of halogen atoms, a $C_1$-$C_5$ alkyl group, a $C_3$-$C_6$ cycloalkyl group, a $C_3$-$C_6$ cycloalkyloxy group, a $C_1$-$C_5$ alkoxy group, a $C_4$-$C_7$ cycloalkylalkoxy, a $C_1$-$C_5$ alkylthio group, a $C_1$-$C_5$ alkylsulfonyl group, a $C_1$-$C_5$ halogenated alkyl, and a benzene ring.

When the benzene ring, the naphthalene ring or the heterocyclic ring has one or more substituents, the substituent may further have one or more substituents selected from the group consisting of a $C_1$-$C_5$ alkyl group such as methyl group, ethyl group, propyl group, isopropyl group, butyl group, isobutyl group, sec-butyl group, tert-butyl group, pentyl group, isopentyl group, neopentyl group, 1,1-dimethylpropyl group; $C_3$-$C_6$ cycloalkyl group such as cyclopropyl group, cyclobutyl group, cyclopentyl group, cyclohexyl group; a $C_3$-$C_6$ cycloalkyloxy group such as cyclopropyloxy group, cyclobutyloxy group, cyclopentyloxy group, cyclohexyloxy group; a $C_1$-$C_5$ alkoxy group such as methoxy group, ethoxy group, propoxy group, isopropoxy group, butoxy group, isobutoxy group, tert-butoxy group, pentyloxy group, and isopentyloxy group; a $C_4$-$C_7$ cycloalkylalkoxy group such as cyclopropylmethoxy group, cyclopentylmethoxy group; a $C_1$-$C_5$ alkylthio group such as methylthio group, ethylthio group, propylthio group, butylthio group, and pentylthio group; a $C_1$-$C_5$ alkylsulfonyl group such as methanesulfonyl group, ethanesulfonyl group, propanesulfonyl group, butanesulfonyl group, and pentanesulfonyl group; a halogen atom such as fluorine atom, chlorine atom, bromine atom, and iodine atom; a $C_1$-$C_5$ halogenated alkyl group such as trifluoromethyl group; a $C_1$-$C_5$ halogenated alkoxy group such as trifluoromethoxy group, 2,2,2-trifluoroethoxy group; hydroxyl group; cyano group; nitro group; formyl group; a $C_2$-$C_6$ alkylcarbonyl group such as acetyl group, propionyl group, butyryl group, and valeryl group; amino group; a $C_1$-$C_5$ monoalkylamino group such as methylamino group, ethylamino group, propylamino group, isopropylamino group, butylamino group, isobutylamino group, tert-butylamino group, pentylamino group, and isopentylamino group; a $C_2$-$C_{10}$ dialkylamino group such as dimethylamino group, ethylmethylamino group, diethylamino group, methylpropylamino group, and diisopropylamino group; a $C_2$-$C_{10}$ monoalkylaminomethyl group such as methylaminomethyl group, ethylaminomethyl group, propylaminomethyl. group, isopropylaminomethyl group, butylaminomethyl group, isobutylaminomethyl group, tert-butylaminomethyl group, pentylaminomethyl group, isopentylaminomethyl group; a $C_3$-$C_{11}$ dialkylaminomethyl group such as dimethylaminomethyl group, diethylaminomethyl group, ethylmethylaminomethyl group, methylpropylaminomethyl group and the like.

$R^1$ may preferably be a $C_1$-$C_3$ alkyl group, more preferably a methyl group.

$R^2$ may preferably be a hydrogen atom.

$R^3$ may preferably be a hydrogen atom.

$R^4$ may preferably be a benzene ring which may be substituted.

$R^5$ may preferably be a benzene ring or a naphthalene ring which may be substituted.

$R^6$ may preferably be a hydrogen atom.

$R^7$ and $R^8$ may preferably be a hydrogen atom or a $C_1$-$C_3$ alkyl group.

$R^9$ or $R^{10}$ may preferably be a benzene ring which may be substituted.

$R^{10}$ may preferably be a heterocyclic ring having 1-4 hetero atoms selected oxygen atom, sulfur atom and nitrogen atom, and having total ring-constituting atoms of 5-10 which may be substituted. Particularly preferred $R^{10}$ is a benzene ring which may be substituted, a 2,3-dihydroindole ring which may be substituted, or 3,4-dihydro-2H-quinoline ring which may be substituted.

Particularly preferred X is $CH_2$ or O.

The compounds represented by the aforementioned formula (I) may form a salt. Examples of the salt include, when an acidic group exists, salts of alkali metals and alkaline earth metals such as lithium, sodium, potassium, magnesium, and calcium; salts of ammonia and amines such as methylamine, dimethylamine, trimethylamine, dicyclohexylamine, tris(hydroxymethyl)aminomethane, N,N-bis(hydroxyethyl)piperazine, 2-amino-2-methyl-1-propanol, ethanolamine, N-methylglucamine, and L-glucamine; or salts with basic amino acids such as lysine, 6-hydroxylysine, and arginine. When a basic group exists, examples include salts with mineral acids such as hydrochloric acid, hydrobromic acid, sulfuric acid, nitric acid, phosphoric acid; salts with organic acids such as methanesulfonic acid, benzenesulfonic acid, p-toluenesulfonic acid, acetic acid, propionic acid, tartaric acid, fumaric acid, maleic acid, malic acid, oxalic acid, succinic acid, citric acid, benzoic acid, mandelic acid, cinnamic acid, lactic acid, glycolic acid, glucuronic acid, ascorbic acid, nicotinic acid, and salicylic acid; or salts with acidic amino acids such as aspartic acid, and glutamic acid.

In addition to the 3-substituted-4-pyrimidone derivatives represented by the aforementioned formula (I) and salts thereof, their solvates and hydrates also fall within the scope of the present invention. The 3-substituted-4-pyrimidone derivatives represented by the aforementioned formula (I) may have one or more asymmetric carbon atoms. As for the stereochemistry of such asymmetric carbon atoms, they may independently be in either (R) and (S) configuration, and the pyrimidone derivative may exist as stereoisomers such as optical isomers, or diastereoisomers. Any stereoisomers of pure form, any mixtures of stereoisomers, racemates and the like fall within the scope of the present invention Examples of preferred compounds of the present invention are shown in the table below. However, the scope of the present invention is not limited by the following compounds.

| Compound No. | STRUCTURE |
|---|---|
| A119 | 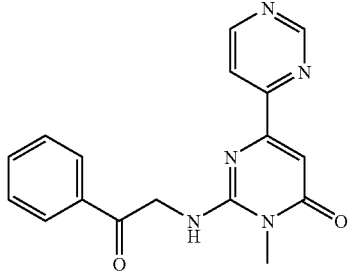 |
| A120 | 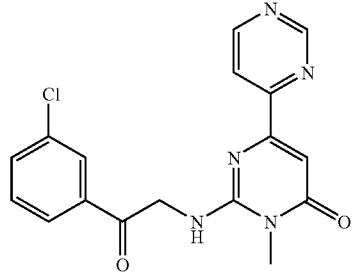 |
| A121 | 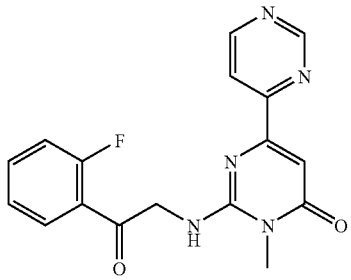 |
| A122 | 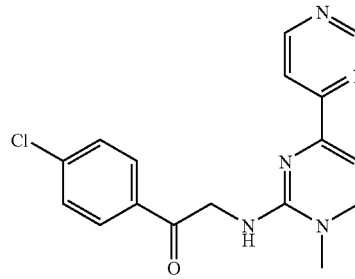 |
| A123 | 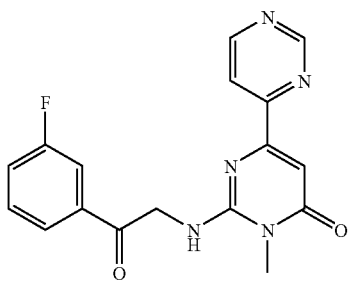 |
-continued
| Compound No. | STRUCTURE |
|---|---|
| A124 | 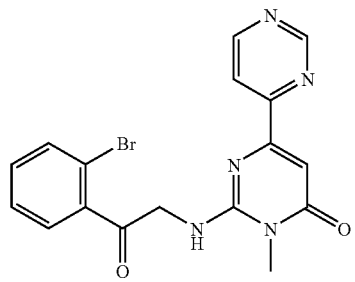 |
| A125 | 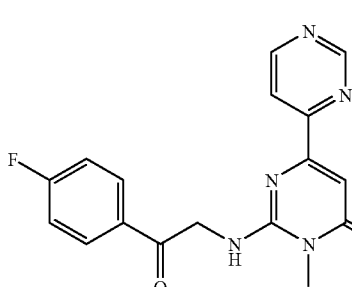 |
| A126 | 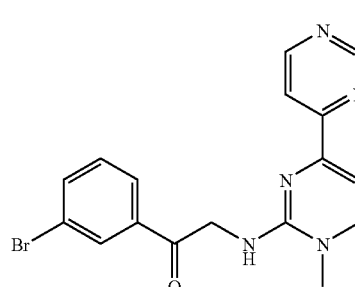 |
| A127 | 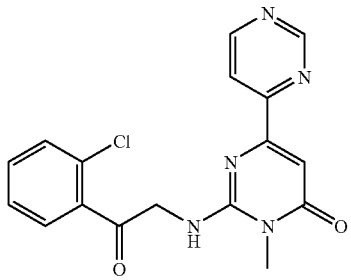 |
| A128 | 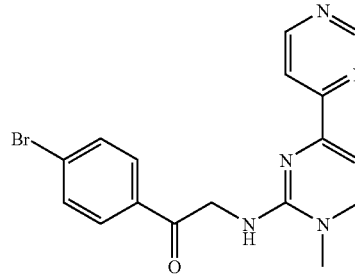 |

-continued
| Compound No. | STRUCTURE |
|---|---|
| A129 | 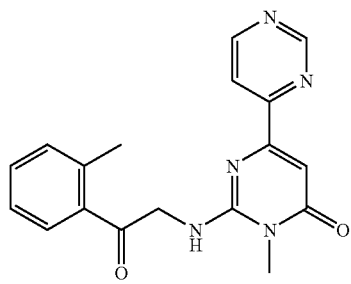 |
| A130 | 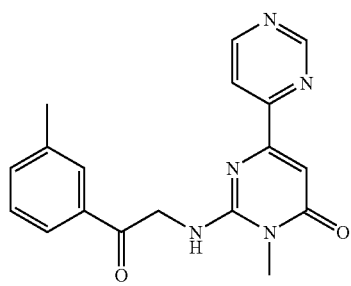 |
| A131 | 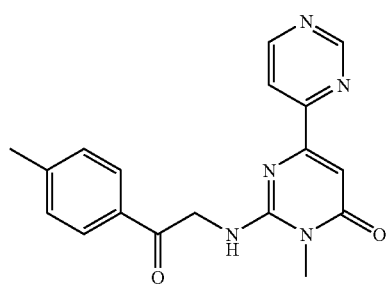 |
| A132 | 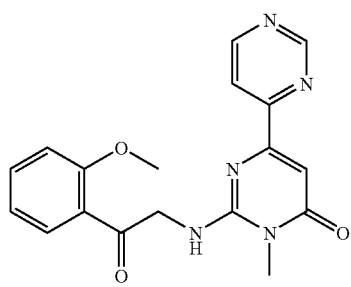 |
| A133 | 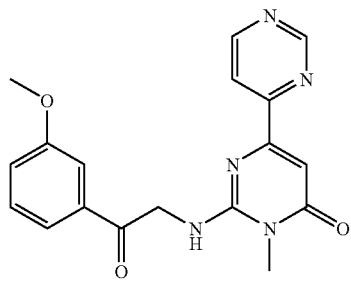 |
-continued
| Compound No. | STRUCTURE |
|---|---|
| A134 | 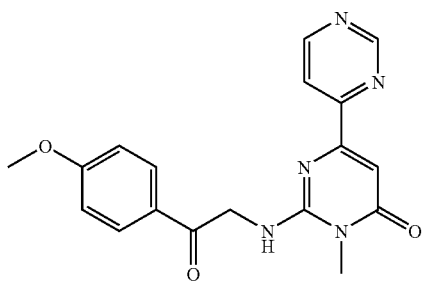 |
| A135 | 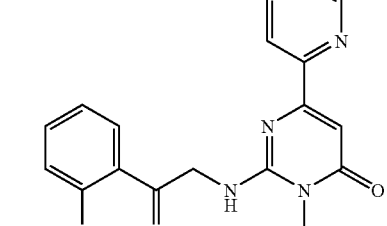 |
| A136 | 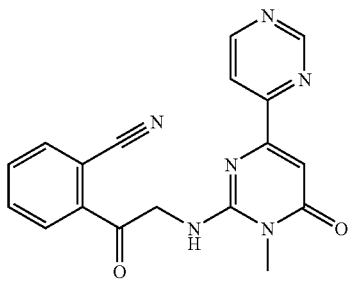 |
| A137 | 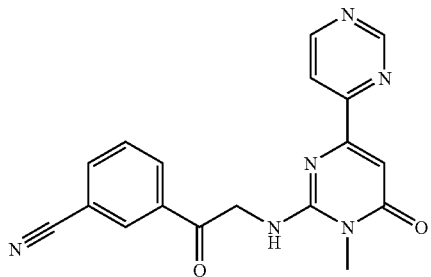 |
| A138 | 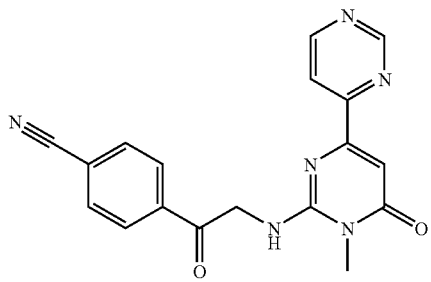 |

-continued
| Compound No. | STRUCTURE |
|---|---|
| A139 | 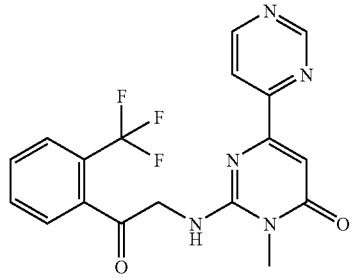 |
| A140 | 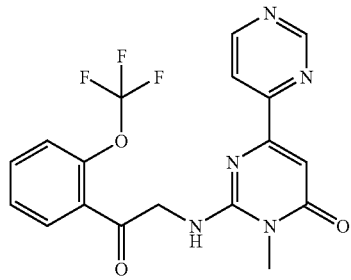 |
| A141 | 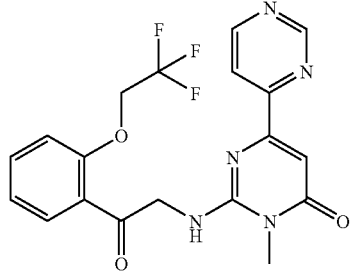 |
| A142 | 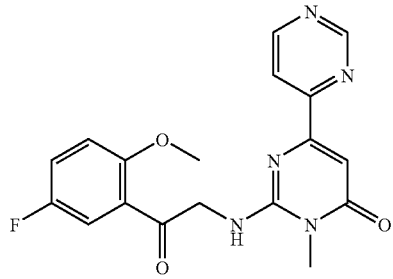 |
| A143 | 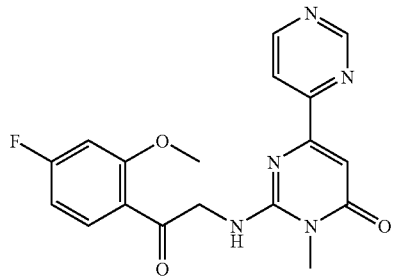 |
-continued
| Compound No. | STRUCTURE |
|---|---|
| A144 | 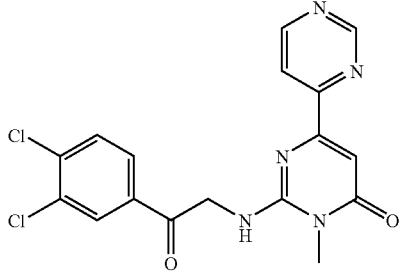 |
| A145 | 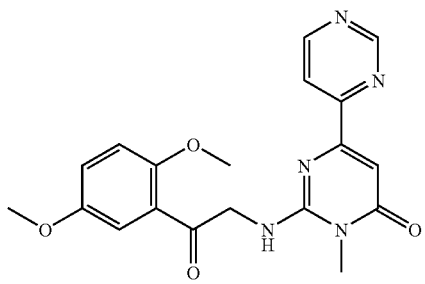 |
| A146 | 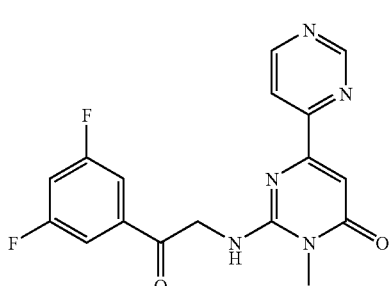 |
| A147 | 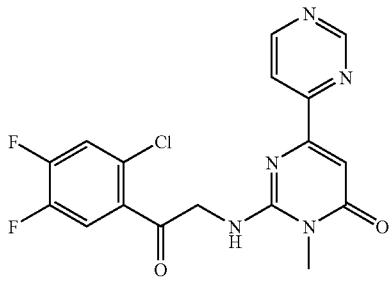 |
| A148 | 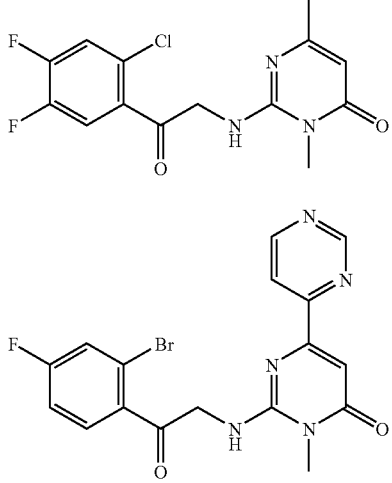 |

-continued

| Compound No. | STRUCTURE |
|---|---|
| A149 | 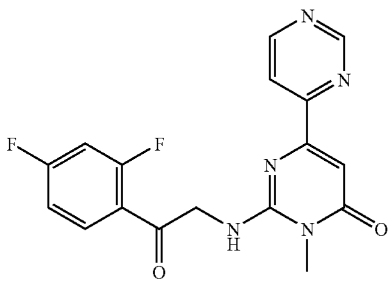 |
| A150 | 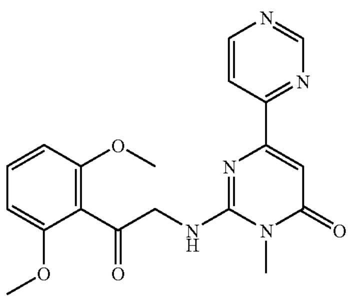 |
| A151 | 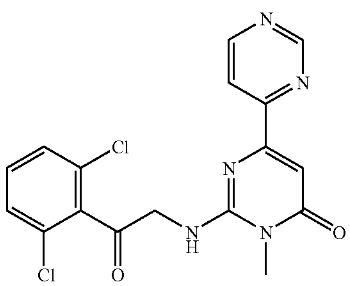 |
| A152 | 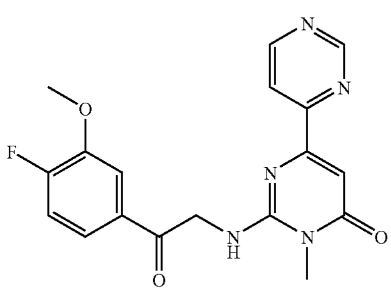 |
| A153 | 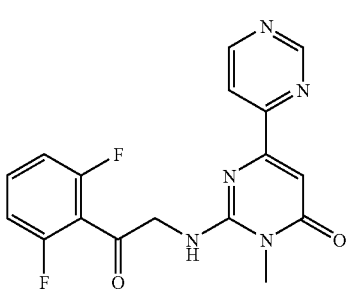 |

-continued

| Compound No. | STRUCTURE |
|---|---|
| A154 | 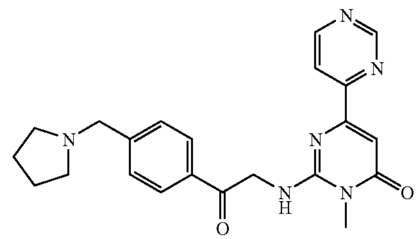 |
| A155 | 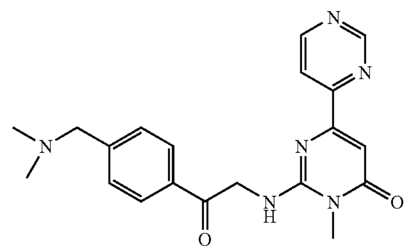 |
| A156 | 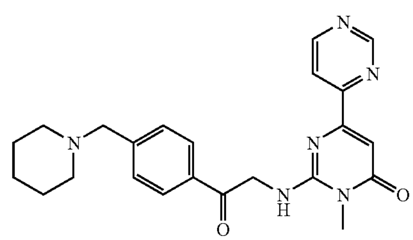 |
| A157 | 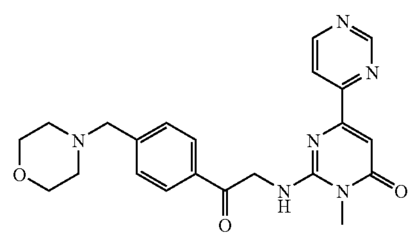 |
| A158 | 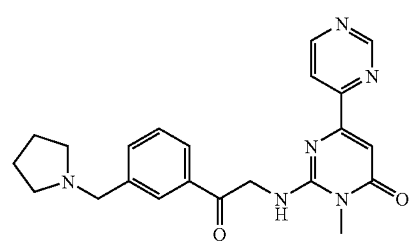 |
| A159 | 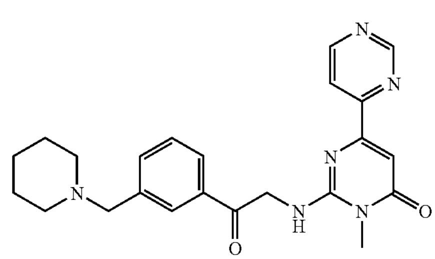 |

| Compound No. | STRUCTURE |
|---|---|
| A160 | 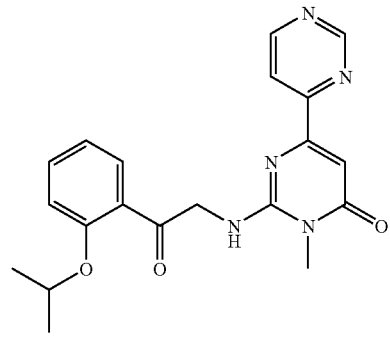 |
| A161 | 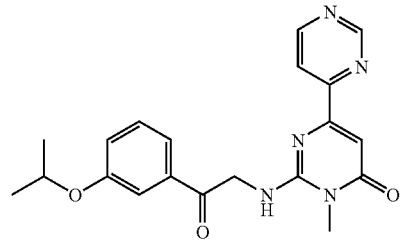 |
| A162 | 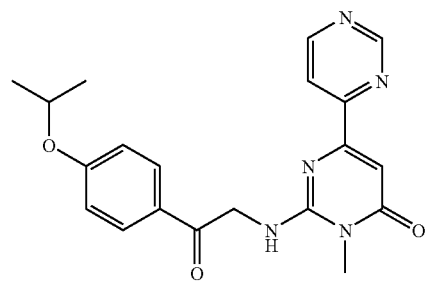 |
| A163 | 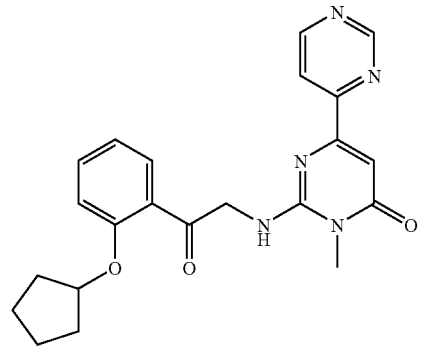 |
| A164 | 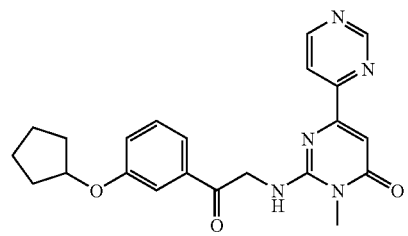 |
| Compound No. | STRUCTURE |
|---|---|
| A165 | 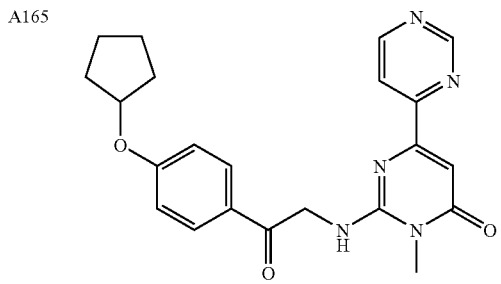 |
| A166 | 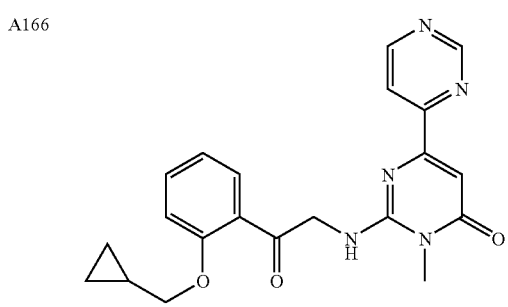 |
| A167 | 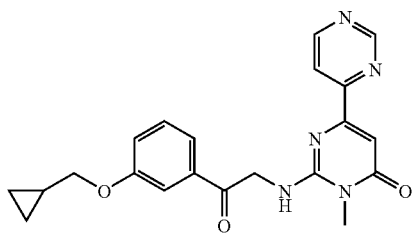 |
| A168 | 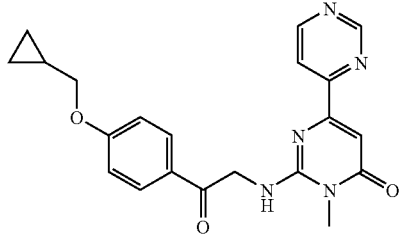 |
| A169 | 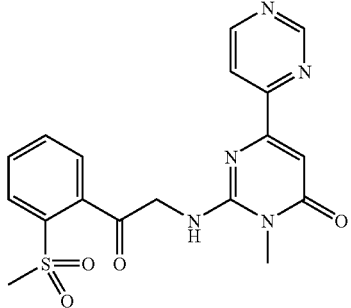 |

-continued
| Compound No. | STRUCTURE |
|---|---|
| A170 | 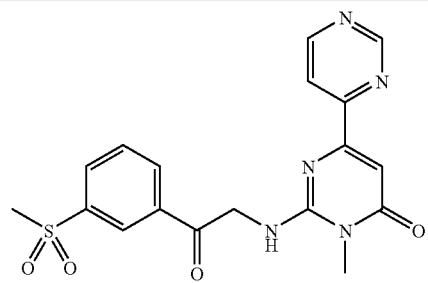 |
| A171 | 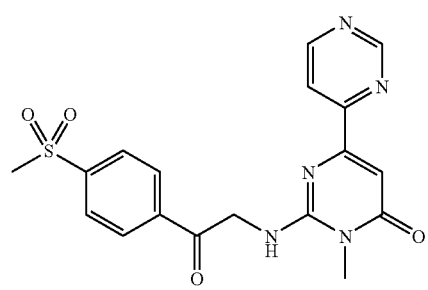 |
| A172 | 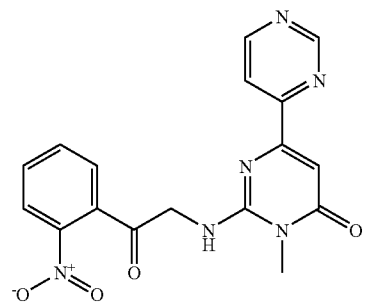 |
| A173 | 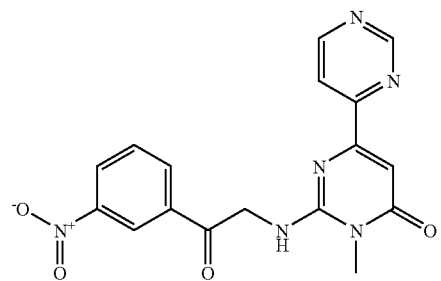 |
| A174 | 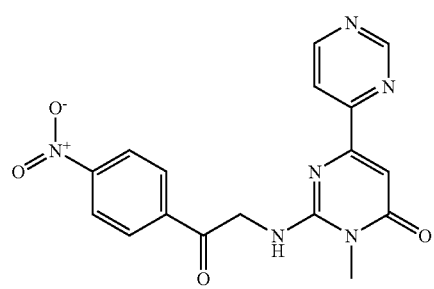 |
-continued
| Compound No. | STRUCTURE |
|---|---|
| A175 | 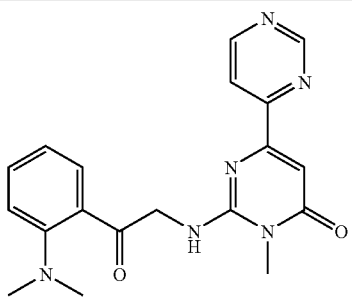 |
| A176 | 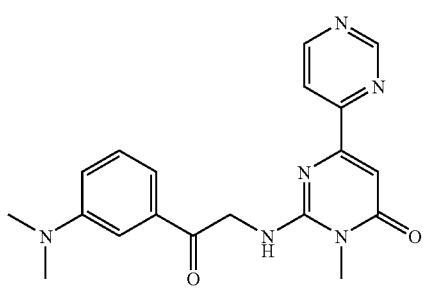 |
| A177 | 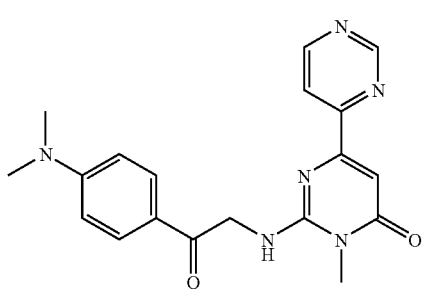 |
| A178 | 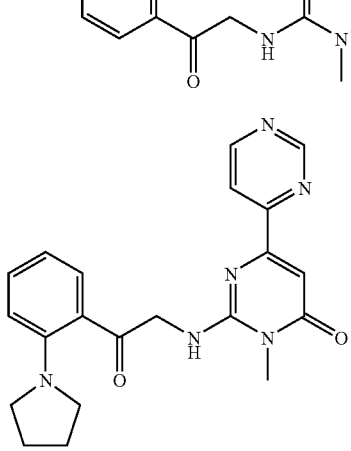 |
| A179 | 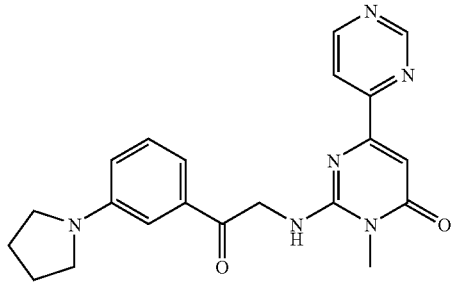 |

-continued
| Compound No. | STRUCTURE |
|---|---|
| A180 | 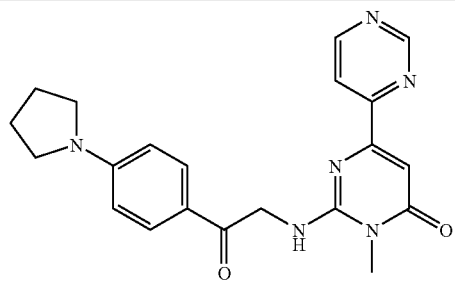 |
| A181 | 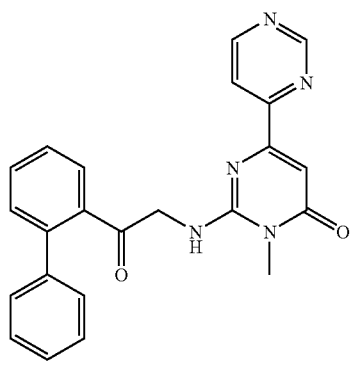 |
| A182 | 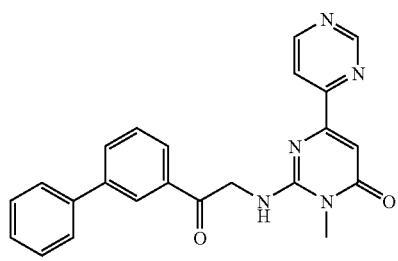 |
| A183 | 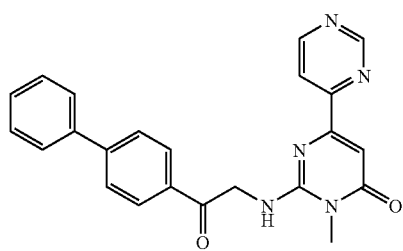 |
| A184 | 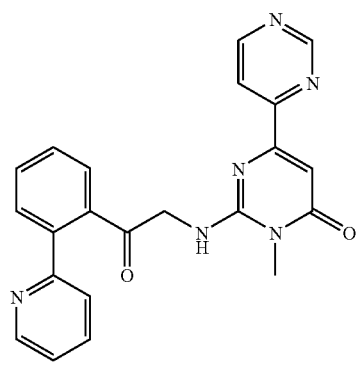 |
-continued
| Compound No. | STRUCTURE |
|---|---|
| A185 | 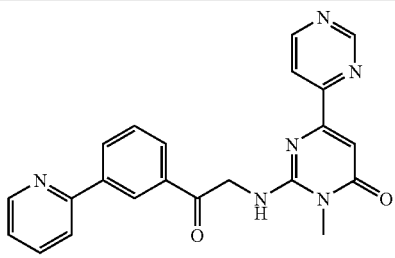 |
| A186 | 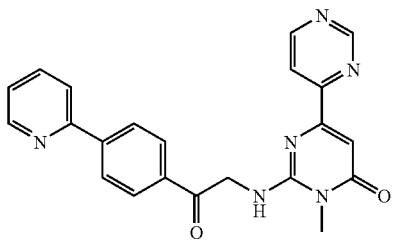 |
| A187 | 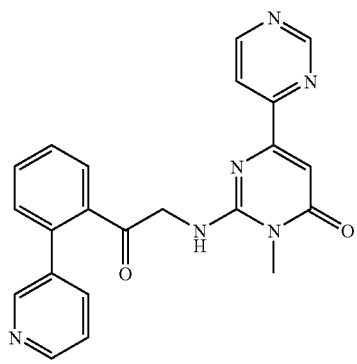 |
| A188 | 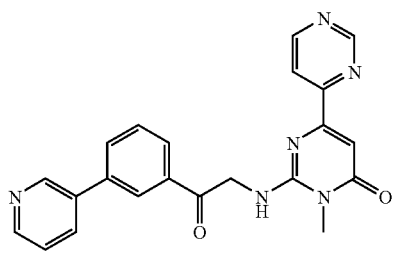 |
| A189 | 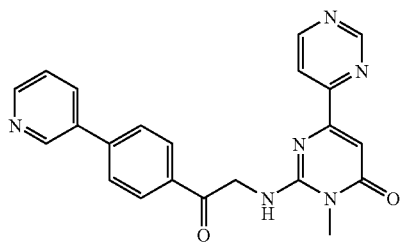 |

-continued

| Compound No. | STRUCTURE |
|---|---|
| A190 | 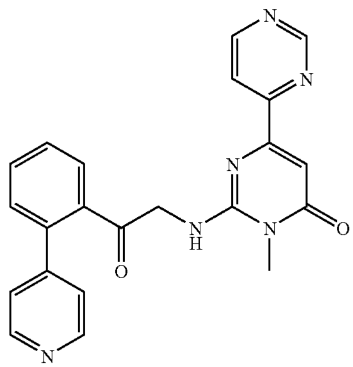 |
| A191 | 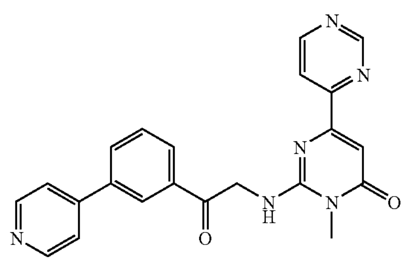 |
| A192 | 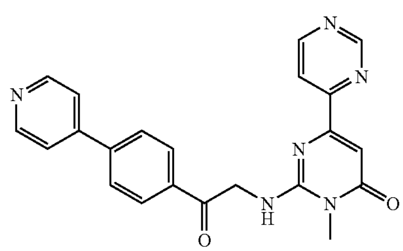 |
| A193 | 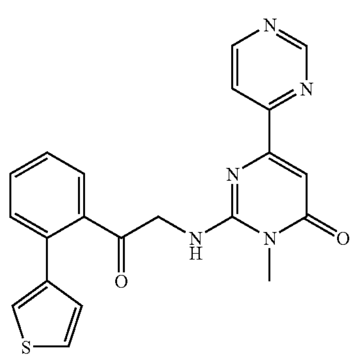 |
| A194 | 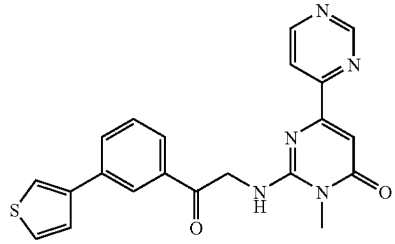 |

-continued

| Compound No. | STRUCTURE |
|---|---|
| A195 | 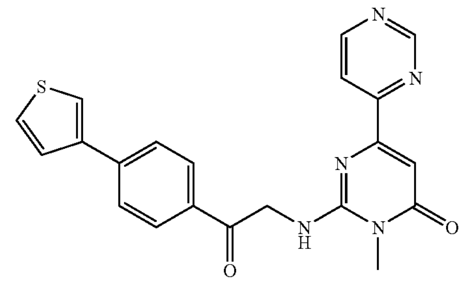 |
| A196 | 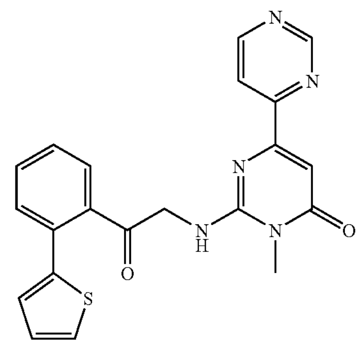 |
| A197 | 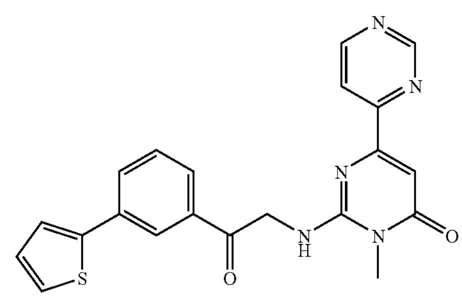 |
| A198 | 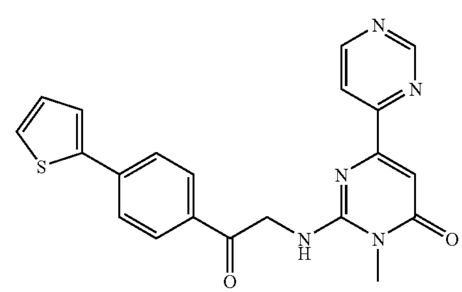 |
| A199 | 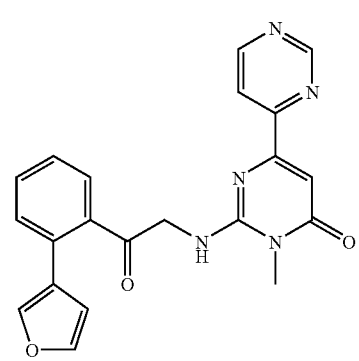 |

-continued
| Compound No. | STRUCTURE |
|---|---|
| A200 | 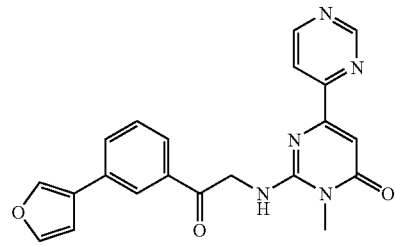 |
| A201 | 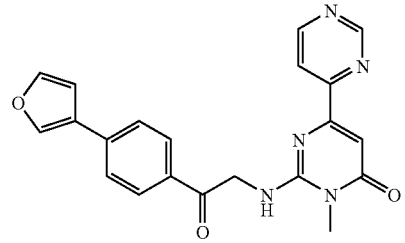 |
| A202 | 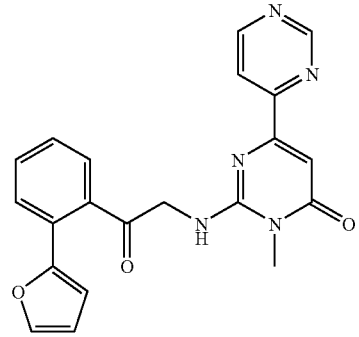 |
| A203 | 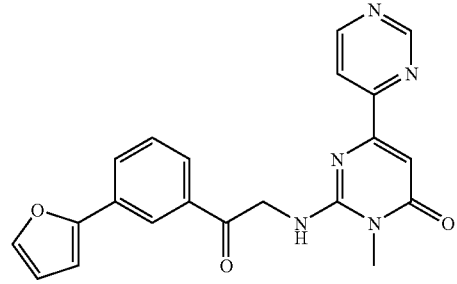 |
| A204 | 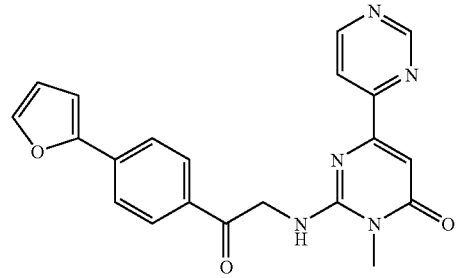 |
-continued
| Compound No. | STRUCTURE |
|---|---|
| A205 | 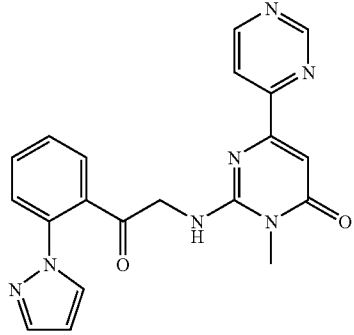 |
| A206 | 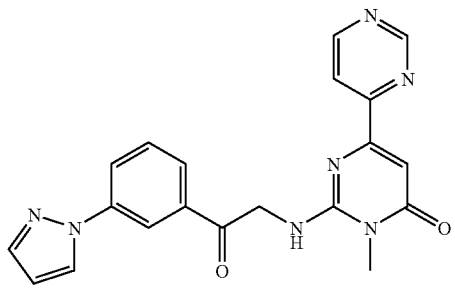 |
| A207 | 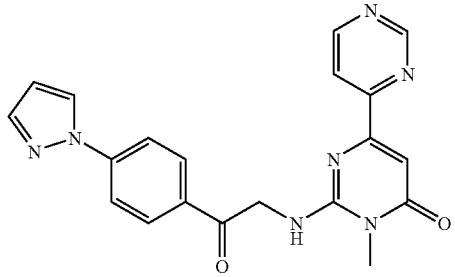 |
| A208 | 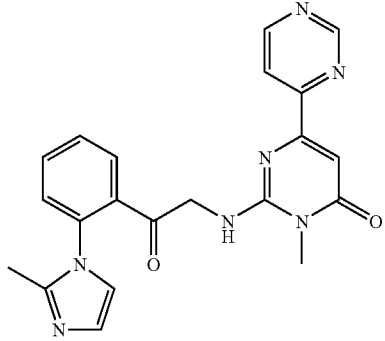 |
| A209 | 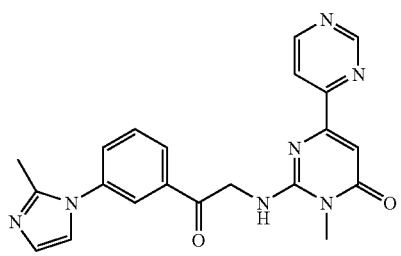 |

-continued
| Compound No. | STRUCTURE |
|---|---|
| A210 | 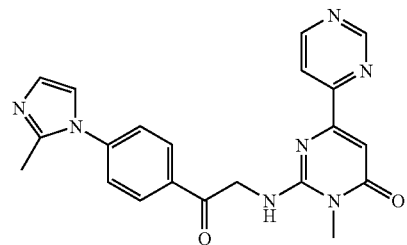 |
| A211 | 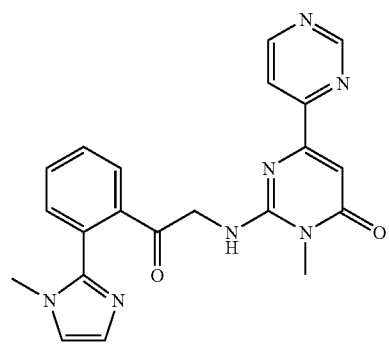 |
| A212 | 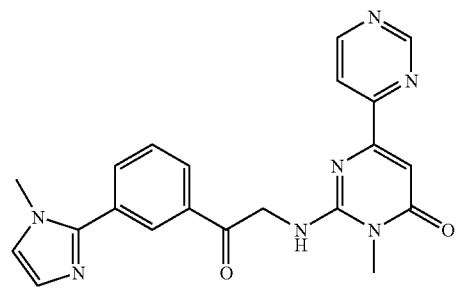 |
| A213 | 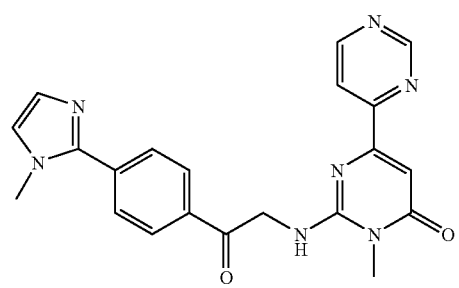 |
| A214 | 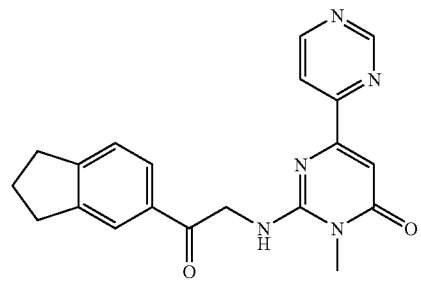 |
-continued
| Compound No. | STRUCTURE |
|---|---|
| A215 | 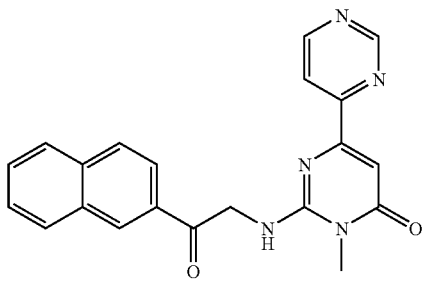 |
| A216 | 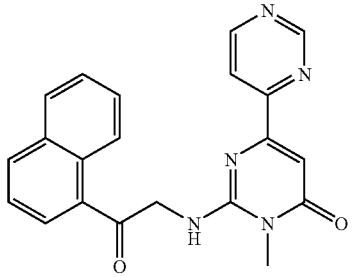 |
| A217 | 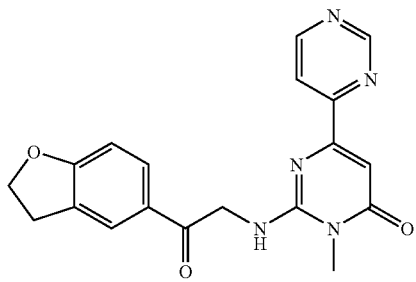 |
| A218 | 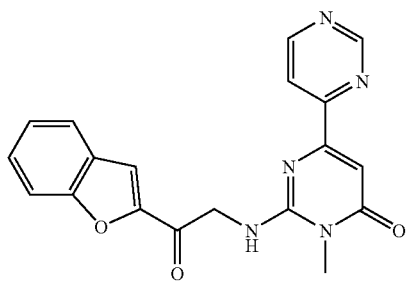 |
| A219 | 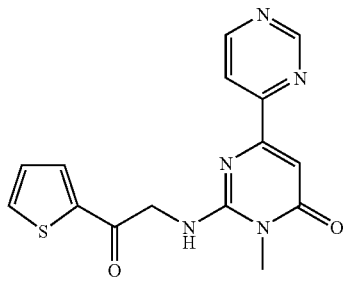 |

-continued
| Compound No. | STRUCTURE |
|---|---|
| A220 | 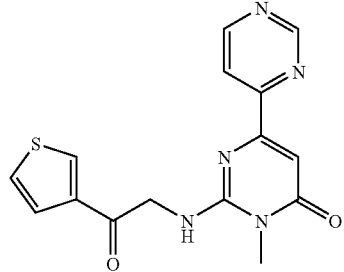 |
| A221 | 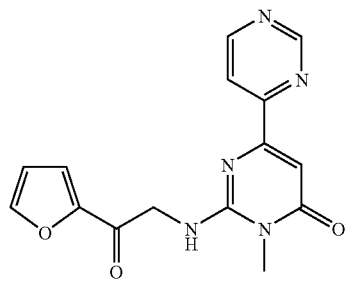 |
| A222 | 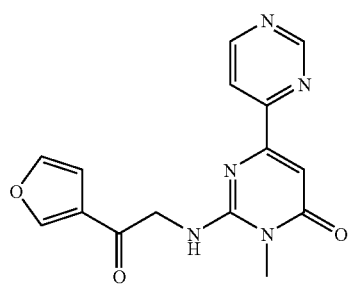 |
| A223 | 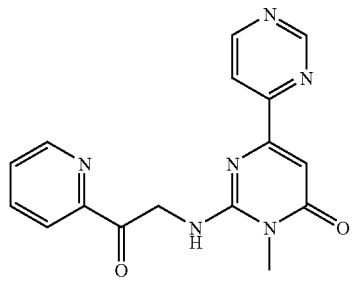 |
| A224 | 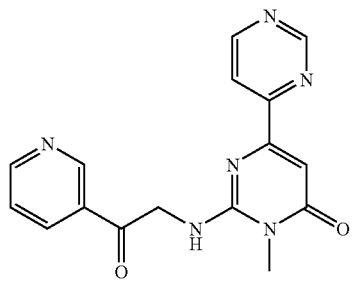 |
-continued
| Compound No. | STRUCTURE |
|---|---|
| A225 | 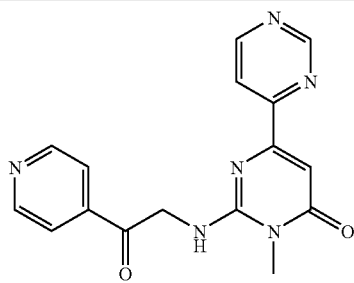 |
| A226 | 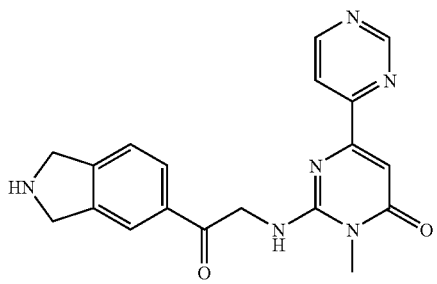 |
| A227 | 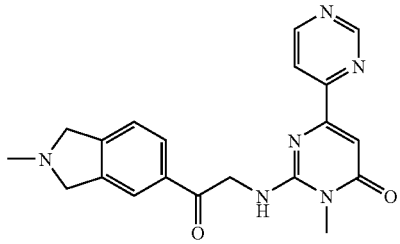 |
| A228 | 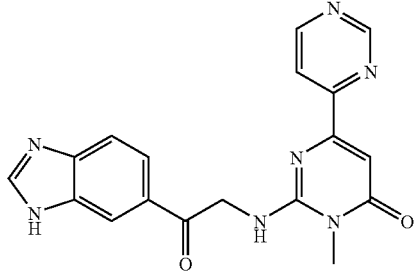 |
| A229 | 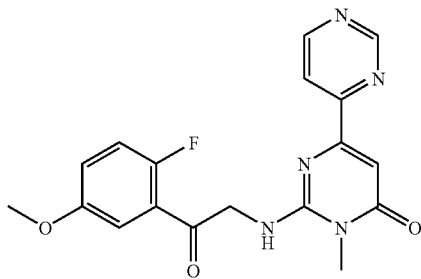 |

-continued
| Compound No. | STRUCTURE |
|---|---|
| A230 | 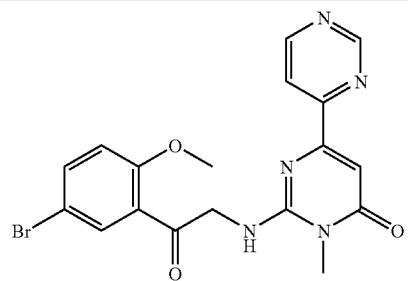 |
| A231 | 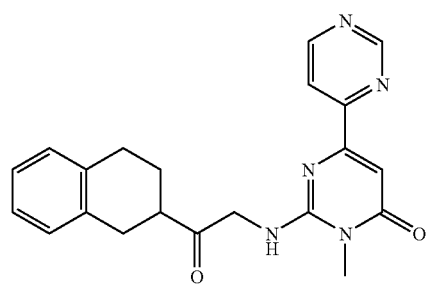 |
| A232 | 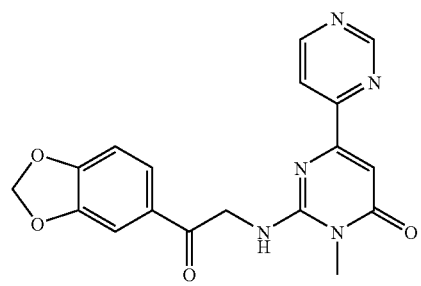 |
| A233 | 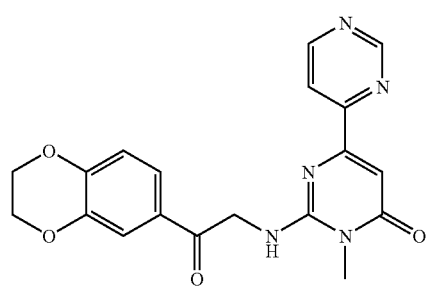 |
| A234 | 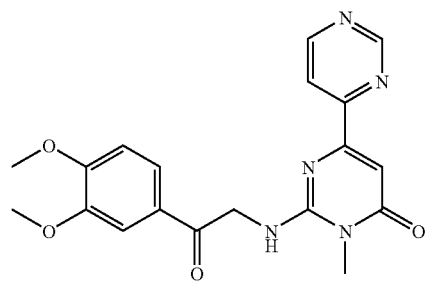 |
-continued
| Compound No. | STRUCTURE |
|---|---|
| A235 | 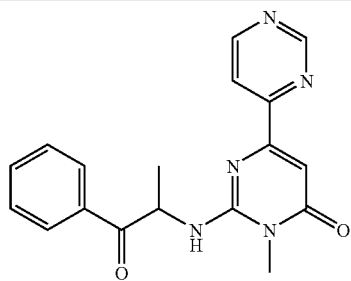 |
| A236 | 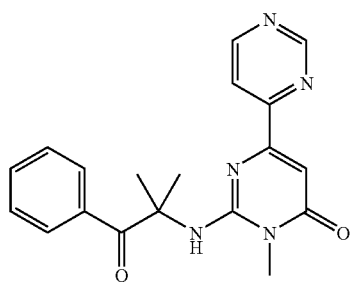 |
| B001 | 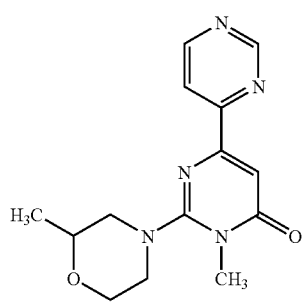 |
| B002 | 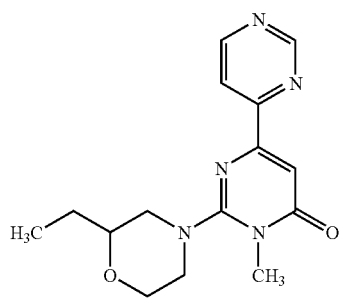 |
| B003 | 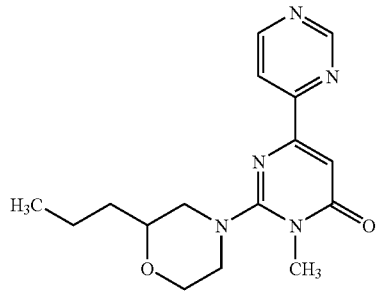 |

-continued
| Compound No. | STRUCTURE |
|---|---|
| B004 | 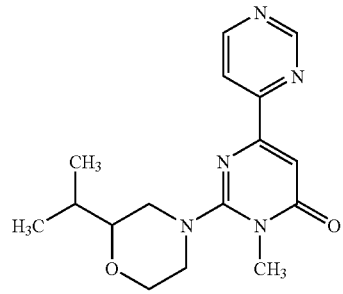 |
| B005 | 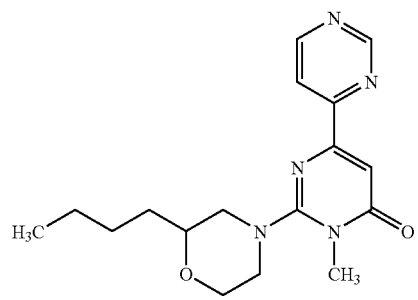 |
| B006 | 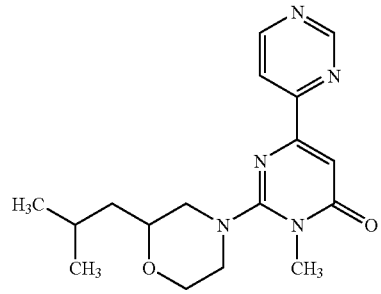 |
| B007 | 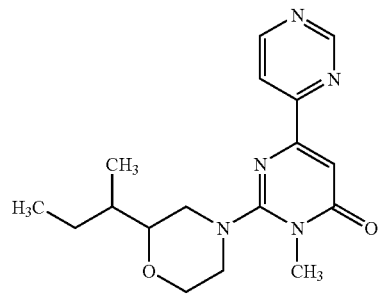 |
| B008 | 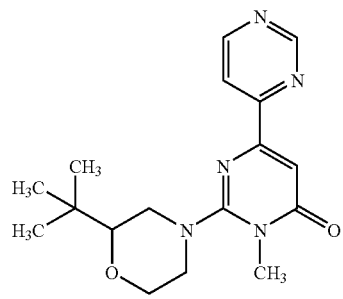 |
-continued
| Compound No. | STRUCTURE |
|---|---|
| B009 | 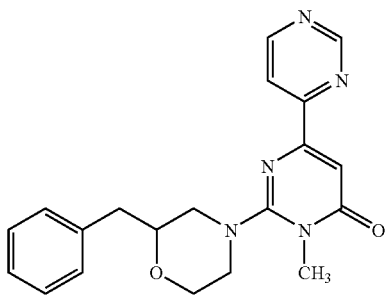 |
| B010 | 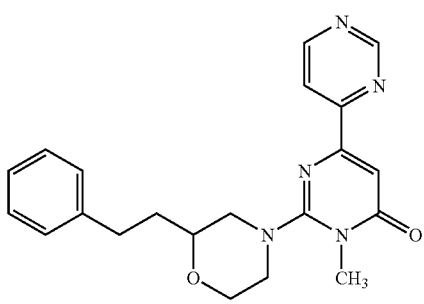 |
| B011 | 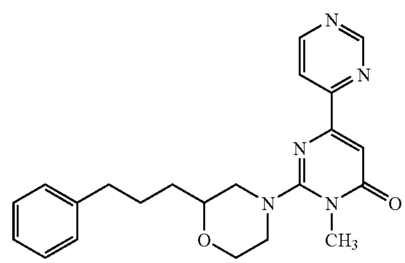 |
| B012 | 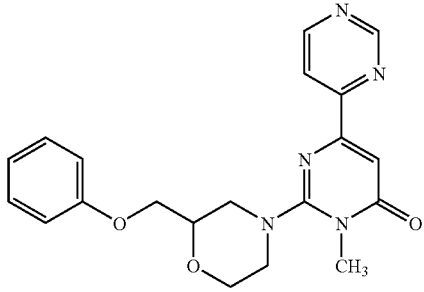 |
| B013 | 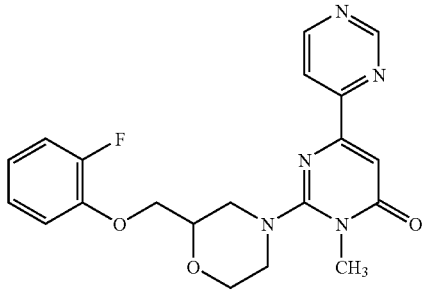 |

-continued
| Compound No. | STRUCTURE |
|---|---|
| B014 | 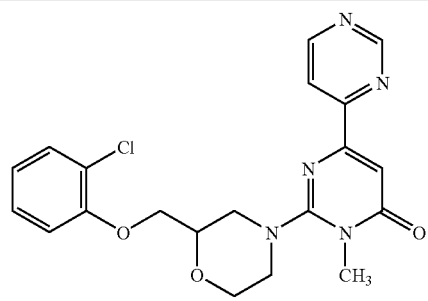 |
| B015 | 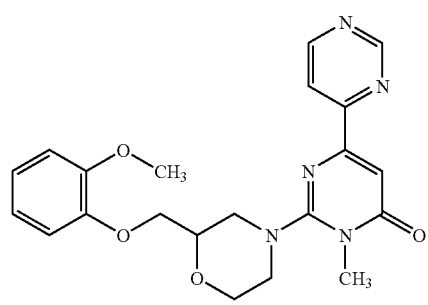 |
| B016 | 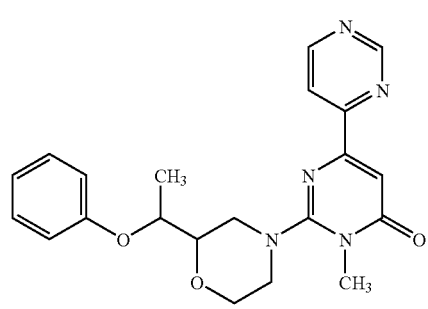 |
| B017 | 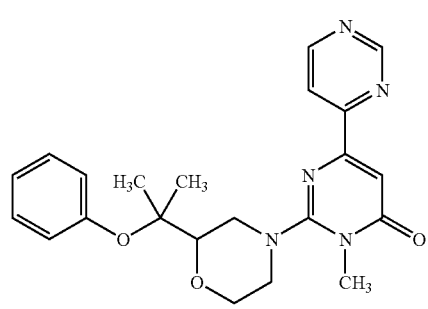 |
| B018 | 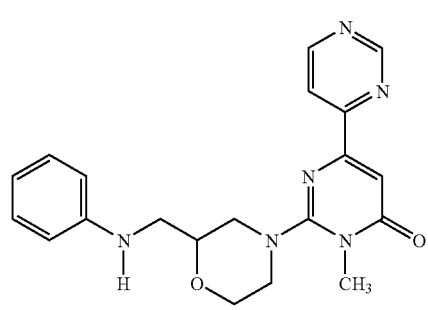 |
-continued
| Compound No. | STRUCTURE |
|---|---|
| B019 | 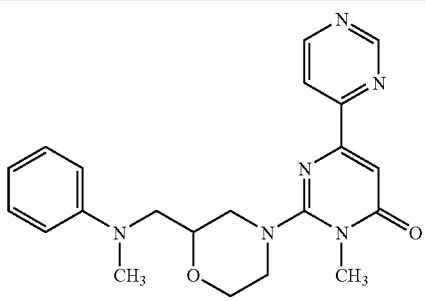 |
| B020 | 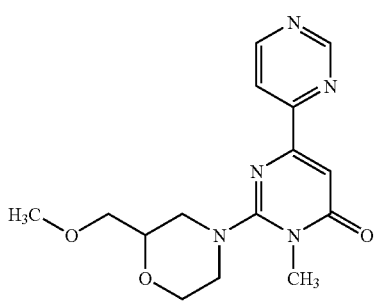 |
| B021 | 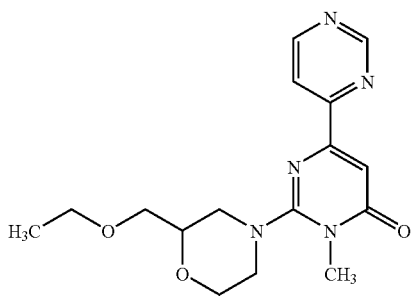 |
| B022 | 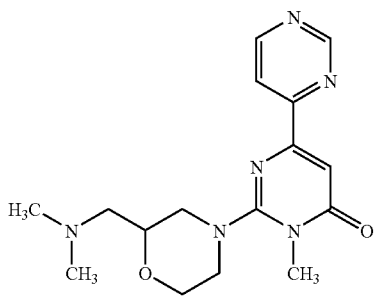 |
| B023 | 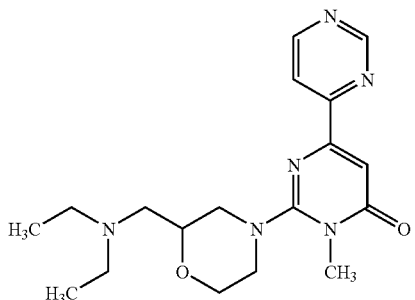 |

-continued
| Compound No. | STRUCTURE |
|---|---|
| B024 | 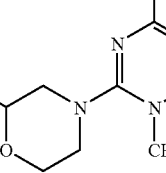 |
| B025 | 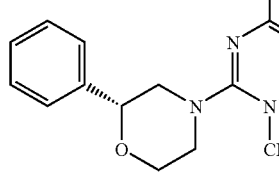 |
| B026 | 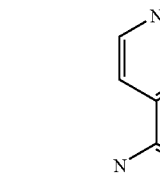 |
| B027 | 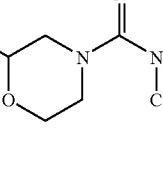 |
| B028 | 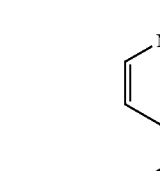 |
-continued
| Compound No. | STRUCTURE |
|---|---|
| B029 | 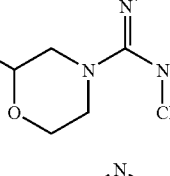 |
| B030 | 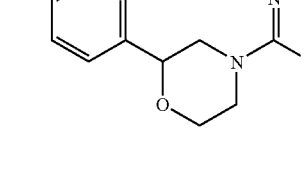 |
| B031 | 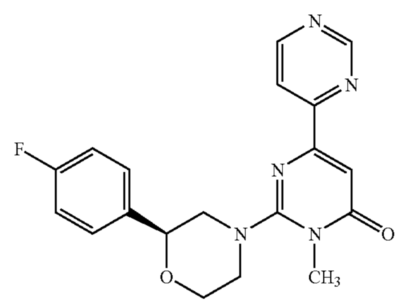 |
| B032 | 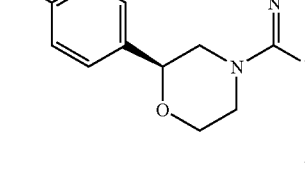 |
| B033 | 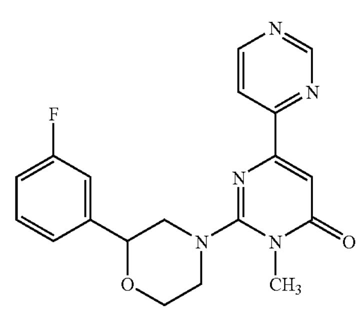 |

-continued
| Compound No. | STRUCTURE |
|---|---|
| B034 | 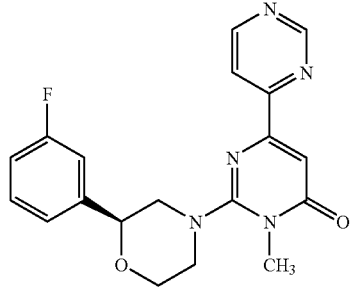 |
| B035 | 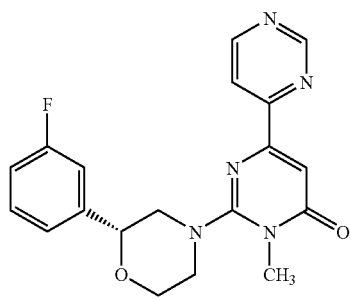 |
| B036 | 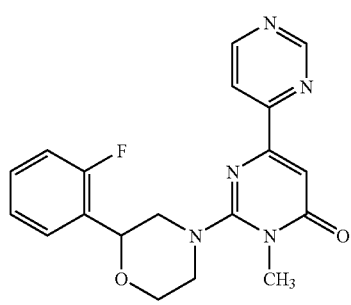 |
| B037 | 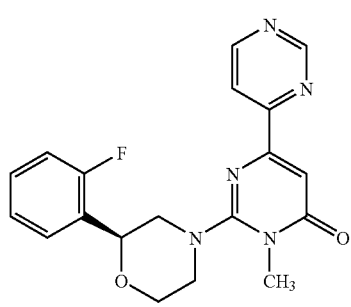 |
| B038 | 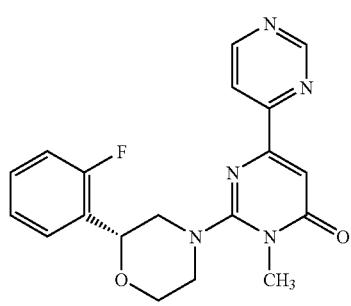 |
-continued
| Compound No. | STRUCTURE |
|---|---|
| B039 | 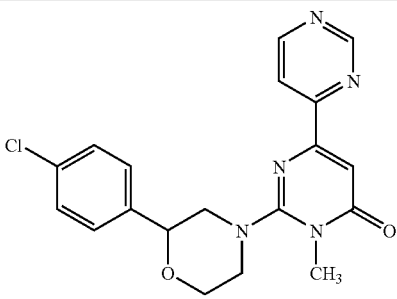 |
| B040 | 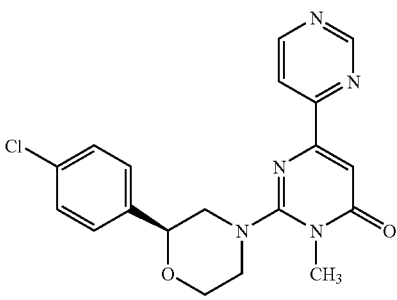 |
| B041 | 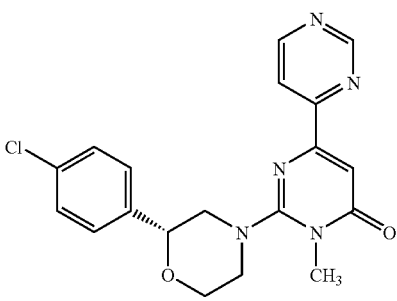 |
| B042 | 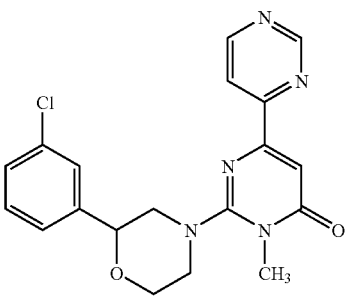 |
| B043 | 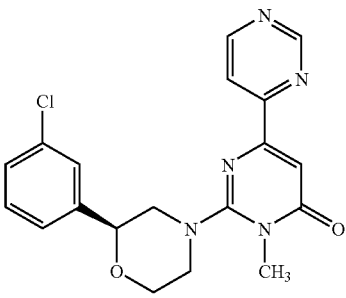 |

-continued
| Compound No. | STRUCTURE |
|---|---|
| B044 | 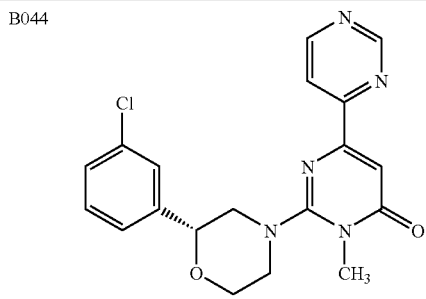 |
| B045 | 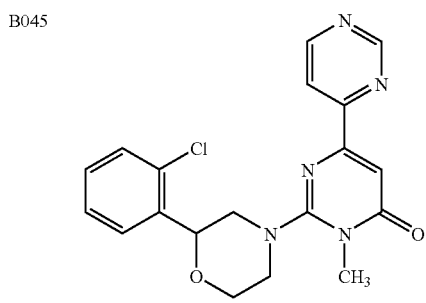 |
| B046 | 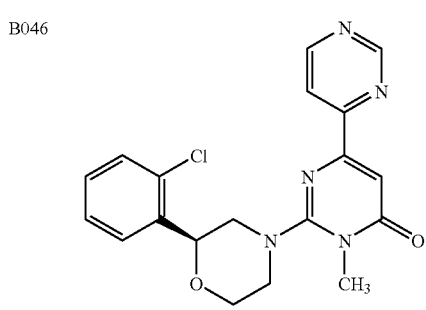 |
| B047 | 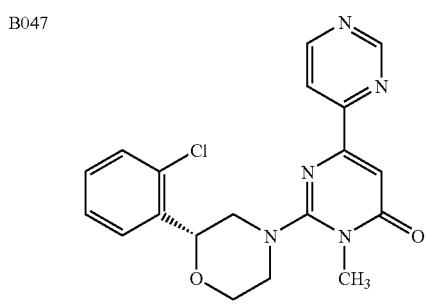 |
| B048 | 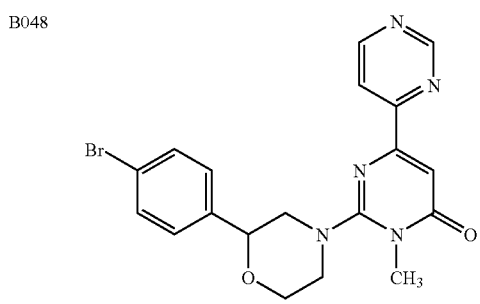 |
-continued
| Compound No. | STRUCTURE |
|---|---|
| B049 | 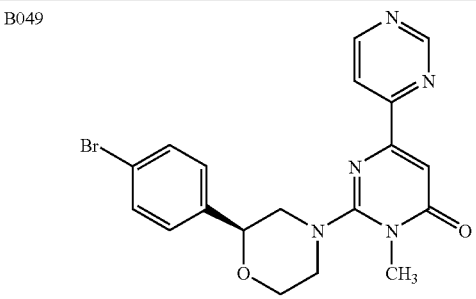 |
| B050 | 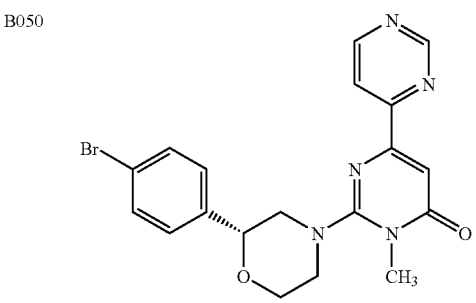 |
| B051 | 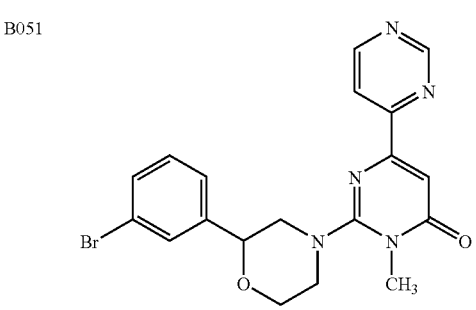 |
| B052 | 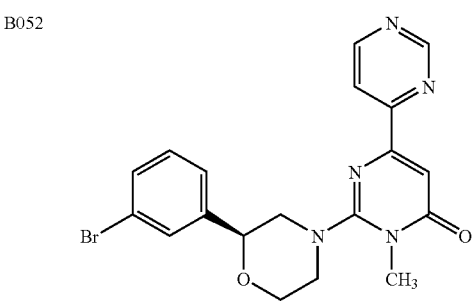 |
| B053 | 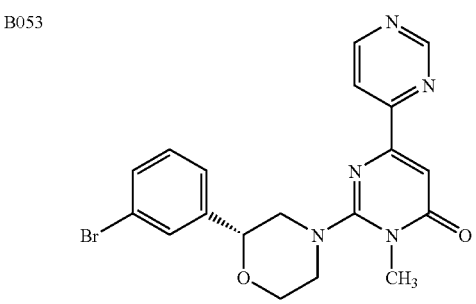 |

-continued
| Compound No. | STRUCTURE |
|---|---|
| B054 | 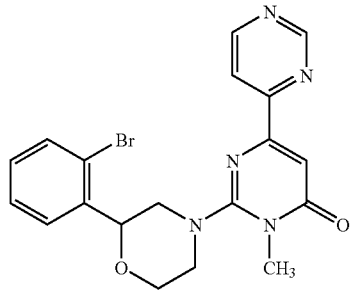 |
| B055 | 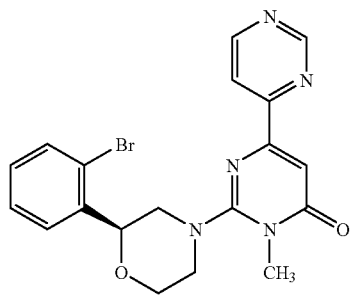 |
| B056 | 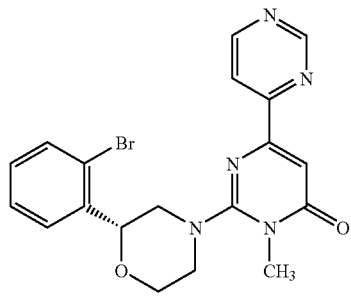 |
| B057 | 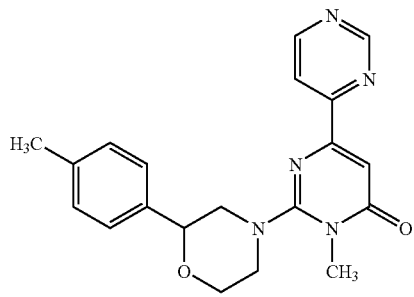 |
| B058 | 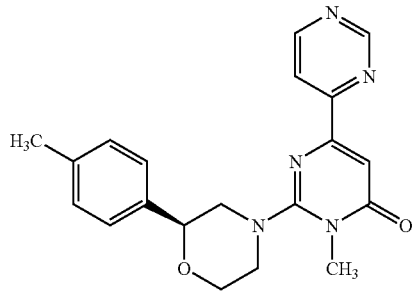 |
-continued
| Compound No. | STRUCTURE |
|---|---|
| B059 | 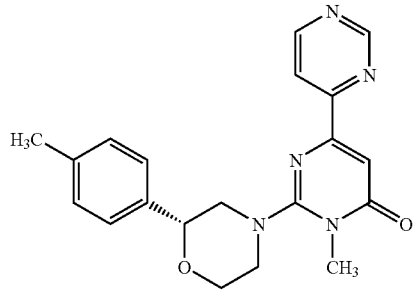 |
| B060 | 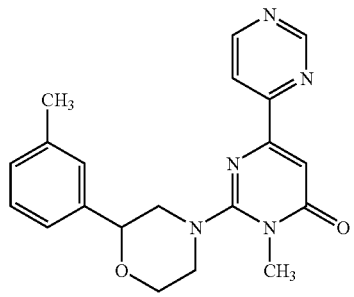 |
| B061 | 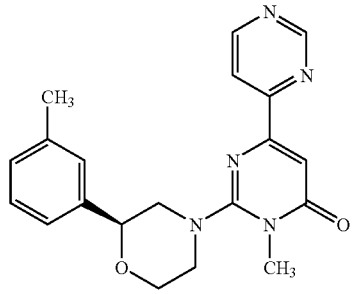 |
| B062 | 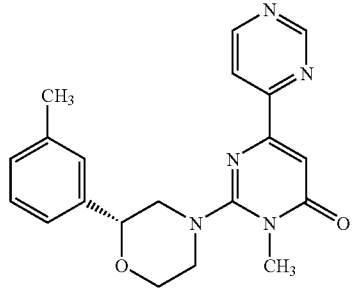 |
| B063 | 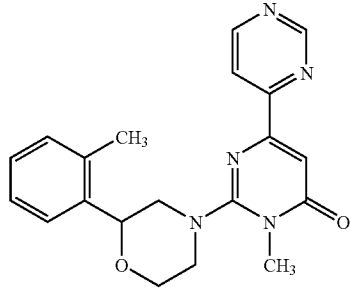 |

-continued
| Compound No. | STRUCTURE |
|---|---|
| B064 | 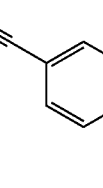 |
| B065 | 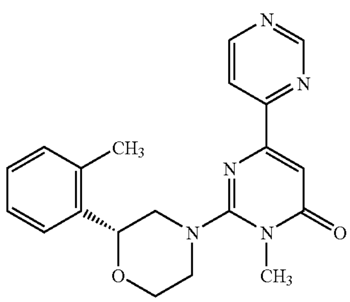 |
| B066 | 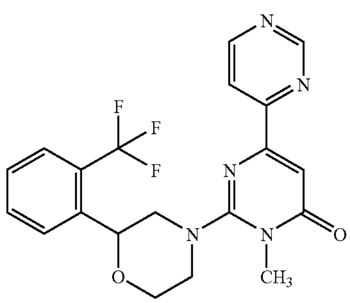 |
| B067 | 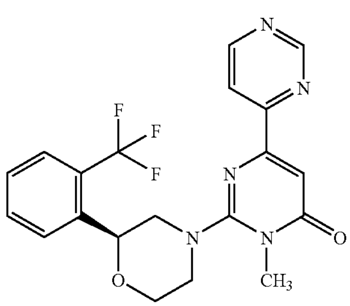 |
| B068 | 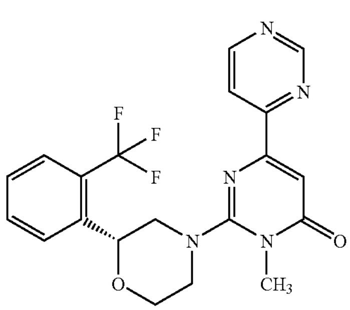 |
-continued
| Compound No. | STRUCTURE |
|---|---|
| B069 | 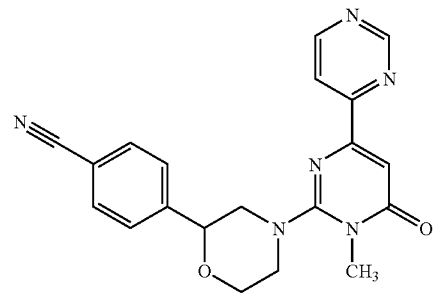 |
| B070 | 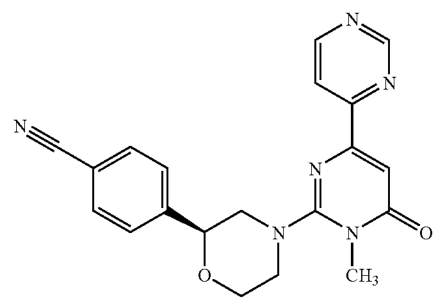 |
| B071 | 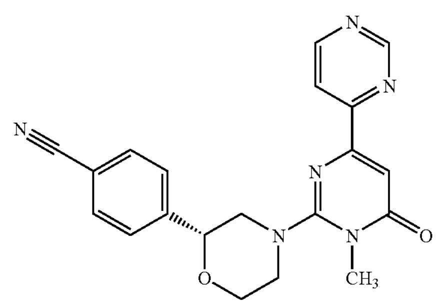 |
| B072 | 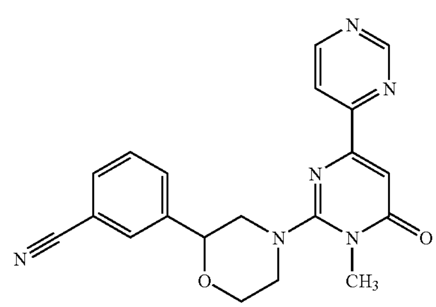 |
| B073 | 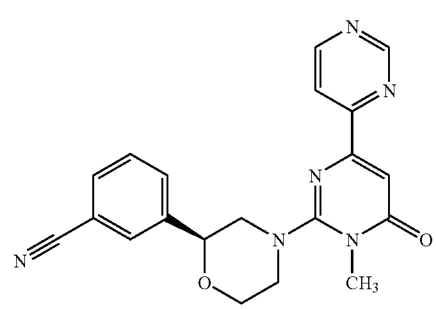 |

-continued
| Compound No. | STRUCTURE |
|---|---|
| B074 | 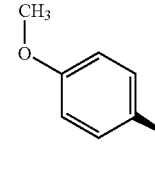 |
| B075 | 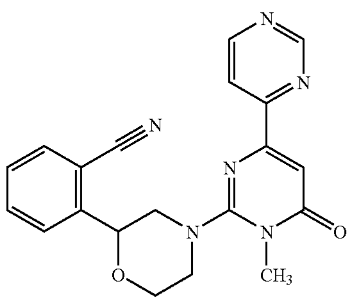 |
| B076 | 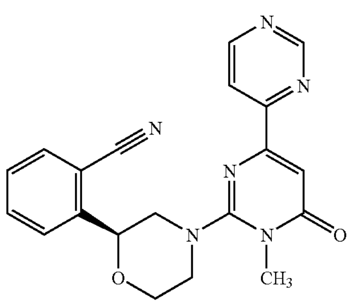 |
| B077 | 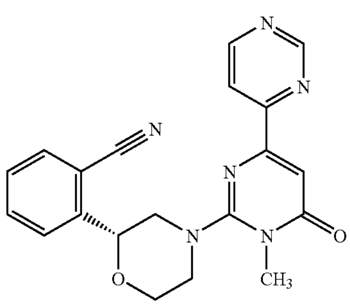 |
| B078 | 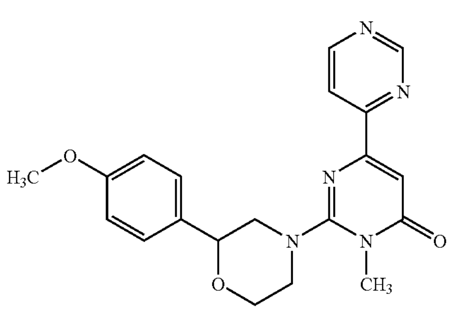 |
-continued
| Compound No. | STRUCTURE |
|---|---|
| B079 | 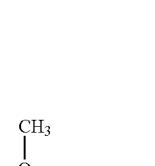 |
| B080 | 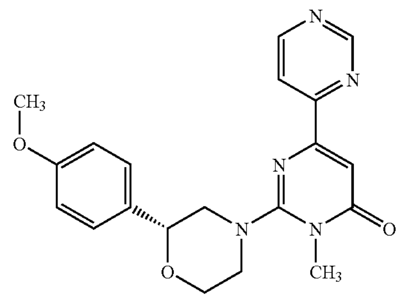 |
| B081 | 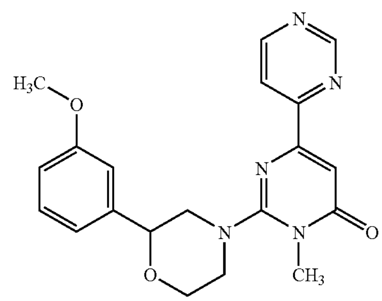 |
| B082 | 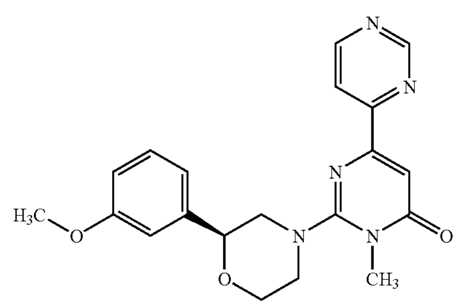 |
| B083 | 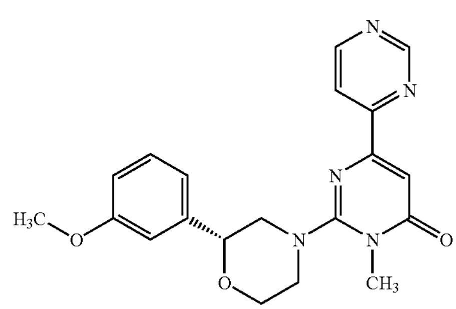 |

-continued
| Compound No. | STRUCTURE |
|---|---|
| B084 | 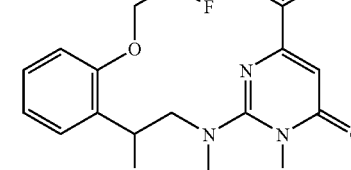 |
| B085 | 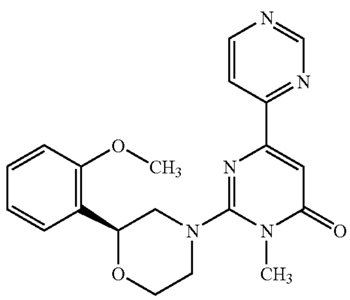 |
| B086 | 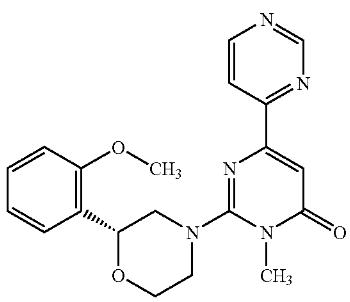 |
| B087 | 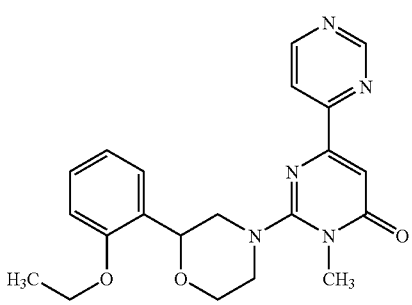 |
| B088 | 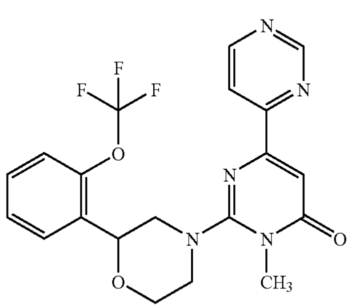 |
-continued
| Compound No. | STRUCTURE |
|---|---|
| B089 | 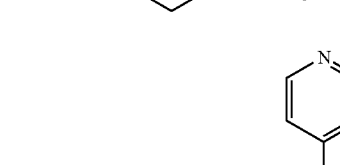 |
| B090 | 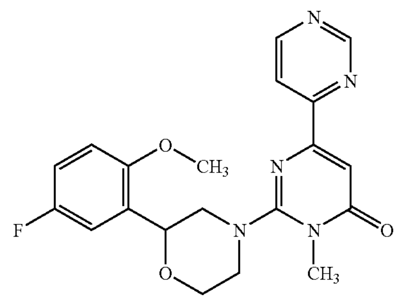 |
| B091 | 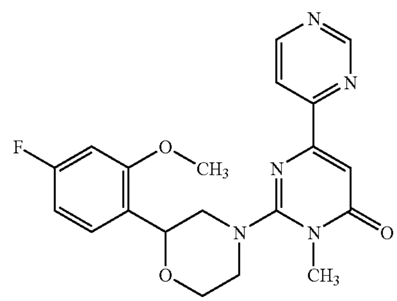 |
| B092 | 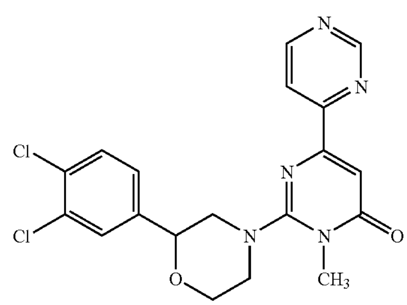 |
| B093 | 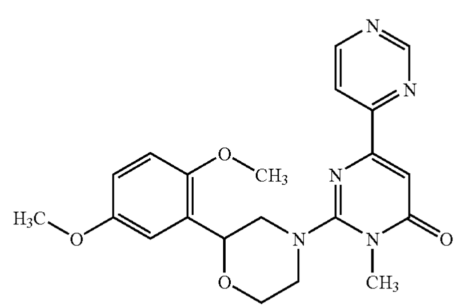 |

-continued
| Compound No. | STRUCTURE |
|---|---|
| B094 | 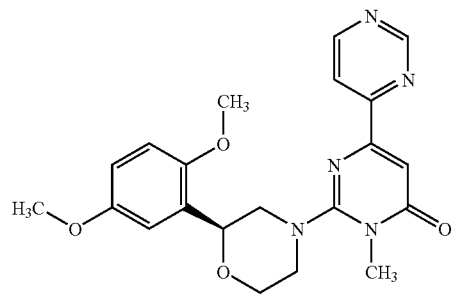 |
| B095 | 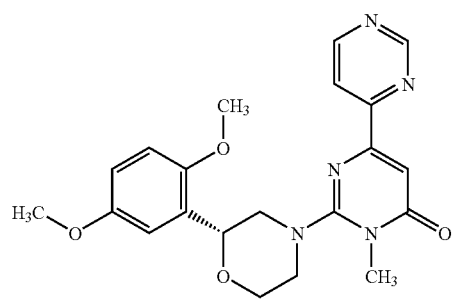 |
| B096 | 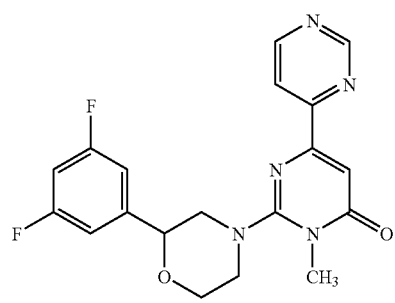 |
| B097 | 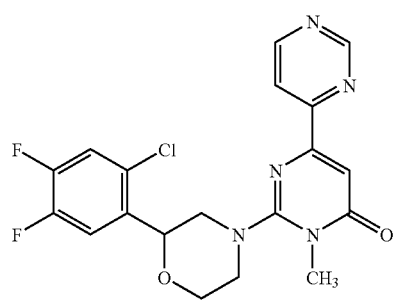 |
| B098 | 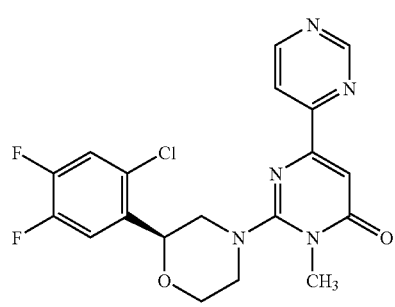 |
-continued
| Compound No. | STRUCTURE |
|---|---|
| B099 | 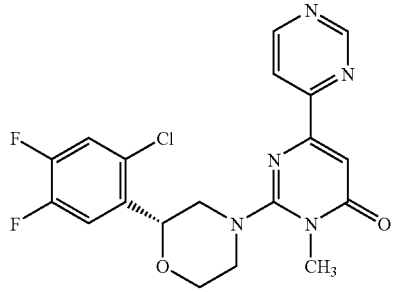 |
| B100 | 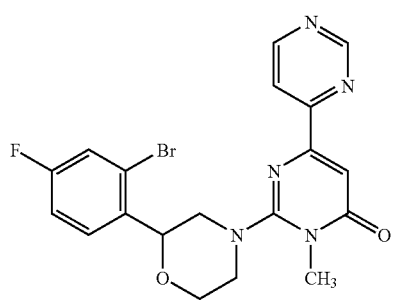 |
| B101 | 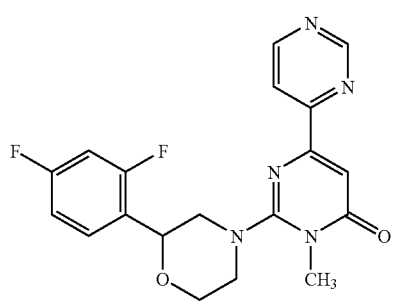 |
| B102 | 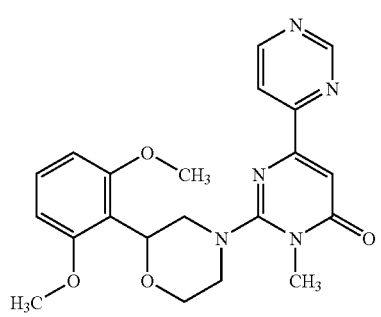 |
| B103 | 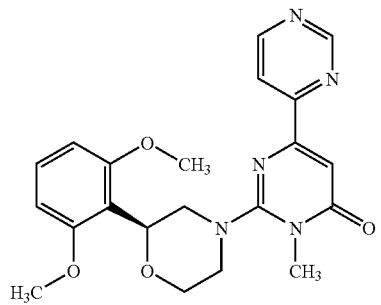 |

-continued
| Compound No. | STRUCTURE |
|---|---|
| B104 | 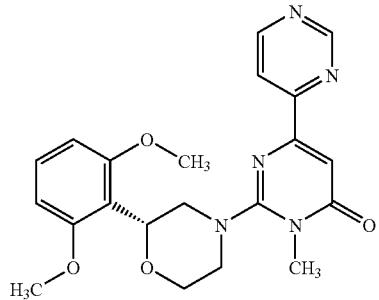 |
| B105 | 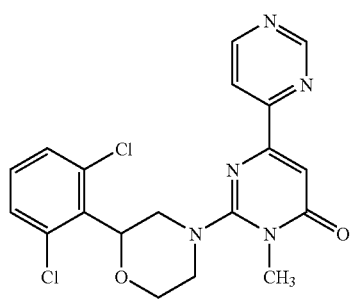 |
| B106 | 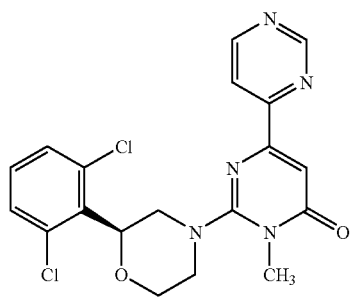 |
| B107 | 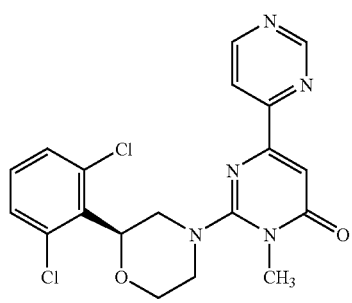 |
| B108 | 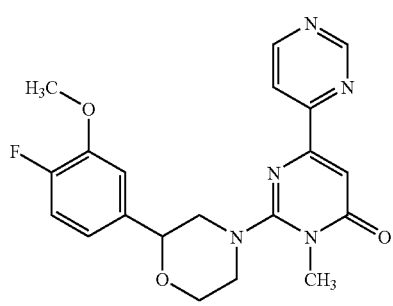 |
-continued
| Compound No. | STRUCTURE |
|---|---|
| B109 | 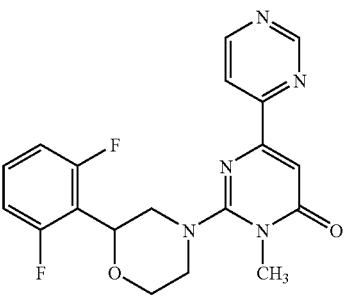 |
| B110 | 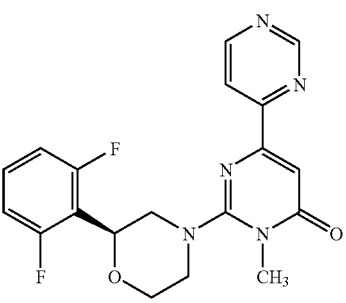 |
| B111 | 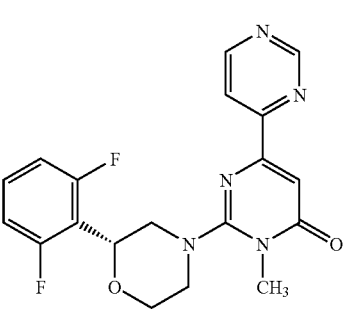 |
| B112 | 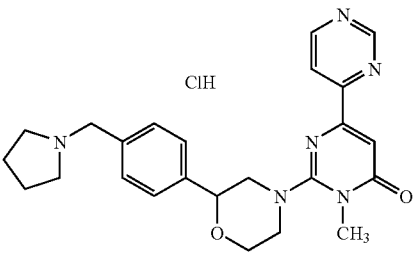 |
| B113 | 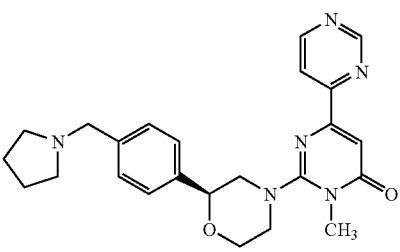 |

-continued
| Compound No. | STRUCTURE |
|---|---|
| B114 | 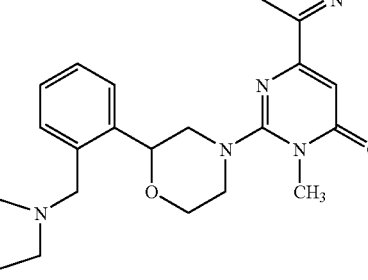 |
| B115 | 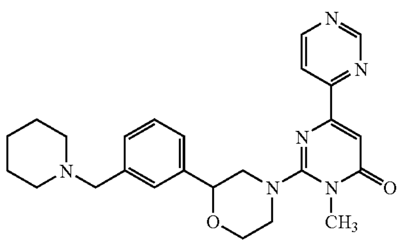 |
| B116 | 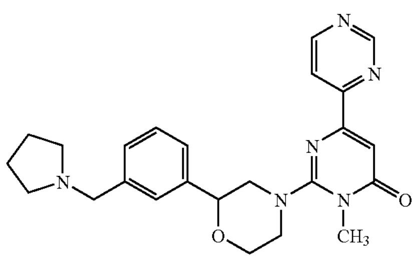 |
| B117 | 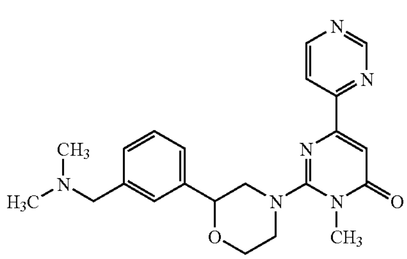 |
| B118 | 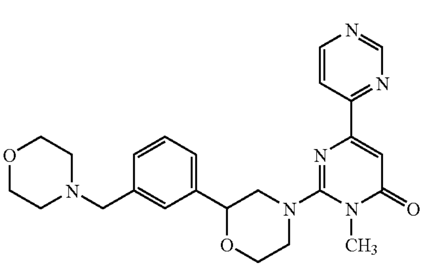 |
-continued
| Compound No. | STRUCTURE |
|---|---|
| B119 | 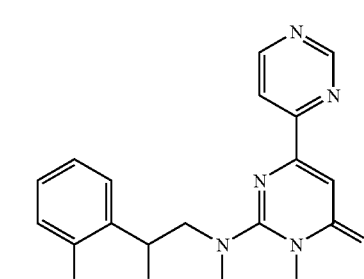 |
| B120 | 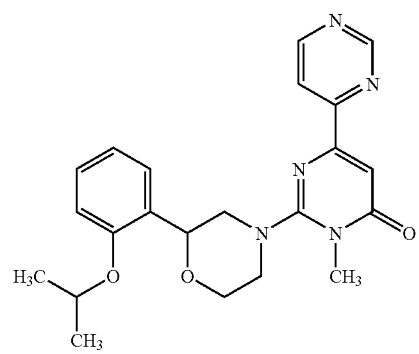 |
| B121 | 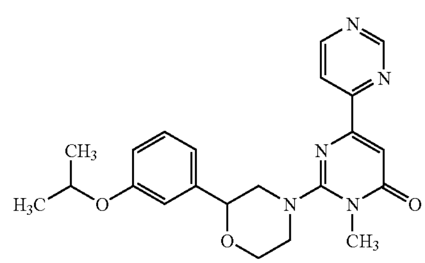 |
| B122 | 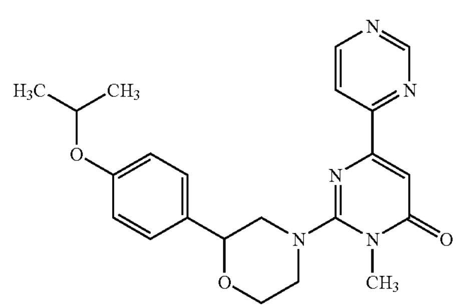 |

| Compound No. | STRUCTURE |
|---|---|
| B123 | 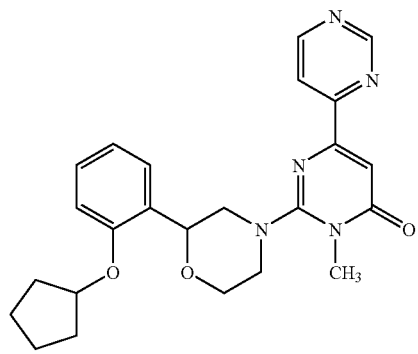 |
| B124 | 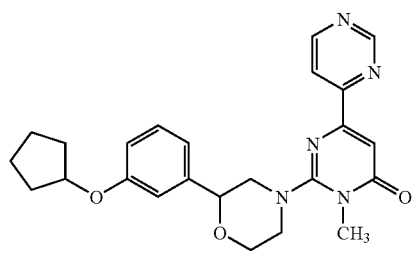 |
| B125 | 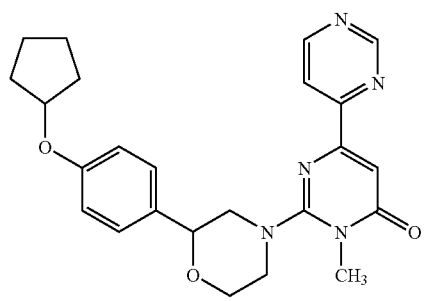 |
| B126 | 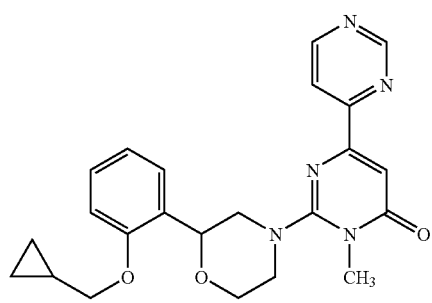 |
| B127 | 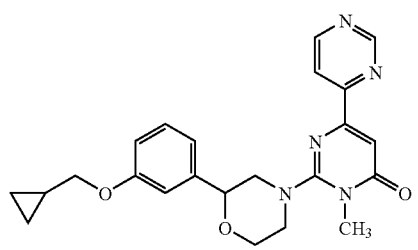 |
| B128 | 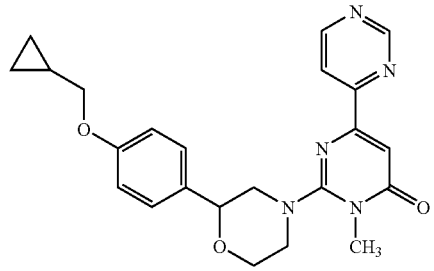 |
| B129 | 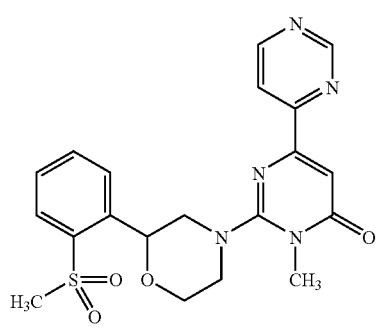 |
| B130 | 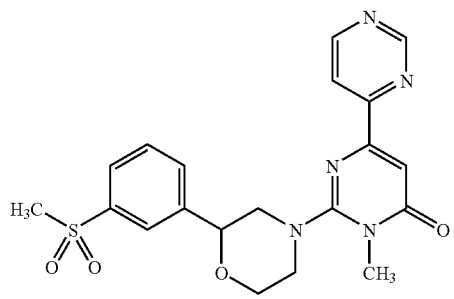 |
| B131 | 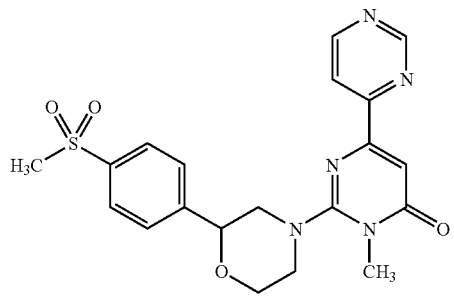 |
| B132 | 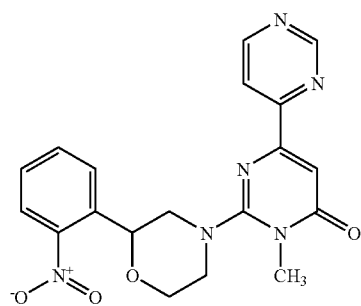 |

-continued
| Compound No. | STRUCTURE |
|---|---|
| B133 | 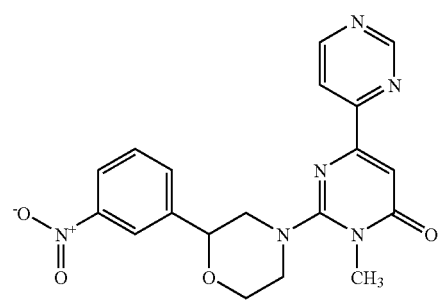 |
| B134 | 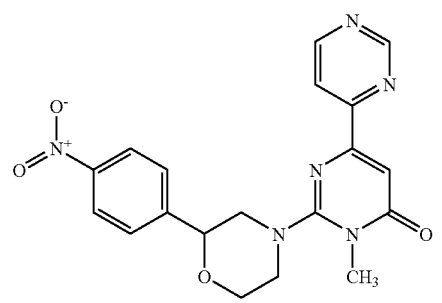 |
| B135 | 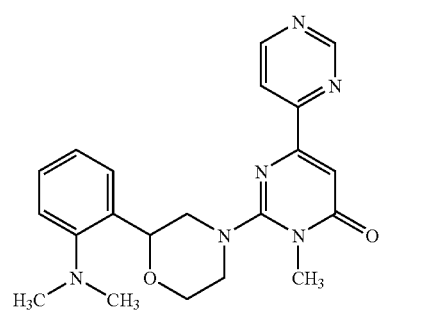 |
| B136 | 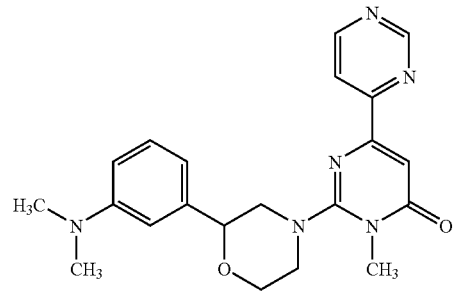 |
| B137 | 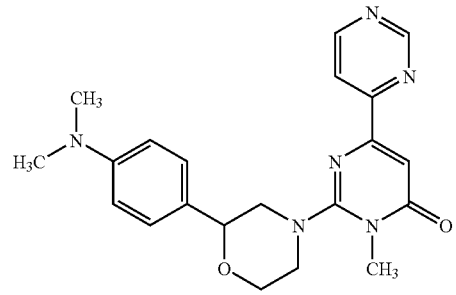 |
-continued
| Compound No. | STRUCTURE |
|---|---|
| B138 | 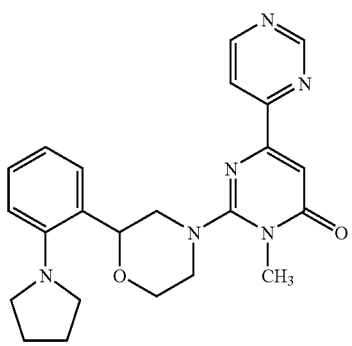 |
| B139 | 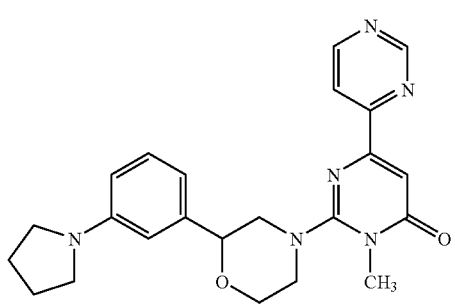 |
| B140 | 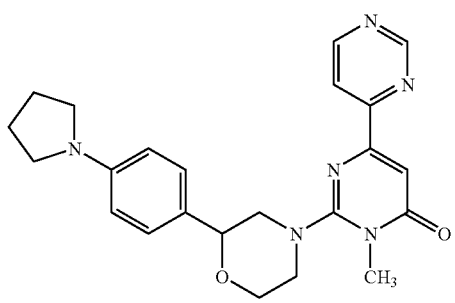 |
| B141 | 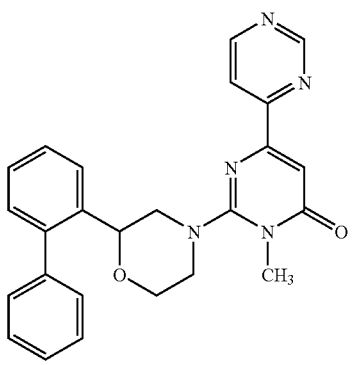 |

-continued
| Compound No. | STRUCTURE |
|---|---|
| B142 | 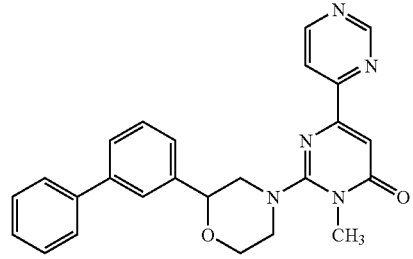 |
| B143 | 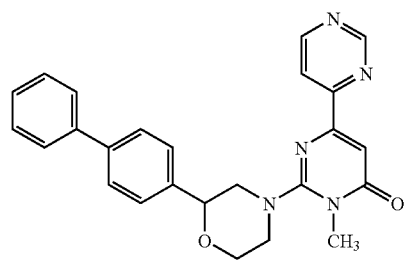 |
| B144 | 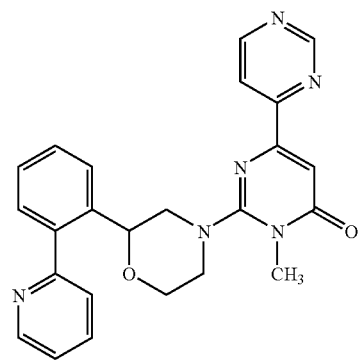 |
| B145 | 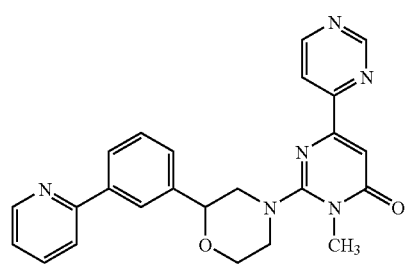 |
| B146 | 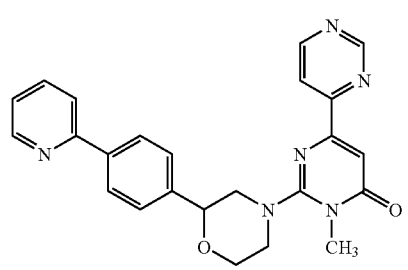 |
-continued
| Compound No. | STRUCTURE |
|---|---|
| B147 | 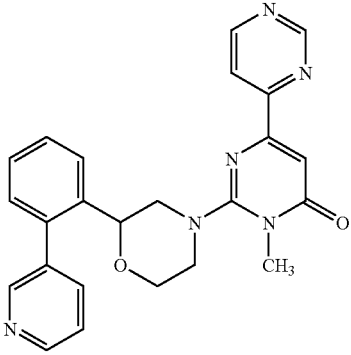 |
| B148 | 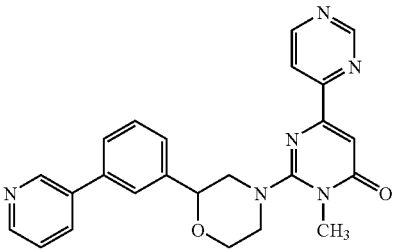 |
| B149 | 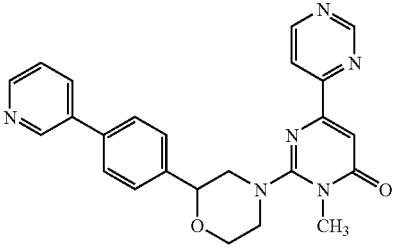 |
| B150 | 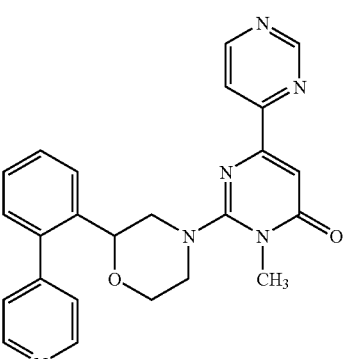 |
| B151 | 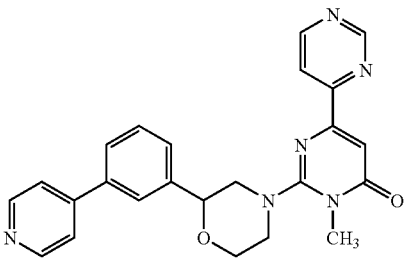 |

| Compound No. | STRUCTURE |
|---|---|
| B152 | 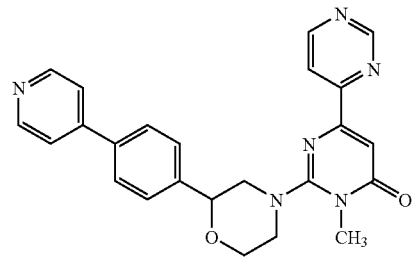 |
| B153 | 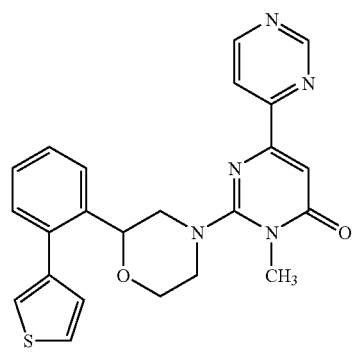 |
| B154 | 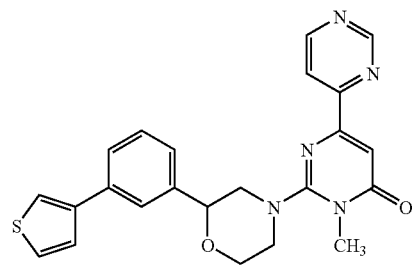 |
| B155 | 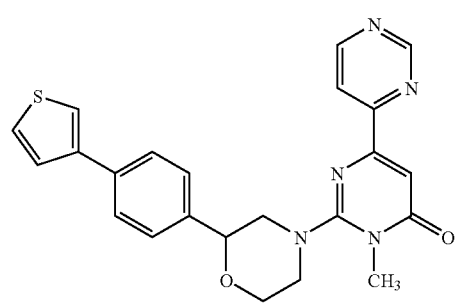 |
| B156 | 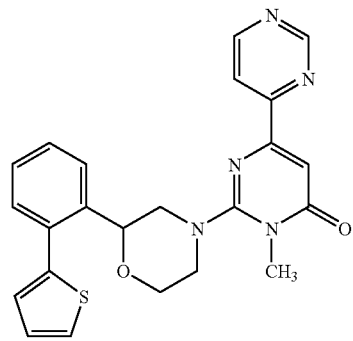 |
| Compound No. | STRUCTURE |
|---|---|
| B157 | 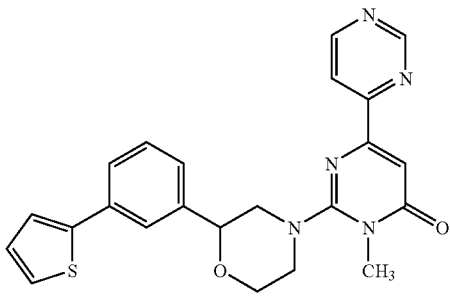 |
| B158 | 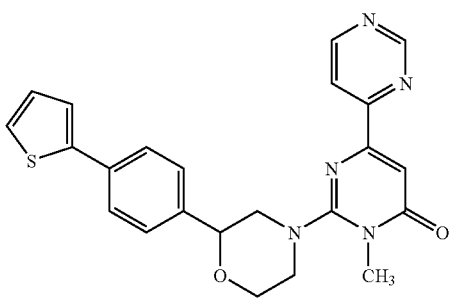 |
| B159 | 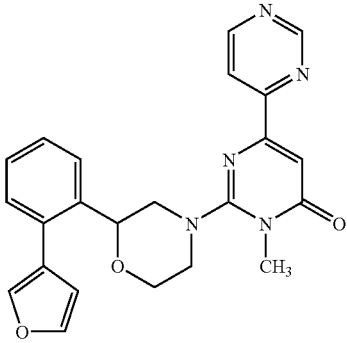 |
| B160 | 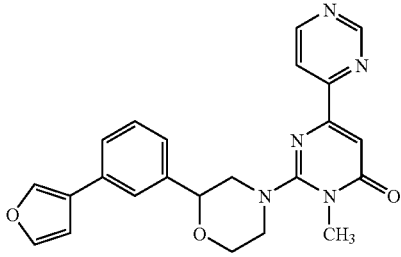 |
| B161 | 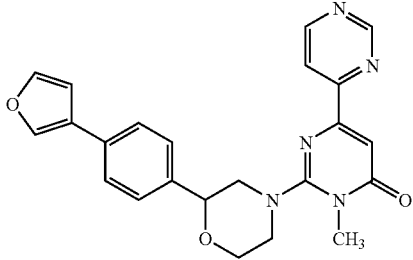 |

| Compound No. | STRUCTURE |
|---|---|
| B162 | 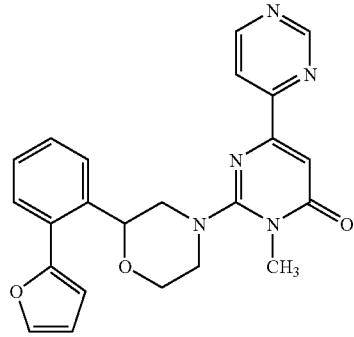 |
| B163 | 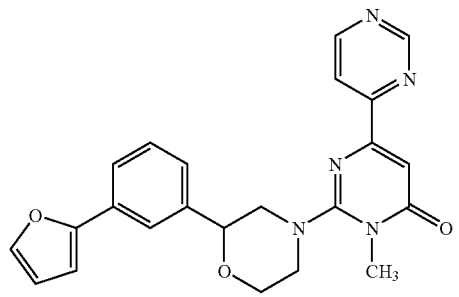 |
| B164 | 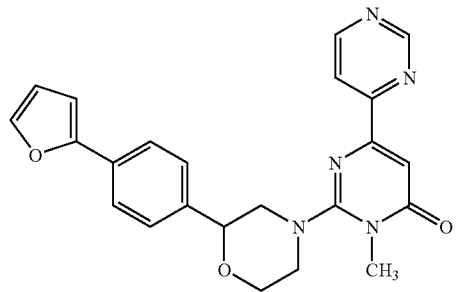 |
| B165 | 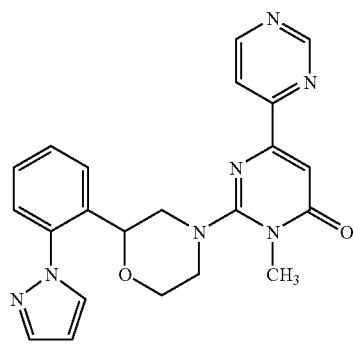 |
| Compound No. | STRUCTURE |
|---|---|
| B166 | 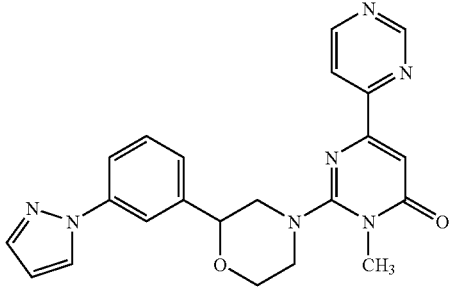 |
| B167 | 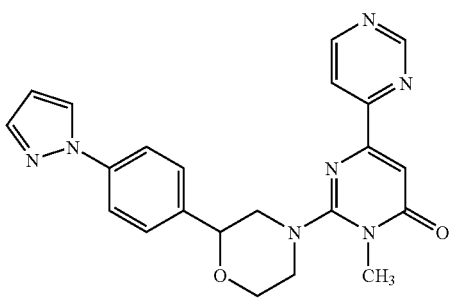 |
| B168 | 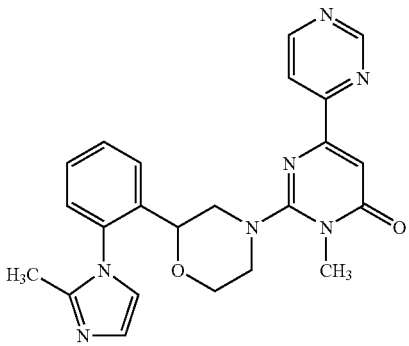 |
| B169 | 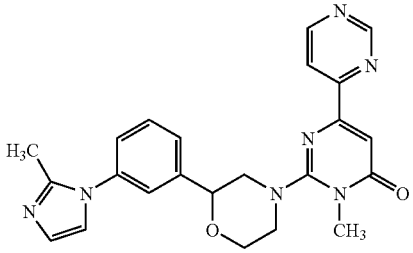 |
| B170 | 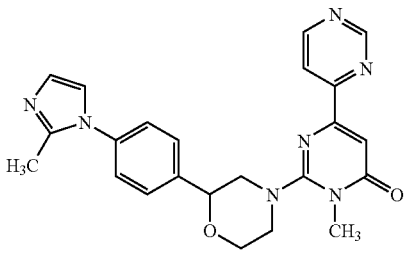 |

-continued
| Compound No. | STRUCTURE |
|---|---|
| B171 | 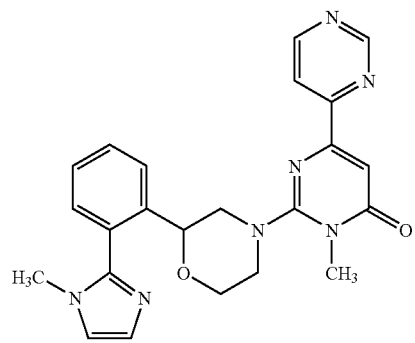 |
| B172 | 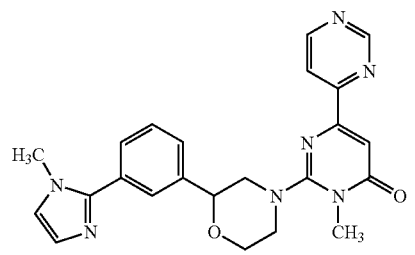 |
| B173 | 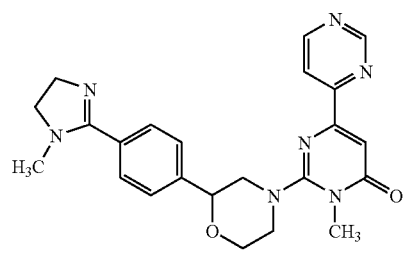 |
| B174 | 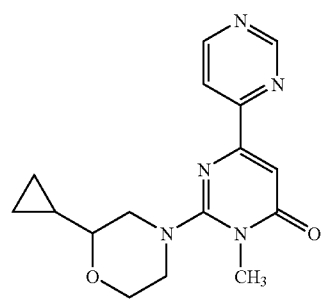 |
| B175 | 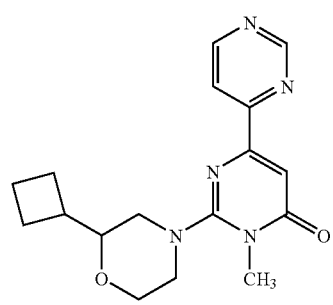 |
-continued
| Compound No. | STRUCTURE |
|---|---|
| B176 | 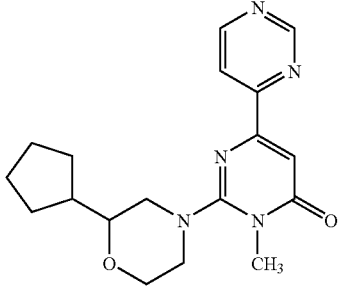 |
| B177 | 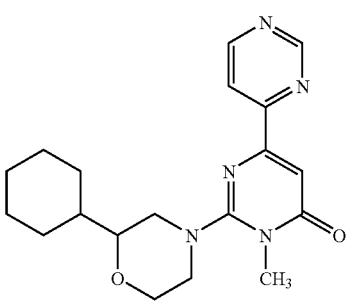 |
| B178 | 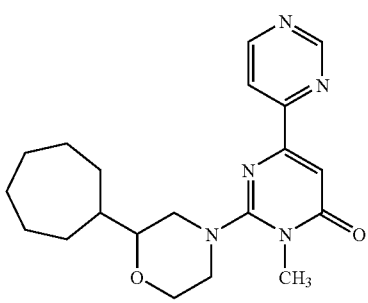 |
| B179 | 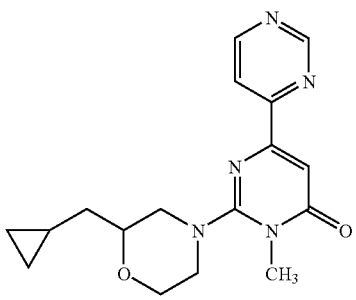 |
| B180 | 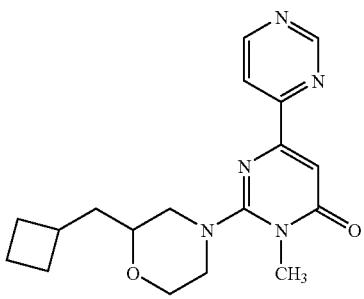 |

-continued
| Compound No. | STRUCTURE |
|---|---|
| B181 | 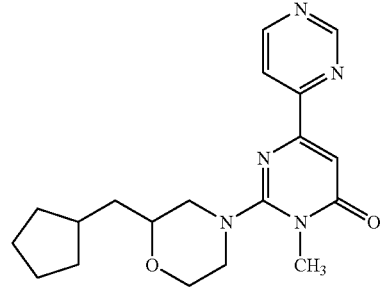 |
| B182 | 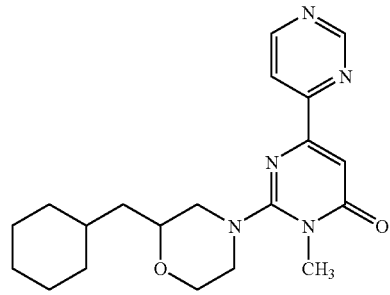 |
| B183 | 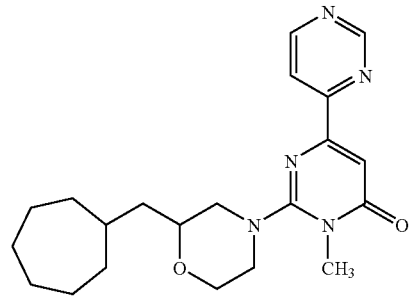 |
| B184 | 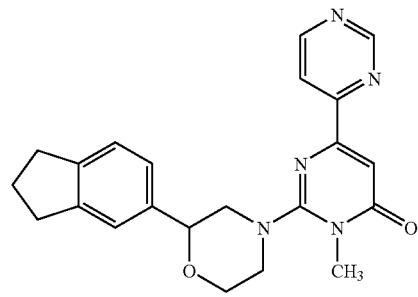 |
| B185 | 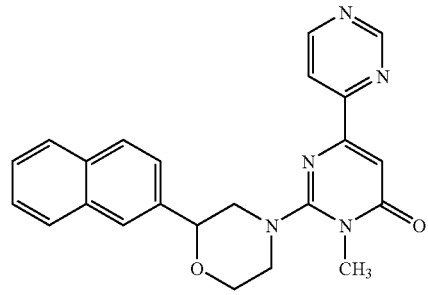 |
-continued
| Compound No. | STRUCTURE |
|---|---|
| B186 | 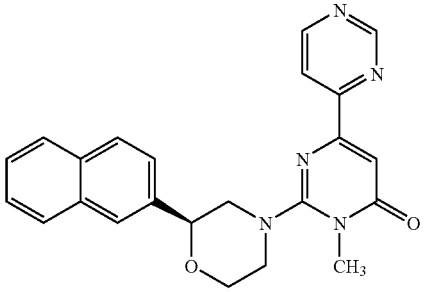 |
| B187 | 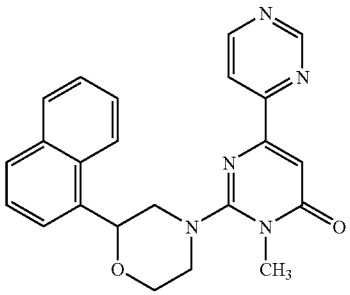 |
| B188 | 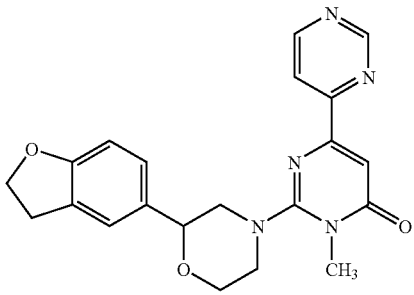 |
| B189 | 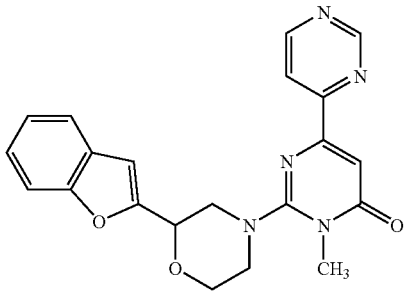 |
| B190 | 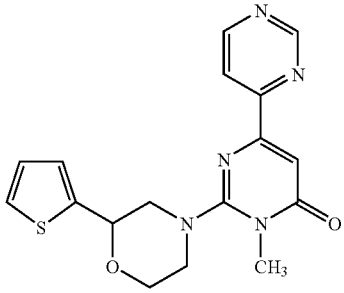 |

-continued
| Compound No. | STRUCTURE |
|---|---|
| B191 | 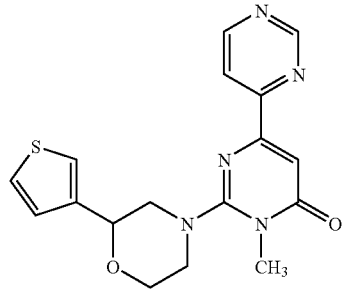 |
| B192 | 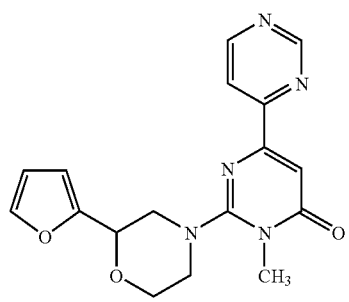 |
| B193 | 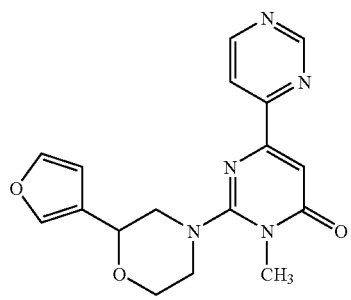 |
| B194 | 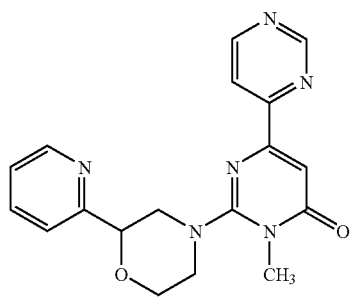 |
| B195 | 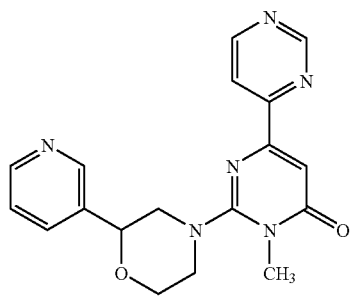 |
-continued
| Compound No. | STRUCTURE |
|---|---|
| B196 | 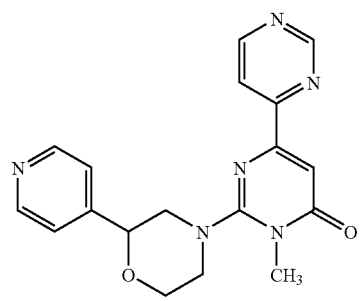 |
| B197 | 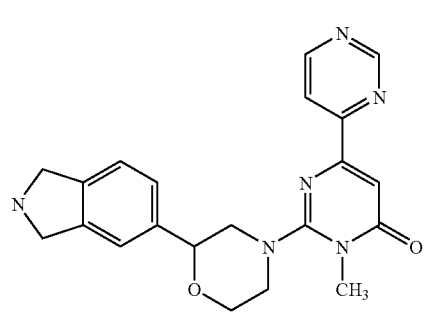 |
| B198 | 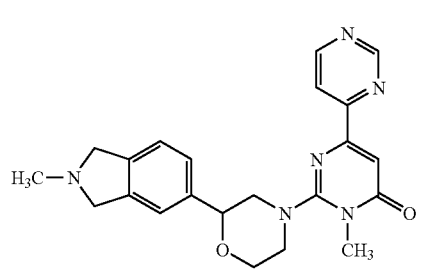 |
| B199 | 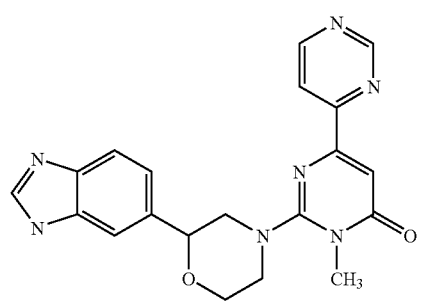 |
| B200 | 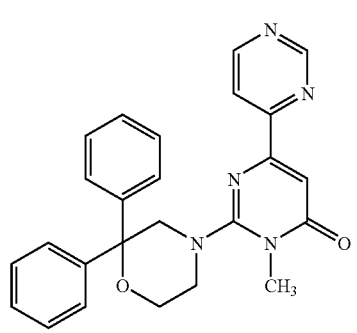 |

-continued
| Compound No. | STRUCTURE |
|---|---|
| B201 | 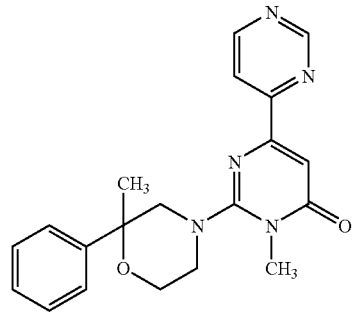 |
| B202 | 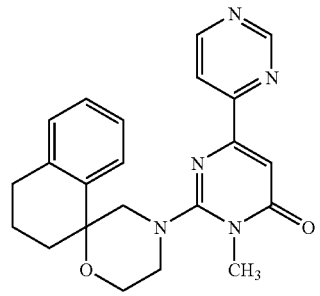 |
| B203 | 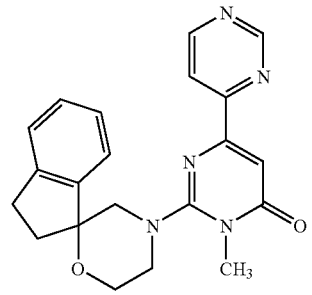 |
| B205 | 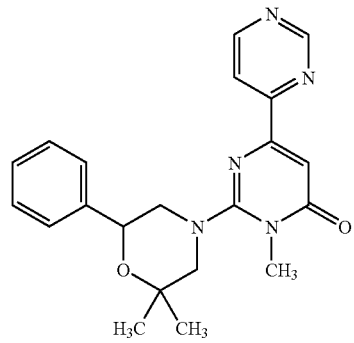 |
-continued
| Compound No. | STRUCTURE |
|---|---|
| B206 | 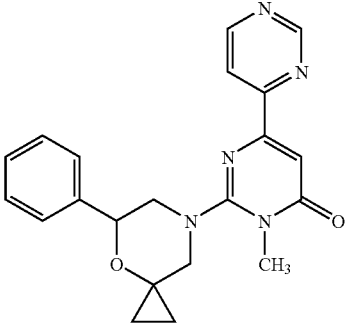 |
| B207 | 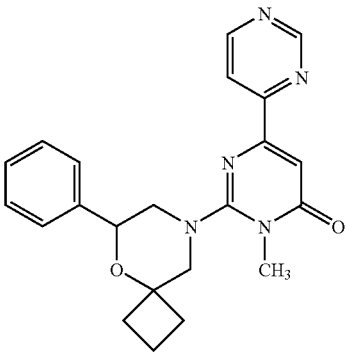 |
| B208 | 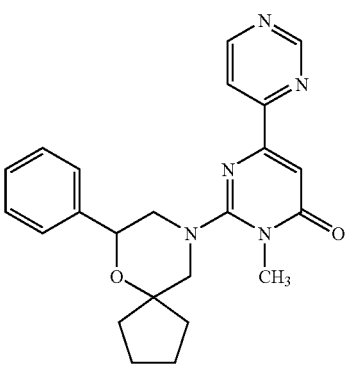 |
| B209 | 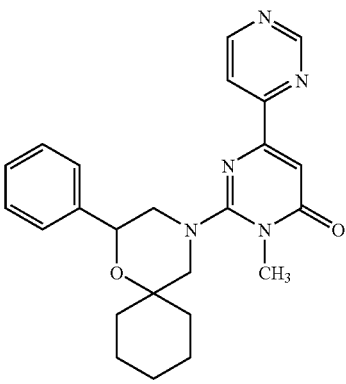 |

-continued
| Compound No. | STRUCTURE |
|---|---|
| B213 | 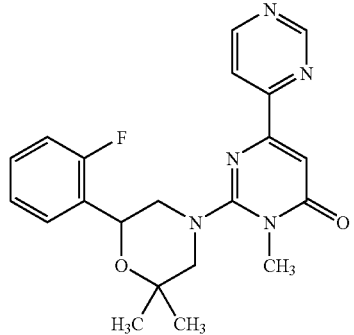 |
| B214 | 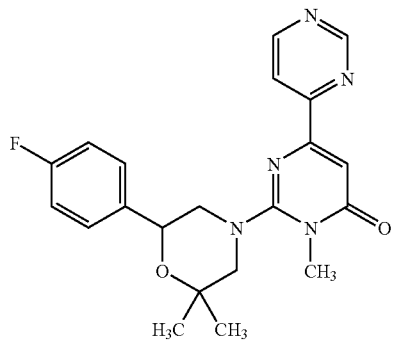 |
| B215 | 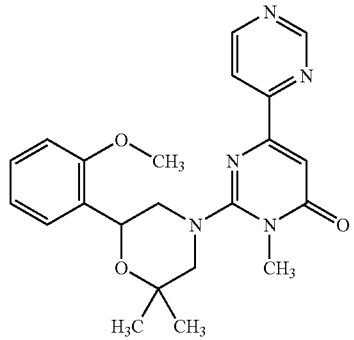 |
| B216 | 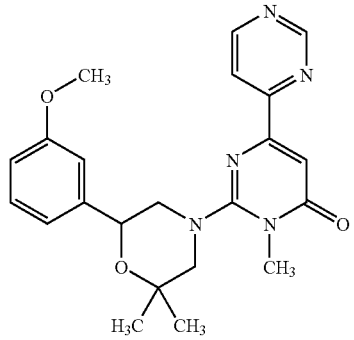 |
-continued
| Compound No. | STRUCTURE |
|---|---|
| B217 | 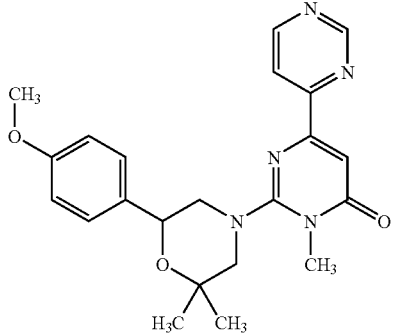 |
| B218 | 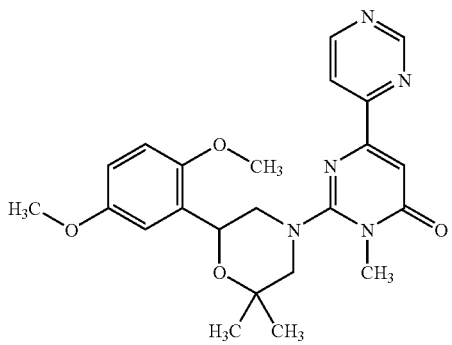 |
| B219 | 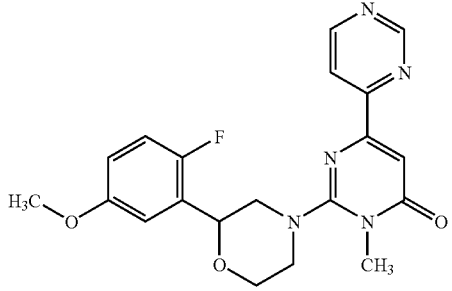 |
| B220 | 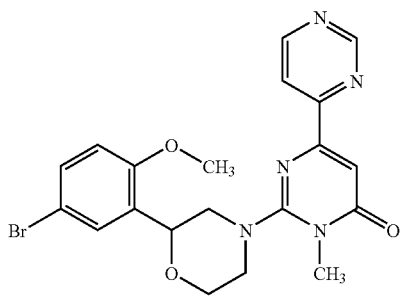 |

| Compound No. | STRUCTURE |
|---|---|
| B221 | 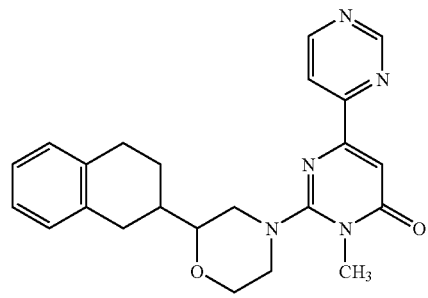 |
| B222 | 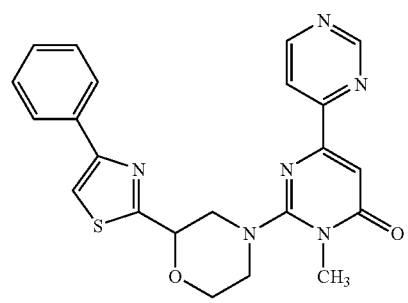 |
| B223 | 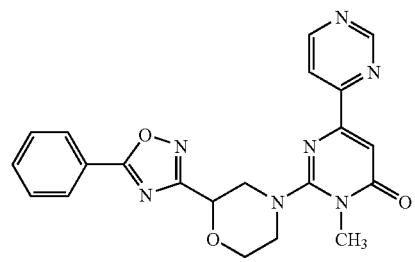 |
| B224 | 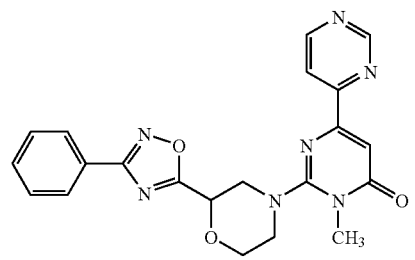 |
| B225 | 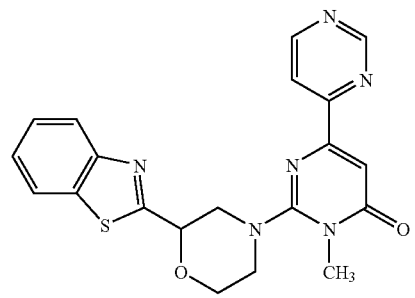 |
| B226 | 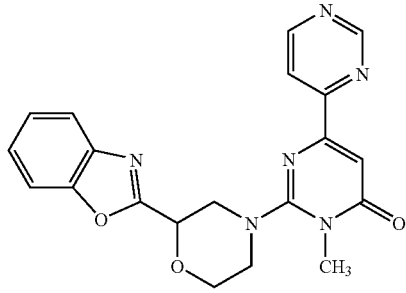 |
| B227 | 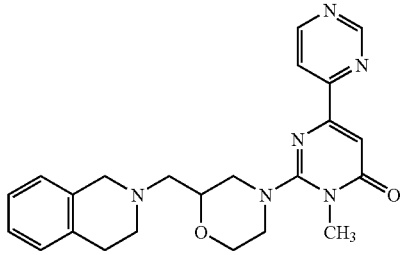 |
| B228 | 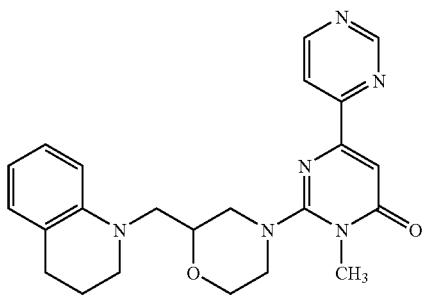 |
| B229 | 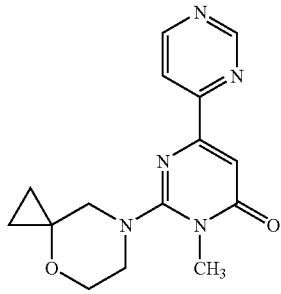 |
| B230 | 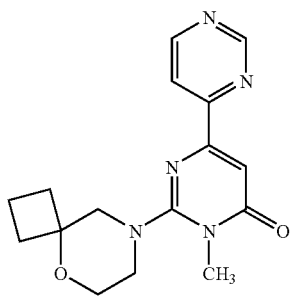 |

-continued
| Compound No. | STRUCTURE |
|---|---|
| B231 | 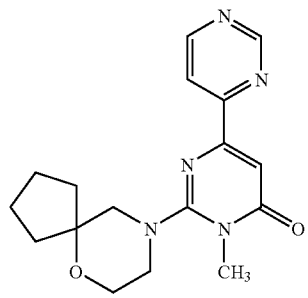 |
| B232 | 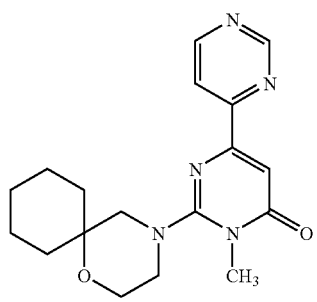 |
-continued
| Compound No. | STRUCTURE |
|---|---|
| B233 | 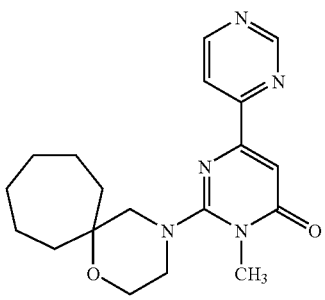 |
| B234 | 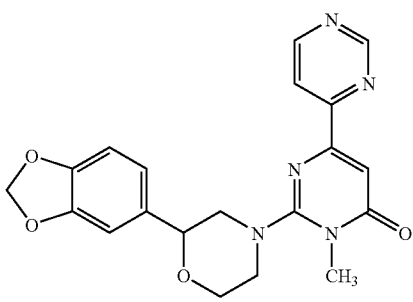 |
| Compound No. | STRUCTURE |
|---|---|
| B235 | 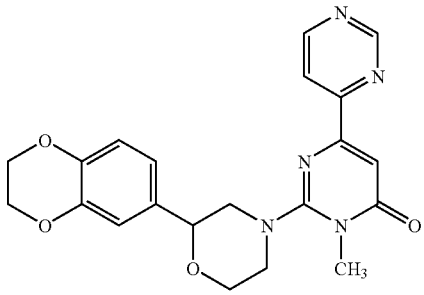 |
| B236 | 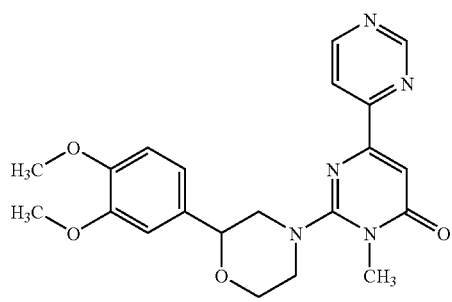 |

-continued
| Compound No. | STRUCTURE |
|---|---|
| B237 | 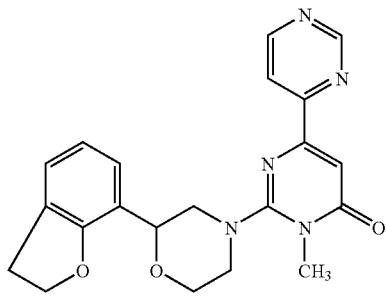 |
| B238 | 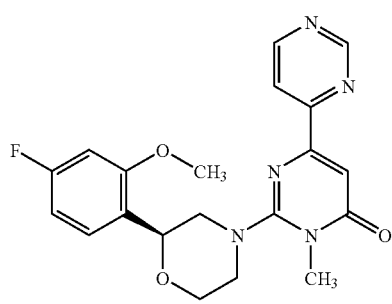 |
| B239 | 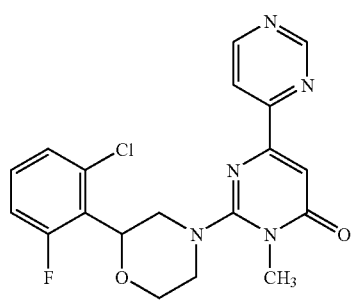 |
| B240 | 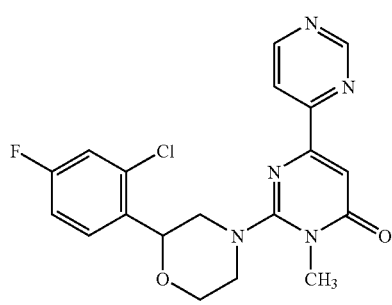 |
| B241 | 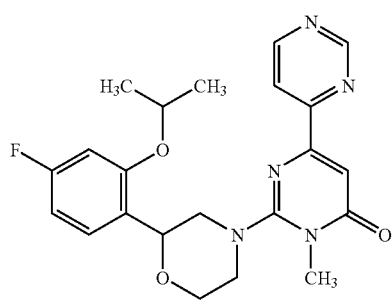 |

-continued
| Compound No. | STRUCTURE |
|---|---|
| B242 | 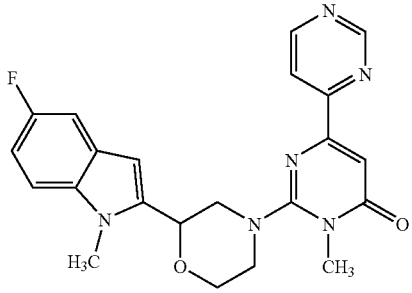 |
| B243 | 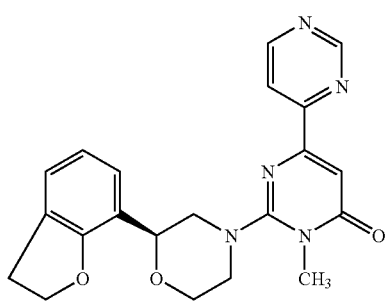 |
| B244 | 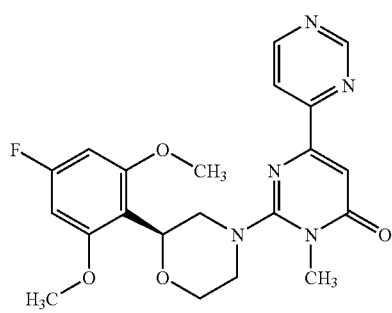 |
| B245 | 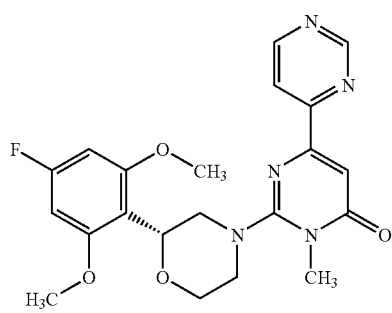 |
| B246 | 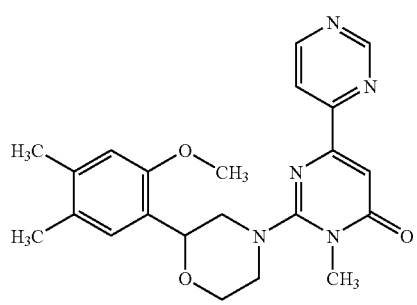 |

-continued

| Compound No. | STRUCTURE |
|---|---|
| B247 | 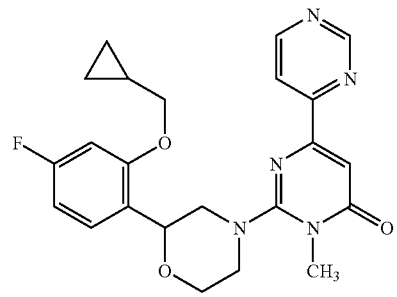 |
| B248 | 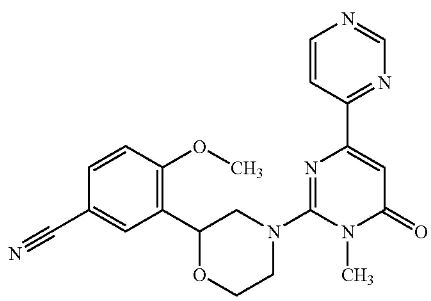 |
| B249 | 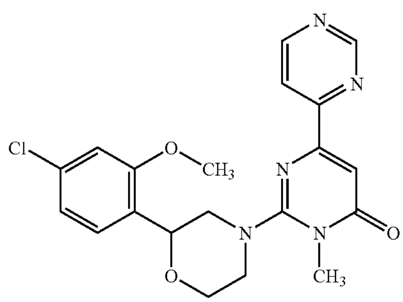 |
| B250 | 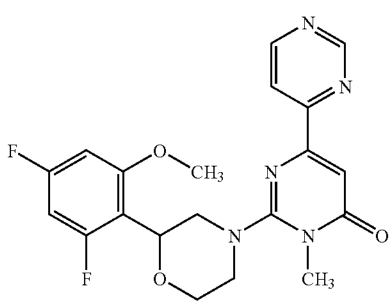 |
| B251 | 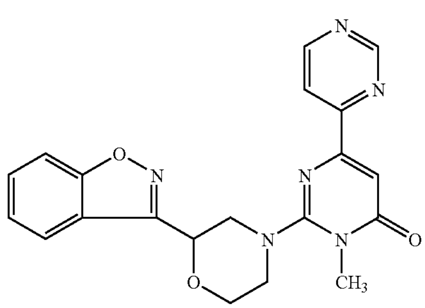 |

-continued
| Compound No. | STRUCTURE |
|---|---|
| B252 | 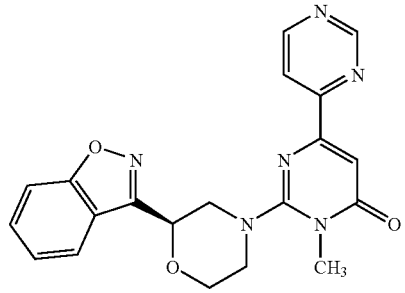 |
| B253 | 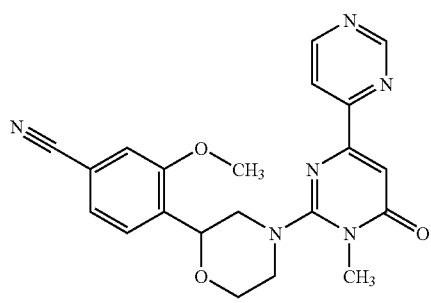 |
| B254 | 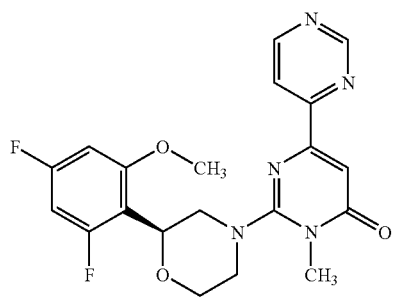 |
| B255 | 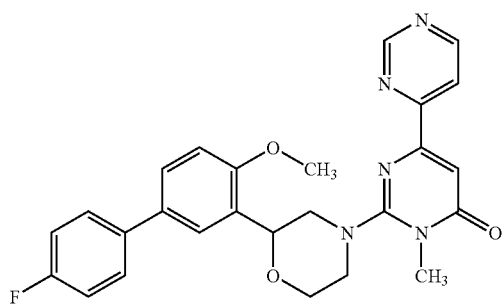 |
| B256 | 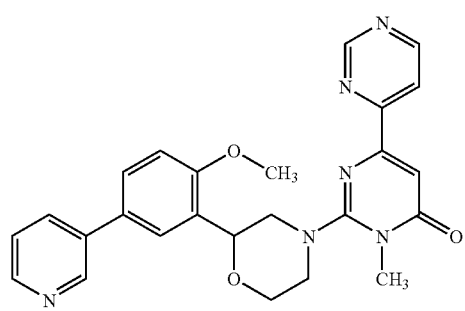 |

-continued
| Compound No. | STRUCTURE |
|---|---|
| B257 | 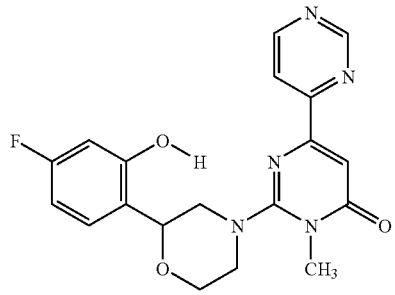 |
| B258 | 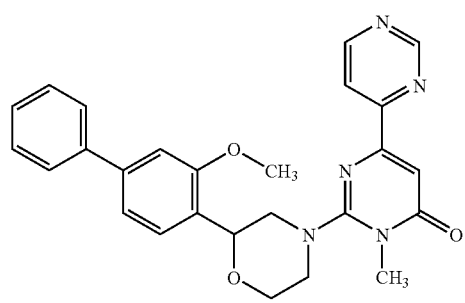 |
| B259 | 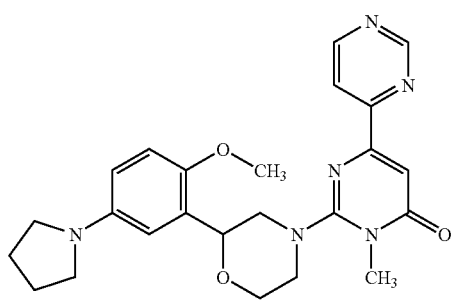 |
| B260 | 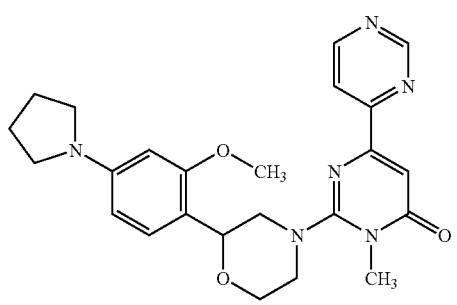 |
| B261 | 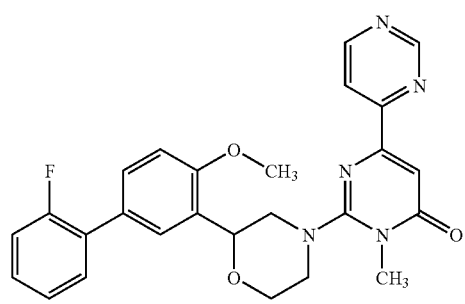 |

-continued
| Compound No. | STRUCTURE |
|---|---|
| B262 | 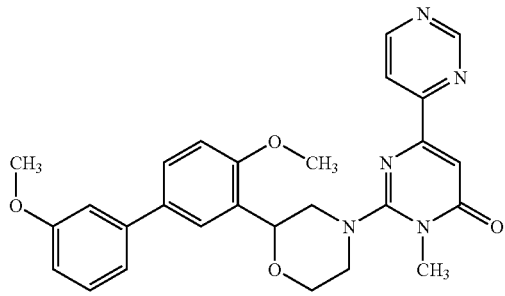 |
| B263 | 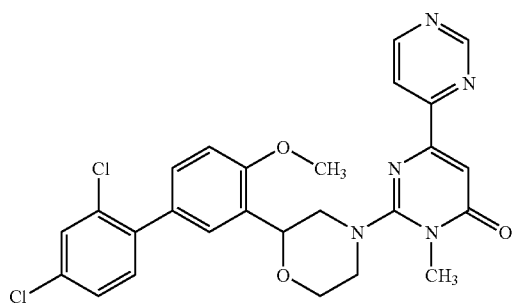 |
| B264 | 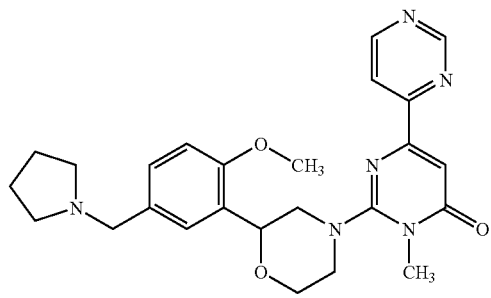 |
| B265 | 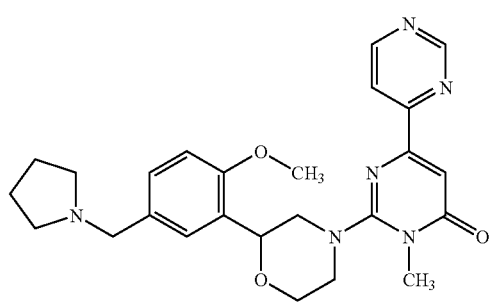 |
| B266 | 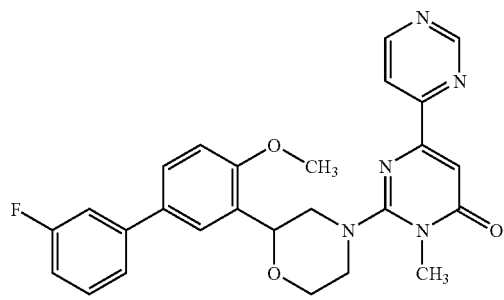 |

|Compound No.|STRUCTURE|
|---|---|
|B267|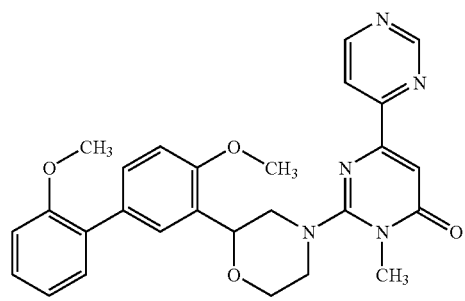|
|B268|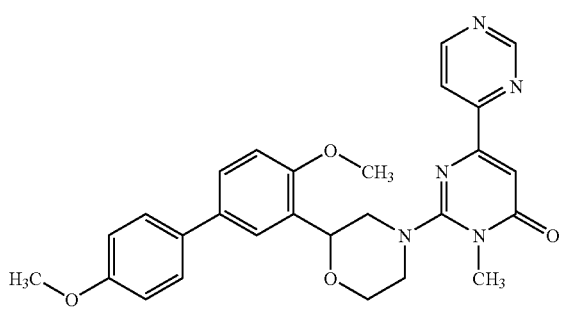|
|B269|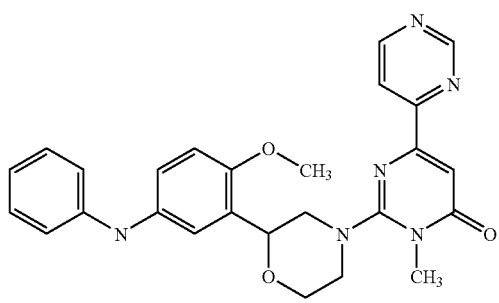|
|B270|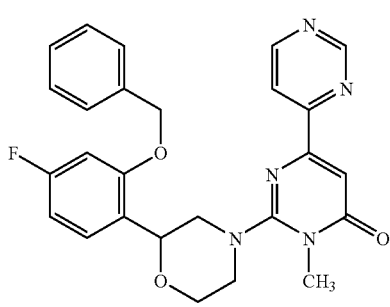|
|B271|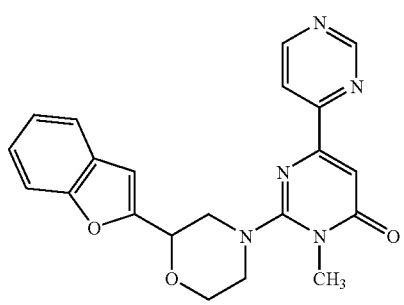|

-continued
| Compound No. | STRUCTURE |
|---|---|
| B272 | 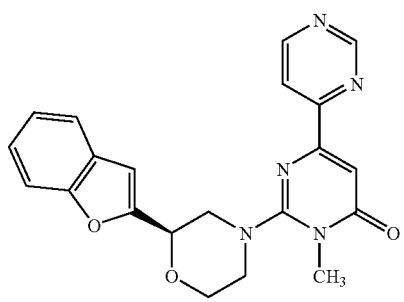 |
| B273 | 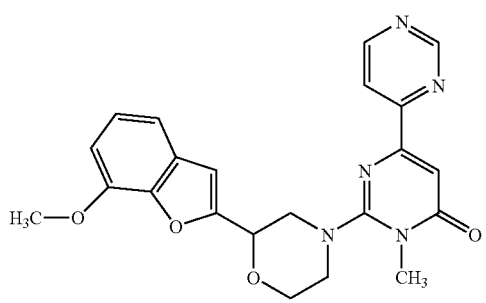 |
| B274 | 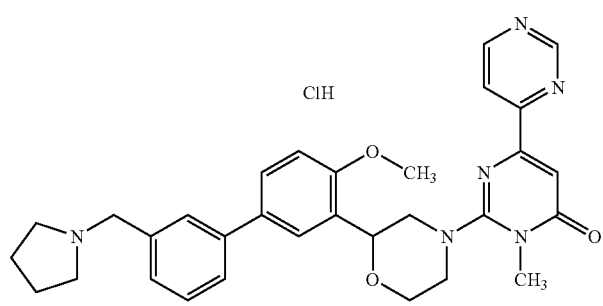 |
| B275 | 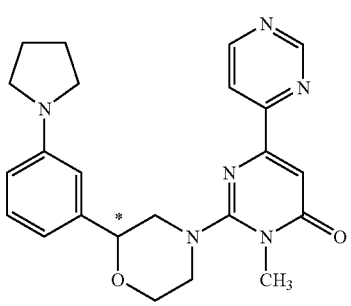 |
| B276 | 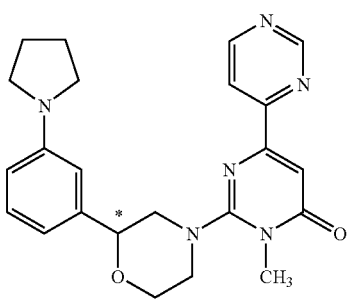 |

| Compound No. | STRUCTURE |
|---|---|
| B277 | 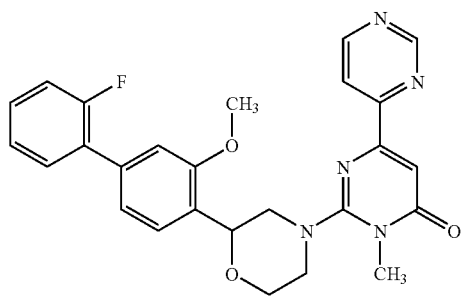 |
| B278 | 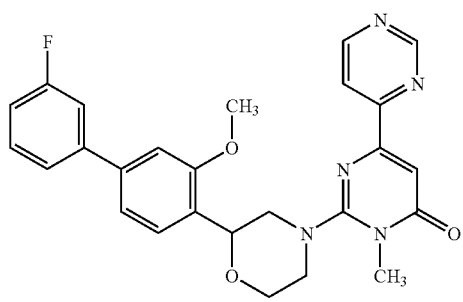 |
| B279 | 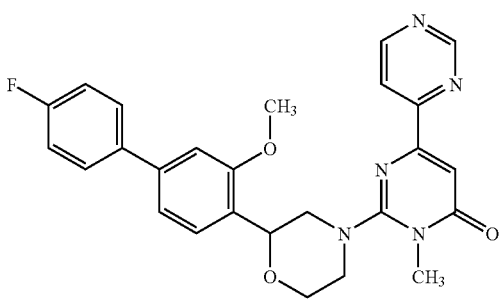 |
| B280 | 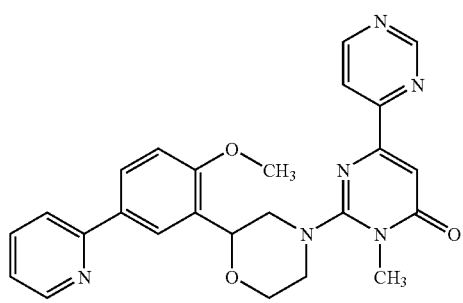 |

-continued
| Compound No. | STRUCTURE |
|---|---|
| B281 | 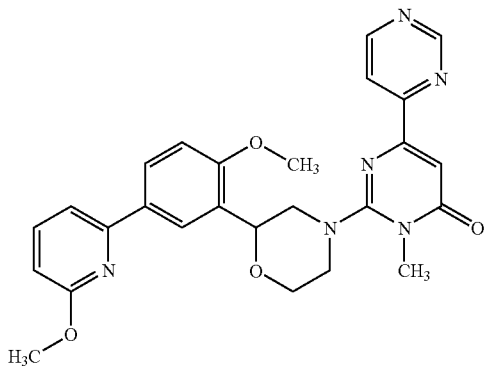 |
| B282 | 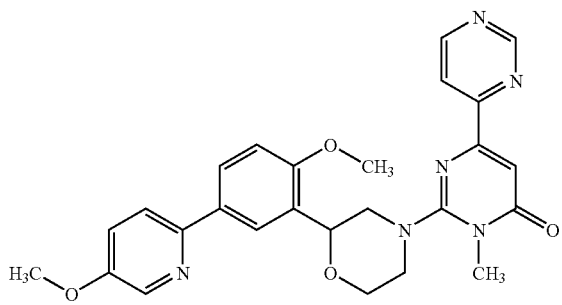 |
| B283 | 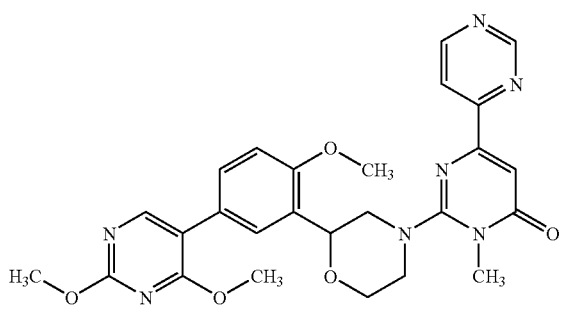 |
| B284 | 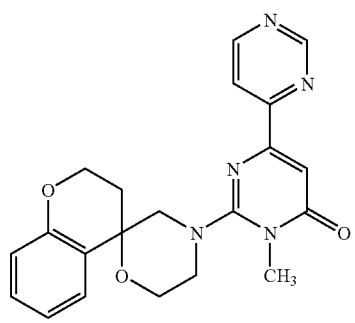 |

-continued
| Compound No. | STRUCTURE |
|---|---|
| B285 | 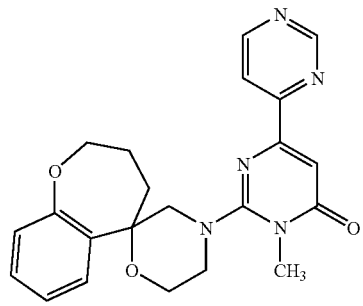 |
| C401 | 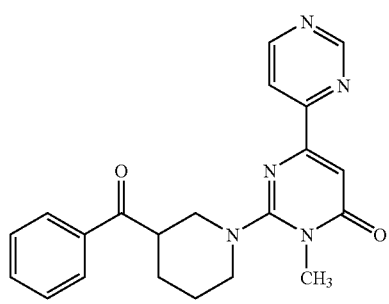 |
| C402 | 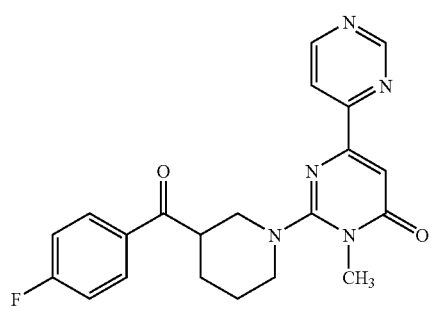 |
| C403 | 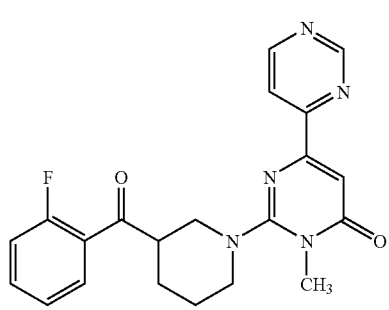 |
| C404 | 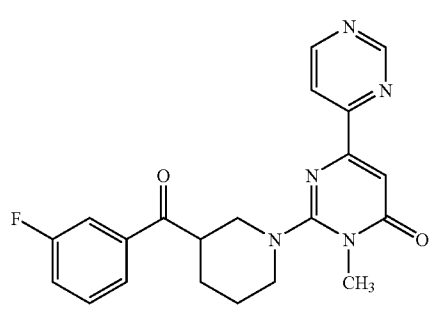 |

-continued
| Compound No. | STRUCTURE |
|---|---|
| C405 | 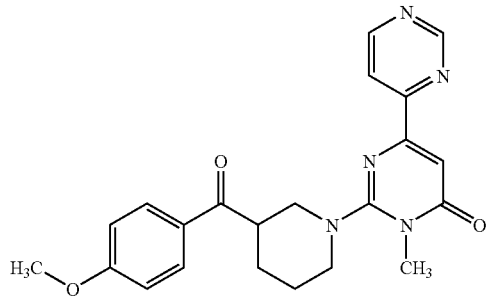 |
| C406 | 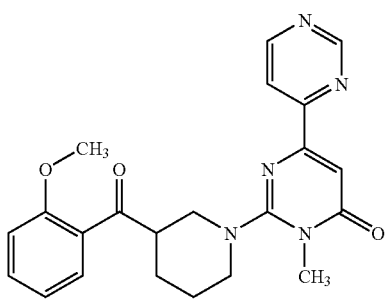 |
| C407 | 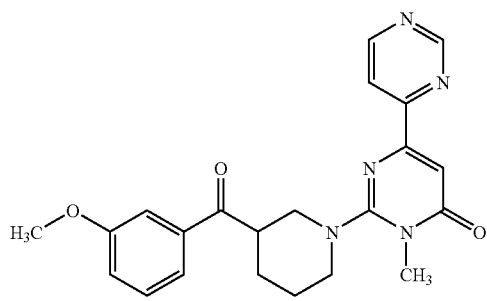 |
| C408 | 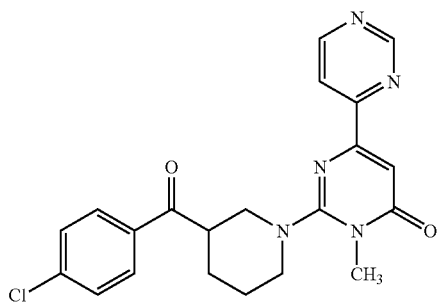 |
| C409 | 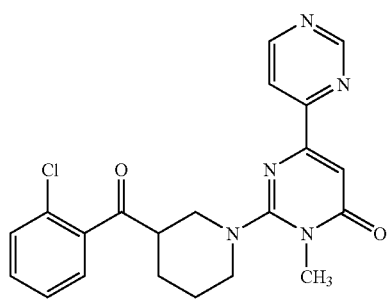 |

-continued
| Compound No. | STRUCTURE |
|---|---|
| C410 | 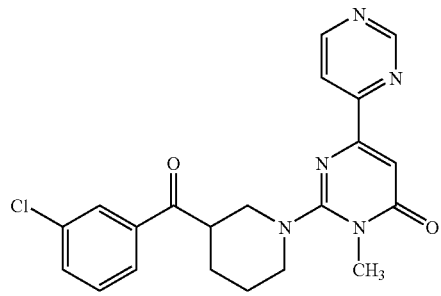 |
| C411 | 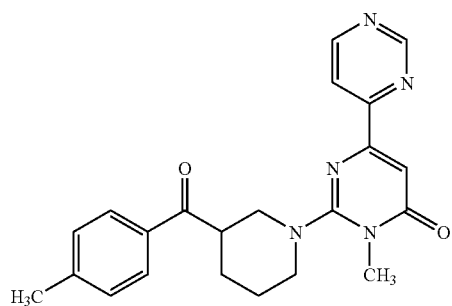 |
| C412 | 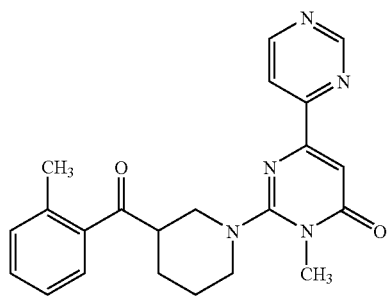 |
| C413 | 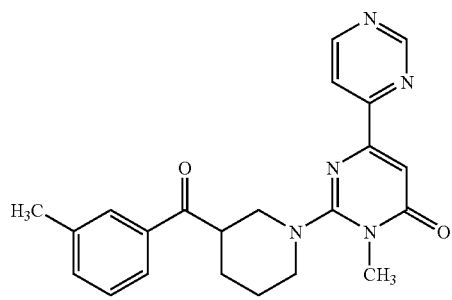 |
| C414 | 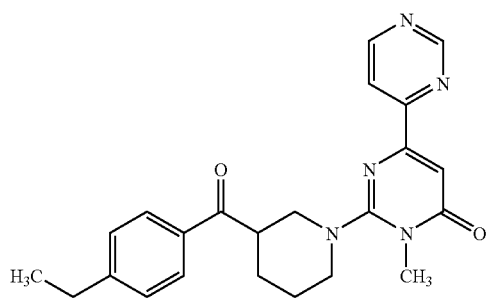 |

| Compound No. | STRUCTURE |
|---|---|
| C415 | 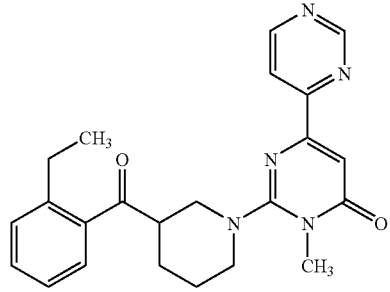 |
| C416 | 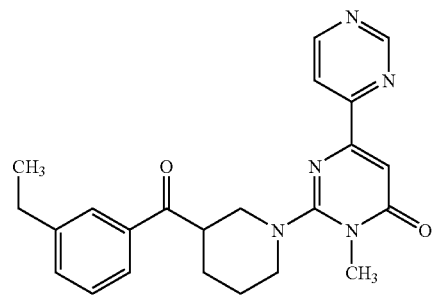 |
| C417 | 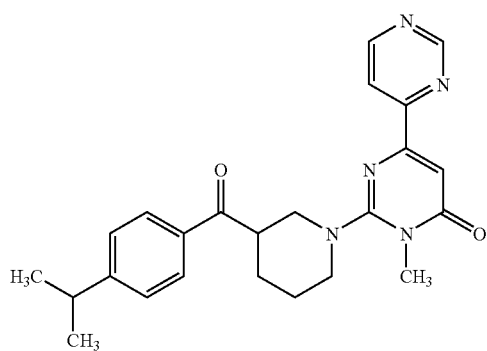 |
| C418 | 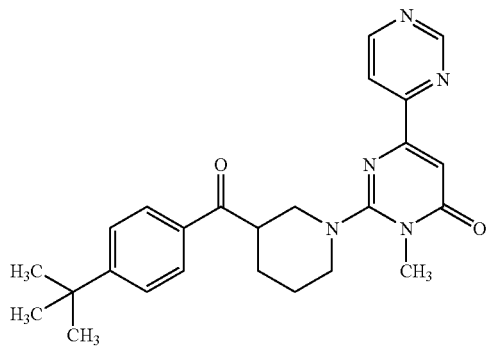 |

| Compound No. | STRUCTURE |
|---|---|
| C419 | 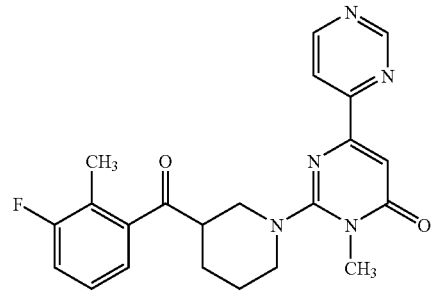 |
| C420 | 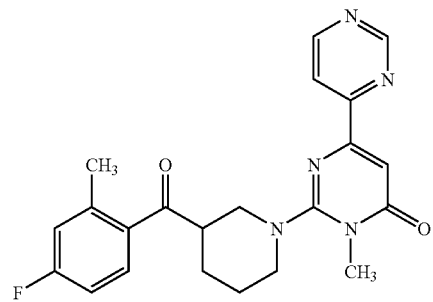 |
| C421 | 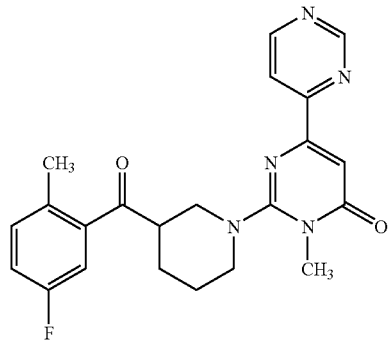 |
| C422 | 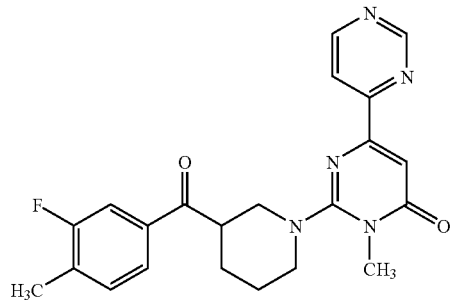 |

| Compound No. | STRUCTURE |
|---|---|
| C423 | 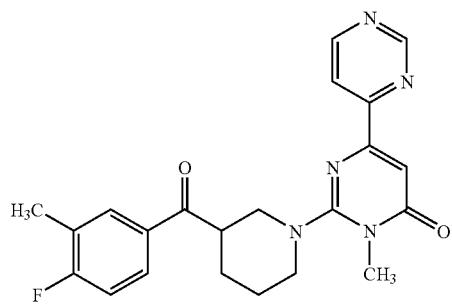 |
| C424 | 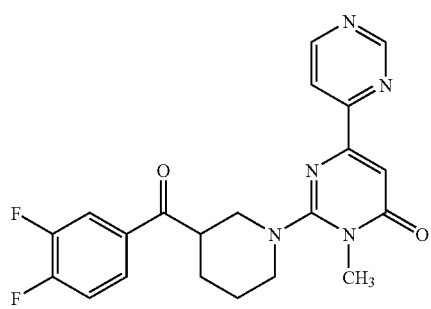 |
| C425 | 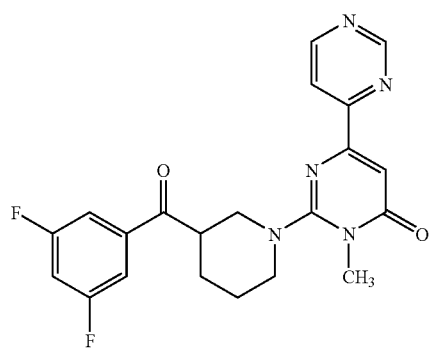 |
| C426 | 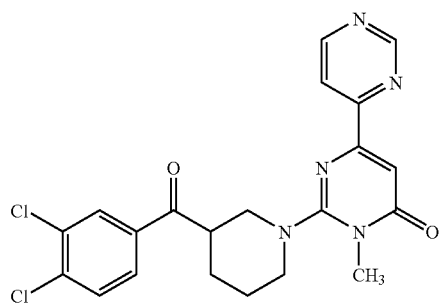 |

| Compound No. | STRUCTURE |
|---|---|
| C427 | 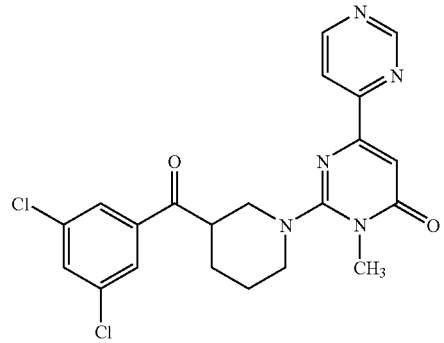 |
| C428 | 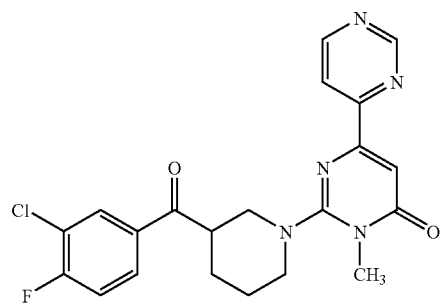 |
| C429 | 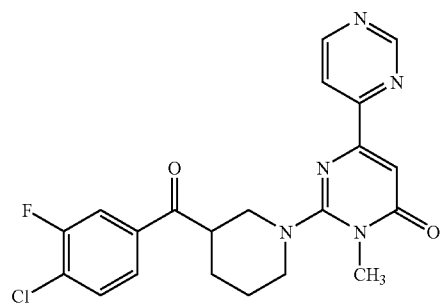 |
| C430 | 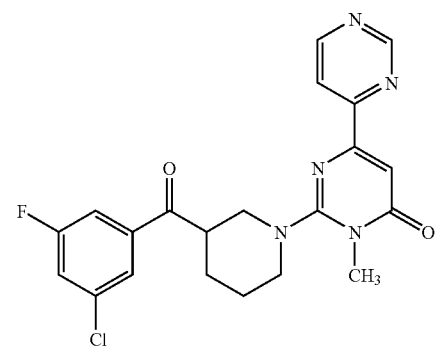 |

-continued
| Compound No. | STRUCTURE |
|---|---|
| C431 | 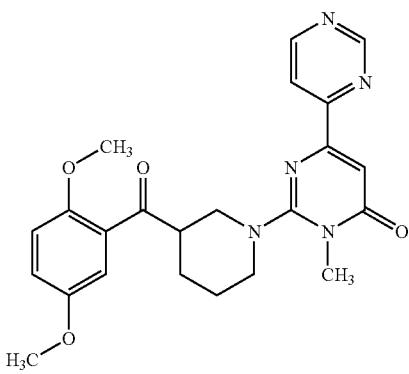 |
| C432 | 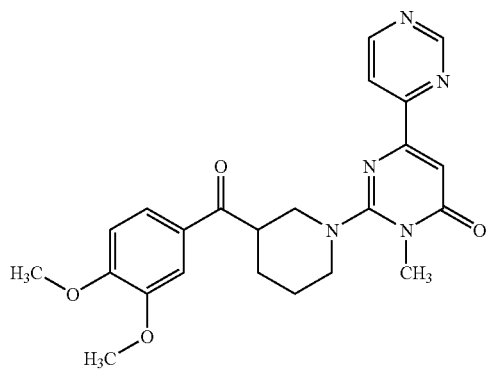 |
| C433 | 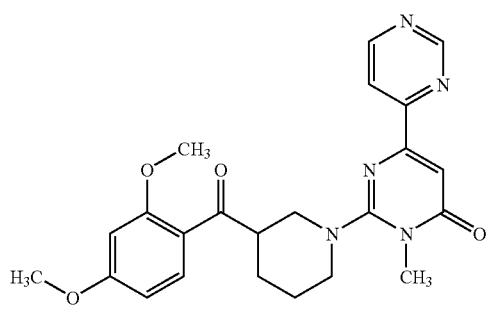 |
| C434 | 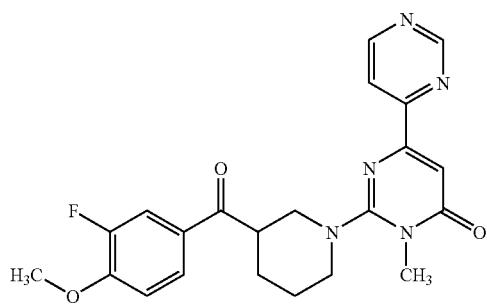 |

-continued
| Compound No. | STRUCTURE |
|---|---|
| C435 | 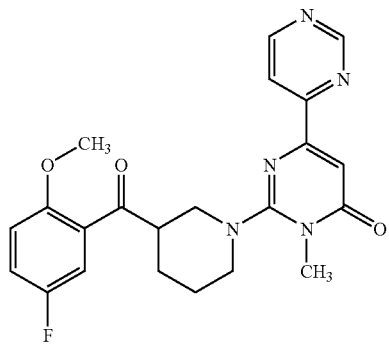 |
| C436 | 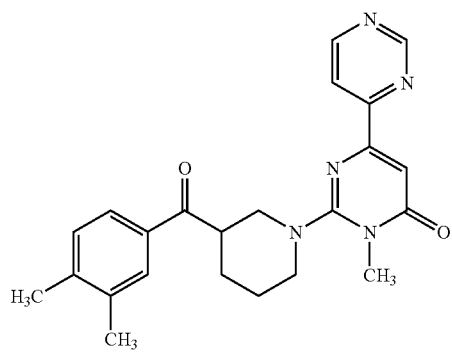 |
| C437 | 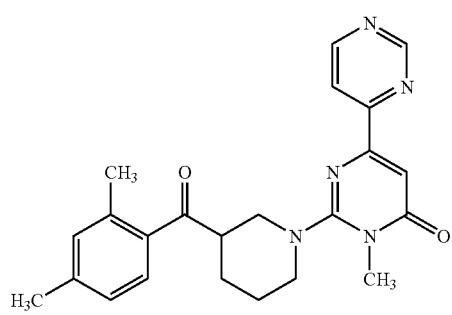 |
| C438 | 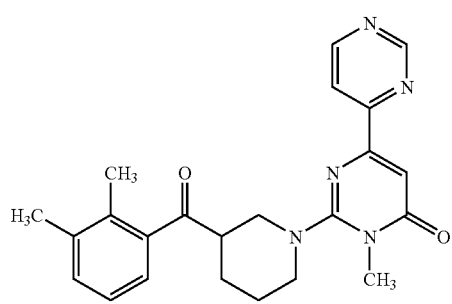 |

-continued
| Compound No. | STRUCTURE |
|---|---|
| C439 | 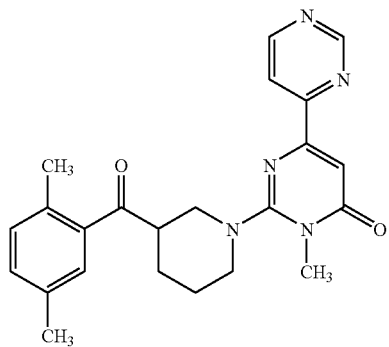 |
| C440 | 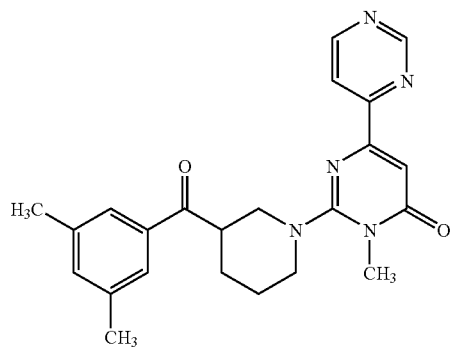 |
| C441 | 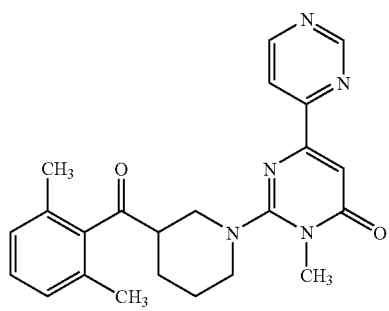 |
| C442 | 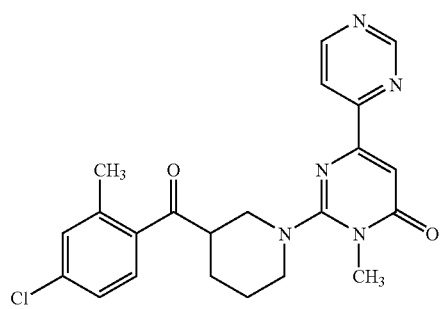 |

-continued
| Compound No. | STRUCTURE |
|---|---|
| C443 | 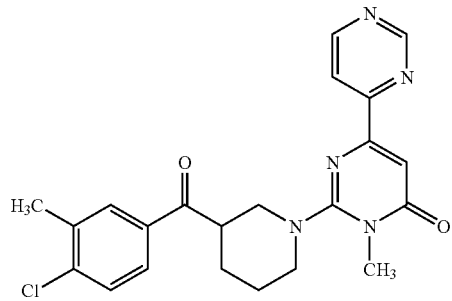 |
| C444 | 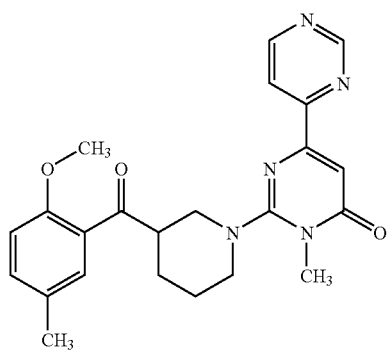 |
| C445 | 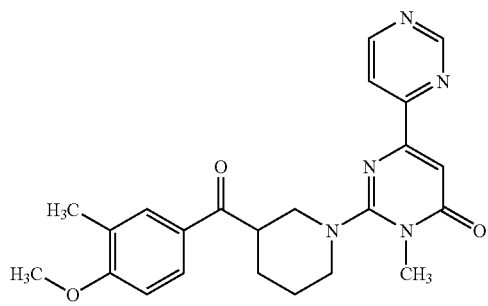 |
| C446 | 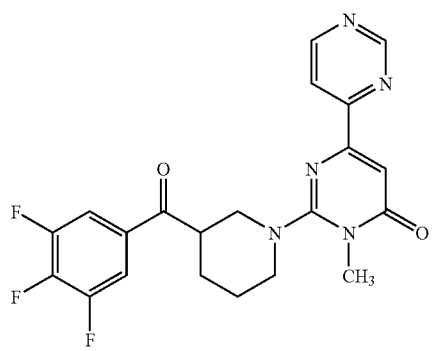 |

-continued
| Compound No. | STRUCTURE |
|---|---|
| C447 | 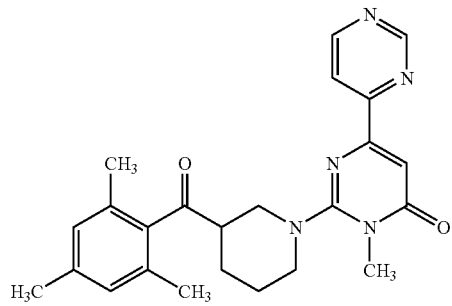 |
| C448 | 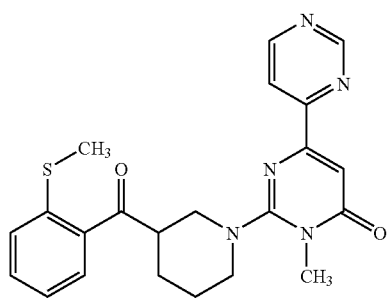 |
| C449 | 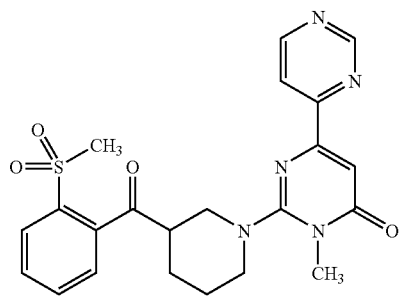 |
| C450 | 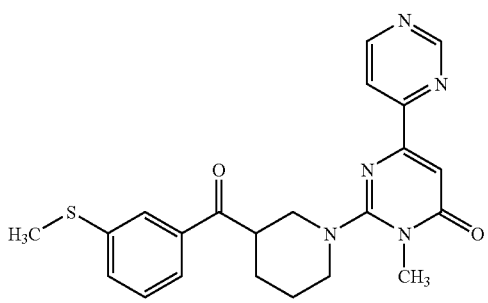 |
| C451 | 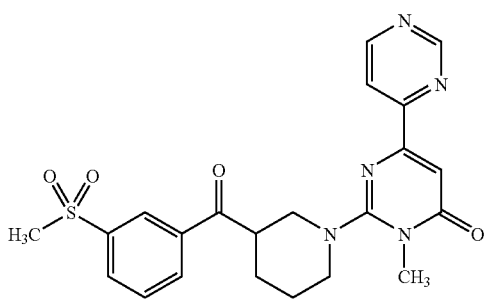 |

-continued
| Compound No. | STRUCTURE |
|---|---|
| C452 | 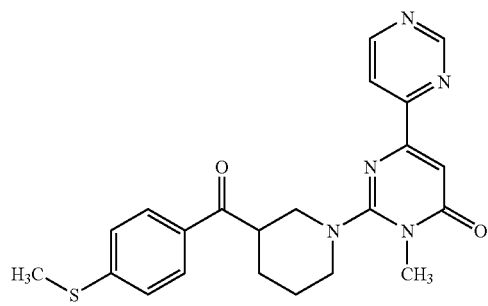 |
| C453 | 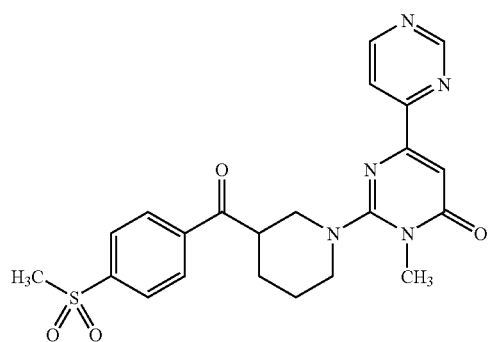 |
| C454 | 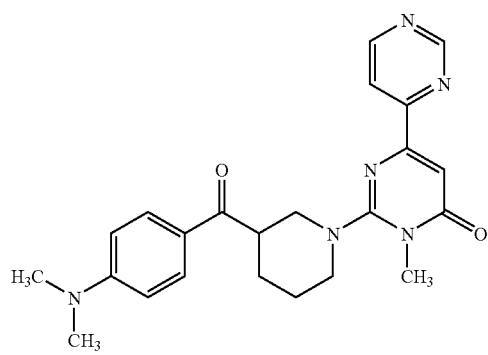 |
| C455 | 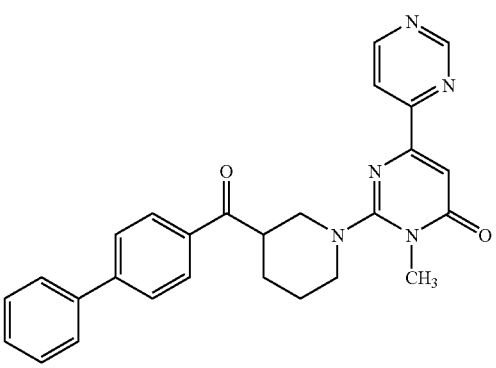 |

| Compound No. | STRUCTURE |
|---|---|
| C456 | 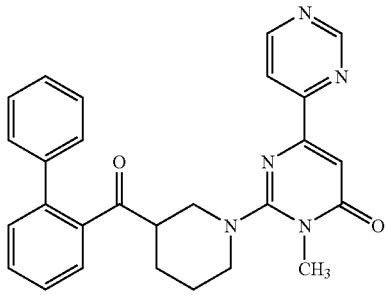 |
| C457 | 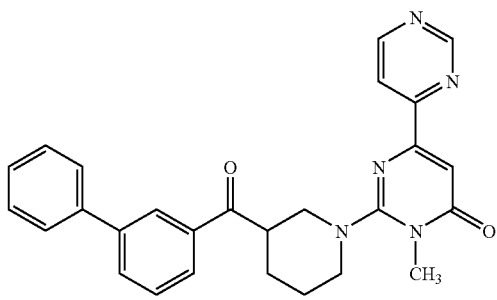 |
| C458 | 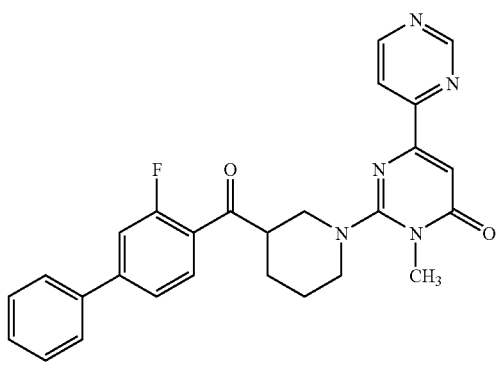 |
| C459 | 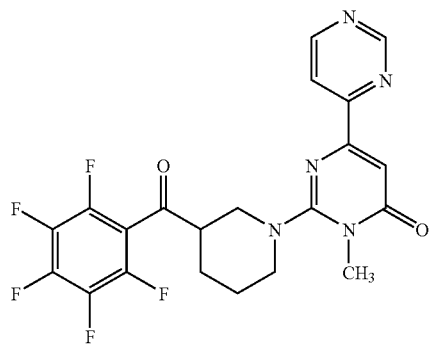 |

-continued
| Compound No. | STRUCTURE |
|---|---|
| C460 | 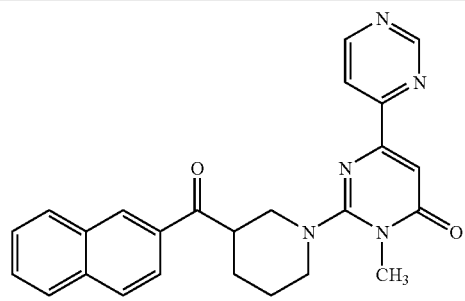 |
| C461 | 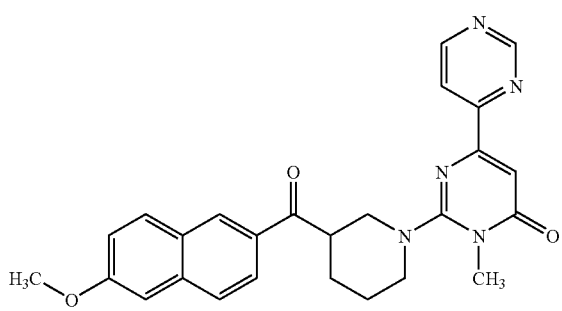 |
| C462 | 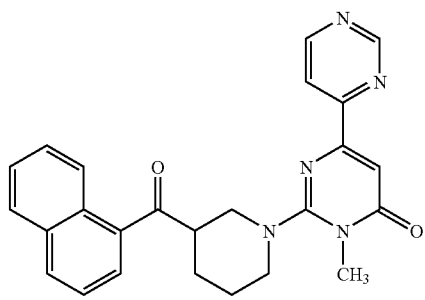 |
| C463 | 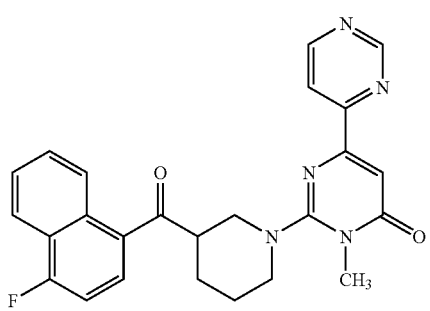 |
| C464 | 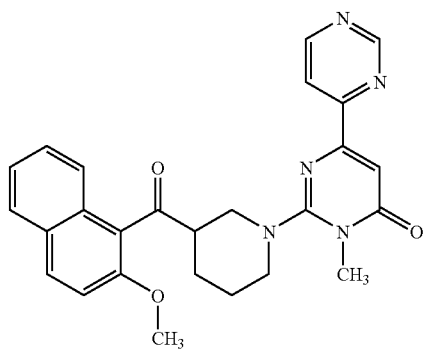 |

| Compound No. | STRUCTURE |
|---|---|
| C465 | 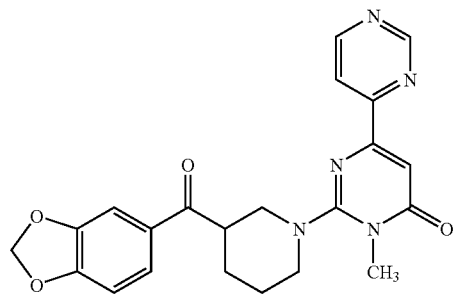 |
| C466 | 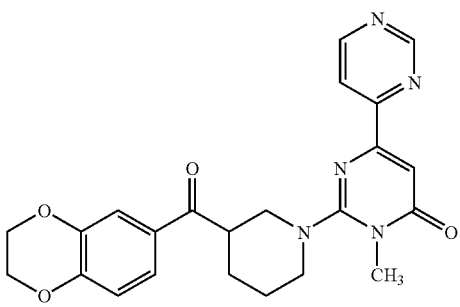 |
| C467 | 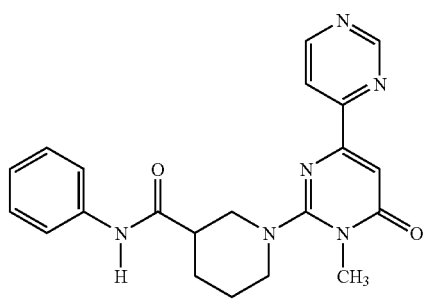 |
| C468 | 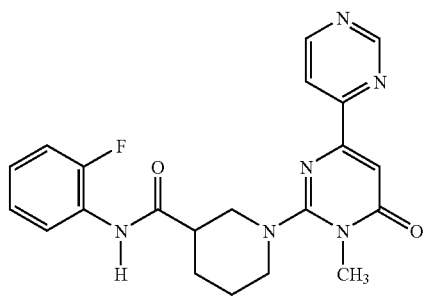 |
| C469 | 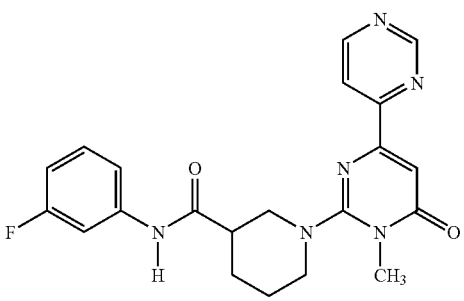 |

-continued
| Compound No. | STRUCTURE |
|---|---|
| C470 | 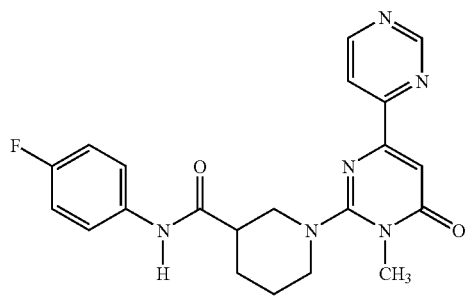 |
| C471 | 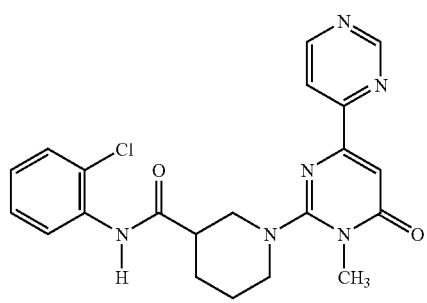 |
| C472 | 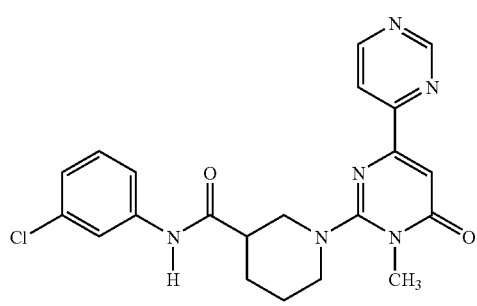 |
| C473 | 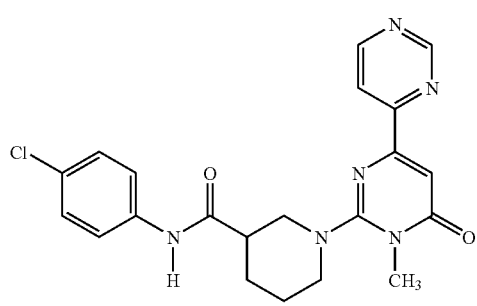 |
| C474 | 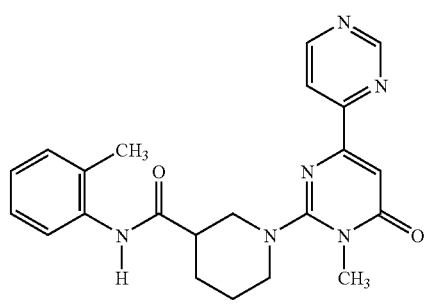 |

-continued
| Compound No. | STRUCTURE |
|---|---|
| C475 | 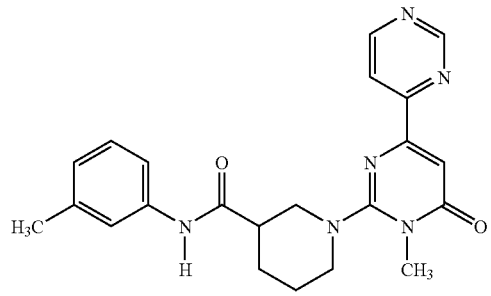 |
| C476 | 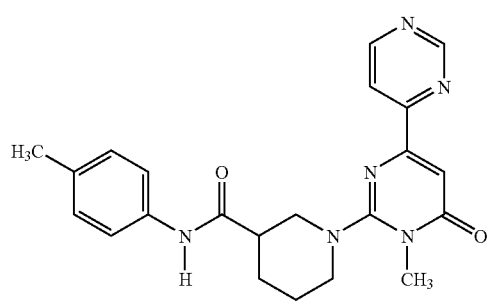 |
| C477 | 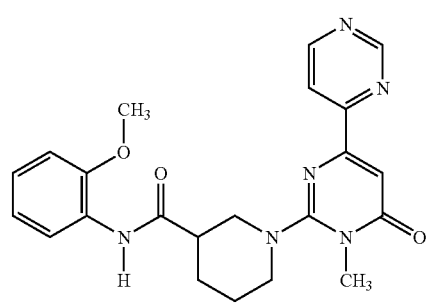 |
| C478 | 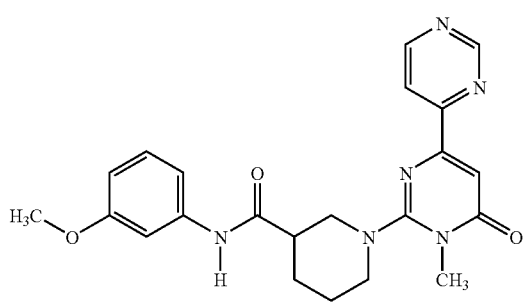 |
| C479 | 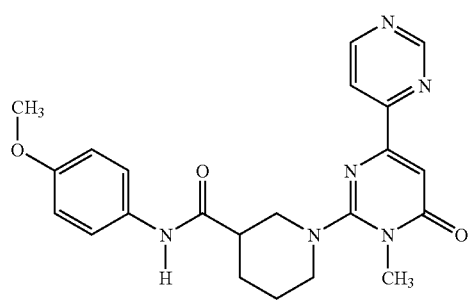 |

-continued
| Compound No. | STRUCTURE |
|---|---|
| C480 | 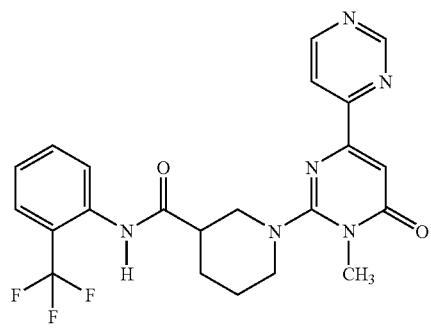 |
| C481 | 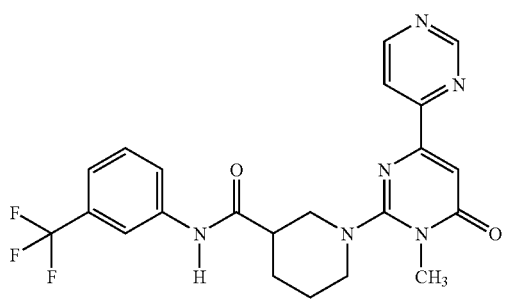 |
| C482 | 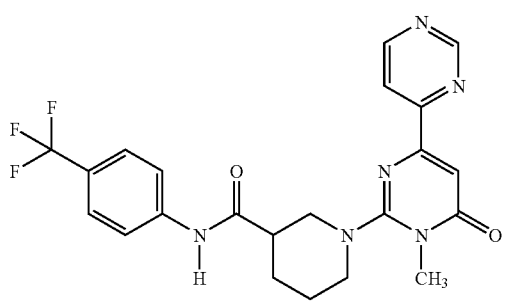 |
| C483 | 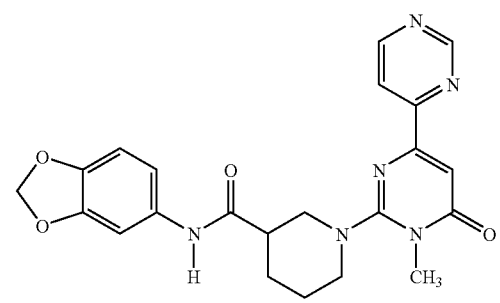 |
| C484 | 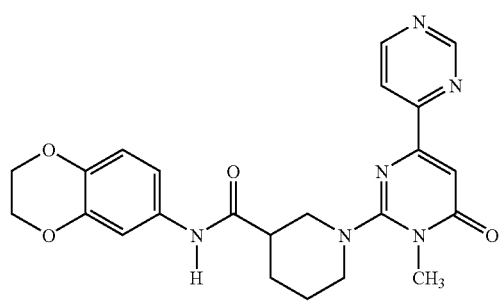 |

-continued
| Compound No. | STRUCTURE |
|---|---|
| C485 | 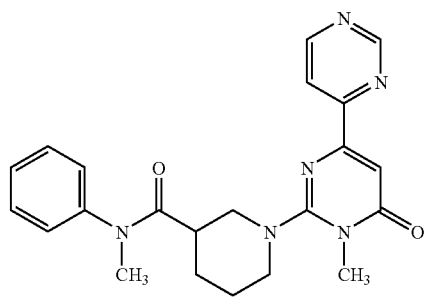 |
| C486 | 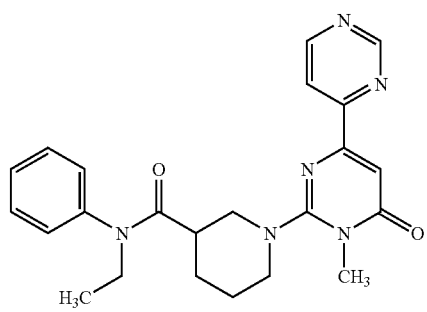 |
| C487 | 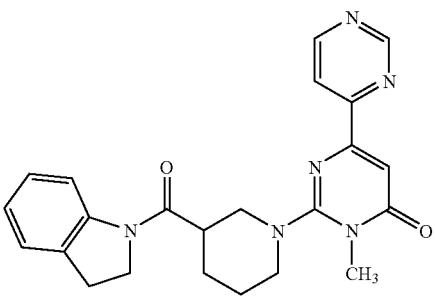 |
| C488 | 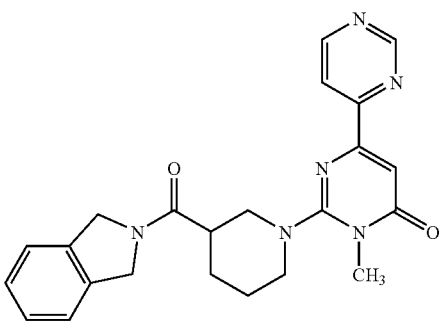 |
| C489 | 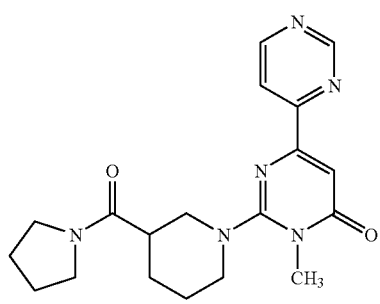 |

-continued
| Compound No. | STRUCTURE |
|---|---|
| C490 | 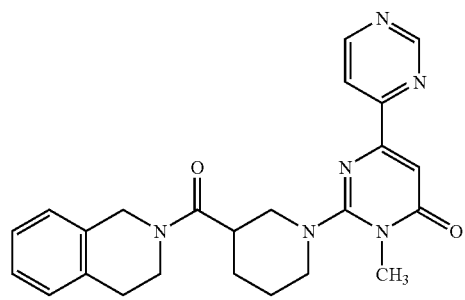 |
| C491 | 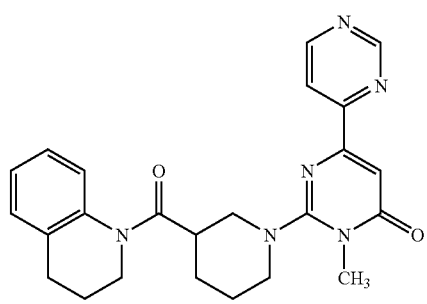 |
| C492 | 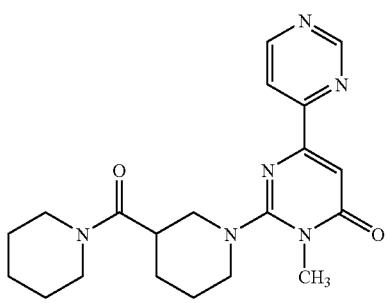 |
| C493 | 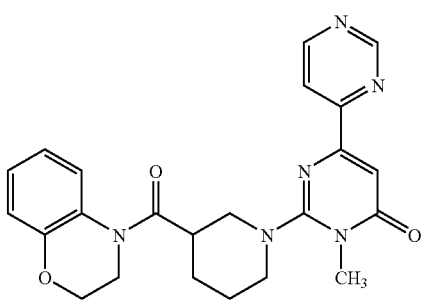 |
| C494 | 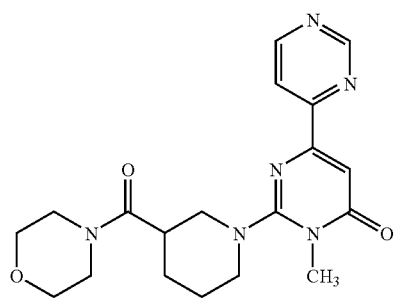 |

-continued
| Compound No. | STRUCTURE |
|---|---|
| C495 | 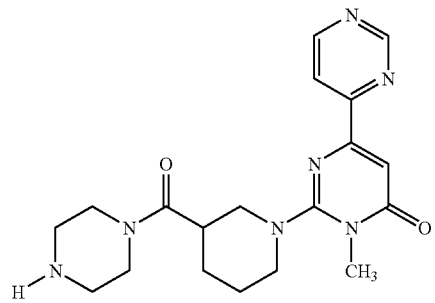 |
| C496 | 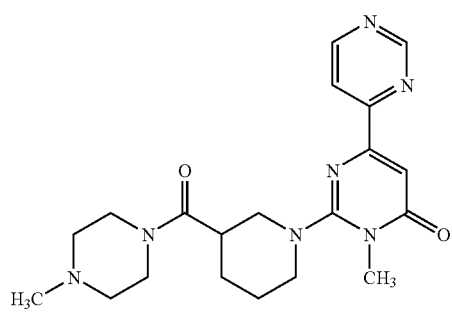 |
| C497 | 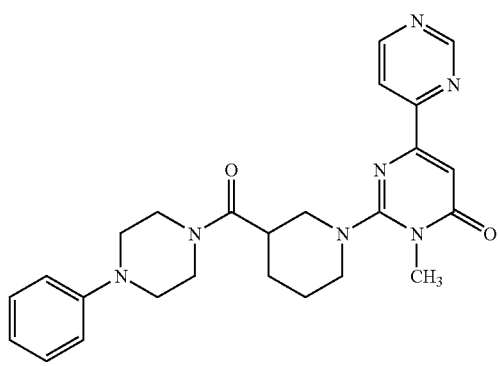 |
| C498 | 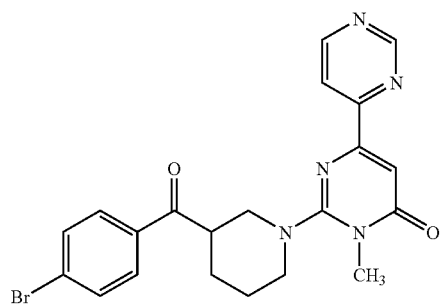 |

-continued
| Compound No. | STRUCTURE |
|---|---|
| C499 | 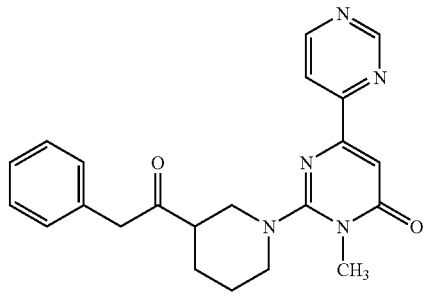 |
| C501 | 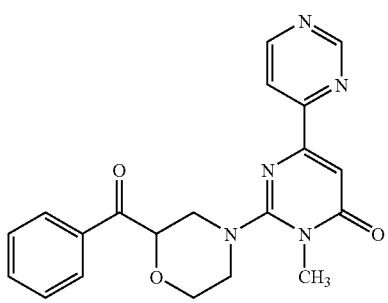 |
| C502 | 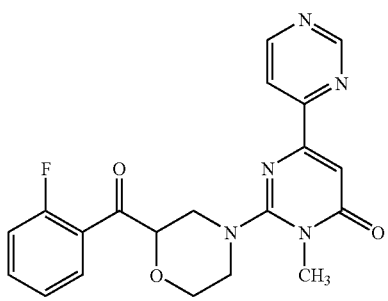 |
| C503 | 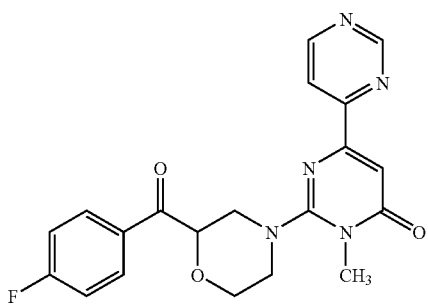 |
| C504 | 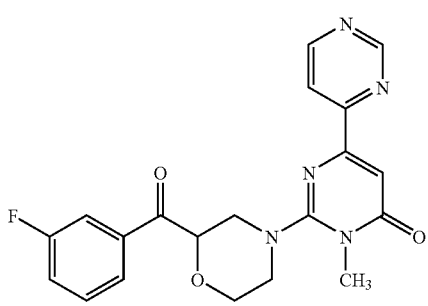 |

-continued
| Compound No. | STRUCTURE |
|---|---|
| C505 | 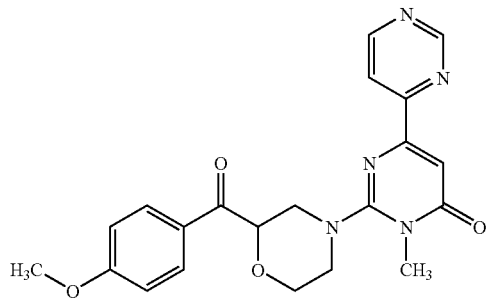 |
| C506 | 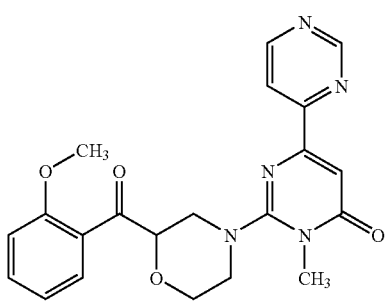 |
| C507 | 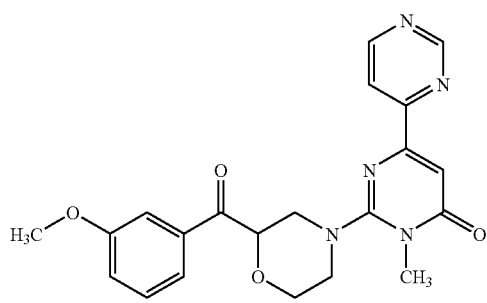 |
| C508 | 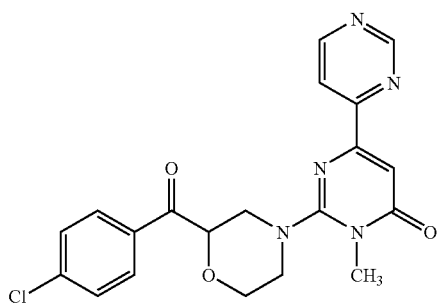 |
| C509 | 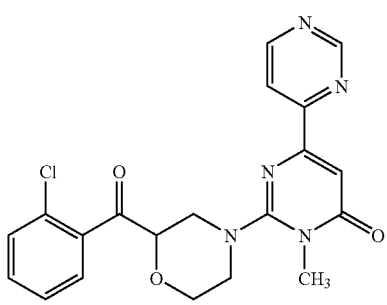 |

-continued
| Compound No. | STRUCTURE |
|---|---|
| C510 | 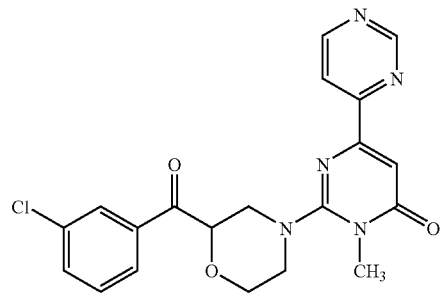 |
| C511 | 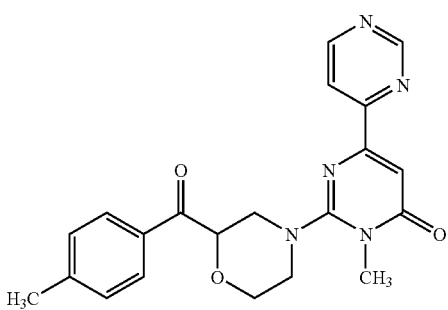 |
| C512 | 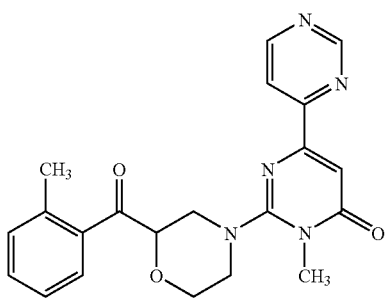 |
| C513 | 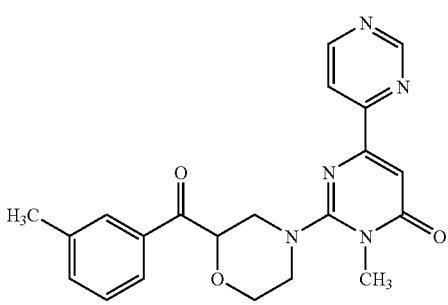 |
| C514 | 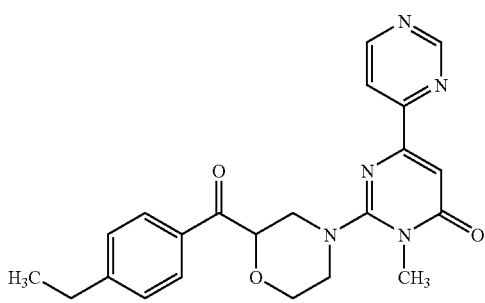 |

-continued
| Compound No. | STRUCTURE |
|---|---|
| C515 | 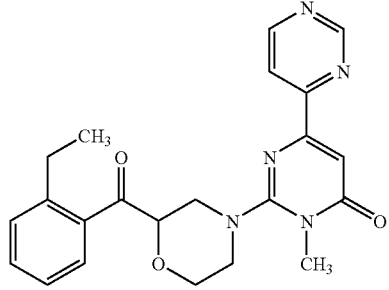 |
| C516 | 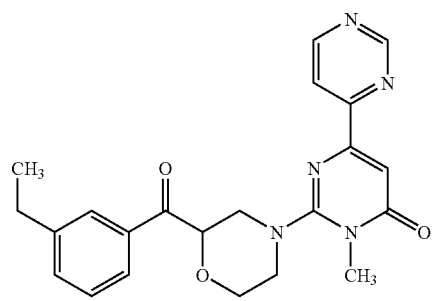 |
| C517 | 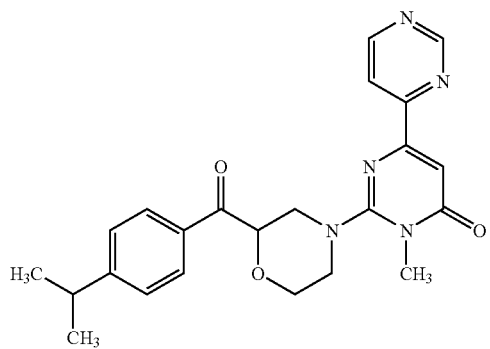 |
| C518 | 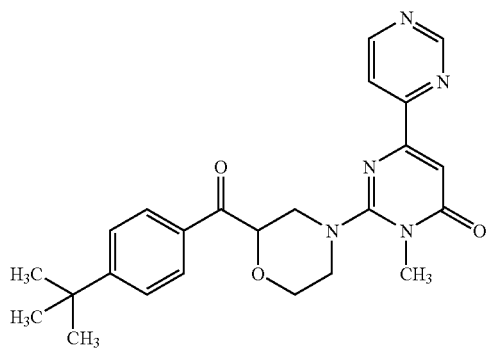 |

-continued
| Compound No. | STRUCTURE |
|---|---|
| C519 | 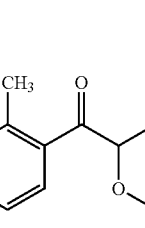 |
| C520 | 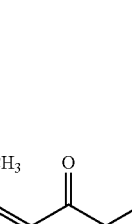 |
| C521 | 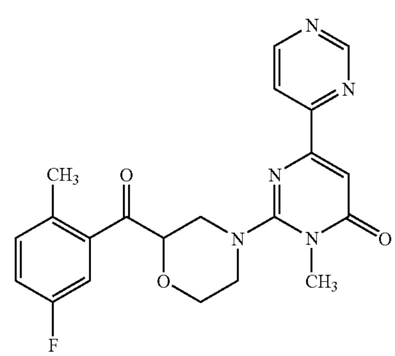 |
| C522 | 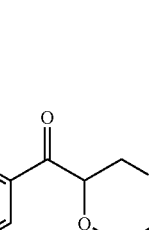 |

-continued
| Compound No. | STRUCTURE |
|---|---|
| C523 | 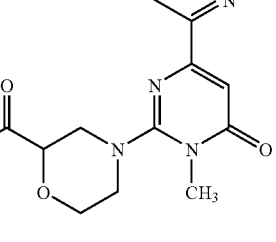 |
| C524 | 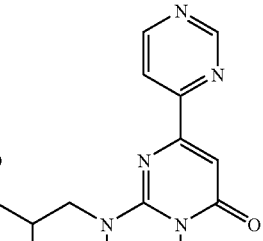 |
| C525 | 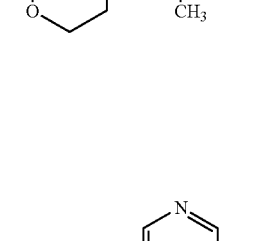 |
| C526 | 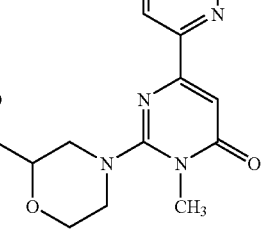 |

| Compound No. | STRUCTURE |
|---|---|
| C527 | 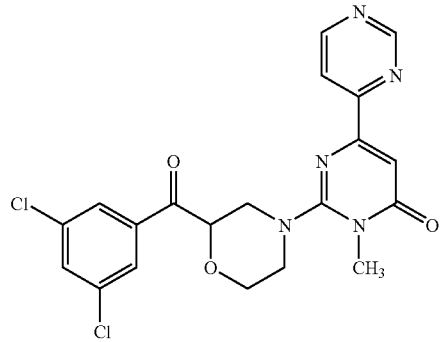 |
| C528 | 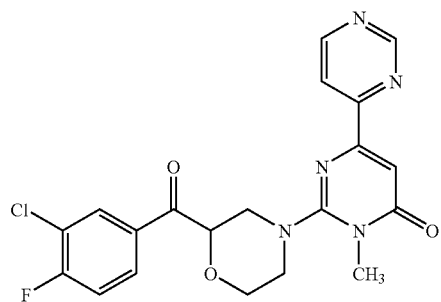 |
| C529 | 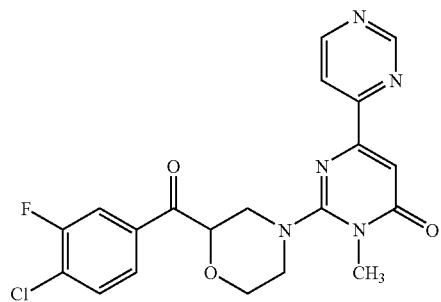 |
| C530 | 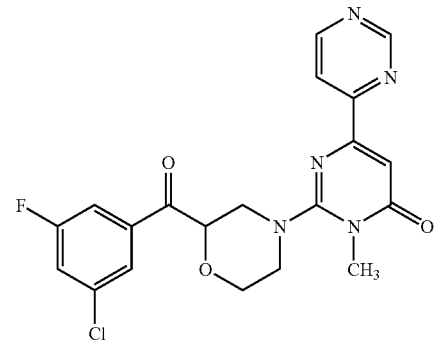 |

| Compound No. | STRUCTURE |
|---|---|
| C531 | 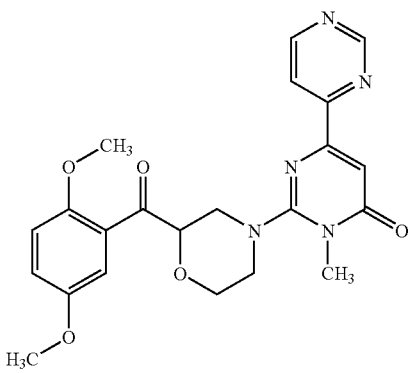 |
| C532 | 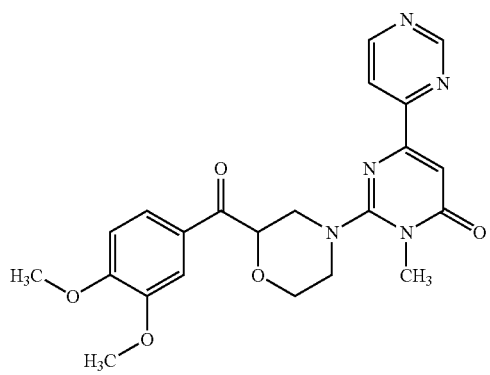 |
| C533 | 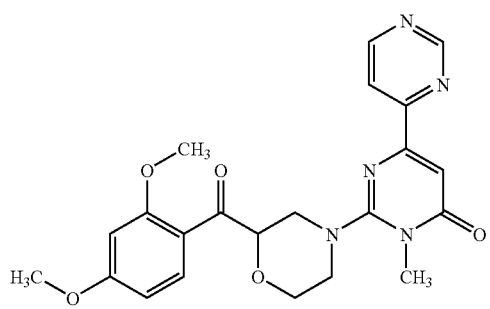 |
| C534 | 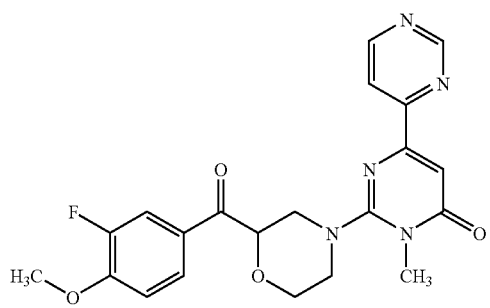 |

| Compound No. | STRUCTURE |
|---|---|
| C535 | 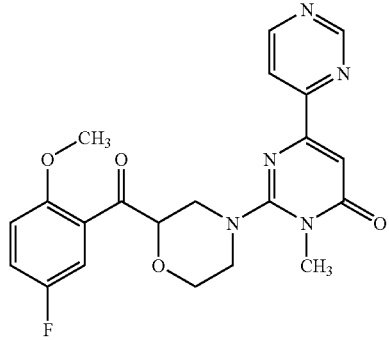 |
| C536 | 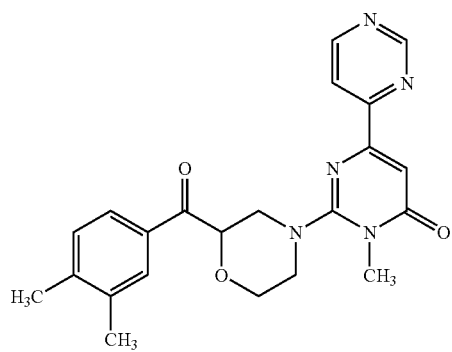 |
| C537 | 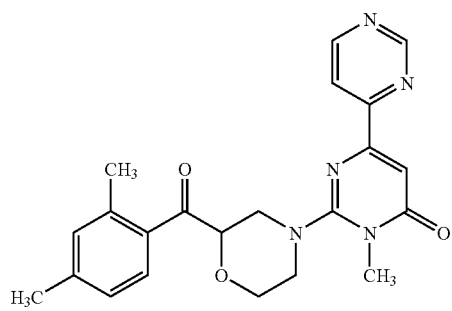 |
| C538 | 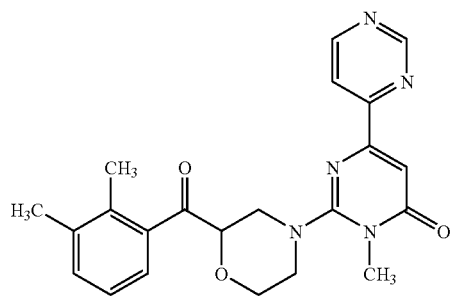 |

-continued
| Compound No. | STRUCTURE |
|---|---|
| C539 | 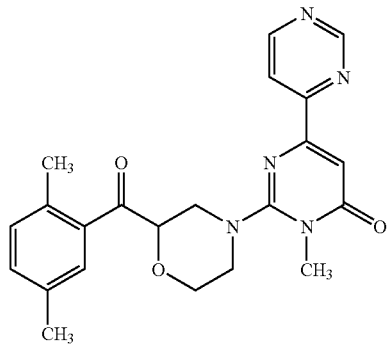 |
| C540 | 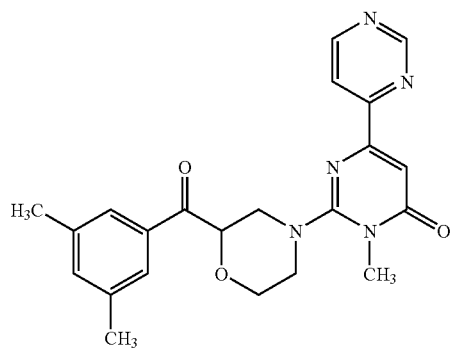 |
| C541 | 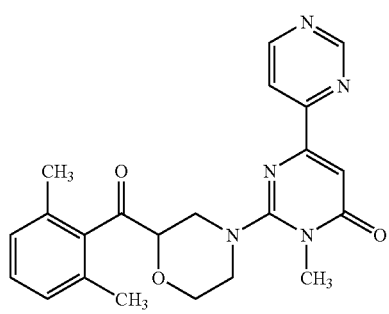 |
| C542 | 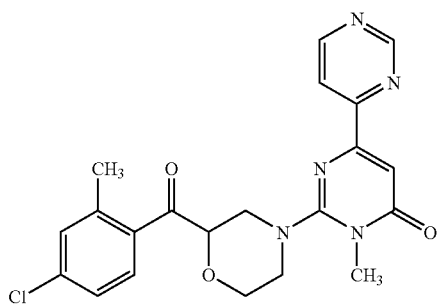 |

| Compound No. | STRUCTURE |
|---|---|
| C543 | 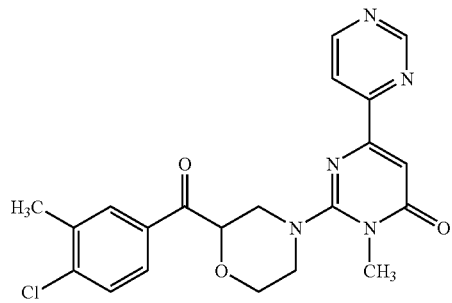 |
| C544 | 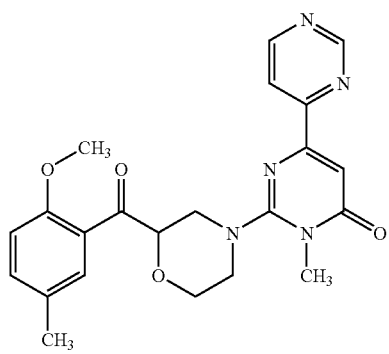 |
| C545 | 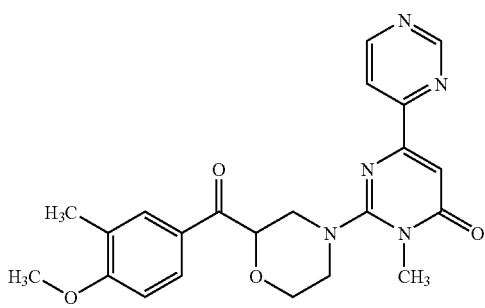 |
| C546 | 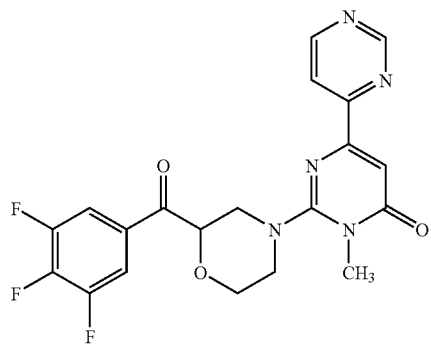 |

-continued
| Compound No. | STRUCTURE |
|---|---|
| C547 | 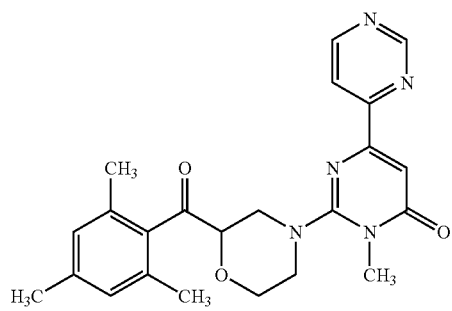 |
| C548 | 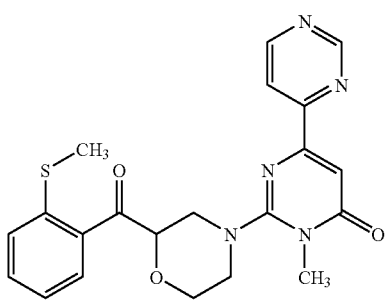 |
| C549 | 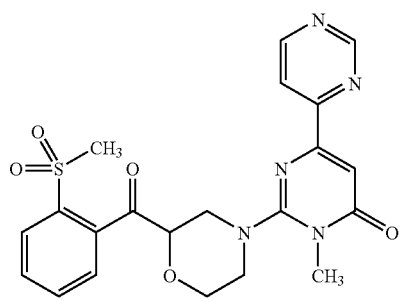 |
| C550 | 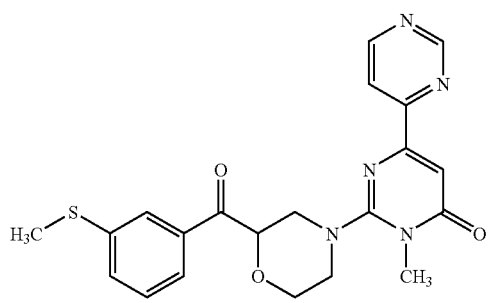 |
| C551 | 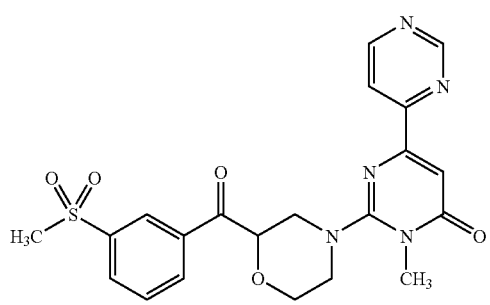 |

-continued
| Compound No. | STRUCTURE |
|---|---|
| C552 | 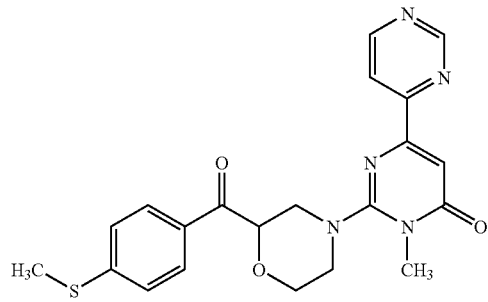 |
| C553 | 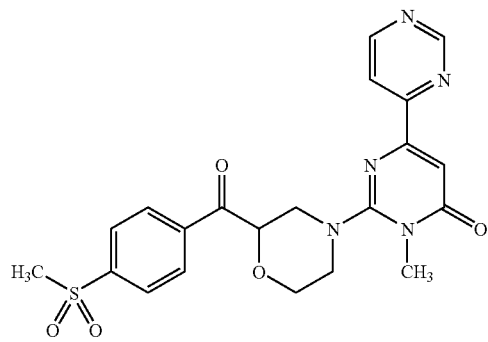 |
| C554 | 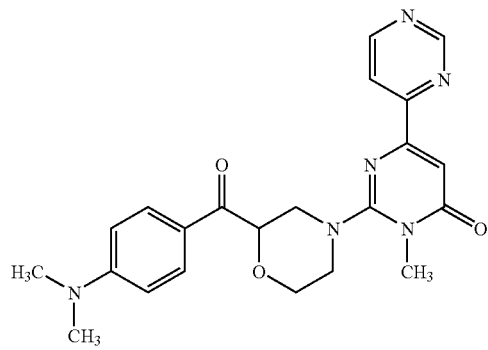 |
| C555 | 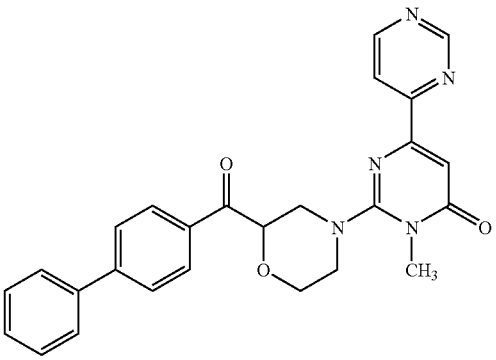 |

| Compound No. | STRUCTURE |
|---|---|
| C556 | 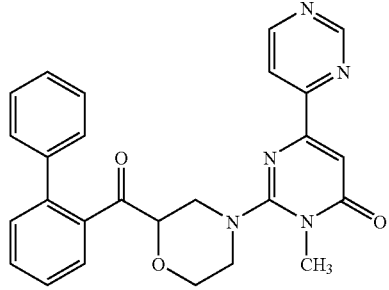 |
| C557 | 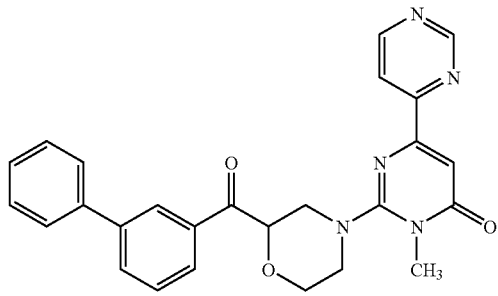 |
| C558 | 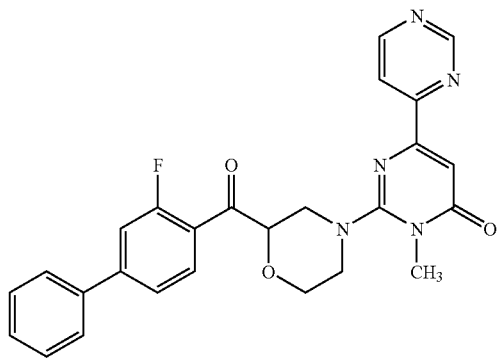 |
| C559 | 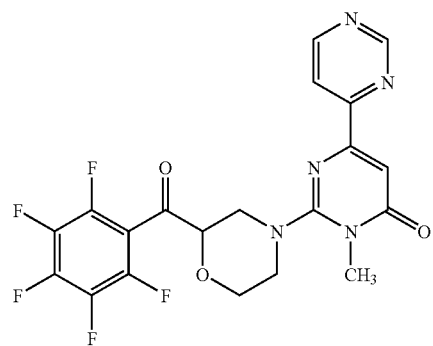 |

| Compound No. | STRUCTURE |
|---|---|
| C560 | 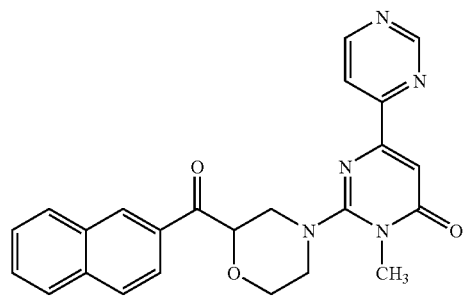 |
| C561 | 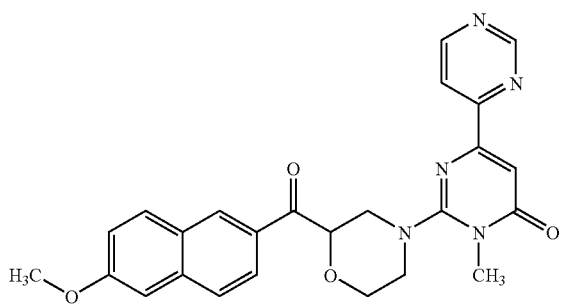 |
| C562 | 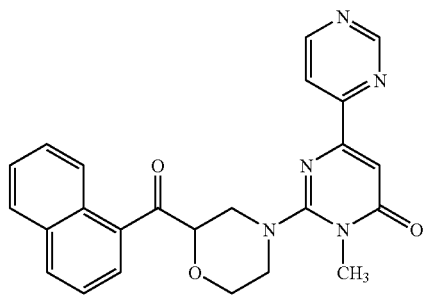 |
| C563 | 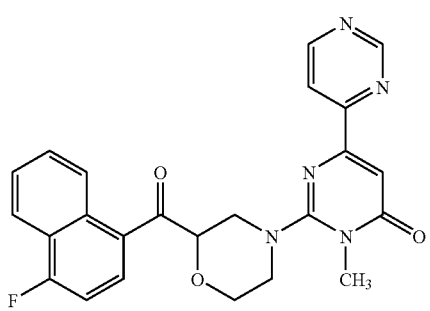 |
| C564 | 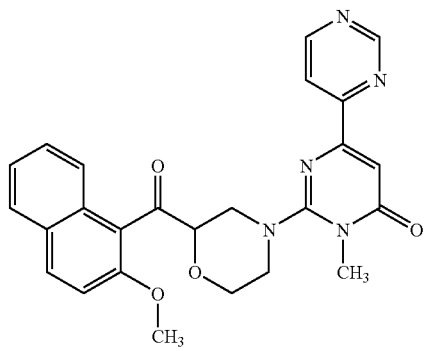 |

-continued
| Compound No. | STRUCTURE |
|---|---|
| C565 | 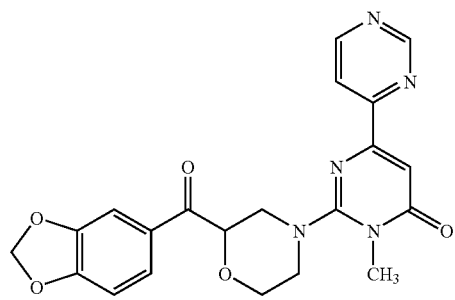 |
| C566 | 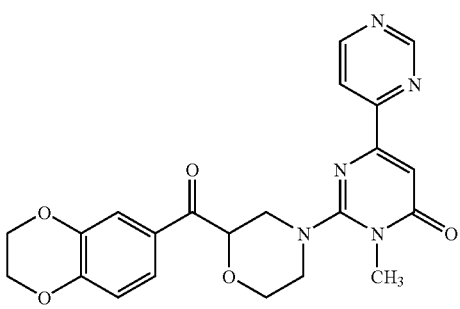 |
| C567 | 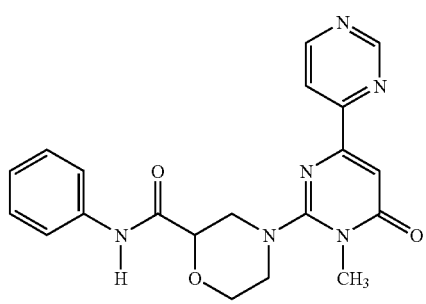 |
| C568 | 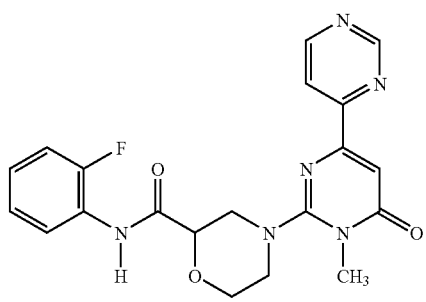 |
| C569 | 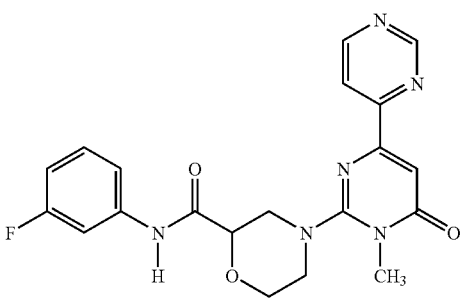 |

-continued
| Compound No. | STRUCTURE |
|---|---|
| C570 | 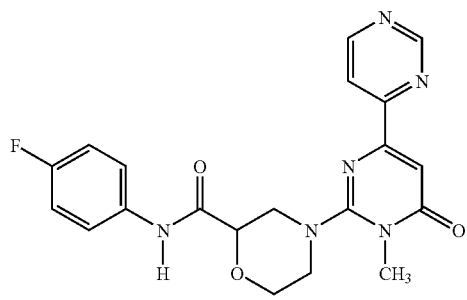 |
| C571 | 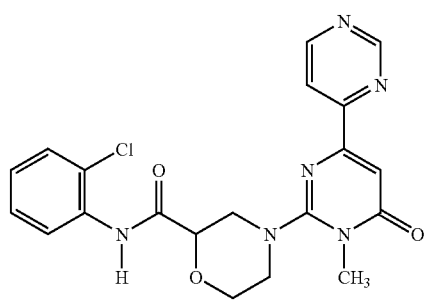 |
| C572 | 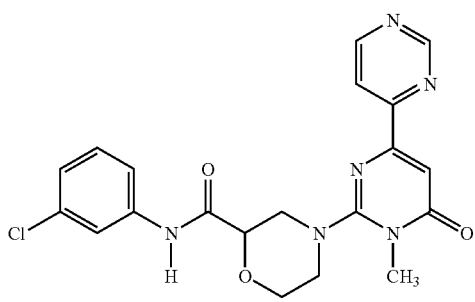 |
| C573 | 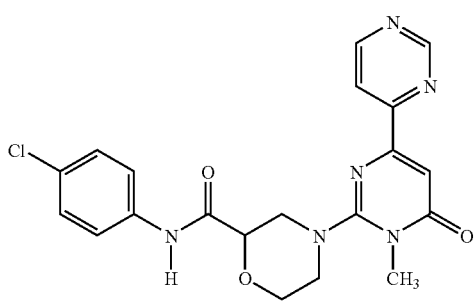 |
| C574 | 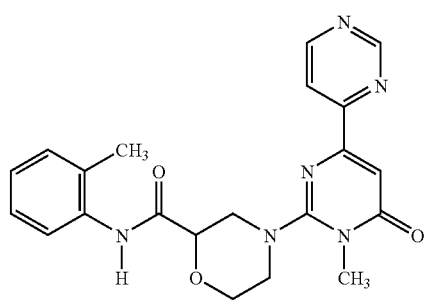 |

-continued
| Compound No. | STRUCTURE |
|---|---|
| C575 | 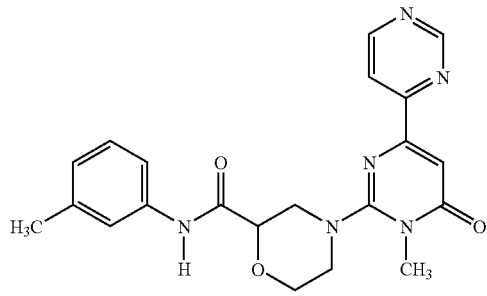 |
| C576 | 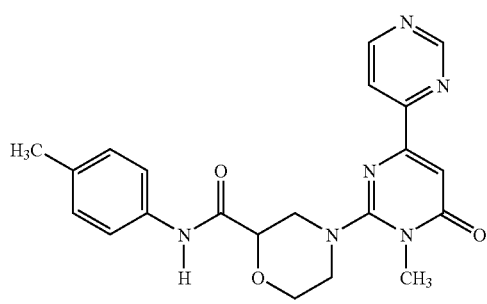 |
| C577 | 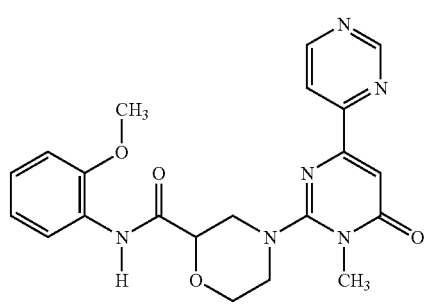 |
| C578 | 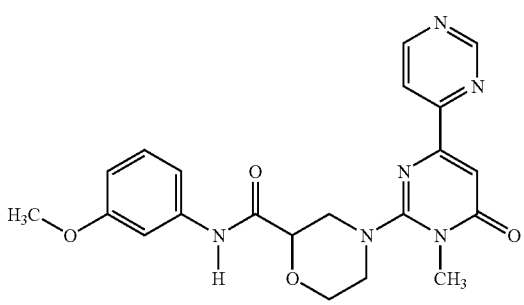 |
| C579 | 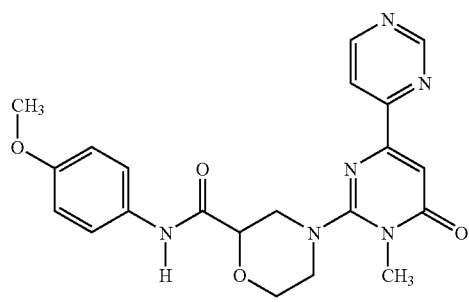 |

-continued
| Compound No. | STRUCTURE |
|---|---|
| C580 | 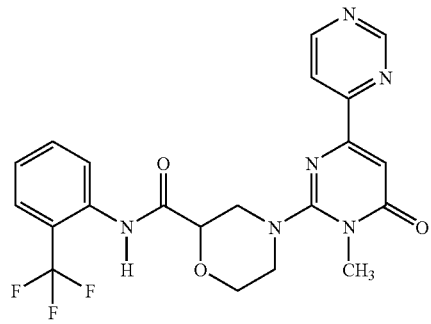 |
| C581 | 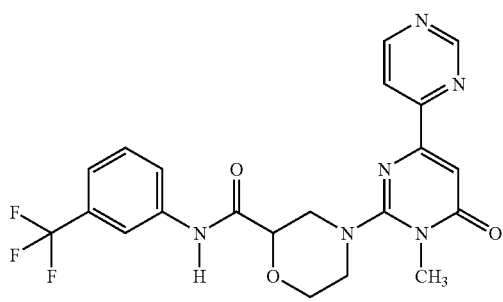 |
| C582 | 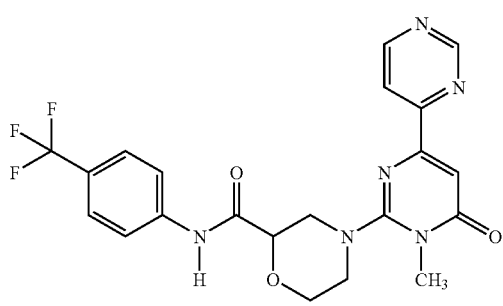 |
| C583 | 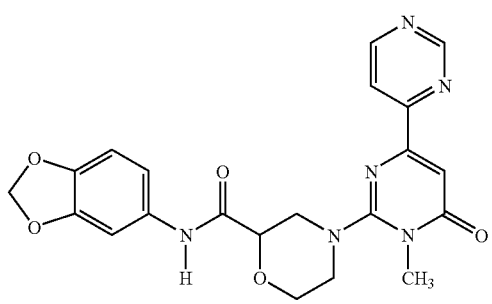 |
| C584 | 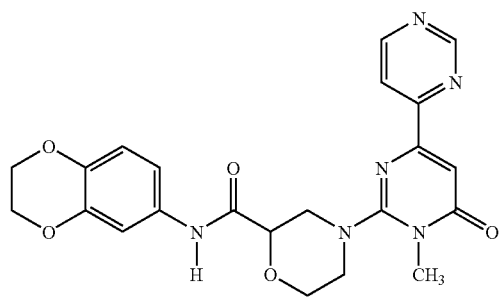 |

| Compound No. | STRUCTURE |
|---|---|
| C585 | 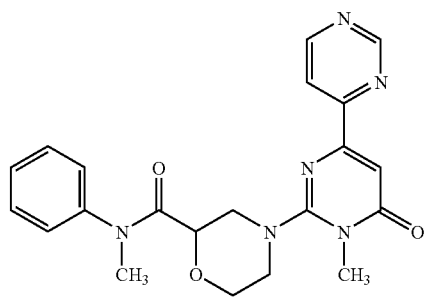 |
| C586 | 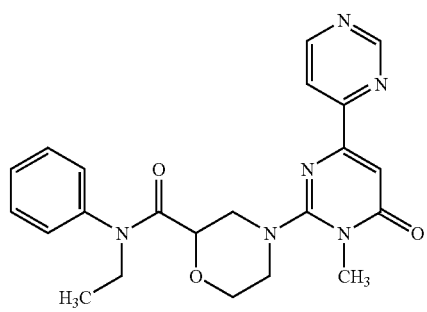 |
| C587 | 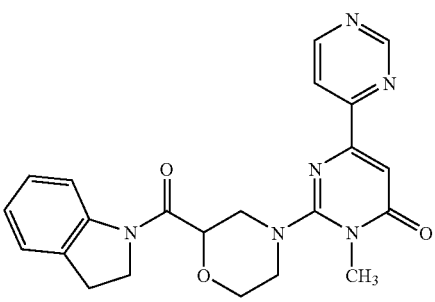 |
| C588 | 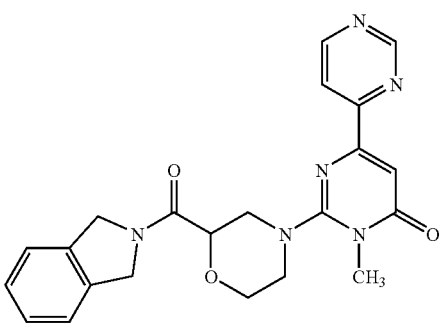 |
| C589 | 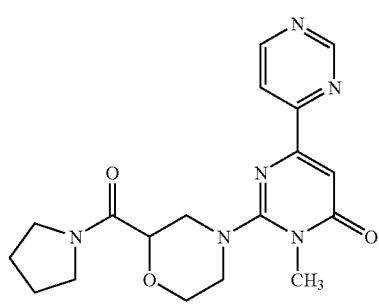 |

-continued
| Compound No. | STRUCTURE |
|---|---|
| C590 | 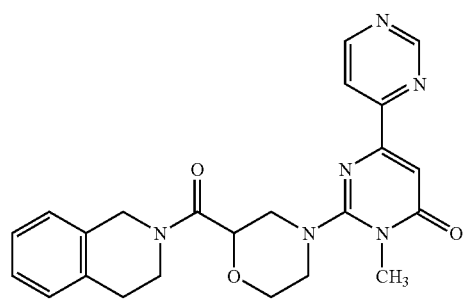 |
| C591 | 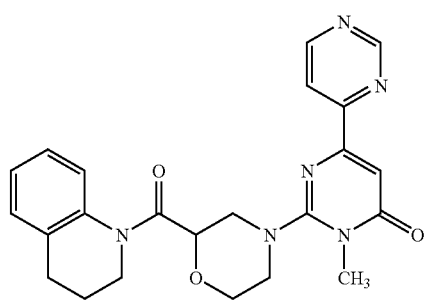 |
| C592 | 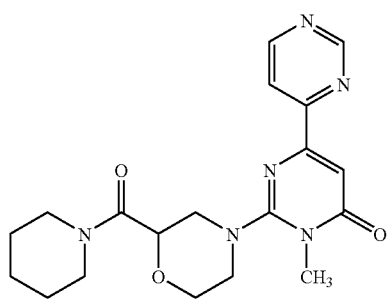 |
| C593 | 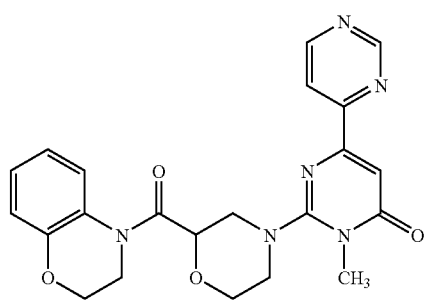 |
| C594 | 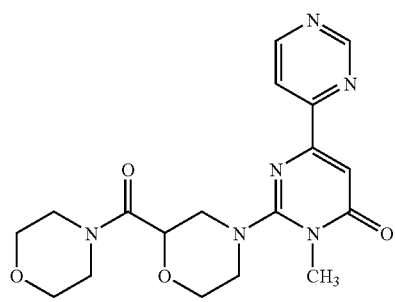 |

| Compound No. | STRUCTURE |
|---|---|
| C595 | 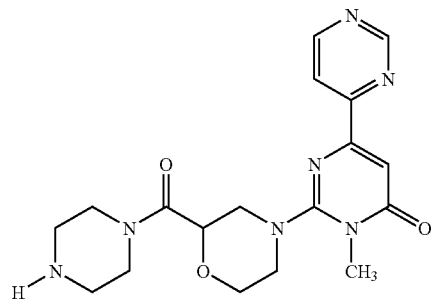 |
| C596 | 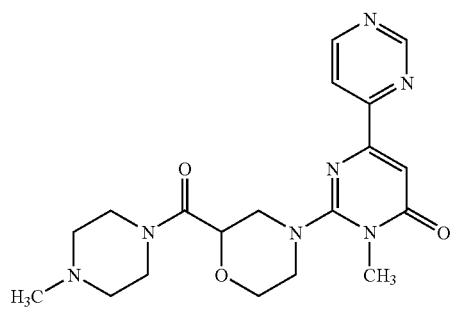 |
| C597 | 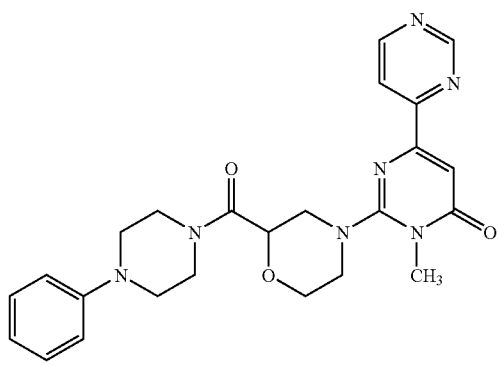 |
| C598 | 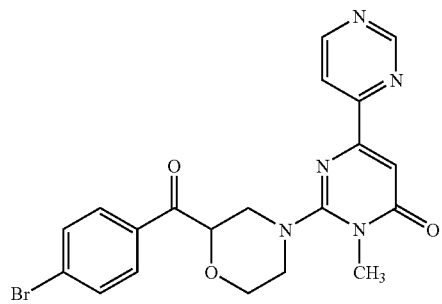 |

| Compound No. | STRUCTURE |
|---|---|
| C599 | 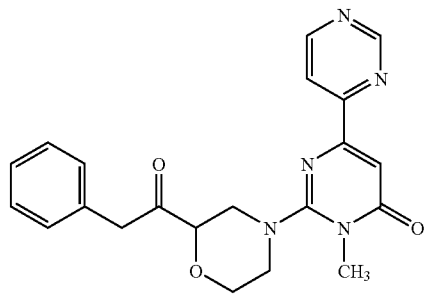 |
| C601 | 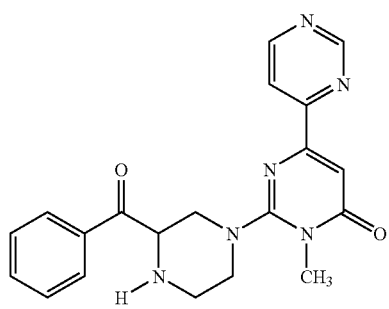 |
| C602 | 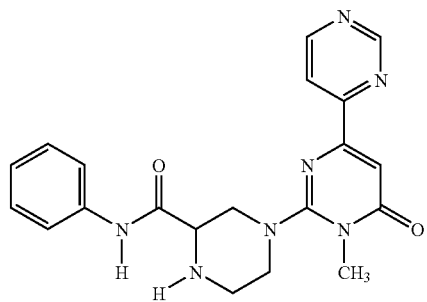 |
| C603 | 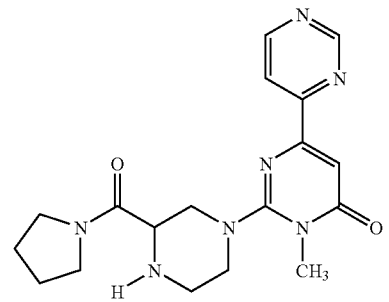 |
| C604 | 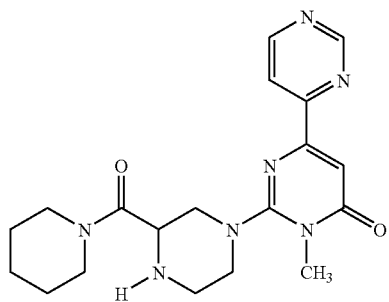 |

-continued
| Compound No. | STRUCTURE |
|---|---|
| C605 | 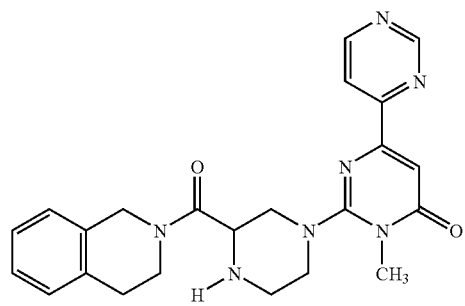 |
| C606 | 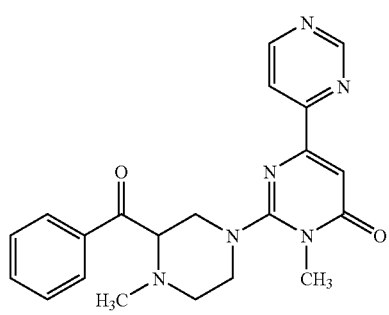 |
| C607 | 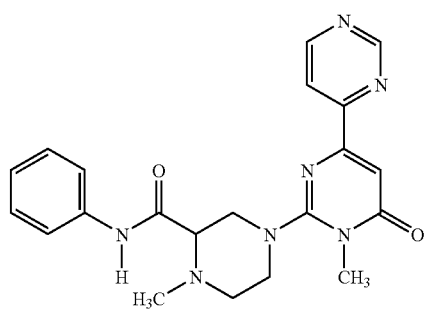 |
| C608 | 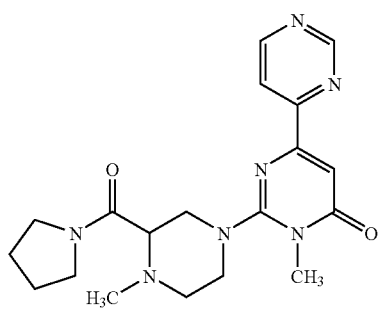 |
| C609 | 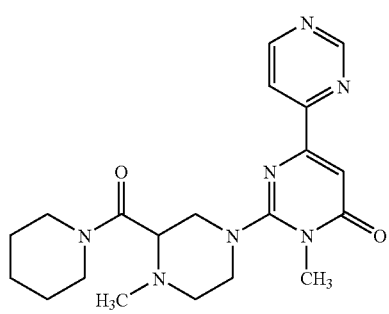 |

-continued
| Compound No. | STRUCTURE |
|---|---|
| C610 | 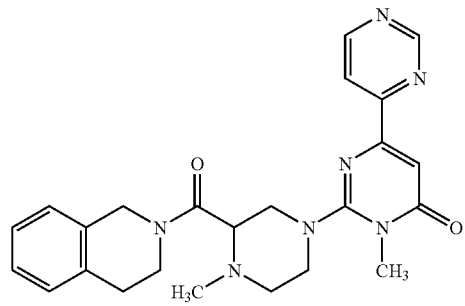 |
| C650 | 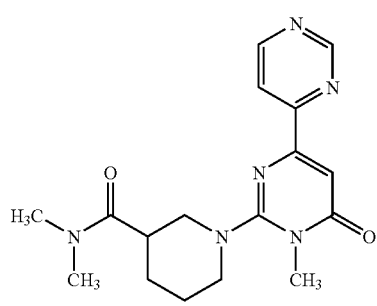 |
| C651 | 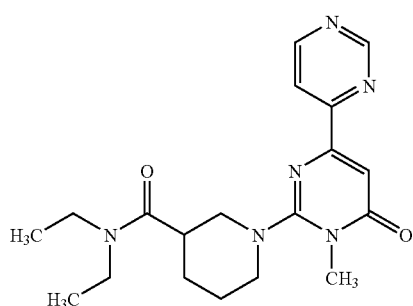 |
| C660 | 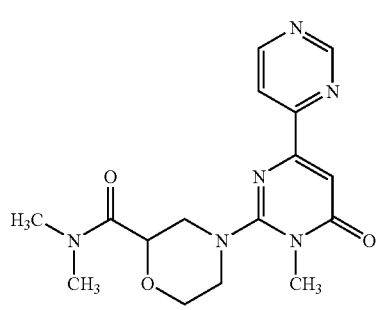 |
| C661 | 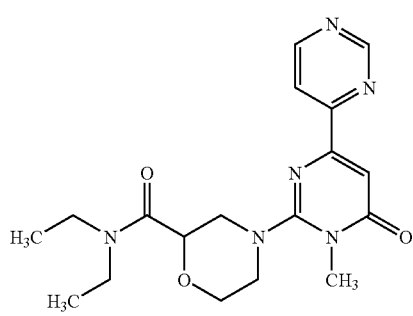 |

-continued
| Compound No. | STRUCTURE |
|---|---|
| C751 | 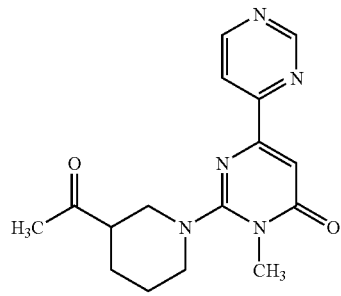 |
| C752 | 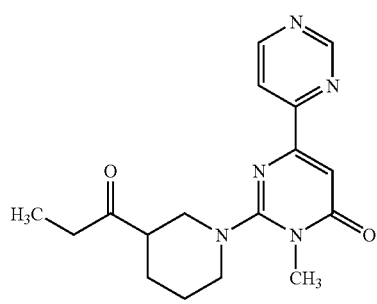 |
| C753 | 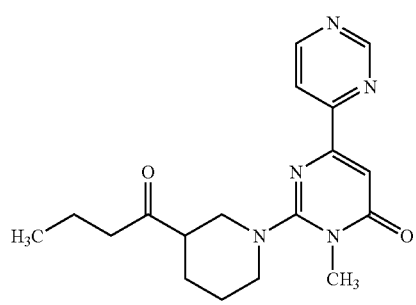 |
| 754 | 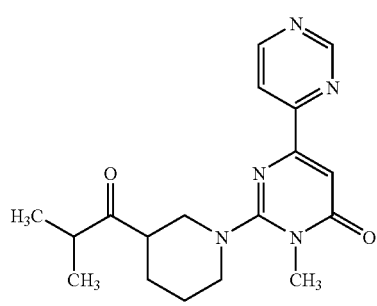 |
| C755 | 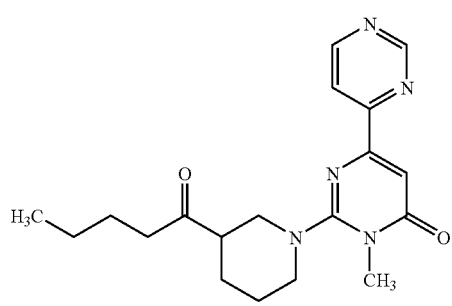 |

-continued
| Compound No. | STRUCTURE |
|---|---|
| C756 | 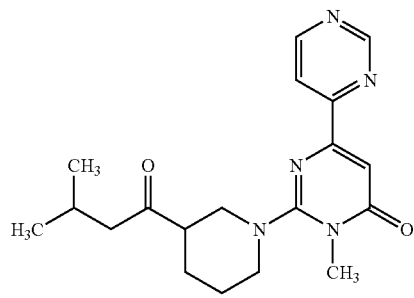 |
| C757 | 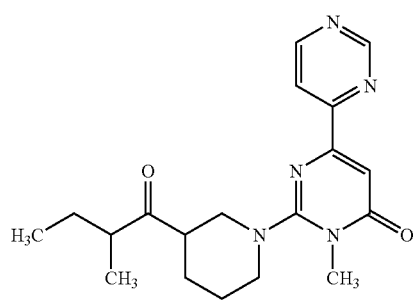 |
| C758 | 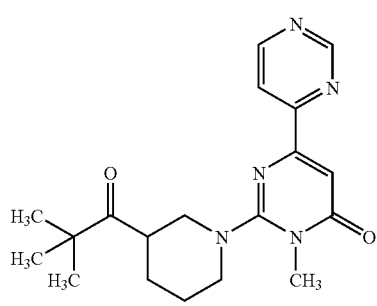 |
| C759 | 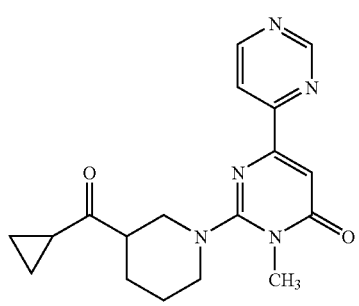 |
| C760 | 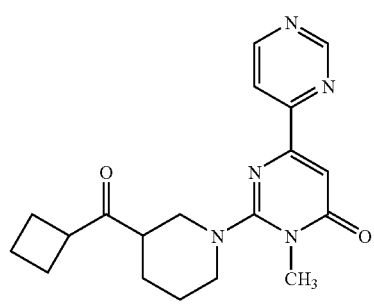 |

-continued
| Compound No. | STRUCTURE |
|---|---|
| C761 | 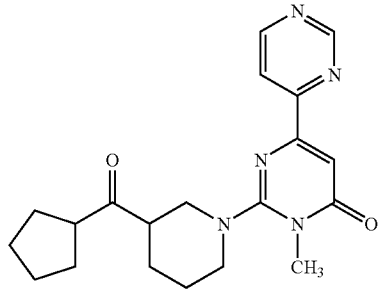 |
| C762 | 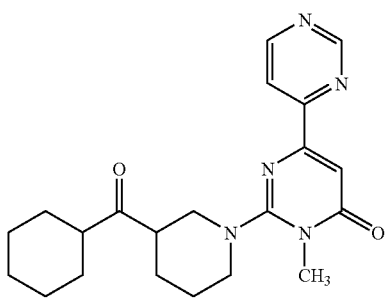 |
| C763 | 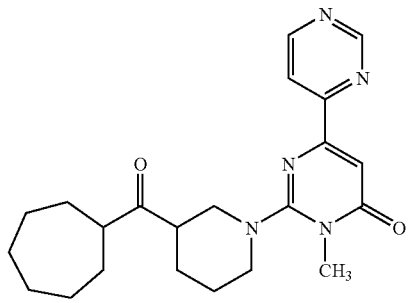 |
| C764 | 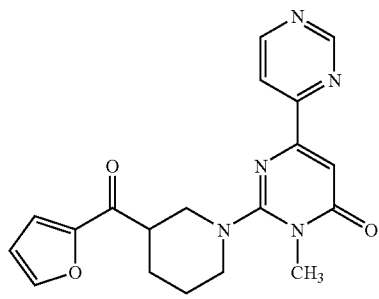 |
| C765 | 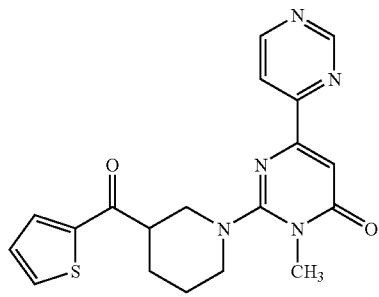 |

| Compound No. | STRUCTURE |
|---|---|
| C766 | 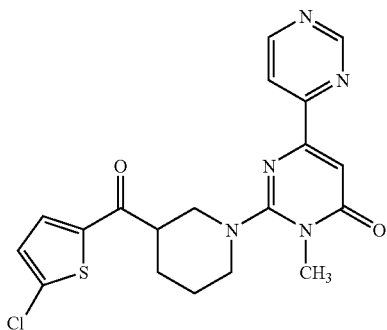 |
| C767 | 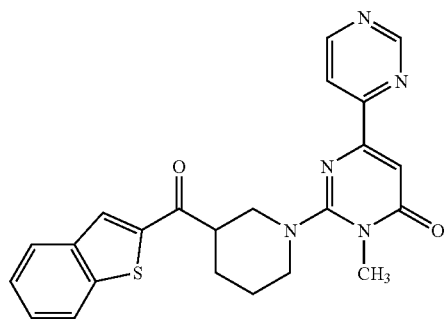 |
| C768 | 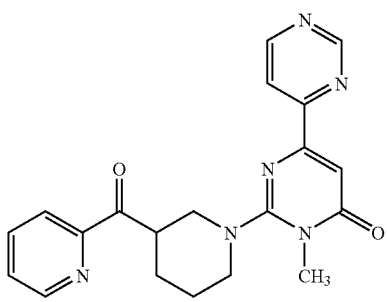 |
| C784 | 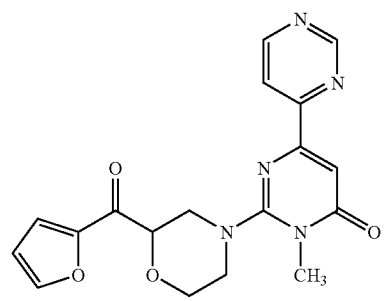 |
| C785 | 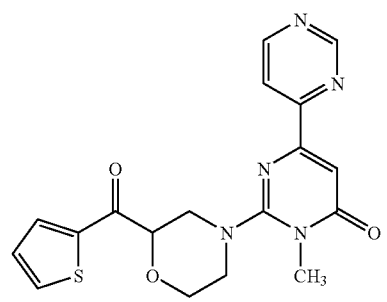 |

|Compound No.|STRUCTURE|
|---|---|
|C786|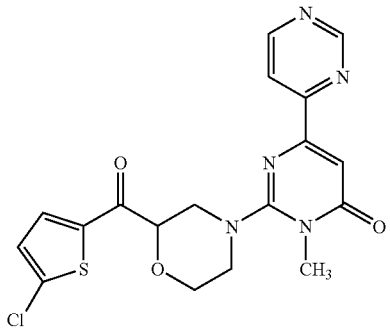|
|C787|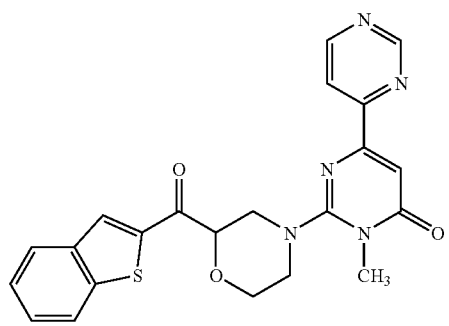|
|C788|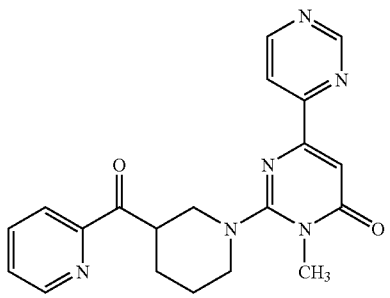|
|C789|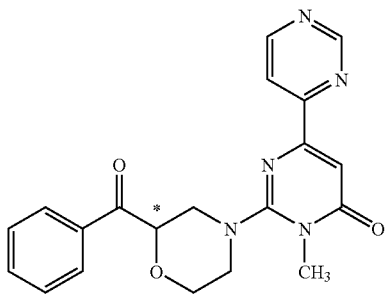|

|Compound No.|STRUCTURE|
|---|---|
|C790|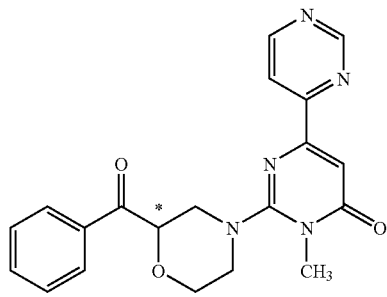|
|D026|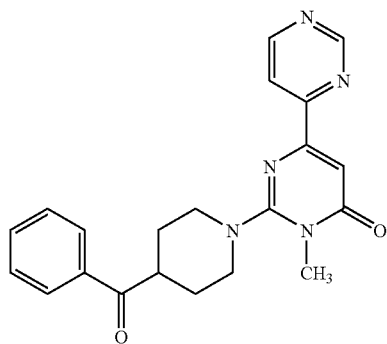|
|D027|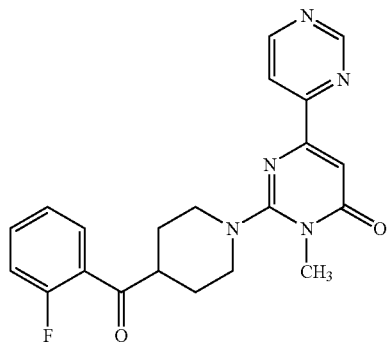|
|D028|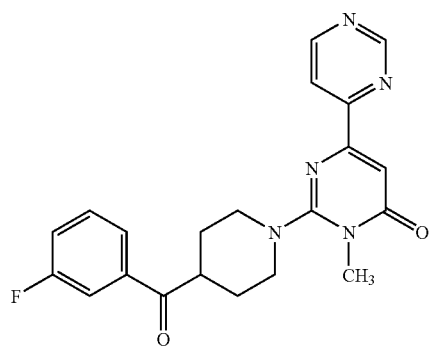|

-continued
| Compound No. | STRUCTURE |
|---|---|
| D029 | 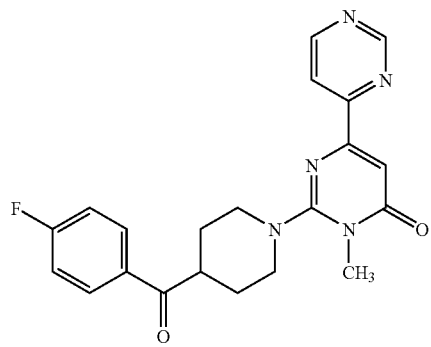 |
| D030 | 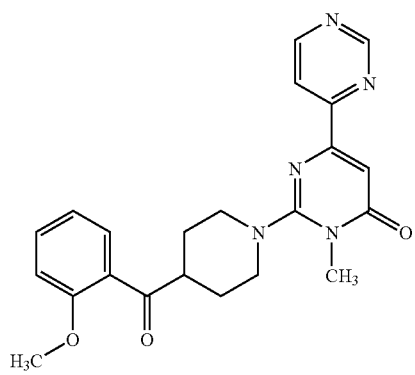 |
| D031 | 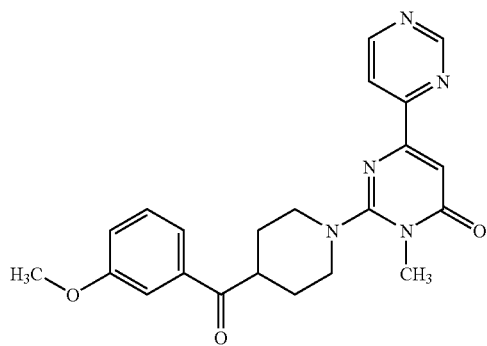 |
| D032 | 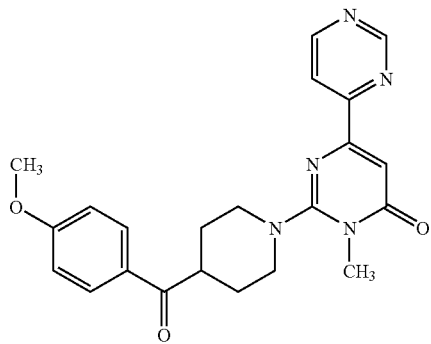 |

-continued
| Compound No. | STRUCTURE |
|---|---|
| D033 | 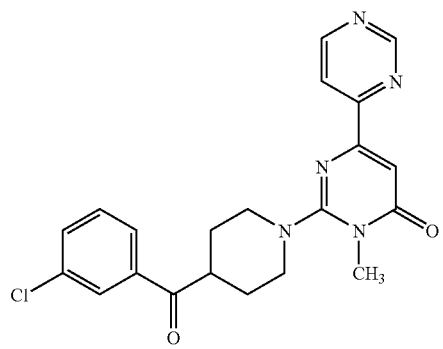 |
| D034 | 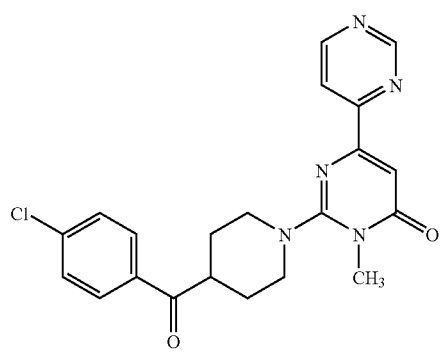 |
| D035 | 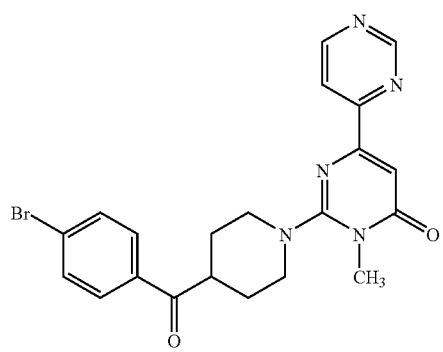 |
| D036 | 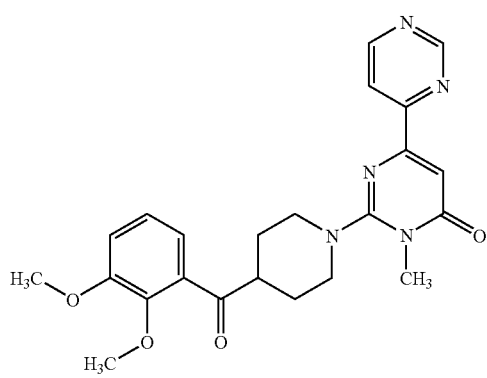 |

-continued
| Compound No. | STRUCTURE |
|---|---|
| D037 | 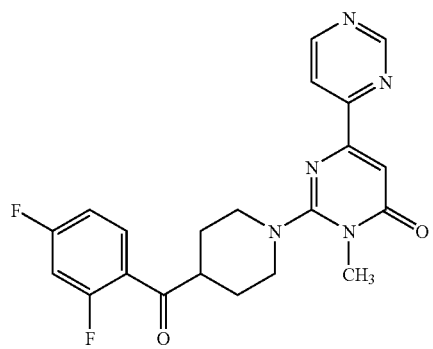 |
| D038 | 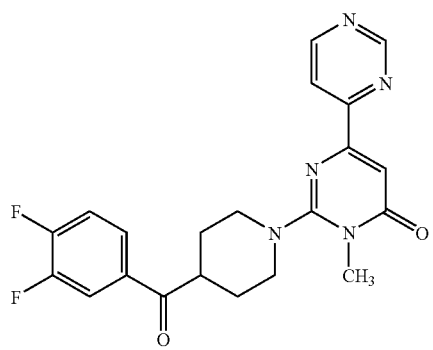 |
| D039 | 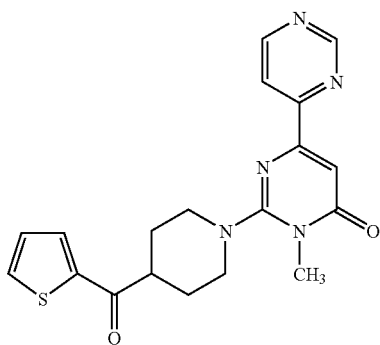 |
| D040 | 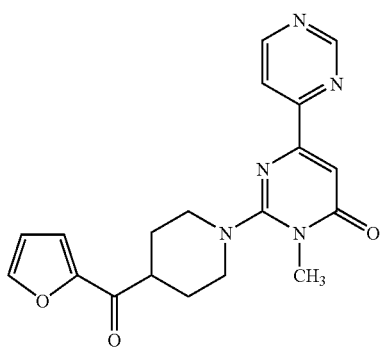 |

-continued
| Compound No. | STRUCTURE |
|---|---|
| D041 | 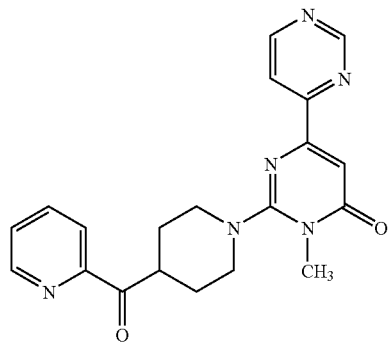 |
| D042 | 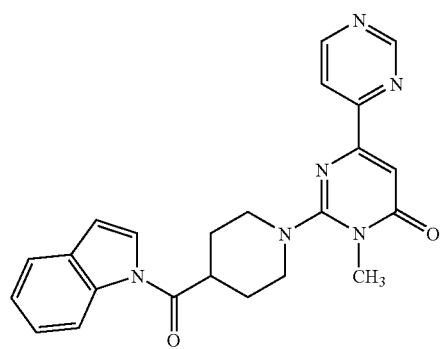 |
| D043 | 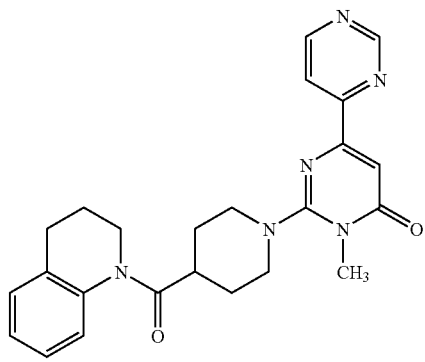 |
| D044 | 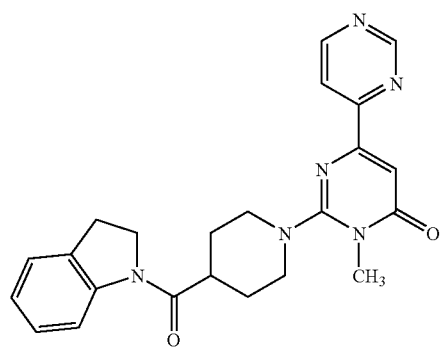 |

-continued
| Compound No. | STRUCTURE |
|---|---|
| D045 | 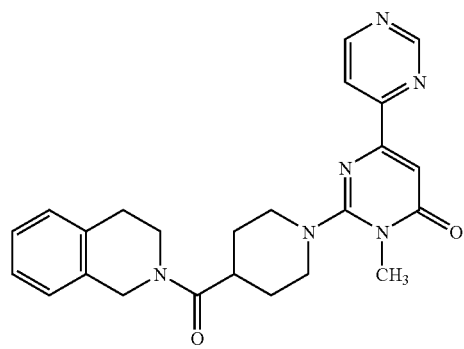 |
| D046 | 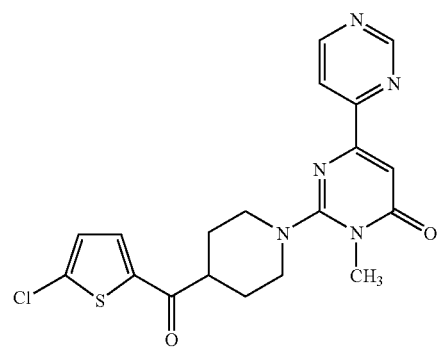 |
| D047 | 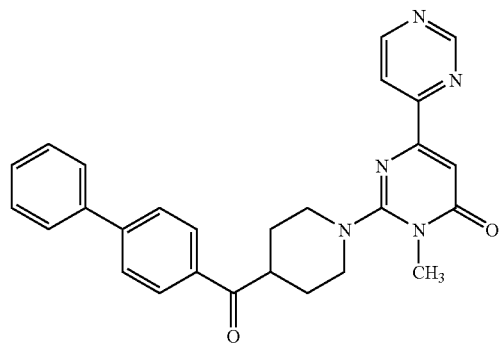 |
| D048 | 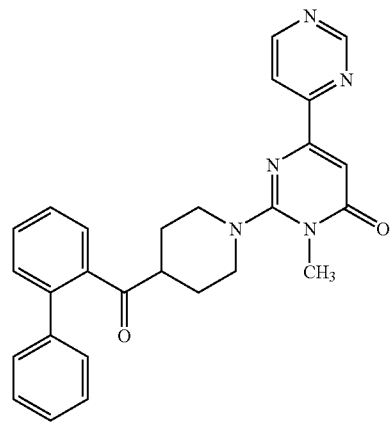 |

| Compound No. | STRUCTURE |
|---|---|
| D049 | 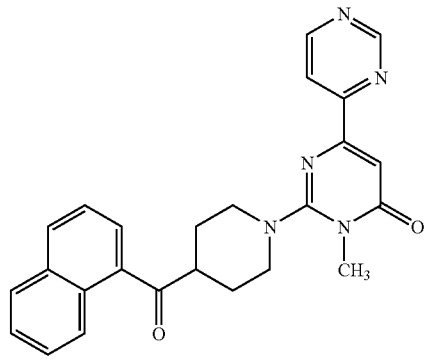 |
| D050 | 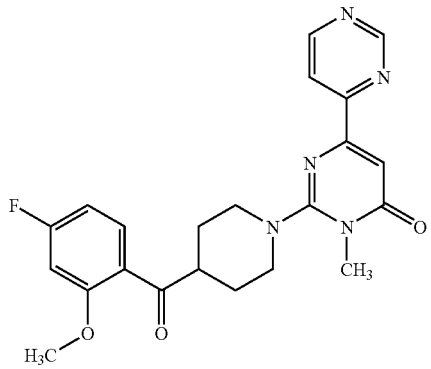 |

Compound B275 and B276
  Measurement condition
  CHIRALPAK AD
  Mobile phase: n-hexane: i-propanol=80:20
  Flow rate: 1.0 ml/min
  Temperature: 30° C.
  * Retention time
  B275: 19.1 min
  B276: 21.5 min Compound C789 and C790
  Measurement condition
  CHIRALPAK AD
  Mobile phase: n-hexane: i-propanol=60:40
  Flow rate: 1.0 ml/min
  Temperature: 30° C.
  Retention time
  B789: 17.7 min
  B790: 14.0 min Particularly preferred compounds of the present invention represented by formula (I) include:
3-methyl-2-(2-oxo-2-phenylethylamino)-6-pyrimidin-4-yl-3H-pyrimidin-4-one;
3-methyl-2-(2-oxo-2-(3-fluorophenyl)ethylamino)-6-pyrimidin-4-yl-3H-pyrimidin-4-one;
3-methyl-2-(2-oxo-2-(4-fluorophenyl)ethylamino)-6-pyrimidin-4-yl-3H-pyrimidin-4-one;
3-methyl-2-(2-oxo-2-(3-chlorophenyl)ethylamino)-6-pyrimidin-4-yl-3H-pyrimidin-4-one;
3-methyl-2-(2-oxo-2-(3-methylphenyl)ethylamino)-6-pyrimidin-4-yl-3H-pyrimidin-4-one;
2-[2-(4-Fluorophenyl)morpholin-4-yl]-3-methyl-6-pyrimidin-4-yl-3H-pyrimidin-4-one;
(S)-2-[2-(4-Fluorophenyl)morpholin-4-yl]-3-methyl-6-pyrimidin-4-yl-3H-pyrimidin-4-one;
2-[2-(2-Fluorophenyl)morpholin-4-yl]-3-methyl-6-pyrimidin-4-yl-3H-pyrimidin-4-one;
(S)-2-[2-(2-Fluorophenyl)morpholin-4-yl]-3-methyl-6-pyrimidin-4-yl-3H-pyrimidin-4-one;
2-[2-(4-Chlorophenyl)morpholin-4-yl]-3-methyl-6-pyrimidin-4-yl-3H-pyrimidin-4-one;
2-[2-(3-Chlorophenyl)morpholin-4-yl]-3-methyl-6-pyrimidin-4-yl-3H-pyrimidin-4-one;
2-[2-(2-Chlorophenyl)morpholin-4-yl]-3-methyl-6-pyrimidin-4-yl-3H-pyrimidin-4-one;
(S)-2-[2-(2-Chlorophenyl)morpholin-4-yl]-3-methyl-6-pyrimidin-4-yl-3H-pyrimidin-4-one;
2-[2-(4-Bromophenyl)morpholin-4-yl]-3-methyl-6-pyrimidin-4-yl-3H-pyrimidin-4-one;
(S)-2-[2-(4-Bromophenyl)morpholin-4-yl]-3-methyl-6-pyrimidin-4-yl-3H-pyrimidin-4-one;
2-[2-(3-Bromophenyl)morpholin-4-yl]-3-methyl-6-pyrimidin-4-yl-3H-pyrimidin-4-one;
(S)-2-[2-(3-Bromophenyl)morpholin-4-yl]-3-methyl-6-pyrimidin-4-yl-3H-pyrimidin-4-one;
2-[2-(2-Bromophenyl)morpholin-4-yl]-3-methyl-6-pyrimidin-4-yl-3H-pyrimidin-4-one;
2-[2-(4-Methylphenyl)morpholin-4-yl]-3-methyl-6-pyrimidin-4-yl-3H-pyrimidin-4-one;
2-[2-(3-Methylphenyl)morpholin-4-yl]-3-methyl-6-pyrimidin-4-yl-3H-pyrimidin-4-one 2-[2-(2-Methylphenyl)morpholin-4-yl]-3-methyl-6-pyrimidin-4-yl-3H-pyrimidin-4-one;
(S)-2-[2-(2-Methylphenyl)morpholin-4-yl]-3-methyl-6-pyrimidin-4-yl-3H-pyrimidin-4-one;
2-[2-(4-Cyanophenyl)morpholin-4-yl]-3-methyl-6-pyrimidin-4-yl-3H-pyrimidin-4-one;
2-[2-(3-Cyanophenyi)morpholin-4-yl]-3-methyl-6-pyrimidin-4-yl-3H-pyrimidin-4-one;
(S)-2-[2-(3-Cyanophenyl)morpholin-4-yl]-3-methyl-6-pyrimidin-4-yl-3H-pyrimidin-4-one;
2-[2-(2-Cyanophenyl)morpholin-4-yl]-3-methyl-6-pyrimidin-4-yl-3H-pyrimidin-4-one;
2-[2-(4-Methoxyphenyl)morpholin-4-yl]-3-methyl-6-pyrimidin-4-yl-3H-pyrimidin-4-one;
(S)-2-[2-(4-Methoxyphenyl)morpholin-4-yl]-3-methyl-6-pyrimidin-4-yl-3H-pyrimidin-4-one;
2-[2-(3-Methoxyphenyl)morpholin-4-yl]-3-methyl-6-pyrimidin-4-yl-3H-pyrimidin-4-one;
(S)-2-[2-(3-Methoxyphenyl)morpholin-4-yl]-3-methyl-6-pyrimidin-4-yl-3H-pyrimidin-4-one;
2-[2-(2-Methoxyphenyl)morpholin-4-yl]-3-methyl-6-pyrimidin-4-yl-3H-pyrimidin-4-one;
(S)-2-[2-(2-Methoxyphenyl)morpholin-4-yl]-3-methyl-6-pyrimidin-4-yl-3H-pyrimidin-4-one;
2-[2-(2-Ethoxyphenyl)morpholin-4-yl]-3-methyl-6-pyrimidin-4-yl-3H-pyrimidin-4-one;
2-[2-(2-Tifluoromethoxyphenyl)morpholin-4-yl]-3-methyl-6-pyrimidin-4-yl-3H-pyrimidin-4-one;
2-[2-(5-Fluoro-2-methoxyphenyl)morpholin-4-yl]-3-methyl-6-pyrimidin-4-yl-3H-pyrimidin-4-one;
2-[2-(4-Fluoro-2-methoxyphenyl)morpholin-4-yl]-3-methyl-6-pyrimidin-4-yl-3H-pyrimidin-4-one;
(S)-2-[2-(4-Fluoro-2-methoxyphenyl)morpholin-4-yl]-3-methyl-6-pyrimidin-4-yl-3H-pyrimidin-4-one;
2-[2-(2,5-Dimethoxyphenyl)morpholin-4-yl]-3-methyl-6-pyrimidin-4-yl-3H-pyrimidin-4-one;
(S)-2-[2-(2,5-Dimethoxyphenyl)morpholin-4-yl]-3-methyl-6-pyrimidin-4-yl-3H-pyrimidin-4-one;
2-[2-(2-Chloro-4,5-difluorophenyl)morpholin-4-yl]-3-methyl-6-pyrimidin-4-yl-3H-pyrimidin-4-one;
(S)-2-[2-(2-Chloro-4,5-difluorophenyl)morpholin-4-yl]-3-methyl-6-pyrimidin-4-yl-3H-pyrimidin-4-one;
2-[2-(2-Bromo-4-fluorophenyl)morpholin-4-yl]-3-methyl-6-pyrimidin-4-yl-3H-pyrimidin-4-one;
2-[2-(2,4-Difluorophenyl)morpholin-4-yl]-3-methyl-6-pyrimidin-4-yl-3H-pyrimidin-4-one;
(S)-2-[2-(2,4-Difluorophenyl)morpholin-4-yl]-3-methyl-6-pyrimidin-4-yl-3H-pyrimidin-4-one;
2-[2-(2,6-Dimethoxyphenyl)morpholin-4-yl]-3-methyl-6-pyrimidin-4-yl-3H-pyrimidin-4-one;
(S)-2-[2-(2,6-Dimethoxyphenyl)morpholin-4-yl]-3-methyl-6-pyrimidin-4-yl-3H-pyrimidin-4-one;
2-[2-(2,4-Dimethoxyphenyl)morpholin-4-yl]-3-methyl-6-pyrimidin-4-yl-3H-pyrimidin-4-one;
(S S-2-[2-(2,4-Dimethoxyphenyl)morpholin-4-yl]-3-methyl-6-pyrimidin-4-yl-3H-pyrimidin-4-one;
2-[2-(2,6-Dichlorophenyl)morpholin-4-yl]-3-methyl-6-pyrimidin-4-yl-3H-pyrimidin-4-one;
(S)-2-[2-(2,6-Dichlorophenyl)morpholin-4-yl]-3-methyl-6-pyrimidin-4-yl-3H-pyrimidin-4-one;
2-[2-(2,6-Difluorophenyl)morpholin-4-yl]-3-methyl-6-pyrimidin-4-yl-3H-pyrimidin-4-one;
(S)-2-[2-(2,6-Difluorophenyl)morpholin-4-yl]-3-methyl-6-pyrimidin-4-yl-3H-pyrimidin-4-one;
2-[2-(2-Chloro-6-fluorophenyl)morpholin-4-yl]-3-methyl-6-pyrimidin-4-yl-3H-pyrimidin-4-one;
(S)-2-[2-(2-Chloro-6-fluorophenyl)morpholin-4-yl]-3-methyl-6-pyrimidin-4-yl-3H-pyrimidin-4-one;
2-[2-(4-Fluoro-3-methoxyphenyl)morpholin-4-yl]-3-methyl-6-pyrimidin-4-yl-3H-pyrimidin-4-one;
2-[2-(5-Cyano-2-methoxyphenyl)morpholin-4-yl]-3-methyl-6-pyrimidin-4-yl-3H-pyrimidin-4-one;
(S)-2-[2-(5-Cyano-2-methoxyphenyl)morpholin-4-yl]-3-methyl-6-pyrimidin-4-yl-3H-pyrimidin-4-one;
2-[2-(4-Cyano-2-methoxyphenyl)morpholin-4-yl]-3-methyl-6-pyrimidin-4-yl-3H-pyrimidin-4-one;
(S)-2-[2-(4-Cyano-2-methoxyphenyl)morpholin-4-yl]-3-methyl-6-pyrimidin-4-y1-3H-pyrimidin-4-one;
2-[2-(2,4-Difluoro-6-methoxyphenyl )morpholin-4-yl]-3-methyl-6-pyrimidin-4-yl-3H-pyrimidin-4-one;
(S)-2-[2-(2,4-Difuoro-6-methoxyphenyl)morpholin-4-yl]-3-methyl-6-pyrimidin-4-yl-3H-pyrimidin-4-one;
2-[2-(4-(Pyrrolidin-1-yl-methyl)phenyl)morpholino-4-yl]-3-methyl-6-pyrimidin-4-yl-3H-pyrimidin-4-one;
(S)-2-[2-(4-(Pyrrolidin-1-yl]-methyl)phenyl)morpholino-4-yl)-3-methyl-6-pyrimidin-4-yl-3H-pyrimidin-4-one;
2-[2-(1-Naphthyl)morpholin-4-yl]-3-methyl-6-pyrimidin-4-yl-3H-pyrimidin-4-one;
2-[2-(2-Naphthyl)morpholin-4-yl]-3-methyl-6-pyrimidin-4-yl-3H-pyrimidin-4-one;
(S)-2-[2-(2-Naphthyl)morpholin-4-yl]-3-methyl-6-pyrimidin-4-yl-3H-pyrimidin-4-one;
2-[2-(2,3-Dihydrobenzofuran-7-yl)morpholin-4-yl]-3-methyl-6-pyrimidin-4-yl-3H-pyrimidin-4-one;
(S)-2-[2-(2,3-Dihydrobenzofuran-7-yl)morpholin-4-yl]-3-methyl-6-pyrimidin-4-yl-3H-pyrimidin-4-one;
2-[2-(Benzofuran-2-yl)morpholin-4-yl]-3-methyl-6-pyrimidin-4-yl-3H-pyrimidin-4-one;
(S)-2-[2-(Benzofuran-2-yl)morpholin-4-yl]-3-methyl-6-pyrimidin-4-yl-3H-pyrimidin-4-one;
2-[3-(4-Fluorobenzoyl)piperidin-1-yl]-3-methyl-6-pyrimidin-4-yl-3H-pyrimidin-4-one;
2-(3-Benzoylpiperidin-1-yl)-3-methyl-6-pyrimidin-4-yl-3H-pyrimidin-4-one;
2-[3-(2-Methoxybenzoyl)piperidin-1-yl]-3-methyl-6-pyrimidin-4-yl-3H-pyrimidin-4-one;
2-[3-(4-Methoxybenzoyl)piperidin-1-yl]-3-methyl-6-pyrimidin-4-yl-3H-pyrimidin-4-one;
2-[2-(4-Fluorobenzoyl)morpholine-4-yl]-3-methyl-6-pyrimidin-4-yl-3H-pyrimidin-4-one
2-(2-Benzoylmorpholine-4-yl)-3-methyl-6-pyrimidin-4-yl-3H-pyrimidin-4-one;
2-[2-(2-Methoxybenzoyl)morpholine-4-yl]-3-methyl-6-pyrimidin-4-yl-3H-pyrimidin-4-one;
2-[2-(4-Methoxybenzoyl)morpholine-4-yl]-3-methyl-6-pyrimidin-4-yl-3H-pyrimidin-4-one; and
2-[4-(4-Chlorobenzoyl)piperidin-1-yl]-3-methyl-6-pyrimidin-4-yl-3H-pyrimidin-4-one.

Salts of the aforementioned preferred compound, and solvates or hydrates of the aforementioned compounds and salts thereof are also preferred.

The 3-substituted-4-pyrimidone compounds represented by the aforementioned formula (I) wherein R is the group represented by formula (II) can be prepared, for example, according to the method explained below.

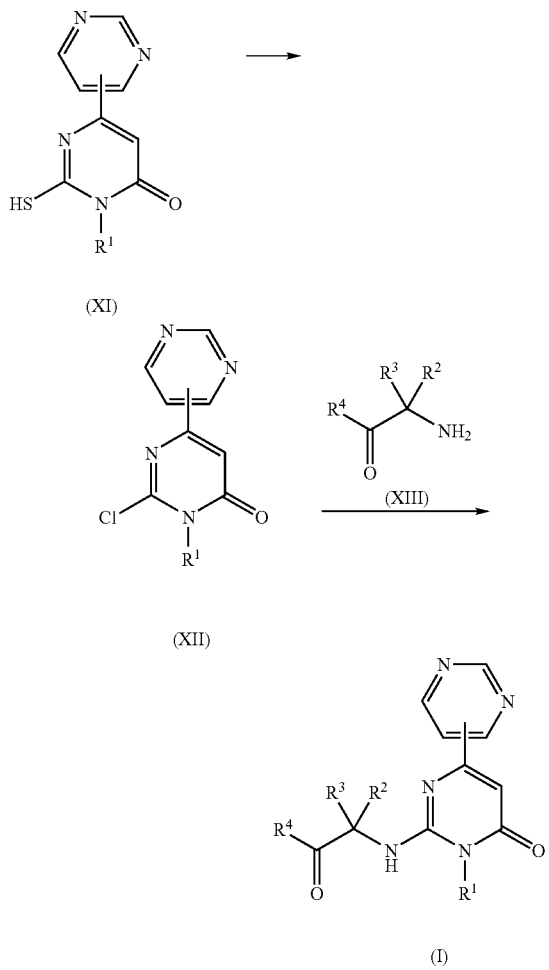

(In the above scheme, definitions of $R^1$, $R^2$, $R^3$ and $R^4$ are the same as those already described.)

The 2-thiopyrimidone represented by the above formula (XI) is prepared easily by a modification of the method described in EP 354,179. The reaction is carried out in the presence of a base such as sodium hydroxide, potassium hydroxide, sodium methoxide, sodium ethoxide, potassium t-butoxide, sodium carbonate, sodium hydrogencarbonate, potassium carbonate, triethylamine, diisopropylethylamine, and 1,8-diazabicyclo[5,4,0]undec-7-en for 1 to 100 hours at a suitable temperature ranging from 0° C. to 200° C. under nitrogen or argon atmosphere or under ordinary air to afford the desired compound (XI). Examples of a solvent for the reactions include, for example, alcoholic solvent such as methanol, ethanol, 1-propanol, isopropanol, tert-butanol, ethylene glycol, propylene glycol; etheric solvents such as diethyl ether, tert-butyl methyl ether, tetrahydrofuran, isopropyl ether; hydrocarbonic solvents such as benzene, toluene, xylene; halogenated hydrocarbonic solvents such as dichloromethane, chloroform, dichloroethane; aprotic polar solvents such as formamide, N,N-dimethylformamide, N,N-dimethylacetamide, N-methylpyrrolidone, dimethyl sulfoxide, sulfolane, hexamethylphosphoric triamide, water and the like. Generally, a single solvent or a mixture of two or more solvents may be used so as to be suitable to a base used.

Then the 2-thiopyrimidone derivative (XI) is transformed into the 2-chloropyrimidone (XII) by a chlorinating agent. The reaction time and temperature depend on the chlorinating agent used. Examples of a chlorinating agent for the reactions include, for example, thionyl chloride, thionyl chloride and dimethylformamide, phosphorus oxychloride, phosphorus oxychloride and dimethylformamide, oxalyl chloride, phosphorous oxychloride and dimethylformamide, and phosphorus pentachloride.

The amine represented by the above formula (XIII) or salts thereof is may be prepared by a modification of the method described in the literature (Tetrahedron Lett., 30, 5285 (1989), Synthesis, 122 (1990)).

Then the chloride derivative (XII) is allowed to react with the amine (XIII) or salts thereof in the presence of a base such as sodium hydroxide, potassium hydroxide, sodium methoxide, sodium ethoxide, sodium carbonate, sodium hydrogencarbonate, potassium carbonate, triethylamine, diisopropylethylamine, and 1,8-diazabicyclo[5,4,0]undec-7-en for 1 to 100 hours at a suitable temperature ranging from 0° C. to 200° C. under nitrogen or argon atmosphere or under ordinary air to afford the desired compound (I). 4-Dimethylaminopyridine may be used as a catalyst.

Examples of a solvent for the reactions include, for example, alcoholic solvent such as methanol, ethanol, 1-propanol, isopropanol, tert-butanol, ethylene glycol, propylene glycol; etheric solvents such as diethyl ether, tert-butyl methyl ether, tetrahydrofuran, isopropyl ether; hydrocarbonic solvents such as benzene, toluene, xylene; halogenated hydrocarbonic solvents such as dichloromethane, chloroform, dichloroethane; aprotic polar solvents such as formamide, N,N-dimethylformamide, N,N-dimethylacetamide, N-methylpyrrolidone, dimethyl sulfoxide, sulfolane, hexamethylphosphoric triamide, water and the like. Generally, a single solvent or a mixture of two or more solvents may be used so as to be suitable to a base used.

The 3-substituted-4-pyrimidone compounds represented by the aforementioned formula (I) wherein R is the group represented by formula (III) can be prepared, for example, according to the method explained below.

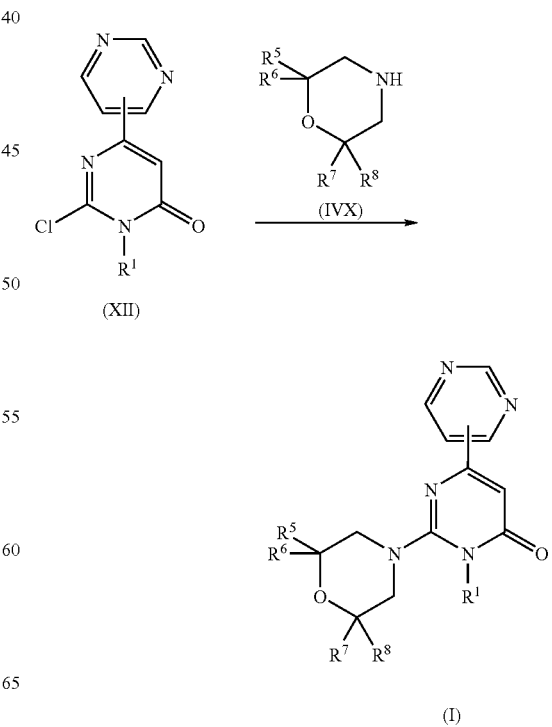

(In the above scheme, definitions of $R^1$, $R^5$, $R^6$, $R^7$ and $R^8$ are the same as those already described.)

The chloride derivative (XII) is allowed to react with the amine (IVX) or salts thereof in the presence of a base such as sodium hydroxide, potassium hydroxide, sodium methoxide, sodium ethoxide, sodium carbonate, sodium hydrogencarbonate, potassium carbonate, triethylamine, diisopropylethylamine, and 1,8-diazabicyclo[5,4,0]undec-7-en for 1 to 100 hours at a suitable temperature ranging from 0° C. to 200° C. under nitrogen or argon atmosphere or under ordinary air to afford the desired compound (I).

Examples of a solvent for the reactions include, for example, alcoholic solvent such as methanol, ethanol, 1-propanol, isopropanol, tert-butanol, ethylene glycol, propylene glycol; etheric solvents such as diethyl ether, tert-butyl methyl ether, tetrahydrofuran, isopropyl ether; hydrocarbonic solvents such as benzene, toluene, xylene; halogenated hydrocarbonic solvents such as dichloromethane, chloroform, dichloroethane; aprotic polar solvents such as formamide, N,N-dimethylformamide, N,N-dimethylacetamide, N-methylpyrrolidone, dimethyl sulfoxide, sulfolane, hexamethylphosphoric triamide, water and the like. Generally, a single solvent or a mixture of two or more solvents may be used so as to be suitable to a base used.

The 3-substituted-4-pyrimidone compounds represented by the aforementioned formula (I) wherein R is the group represented by formula (IV) can be prepared, for example, according to the method explained below.

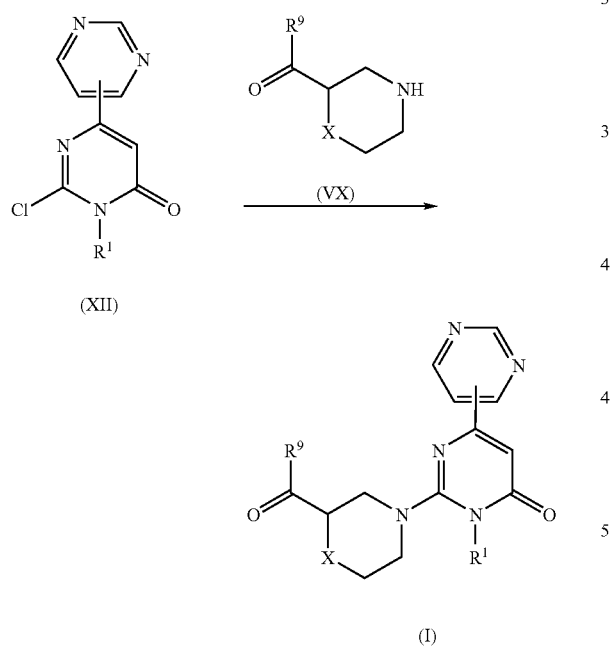

(In the above scheme, definitions of $R^1$, $R^{9'}$ and X are the same as those already described.)

The amine represented by the above formula (VX) may be prepared by a modification of the method described in the literature (J. Med. Chem., 13, 1 (1970), J. Med. Chem., 41, 591 (1998)) or according to well-known methods of one skilled in the art.

Then the chloride derivative (XII) is allowed to react with the amine (VX) or salts thereof in the presence of a base such as sodium hydroxide, potassium hydroxide, sodium methoxide, sodium ethoxide, sodium carbonate, sodium hydrogencarbonate, potassium carbonate, triethylamine, diisopropylethylamine, and 1,8-diazabicyclo[5,4,0]undec-7-en for 1 to 100 hours at a suitable temperature ranging from 0° C. to 200° C. under nitrogen or argon atmosphere or under ordinary air to afford the desired compound (I).

Examples of a solvent for the reactions include, for example, alcoholic solvent such as methanol, ethanol, 1-propanol, isopropanol, tert-butanol, ethylene glycol, propylene glycol; etheric solvents such as diethyl ether, tert-butyl methyl ether, tetrahydrofuran, isopropyl ether; hydrocarbonic solvents such as benzene, toluene, xylene; halogenated hydrocarbonic solvents such as dichloromethane, chloroform, dichloroethane; aprotic polar solvents such as formamide, N,N-dimethylformamide, N,N-dimethylacetamide, N-methylpyrrolidone, dimethyl sulfoxide, sulfolane, hexamethylphosphoric triamide, water and the like. Generally, a single solvent or a mixture of two or more solvents may be used so as to be suitable to a base used.

The 3-substituted-4-pyrimidone compounds represented by the aforementioned formula (I) wherein R is the group represented by formula (V) can be prepared, for example, according to the method explained below.

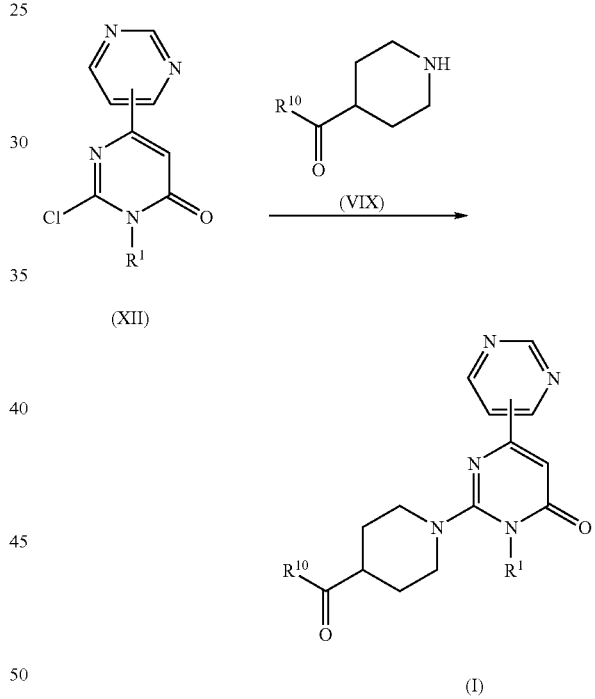

(In the above scheme, definitions of $R^1$ and $R^{10}$ are the same as those already described.)

The amine represented by the above formula (VIX) is commercially available or may be prepared by a modification of the method described in the literature (J. Med. Chem., 13, 1 (1970), J. Med. Chem., 41, 591 (1998)) or according to well-known methods of one skilled in the art.

Then the chloride derivative (XII) is allowed to react with the amine (VIX) or salts thereof in the presence of a base such as sodium hydroxide, potassium hydroxide, sodium methoxide, sodium ethoxide, sodium carbonate, sodium hydrogencarbonate, potassium carbonate, triethylamine, diisopropylethylamine, and 1,8-diazabicyclo[5,4,0]undec-7-en for 1 to 100 hours at a suitable temperature ranging from 0° C. to 200°

C. under nitrogen or argon atmosphere or under ordinary air to afford the desired compound (I).

Examples of a solvent for the reactions include, for example, alcoholic solvent such as methanol, ethanol, 1-propanol, isopropanol, tert-butanol, ethylene glycol, propylene glycol; etheric solvents such as diethyl ether, tert-butyl methyl ether, tetrahydrofuran, isopropyl ether; hydrocarbonic solvents such as benzene, toluene, xylene; halogenated hydrocarbonic solvents such as dichloromethane, chloroform, dichloroethane; aprotic polar solvents such as formamide, N,N-dimethylformamide, N,N-dimethylacetamide, N-methylpyrrolidone, dimethyl sulfoxide, sulfolane, hexamethylphosphoric triamide, water and the like. Generally, a single solvent or a mixture of two or more solvents may be used so as to be suitable to a base used.

The compounds of the present invention have inhibitory activity against TPK1, and they inhibit TPK1 activity in neurodegenerative diseases such as Alzheimer disease, thereby suppress the neurotoxicity of A β and the formation of PHF and inhibit the nerve cell death. Accordingly, the compounds of the present invention are useful as an active ingredient of a medicament which radically enables preventive and/or therapeutic treatment of Alzheimer disease. In addition, the compounds of the present invention are also useful as an active ingredient of a medicament for preventive and/or therapeutic treatment of ischemic cerebrovascular accidents, Down syndrome, cerebral bleeding due to solitary cerebral amyloid angiopathy, progressive supranuclear palsy, subacute sclerosing panencephalitis, postencephalitic parkinsonism, pugilistic encephalosis, Guam parkinsonism-dementia complex, Lewy body disease, Pick's disease, corticobasal degeneration frontotemporal dementia, vascular dementia, traumatic injuries, brain and spinal cord trauma, peripheral neuropathies, retinopathies and glaucoma, non-insulin dependent diabetes, obesity, manic depressive illness, schizophrenia, alopecia, breast cancer, non-small cell lung carcinoma, thyroid cancer, T or B-cell leukemia, and several virus-induced tumors.

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more of pharmaceutical additives. As the active ingredient of the medicament of the present invention, two or more of the aforementioned substance may be used in combination. The above pharmaceutical composition may be supplemented with an active ingredient of other medicament for the treatment of Alzheimer disease and the above-mentioned diseases.

A type of the pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilized preparations, and may be used by dissolving just before use in an appropriate aqueous medium such as physiological saline. Sustained-release preparations such as those coated with a polymer may be directly administered intracerebrally.

Types of pharmaceutical additives used for the manufacture of the pharmaceutical composition, content rations of the pharmaceutical additives relative to the active ingredient, and methods for preparing the pharmaceutical composition may be appropriately chosen by those skilled in the art. Inorganic or organic substances, or solid or liquid substances may be used as pharmaceutical additives. Generally, the pharmaceutical additives may be incorporated in a ratio ranging from 1% by weight to 90% by weight based on the weight of an active ingredient.

Examples of excipients used for the preparation of solid pharmaceutical compositions include, for example, lactose, sucrose, starch, talc, cellulose, dextrin, kaolin, calcium carbonate and the like. For the preparation of liquid compositions for oral administration, a conventional inert diluent such as water or a vegetable oil may be used. The liquid composition may contain, in addition to the inert diluent, auxiliaries such as moistening agents, suspension aids, sweeteners, aromatics, colorants, and preservatives. The liquid composition may be filled in capsules made of an absorbable material such as gelatin. Examples of solvents or suspension mediums used for the preparation of compositions for parenteral administration, e.g. injections, suppositories, include water, propylene-glycol, polyethylene glycol, benzyl alcohol, ethyl oleate, lecithin and the like. Examples of base materials used for suppositories include, for example, cacao butter, emulsified cacao butter, lauric lipid, witepsol.

Dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 100 mg (the weight of an active ingredient) to an adult.

EXAMPLES

The present invention will be explained more specifically with reference to examples. However, the scope of the present invention is not limited to the following examples. The compound number in the examples-corresponds to that in the table above.

Example 1

Synthesis of 2-mercapto-3-methyl-6-pyrimidin-4-yl-3H-pyrimidin-4-one

A solution of ethyl 3-oxo-3-(4-pyrimidyl)propionate (34.1 g, 176 mmol), N-methylthiourea (47.5 g, 527 mmol) and 1,8-diazabicyclo[5,4,0]-7-undecene (26.3 ml, 176 mmol) in ethanol(340 ml) was refluxed for 2 hours and the solution of methanesulfonic acid (16.9 g, 176 mmol) in water (70 ml) was added after cooling by ice-water. The precipitate was washed with water, filtered and dried to give the title compound (30.2 g, 78%).

¹H-NMR (DMSO-d₆) δ: 3.56(s, 3H), 6.88(s, 1H), 8.24(dd, J=1.2, 5.4 Hz, 1H), 9.05 (d, J=5.4 Hz, 1H), 9.38(s, 1H), 11.94(s, 1H). MS[M−H]⁻: 219.

Example 2

Synthesis of 2-chloro-3-methyl-6-pyrimidin-4-yl-3H-pyrimidin-4-one

Phosphorous oxychloride (4.60g, 30 mmol) was added to dimethylformamide(32 ml) and stirred 20 min at 0° C. 2-Mercapto-3-methyl-6-pyrimidin-4-yl-pyrimidin-4-one (4.40 g, 20 mmol) was added to the solution and stirred 5 min and then stirred at 70° C. for 1 hour. The reaction mixture was poured into ice water, neutralized by solid $K_2CO_3$, and extracted with ethyl acetate. The organic layer was washed with brine, dried over $Na_2SO_4$ and evaporated in vacuo. Purification of the residue by silica gel column chromatography (ethyl acetate) gave the title compound (1.20 g, 27%).

¹H-NMR (CDCl₃) δ: 3.74 (s, 3H), 7.56 (s, 1H), 8.18 (d, J=5.1, 1H), 8.92 (d, J=5.1 Hz, 1H), 9.30 (s, 1H). MS[M⁺H]⁺: 223.

Example 3

Synthesis of (S)-2-[2-(4-Methoxyphenyl)morpholin-4-yl]-3-methyl-6-pyrimidin-4-yl-3H-pyrimidin-4-one (Compound No. B079 in Table-1)

A solution of (S)-2-(4-methoxyphenyl)morpholine hydrochloride (0.30 g, 1.35 mmol), 2-chloro-3-methyl-6-(4-pyrimidyl)-pyrimidin-4-one (0.40 g, 1.75 mmol) and triethylamine (0.56 ml, 4.05 mmol) in tetrahydrofuran(6 ml) was refluxed for several hours. The reaction mixture was removed in vacuo. The residue was dissolved in 1N hydrochloric acid and extracted with dichloromethane. The organic phase was washed with saturated aqueous sodium hydrogen carbonate, dried over anhydrous sodium sulfate, and concentrated. The residue was purified by column chromatography on silica gel with ethyl acetate as the eluent to give the title compound (463 mg, 90%)

¹H-NMR (CDCl₃) δ: 3.12(dd, J=10.5, 12.9 Hz, 1H), 3.31 (dd, J=3.3, 12.3 Hz, 1H), 3.51-3.63 (m, 2H), 3.58 (s, 3H), 3.83 (s, 3H), 3.90-4.30 (m, 2H), 4.67 (dd, J=2.1, 10.5 Hz, 1H), 6.91-6.96 (m, 2H), 7.32-7.36(m, 3H), 8.14 (dd, J=1.2, 5.1 Hz, 1H), 8.86 (d, J=5.1 Hz, 1H), 9.27 (d, J=1.2 Hz, 1H). MS[M⁺H]⁺: 380.

Example 4

Synthesis of (S)-2-[2-(4-fluorophenyl)morpholin-4-yl]-3-methyl-6-pyrimidin-4-yl-3H-pyrimidin-4-one (Compound No. B031 in Table-1)

A solution of (S)-2-(4-fluorophenyl)morpholine hydrochloride (108.6 mg, 0.60 mmol), 2-chloro-3-methyl-6-pyrimidyl-4-pyrimidin-4-one (88.4 mg, 0.40 mmol) and triethylamine (0.27 ml, 2.0 mmol) in tetrahydrofuran(2 ml) was stirred at room temperature for several hours. The precipitate was filtered off after cooling and solvent was removed in vacuo. The residue was washed with ethyl acetate to give the title compound (100 mg, 74%).

¹H-NMR (CDCl₃) δ: 3.09 (dd, J=12.9, 10.8 Hz, 1H), 3.29 (m, 1H), 3.52-3.64 (m, 2H), 3.59 (s, 3H), 4.00 (m, 1H), 4.21 (m, 1H), 4.72 (dd, J=10.5, 2.1 Hz, 1H), 7.07-7.13 (m, 2H), 7.38-7.43 (m, 3H), 8.13 (dd, J=5.4, 1.2 Hz, 1H), 8.88 (d, J=5.1 Hz, 1H), 9.28 (s, 1H). MS[M⁺H]⁺: 367.

Example 5

Synthesis of 2-[4-(4-Chlorobenzoyl)piperidin-1-yl]-3-methyl-6-pyrimidin-4-yl-3H-pyrimidin-4-one (Compound No. D034 in Table-1)

A solution of (4-Chlorobenzoyl)piperidine hydrochloride (140 mg, 0.539 mmol), 2-chloro-3-methyl-6-(4-pyrimidyl)-pyrimidine-4-one (120 mg, 0.539 mmol) and triethylamine (0.188 ml, 1.35 mmol) in N,N-dimethylformamide(2 ml) was stirred at room temperature. After stirring for several hours, water was added to the reaction mixture. The precipitate was filtered, washed with water and dried to give the title compound (204 mg, 92%).

The compounds in the following table were prepared in the same manner as the methods described above. The compound numbers in the following table correspond to those shown in the above-described table of preferred compounds.

TABLE 2

| Compound No. | ¹H-NMR (Solvent) δ: | [M + H]+ |
|---|---|---|
| A119 | (CDCl₃): 3.60(s, 3H), 5.03(d, J=3.9Hz, 2H), 6.14(brs, 1H), 7.14(s, 1H), 7.59(t, J=7.8Hz, 2H), 7.69(m, 2H), 8.08(m, 2H), 8.15(m, 1H), 8.86(d, J=5.1Hz, 1H), 9.28(s, 1H). | 322 |
| A121 | (CDCl₃): 3.60(s, 3H), 5.01(d, J=3.9Hz, 2H), 6.06(brs, 1H), 7.14(s, 1H), 7.40-7.89(m, 4H), 8.13(m, 1H), 8.87(d, J=5.1Hz, 1H), 9.28(s, 1H). | 340 |
| A124 | (CDCl₃): 3.61(s, 3H), 5.02(d, J=4.2Hz, 2H), 6.04(brs, 1H), 7.15(s, 1H), 7.51-8.15(m, 5H), 8.89(d, J=5.1Hz, 1H), 9.29(s, 1H). | 356 |
| A130 | (CDCl₃): 2.49(s, 3H), 3.61(s, 3H), 5.01(d, J=3.9Hz, 2H), 6.14(brs, 1H), 7.14(s, 1H), 7.44-8.18(m, 1H), 8.88(d, J=5.1Hz, 1H), 9.28(s, 1H). | 336 |
| B030 | (CDCl₃): 3.09(dd, J=12.9, 10.8Hz, 1H), 3.29(m, 1H), 3.52-3.64(m, 2H), 3.59(s, 3H), 4.00(m, 1H), 4.20(m, 1H), 4.72(dd, J=10.5, 2.1Hz, 1H), 7.07-7.13(m, 2H), 7.38-7.43(m, 3H), 8.13(dd, J=5.1, 1.2Hz, 1H), 8.87(d, J=5.1Hz, 1H), 9.28(s, 1H). | 368 |
| B032 | (CDCl₃): 3.09(1H, m), 3.29(1H, m), 3.52-3.64(5H, m), 4.00(1H, m), 4.21(1H, m), 4.72(1H, m), 7.07-7.13(2H, m), 7.38-7.43(3H, m), 8.13(1H, d, J=5.4Hz), 8.87(d, J=4.2Hz, 1H), 9.28(s, 1H). | 368 |

TABLE 2-continued

| Compound No. | ¹H-NMR (Solvent) δ: | [M + H]+ |
|---|---|---|
| B037 | (CDCl$_3$): 3.01(dd, J=12.9, 10.5Hz, 1H), 3.39(m, 1H), 3.52(m, 1H), 3.60(s, 3H), 3.80-4.22(m, 3H), 5.13(d, J=8.7Hz, 1H), 7.07-7.36(m, 4H), 7.58(m, 1H), 8.20(d, J=2.1Hz, 1H), 8.88(d, J=5.1Hz, 1H), 9.28(s, 1H). | 367 |
| B082 | (CDCl$_3$): 3.12(dd, J=10.5, 13.2Hz, 1H), 3.20-3.40(m, 1H), 3.50-3.70(m, 2H), 3.59(s, 3H), 3.85(s, 3H), 3.90-4.30(m, 2H), 4.72(dd, J=2.1, 10.5Hz, 1H), 6.80-7.00(m, 2H), 7.30-7.40(m, 2H), 8.15(dd, J=1.2, 5.1Hz, 1H), 8.87(d, J=5.1Hz, 1H), 9.28(d, J=1.2Hz, 1H). | 379 |
| B084 | (CDCl$_3$): 2.82(1H, dd, J=10.3, 12.7Hz), 3.34(1H, dt, J=3.1, 12.3Hz), 3.56(1H, d, J=12.8Hz), 3.64(3H, s), 3.81(1H, d, J=12.2Hz), 3.87(3H, s), 4.01(1H, dt, J=2.4, 11.8Hz), 4.23(1H, dd, J=2.4, 11.7Hz), 5.08(1H, dd, J=1.5, 10.1Hz), 6.91(1H, d, J=8.3Hz), 7.03(1H, t, J=7.5Hz), 7.2-7.3(1H, m), 7.34(1H, s), 7.54(1H, d, J=7.5Hz), 8.20(1H, d, J=4.9Hz), 8.86(1H, d, J=5.1Hz), 9.27(1H, s) | 380 |
| B085 | (CDCl$_3$): 2.82(1H, dd, J=10.2, 12.9Hz), 3.2-3.4(1H, m), (3.5-3.6(1H, m), 3.63(3H, s), 3.8-3.9(1H, m), 3.87(3H, s), 4.0-4.2(1H, m), 4.2-4.3(1H, m), 5.08(1H, dd, J=2.1, 10.2Hz), 6.91(1H, d, J=8.4Hz), 7.03(1H, t, J=7.8Hz), 7.2-7.3(1H, m), 7.34(1H, s), 7.54(1H, dd, J=1.5, 7.8Hz), 8.20(1H, dd, J=1.2, 5.1Hz), 8.86(1H, d, J=5.1Hz), 9.27(1H, d, J=1.2Hz) | 380 |
| B102 | (DMSO-d$_6$): 3.2-3.3(1H, m), 3.42(3H, s), 3.5-3.6(1H, m), 3.6-3.7(1H, m), 3.7-3.8(1H, m), 3.79(6H, s), 3.9-4.0(2H, m), 5.3-5.4(1H, m), 6.91(1H, m), 6.69(2H, d, J=8.4Hz), 6.98(1H, s), 7.29(1H, t, J=8.4Hz), 8.21(1H, d, J=5.1Hz), 9.00(1H, d, J=5.1Hz), 9.29(1H, s). | 410 |
| B103 | (CDCl$_3$): 3.4-3.6(6H, m), 3.86(6H, s), 3.9-4.1(2H, m), 4.1-4.2(1H, m), 5.4-5.5(1H, m), 6.61(2H, d, J=8.4Hz), 7.2-7.4(2H, m), 8.2-8.3(1H, m), 8.86(1H, d, J=5.1Hz), 9.28(1H, d, J=0.9Hz) | 410 |
| B104 | (CDCl$_3$): 3.4-3.6(6H, m), 3.86(6H, s), 3.9-4.1(2H, m), 4.1-4.2(1H, m), 5.4-5.5(1H, m), 6.61(2H, d, J=8.4Hz), 7.2-7.4(2H, m), 8.2-8.3(1H, m), 8.86(1H, d, J=5.1Hz), 9.28(1H, d, J=0.9Hz) | 410 |
| B105 | (CDCl$_3$): 3.43-3.54(3H, m), 3.60(3H, s), 3.82(1H, dd, J=12.9, 11.1Hz), 3.98(1H, m), 4.22(1H, m), 5.55(1H, dd, J=11.1, 2.7Hz), 7.18-7.42(4H, m), 8.19(1H, dd, J=5.1, 1.2Hz), 8.87(1H, d, J=5.1Hz), 9.27(1H, s). | 418 |
| B106 | (CDCl$_3$): 3.43-3.54(3H, m), 3.60(3H, s), 3.82(1H, dd, J=12.9, 11.1Hz), 3.98(1H, m), 4.22(1H, m), 5.55(1H, dd, J=11.1, 2.7Hz), 7.18-7.42(4H, m), 8.20(1H, dd, J=5.1, 1.2Hz), 8.87(1H, d, J=5.1Hz), 9.27(1H, s). | 418 |
| B107 | (CDCl$_3$): 3.43-3.54(3H, m), 3.60(3H, s), 3.82(1H, dd, J=12.9, 11.1Hz), 3.98(1H, m), 4.22(1H, m), 5.55(1H, dd, J=11.1, 2.7Hz), 7.18-7.42(4H, m), 8.19(1H, dd, J=5.1, 1.2Hz), 8.87(1H, d, J=5.1Hz), 9.27(1H, s). | 418 |
| B112 | (DMSO-d$_6$): 1.87-2.02(m, 4H), 2.99-3.34(m, 7H), 3.49(s, 3H), 3.69-4.11(m, 3H), 4.33(d, J=5.7, 1H), 4.79(d, J=9.3Hz, 1H), 7.01(s, 1H), 7.52-7.65(m, 4H), 8.21(d, J=4.8Hz, 1H), 9.00(d, J=5.1Hz, 1H), 9.30(s, 1H). | 432 |
| B126 | (CDCl3): 0.3-0.4(2H, m)0.6-0.7(2H, m), 1.2-1.3(1H, m), 2.79(1H, dd, J=10.3, 12.7Hz), 3.3-3.5(1H, m), 2.6-2.7(1H, m), 3.66(3H, s), 3.7-4.0(3H, m), 4.0-4.2(1H, m), 4.2-4.3(1H, m), 5.09(1H, dd, J=2.0, 10.1Hz), 6.85(1H, d, J=8.2Hz), 6.9-7.1(1H, m), 7.2-7.3(1H, m), 7.33(1H, s), 7.53(1H, dd, J=1.6, 7.6Hz), 8.18(1H, dd, J=1.3, 5.1Hz), 8.87(1H, d, J=5.2Hz), 9.27(1H, d, J=1.4Hz) | 420 |
| B140 | (CDCl3): 2.0-2.1(4H, m), 3.16(1H, dd, J=10.7, 12.8Hz), 3.2-3.4(5H, m), 3.5-3.6(2H, m), 3.57(3H, s), 3.9-4.1(1H, m), 4.1-4.2(1H, m), 4.61(1H, dd, J=2.2, 10.7Hz), 6.58(2H, d, J=8.5Hz), 7.27(1H, d, J=8.5Hz), 7.34(1H, s), 8.15(1H, dd, J=1.2, 5.1Hz), 8.86(1H, d, J=5.1Hz), 9.27(1H, d, J=1.2Hz) | 419 |
| B217 | (CDCl$_3$): 1.19(s, 3H), 1.21(s, 3H), 2.89-3.00(m, 2H), 3.38(m, 1H), 3.60(s, 3H), 3.61(m, 1H), 3.82(s, 3H), 5.00(m, 1H), 6.94(d, J=8.5Hz, 2H), 7.34(s, 1H), 7.37(d, J=8.5Hz, 2H), 8.14(dd, 5.4, 1.4Hz, 1H), 8.87 (d, J=5.4Hz, 1H), 9.27(d, J=1.4Hz, 1H). | 408 |
| B225 | (CDCl$_3$): 3.3-3.6(3H, m), 3.64(3H, s), 4.0-4.4(3H, m), 5.22(1H, dd, J=2.7, 9.9Hz), 7.38(1H, s), 7.4-7.6(2H, m), 7.95(1H, d, J=7.7Hz), 8.03(1H, d, J=8.0Hz), 8.17(1H, d, J=1.0, 5.0Hz), 8.87(1H, d, J=5.0Hz), 9.28(1H, d, J=1.0Hz) | 407 |
| B237 | (CDCl$_3$): 2.99(1H, dd, J=12.9, 10.5Hz), 3.22-3.53(4H, m), 3.60(3H, s), 3.83-4.18(3H, m), 4.58-4.66(2H, m), 4.97(1H, dd, J=10.2, 2.1Hz), 6.91(1H, m), 7.17-7.31(2H, m), 7.34(1H, s), 8.26(1H, dd, J=5.1, 1.2Hz), 8.87(1H, d, J=4.8Hz), 9.28(1H, s). | 392 |

TABLE 2-continued

| Compound No. | ¹H-NMR (Solvent) δ: | [M + H]+ |
|---|---|---|
| B238 | (CDCl₃): 2.80(1H, dd, J=12.5, 10.2Hz), 3.32(1H, m), 3.55(1H, m), 3.63(3H, s), 3.75(1H, m), 3.85(3H, s), 4.01(1H, m), 4.21(1H, m), 5.00(1H, d, J=10.2Hz), 6.61-6.75(2H, m), 7.34(1H, s), 7.48(1H, m), 8.19(1H, dd, J=5.2, 1.1Hz), 8.87(d, J=5.1Hz, 1H), 9.28(s, 1H). | 398 |
| B239 | (CDCl₃): 3.4-3.7(4H, m), 3.59(3H, s), 3.9-4.0(1H, m), 4.18(1H, dd, J=1.6, 12.1Hz), 5.38(1H, dd, J=4.1, 9.3Hz), 7.0-7.1(1H, m), 7.2-7.3(2H, m), 7.36(1H, s), 8.20(1H, dd, J=1.2, 5.2Hz), 8.87(1H, d, J=5.2Hz), 9.28(1H, d, J=1.2Hz) | 402 |
| B240 | (CDCl₃): 2.81(1H, dd, J=10.4, 12.8Hz), 3.2-3.4(1H, m), 3.63(3H, s), 3.7-3.8(1H, m), 4.0-4.1(1H, m), 4.2-4.3(1H, m), 5.07(1H, dd, J=2.0, 10.3Hz), 7.0-7.2(2H, m), 7.35(1H, s), 7.63(1H, dd, J=6.2, 8.7Hz), 8.16(1H, dd, J=1.4, 5.2Hz), 8.86(1H, d, J=5.2Hz), 9.27(1H, d, J=1.4Hz) | 402 |
| B241 | (CDCl₃): 1.33(3H, d, J=6.0Hz), 1.38(3H, d, J=6.0Hz), 2.72(1H, dd, J=12.9, 10.5Hz), 3.35(1H, m), 3.55-3.71(5H, m), 4.03-4.21(2H, m), 4.57(1H, m), 4.96(1H, dd, J=9.9, 1.8Hz), 6.58-6.71(2H, m), 7.34(1H, s), 7.46(1H, dd, J=8.7, 7.5Hz), 8.17(1H, dd, J=5.1, 1.2Hz), 8.87(1H, d, J=5.4Hz), 9.28(1H, s). | 426 |
| B242 | (CDCl₃): 3.3-3.4(1H, m), 3.5-3.6(2H, m), 3.60(3H, s), 3.83(3H, s), 3.9-4.0(1H, m), 4.0-4.1(1H, m), 4.1-4.2(1H, m), 4.96(1H, dd, J=2.4, 10.2Hz), 6.50(1H, s), 7.0-7.1(1H, m), 7.2-7.3(2H, m), 7.38(1H, s), 8.15(1H, dd, J=1.2, 4.8Hz), 8.89(1H, d, J=5.4Hz), 9.29(1H, d, J=1.2Hz) | 421 |
| B243 | (CDCl₃): 2.99(1H, dd, J=12.9, 10.5Hz), 3.22-3.53(4H, m), 3.61(3H, s), 3.83-4.18(3H, m), 4.58-4.66(2H, m), 4.97(1H, dd, J=10.2, 2.1Hz), 6.92(1H, m), 7.17-7.31(2H, m), 7.35(1H, s), 8.26(1H, d, J=5.4Hz), 8.87(1H, d, J=5.1Hz), 9.28(1H, s). | 392 |
| B244 | (DMSO-d₆): 3.2-3.4(1H, m), 3.42(3H, s), 3.80(6H, s), 3.5-4.0(5H, m), 5.26(1H, d, J=8.2Hz), 6.58(1H, s), 6.62(1H, s), 6.98(1H, s), 8.21(1H, dd, J=1.2, 5.0Hz), 9.01(1H, d, J=5.1Hz), 9.30 (1H, d, J=1.2Hz) | 428 |
| B245 | (DMSO-d₆): 3.2-3.4(1H, m), 3.42(3H, s), 3.80(6H, s), 3.5-4.0(5H, m), 5.26(1H, d, J=8.2Hz), 6.58(1H, s), 6.62(1H, s), 6.98(1H, s), 8.21(1H, dd, J=1.2, 5.0Hz), 9.01(1H, d, J=5.1Hz), 9.30(1H, d, J=1.2Hz) | 428 |
| B246 | (DMSO-d₆): 2.17(3H, s), 2.27(3H, s), 2.7-2.9(1H, m), 3.1-3.3(1H, m), 3.48(3H, s), 3.6-3.7(1H, m), 3.7-4.0(5H, m), 4.0-4.1(1H, m), 4.9-5.0(1H, m), 6.85(1H, s), 7.00(1H, s), 7.19(1H, s), 8.24(1H, d, J=5.0Hz), 9.01(1H, d, J=4.9Hz), 9.30(1H, s) | 408 |
| B247 | (DMSO-d₆): 0.29-0.31(2H, m), 0.50-0.54(2H, m), 1.18(1H, m), 2.78(1H, m), 3.34(1H, m), 3.52(3H, s), 3.71-4.16(6H, m), 4.92(1H, m), 6.80(1H, m), 6.92(1H, m), 7.01(1H, s), 7.43(1H, m), 8.23(1H, d, J=4.8Hz), 9.00(1H, d, J=2.1Hz), 9.30(1H, s). | 438 |
| B248 | (DMSO-d₆): 2.85(1H, dd, J=10.4, 12.9Hz), 3.2-3.3(1H, m), 3.49(3H, s), 3.6-3.7(1H, m), 3.8-4.0(2H, m), 3.94(3H, s), 4.1-4.2(1H, m), 5.04(1H, d, J=8.9Hz), 7.02(1H, s), 7.27(1H, d, J=8.6Hz), 7.79(1H, s), 7.85(1H, dd, J=2.0, 8.5Hz), 8.25(1H, d, J=5.2Hz), 9.02(1H, d, J=5.2Hz), 9.30(1H, s) | 405 |
| B249 | (DMSO-d₆): 2.79(1H, dd, J=10.2, 12.9Hz), 3.1-3.3(1H, m), 3.48(3H, s), 3.6-3.7(1H, m), 3.8-4.0(2H, m), 3.87(3H, s), 4.0-4.1(1H, m), 4.9-5.0(1H, m), 7.01(1H, s), 7.07(1H, dd, J=1.8, 8.1Hz), 7.14(1H, d, J=2.1Hz), 7.44(1H, d, J=8.1Hz), 8.24(1H, d, J=5.4Hz), 9.01(1H, d, J=5.1Hz), 9.30(1H, s) | 414 |
| B250 | (DMSO-d₆): 3.2-3.6(2H, m), 3.48(3H, s), 3.6-3.7(2H, m), 3.7-4.1(2H, m), 3.87(3H, s), 5.1-5.3(1H, m), 6.7-7.0(2H, m), 7.00(1H, s), 8.2-8.3(1H, m), 9.0-9.1(1H, m), 9.31(1H, s) | 416 |
| B251 | (CDCl₃): 3.3-3.5(1H, m), 3.62(3H, s), 3.5-3.7(2H, m), 4.0-4.4(3H, m), 5.36(1H, dd, J=2.7, 9.9Hz), 7.3-7.4(2H, m), 7.6-7.7(2H, m), 7.9-8.0(1H, m), 8.15(1H, dd, J=1.4, 5.3Hz), 8.87(1H, d, J=5.3Hz), 9.28(1H, d, J=1.2Hz). | 391 |
| B252 | (CDCl₃): 3.3-3.5(1H, m), 3.62(3H, s), 3.5-3.7(2H, m), 3.9-4.3(3H, m), 5.36(1H, dd, J=2.6, 9.8Hz), 7.3-7.4(2H, m), 7.5-7.7(2H, m), 7.97(1H, d, J=8.3Hz), 8.1-8.2(1H, m), 8.87(1H, d, J=5.2Hz), 9.28(1H, s). | 391 |
| B253 | (DMSO-d₆): 2.7-2.9(1H, m), 3.2-3.3(1H, m), 3.49(3H, s), 3.6-3.7(1H, m), 3.9-4.0(5H, m), 4.1-4.2(1H, m), 5.0-5.1(1H, m), 7.02(1H, s), 7.49(1H, d, J=6.8Hz), 7.55(1H, s), 7.62(1H, d, J=7.9Hz), 8.24(1H, d, J=4.0Hz), 9.01(1H, d, J=5.1Hz), 9.29(1H, s) | 405 |
| B254 | (CDCl₃): 3.3-3.5(4H, m), 3.57(3H, s), 3.67(1H, t, J=11.1Hz), 3.87(3H, s), 3.95(1H, t, J=11.7Hz), 4.1-4.2(1H, m), 5.24(1H, d, J=9.3Hz), 6.4-6.6(2H, m), 7.34(1H, s), 8.19(1H, dd, J=1.2, 5.1Hz), 8.87(1H, m), 8.87(1H, d, J=5.1Hz), 9.28(1H, d, J=1.2Hz) | 416 |

TABLE 2-continued

| Compound No. | ¹H-NMR (Solvent) δ: | [M + H]+ |
|---|---|---|
| B255 | (DMSO): 2.92(1H, dd, J=10.1, 12.9Hz), 3.22-3.28(1H, m), 3.50(3H, s), 3.66-3.71(1H, d, J=12.7Hz), 3.82-3.96(2H, m), 3.90(3H, s), 4.13(1H, d, J=12.5Hz), 5.08(1H, d, J=9.0Hz), 7.01(1H, s), 7.15(1H, d, J=8.7Hz), 7.24-7.30(2H, m), 7.58-7.69(4H, m), 8.25(1H, d, J=4.9Hz), 9.01(1H, d, J=5.0Hz), 9.30(1H, s) | 474 |
| B256 | (DMSO): 2.95(1H, dd, J=10.3, 12.8Hz), 3.21-3.34(1H, m), 3.50(3H, s), 3.68(1H, d, J=13.1Hz), 3.87-3.96(2H, m), 3.91(3H, s), 4.13(1H, d, J=11.2Hz), 5.10(1H, d, J=8.1Hz), 7.02(1H, s), 7.20(1H, d, J=8.6Hz), 7.40-7.50(1H, m), 7.64-7.71(1H, m), 7.76(1H, d, J=2.3Hz), 7.98-8.06(1H, m), 8.26(1H, dd, J=1.1, 5.0Hz), 8.53-8.54(1H, m), 8.85(1H, d, J=2.4Hz), 9.01(1H, d, J=5.1Hz), 9.29(1H, d, J=1.3Hz) | 457 |
| B257 | (DMSO-d₆): 2.83(1H, m), 3.26(1H, m), 3.50(3H, s), 3.68(1H, m), 3.84-4.11(3H, m), 5.00(1H, m), 6.62-6.66(2H, m), 7.04(1H, s), 7.38(1H, m), 8.33(1H, d, J=5.1Hz), 8.99(1H, d, J=3.9Hz), 9.28(1H, s), 10.21(1H, s). | 384 |
| B258 | (DMSO-d₆): 2.8-2.9(1H, m), 3.2-3.3(1H, m), 3.50(3H, s), 3.69(1H, dd, J=11.7Hz), 3.8-4.0(5H, m), 4.1-4.2(1H, m), 5.06(1H, d, J=8.7Hz), 7.02(1H, s), 7.2-7.6(6H, m), 7.72(2H, d, J=7.8Hz), 8.26(1H, d, J=4.8Hz), 9.01(1H, d, J=5.1Hz), 9.03(1H, s) | 456 |
| B259 | (CDCl₃): 1.9-2.1(4H, m), 2.83(1H, dd, J=9.9, 12.6Hz), 3.2-3.4(5H, m), 3.5-3.6(1H, m), 3.63(3H, s), 3.79(3H, s), 3.8-3.9(1H, m), 4.0-4.1(1H, m), 4.2-4.3(1H, m), 5.05(1H, dd, J=2.1, 9.9Hz), 6.50(1H, dd, J=3.0, 9.0Hz), 6.8-6.9(2H, m), 7.33(1H, s), 8.21(1H, dd, J=1.2, 5.1Hz), 8.86(1H, d, J=5.1Hz), 9.27(1H, d, J=1.2Hz) | 449 |
| B260 | (CDCl₃): 2.0-2.1(4H, m), 2.89(1H, dd, J=10.2, 12.9Hz), 3.3-3.4(5H, m), 3.4-3.6(1H, m), 3.61(3H, s), 3.7-3.8(1H, m), 3.75(3H, s), 4.0-4.1(1H, m), 4.2-4.3(1H, m), 4.99(1H, dd, J=2.1, 10.2Hz), 6.08(1H, d, J=2.1Hz), 6.21(1H, dd, J=2.1, 8.4Hz), 7.3-7.4(2H, m), 8.20(1H, dd, J=1.5, 5.1Hz), 8.86(1H, d, J=5.1Hz), 9.27(1H, d, J=1.2Hz) | 449 |
| B261 | (DMSO): 2.87(1H, dd J=10.5, 12.9Hz), 3.20-3.29(1H, m), 3.50(3H, s), 3.68(1H, d, J=12.6Hz), 3.85-3.98(2H, m), 3.91(3H, s), 4.12(1H, d, J=9.9Hz), 5.08(1H, d, J=9.3Hz), 7.02(1H, s), 7.18(1H, d, J=8.7Hz), 7.29-7.33(2H, m), 7.36-7.40(1H, m), 7.48-7.54(2H, m), 7.64(1H, s), 8.26(1H, d, J=5.1Hz), 9.01(1H, d, J=5.1Hz), 9.30(1H, s) | 474 |
| B262 | (DMSO): 2.92(1H, dd, J=10.5, 12.3Hz), 3.23-3.31(1H, m), 3.50(3H, s), 3.79(1H, d, J=12.9Hz), 3.82(3H, s), 3.87-3.95(2H, m), 3.90(3H, s), 4.13(1H, d, J=10.8Hz), 5.08(1H, d, J=10.8Hz), 6.91(1H, dd, J=1.5, 8.1Hz), 7.01(1H, s), 7.12-7.19(3H, m), 7.34-7.39(1H, m), 7.63(1H, dd, J=1.5, 7.5Hz), 7.71(1H, s), 8.26(1H, d, J=5.1Hz), 9.01(1H, d, J=5.1Hz), 9.30(1H, s) | 486 |
| B263 | (DMSO): 2.86(1H, dd, J=10.8, 12.3Hz), 3.20-3.27(1H, m), 3.50(3H, s), 3.67(1H, d, J=12.9Hz), 3.87-3.95(2H, m), 3.91(3H, s), 4.10(1H, d, J=10.5Hz), 5.08(1H, d, J=9.3Hz), 7.02(1H, s), 7.17(1H, d, J=8.7Hz), 7.40-7.45(2H, m), 7.49-7.55(2H, m), 7.73(1H, s), 8.26(1H, d, J=5.4Hz), 9.02(1H, d, J=5.1Hz), 9.31(1H, s) | 524 |
| B264 | (DMSO): 1.65-1.74(4H, m), 2.38-2.46(4H, m), 2.78(1H, dd, J=10.2, 12.9Hz), 3.19-3.29(1H, m), 3.49(3H, s), 3.52(2H, d, J=4.0Hz), 3.67(1H, d, J=13.2Hz), 3.80-3.91(2H, m), 3.83(3H, s), 4.11(1H, d, J=13.8Hz), 5.01(1H, d, J=8.5Hz), 6.98(1H, d, J=8.4Hz), 7.00(1H, s), 7.22(1H, dd, J=2.1, 8.4Hz), 7.40(1H, d, J=1.9Hz), 8.25(1H, dd, J=1.3, 5.2Hz), 9.01(1H, d, J=5.1Hz), 9.30(1H, d, J=1.1Hz) | 463 |
| B265 | (DMSO): 3.01(1H, dd, J=11.4, 12.3 HZ), 3.15-3.22(1H, m), 3.47(3H, s), 3.70-3.78(2H, m), 3.89-3.96(1H, m), 4.08(1H, d, J=11.4Hz), 4.76(1H, d, J=9.6Hz), 7.01(1H, s), 7.38-7.44(1H, m), 7.52-7.55(1H, m), 7.79-7.81(1H, m), 8.22(1H, d, J=4.8Hz), 8.99(1H, d, J=5.1Hz), 9.30(1H, s) | 446 |
| B266 | (DMSO): 2.94(1H, dd, J=10.4, 12.8Hz), 3.23-3.31(1H, m), 3.49(3H, s), 3.69(1H, d, J=13.2Hz), 3.85-3.95(2H, m), 3.90(3H, s), 4.13(1H, d, J=10.0Hz), 5.08(1H, d, J=8.9Hz), 7.01(1H, s), 7.13-7.17(2H, m), 7.47-7.50(3H, m), 7.67(1H, dd, J=2.2, 8.5Hz), 7.75(1H, d, J=2.3Hz), 8.25(1H, d, J=5.0Hz), 9.01(1H, d, J=5.3Hz), 9.30(1H, s) | 474 |

TABLE 2-continued

| Compound No. | ¹H-NMR (Solvent) δ: | [M + H]+ |
|---|---|---|
| B267 | (DMSO): 2.85(1H, dd, J=10.4, 12.8Hz), 3.19-3.26(1H, m), 3.50(3H, s), 3.67(1H, d, J=13.2Hz), 3.76(1H, s), 3.87-3.94(2H, m), 3.88(3H, s), 4.10(1H, d, J=9.8Hz), 5.06(1H, d, J=9.7Hz), 6.99-7.04(2H, m), 7.07-7.11(2H, m), 7.24-7.37(2H, m), 7.42-7.46(1H, m), 7.54(1H, s), 8.26(1H, d, J=5.2Hz), 9.01(1H, d, J=5.0Hz), 9.30(1H, s) | 486 |
| B268 | (DMSO): 2.91(1H, dd, J=10.4, 12.8Hz), 3.20-3.31(1H, m), 3.50(3H, s), 3.69(1H, d, J=12.8Hz), 3.79(3H, s), 3.86-3.95(2H, m), 3.88(3H, s), 4.13(1H, d, J=10.1Hz), 5.07(1H, d, J=8.8Hz), 7.00-7.02(3H, m), 7.12(1H, d, J=8.6Hz), 7.53-7.57(3H, m), 7.66(1H, d, J=2.2Hz), 8.26(1H, d, J=5.2Hz), 9.01(1H, d, J=6.0Hz), 9.30(1H, s) | 486 |
| B269 | (DMSO): 2.79(1H, dd, J=10.0, 12.7Hz), 3.12-3.24(1H, m), 3.49(3H, s), 3.67(1H, d, J=12.3Hz), 3.81(3H, s), 3.87-3.91(2H, m), 4.04-4.10(1H, m), 5.00(1H, d, J=8.4Hz), 6.70-6.75(1H, m), 6.92-7.01(5H, m), 7.04-7.08(1H, m), 7.15-7.20(2H, m), 7.24(1H, d, J=2.6Hz), 7.94(1H, s), 8.26(1H, d, J=4.6Hz), 9.01(1H, d, J=5.2Hz), 9.30(1H, s) | 471 |
| B270 | (CDCl₃): 2.71(1H, dd, J=12.5, 10.3Hz), 3.24(3H, s), 3.33(1H, m), 3.51(1H, m), 3.69(1H, m), 4.00(1H, m), 4.22(1H, m), 5.04(1H, m), 5.06(2H, s), 6.68-6.78(2H, m), 7.30(1H, s), 7.36-7.40(5H, m), 7.51(1H, m), 8.15(1H, m), 8.81(1H, d, J=5.1Hz), 9.26(1H, s). | 474 |
| B271 | (CDCl₃): 3.37-3.53(3H, m), 3.60(3H, s), 3.86(1H, m), 4.05(1H, m), 4.18(1H, m), 5.00(1H, m), 6.78(1H, s), 7.25-7.38(3H, m), 7.50-7.61(2H, m), 8.17(1H, dd, J=5.1, 1.2Hz), 8.88(1H, d, J=5.1Hz), 9.29(1H, s). | 390 |
| B272 | (CDCl₃): 3.36-3.53(3H, m), 3.60(3H, s), 3.86(1H, m), 4.05(1H, m), 4.18(1H, m), 5.00(1H, dd, J=10.2, 2.4Hz), 6.78(1H, s), 7.25-7.38(3H, m), 7.50-7.61(2H, m), 8.17(1H, dd, J=5.1, 1.2Hz), 8.88(1H, d, J=5.1Hz), 9.29(1H, s). | 390 |
| B273 | (CDCl₃): 3.36-3.54(3H, m), 3.59(3H, s), 3.87(1H, m), 4.03(1H, m), 4.04(3H, s), 4.18(1H, m), 5.01(1H, m), 6.77(1H, s), 6.83(1H, m), 7.17-7.19(2H, m), 7.38(1H, s), 8.17(1H, d, J=4.2Hz), 8.87(1H, d, J=5.1Hz), 9.28(1H, s). | 420 |
| B274 | (DMSO-d₆): 1.8-2.2(4H, m), 2.9-3.2(3H, m), 3.2-3.5(3H, m), 3.50(3H, s), 3.70(1H, d, J=12.9Hz), 3.91(3H, s), 3.8-4.3(3H, m), 4.41(2H, d, J=4.2Hz), 5.10(1H, d, J=9.9Hz), 7.02(1H, s), 7.18(1H, d, J=8.4Hz), 7.4-7.6(2H, m), 7.6-7.8(2H, m), 7.80(1H, s), 7.96(1H, s), 8.27(1H, d, J=4.5Hz), 9.03(1H, d, J=4.8Hz), 9.31(1H, s), 11.2(1H, brd) | 539 |
| B275 | (CDCl₃): 1.9-2.1(4H, m), 3.17(1H, dd, J=10.613.0Hz), 3.2-3.4(5H, m), 3.5-3.6(1H, m), 3.58(3H, s), 3.6-3.7(1H, m), 3.9-4.1(1H, m), 4.2-4.3(1H, m), 4.6-4.7(1H, m), 6.5-6.6(1H, m), 6.60(1H, s), 6.68(1H, d, J=7.6Hz), 7.2-7.3(1H, m), 7.34(1H, s), 8.16(1H, d, J=5.7Hz), 8.85(1H, d, J=5.1Hz), 9.28(1H, d, J=1.3 HGz) | 419 |
| B276 | (CDCl₃): 1.9-2.1(4H, m), 3.17(1H, dd, J=10.613.0Hz), 3.2-3.4(5H, m), 3.5-3.6(1H, m), 3.58(3H, s), 3.6-3.7(1H, m), 3.9-4.1(1H, m), 4.2-4.3(1H, m), 4.6-4.7(1H, m), 6.5-6.6(1H, m), 6.60(1H, s), 6.68(1H, d, J=7.6Hz), 7.2-7.3(1H, m), 7.34(1H, s), 8.16(1H, d, J=5.7Hz), 8.85(1H, d, J=5.1Hz), 9.28(1H, d, J=1.3 HGz) | 419 |
| B277 | (CDCl₃): 2.88(1H, m), 3.37(1H, m), 3.58(1H, m), 3.65(3H, s), 3.86(1H, m), 3.91(3H, s), 4.03(1H, m), 4.24(1H, m), 5.12(1H, m), 7.09(1H, s), 7.13-7.48(6H, m), 7.60(1H, d, J=4.8Hz), 8.22(1H, d, J=5.1Hz), 8.87(1H, d, J=5.1Hz), 9.28(1H, s). | 474 |
| B278 | (CDCl₃): 2.86(1H, dd, J=12.6, 10.5Hz), 3.36(1H, m), 3.56(1H, m), 3.65(3H, s), 3.84(1H, m), 3.94(3H, s), 4.03(1H, m), 4.24(1H, m), 5.11(1H, m), 7.03-7.07(2H, m), 7.19-7.45(5H, m), 7.60(1H, d, J=4.8Hz), 8.21(1H, d, J=4.2Hz), 8.67(1H, d, J=5.1Hz), 9.28(1H, s). | 474 |
| B279 | (CDCl₃): 2.86(1H, dd, J=12.3, 9.9Hz), 3.36(1H, m), 3.58(1H, m), 3.60(3H, s), 3.84(1H, m), 3.93(3H, s), 4.03(1H, m), 4.24(1H, m), 5.11(1H, m), 7.03(1H, s), 7.04-7.41(3H, m), 7.35(1H, s), 7.52-7.60(3H, m), 8.21(1H, dd, J=5.4, 1.5Hz), 8.67(1H, d, J=5.1Hz), 9.28(1H, d, J=1.5Hz). | 474 |
| B280 | (DMSO): 2.88(1H, dd, J=10.5, 12.6Hz), 3.24-3.32(1H, m), 3.51(3H, s), 3.70(1H, d, J=12.9Hz), 3.89-3.97(2H, m), 3.92(3H, s), 4.15(1H, d, J=11.4Hz), 5.09(1H, d, J=9.0Hz), 7.01(1H, s), 7.17(1H, d, J=8.4Hz), | 457 |

TABLE 2-continued

| Compound No. | ¹H-NMR (Solvent) δ: | [M + H]+ |
|---|---|---|
| | 7.28-7.32(1H, m), 7.80-7.92(2H, m), 8.04(1H, d, J=8.7Hz), 8.25-8.27(2H, m), 8.64(1H, d, J=4.2Hz), 9.01(1H, d, J=5.4Hz), 9.30(1H, s) | |
| B281 | (DMSO): 2.91(1H, dd, J=10.3, 12.9Hz), 3.20-3.30(1H, m), 3.50(3H, s), 3.69(1H, d, J=13.0Hz), 3.88-3.97(2H, m), 3.91(3H, s), 3.95(3H, s), 4.15(1H, d, J=9.9Hz), 5.08(1H, d, J=8.6Hz), 6.73(1H, d, J=8.2Hz), 7.01(1H, s), 7.17(1H, d, J=8.7Hz), 7.48(1H, d, J=7.5Hz), 7.73-7.78(1H, m), 8.06-8.09(1H, m), 8.15(1H, d, J=2.1Hz), 8.25(1H, dd, J=1.1, 5.1Hz), 9.00(1H, d, J=5.2Hz), 9.30(1H, d, J=0.9Hz) | 487 |
| B282 | (DMSO): 2.93(1H, dd, J=10.5, 12.9Hz), 3.22-3.30(1H, m), 3.50(3H, s), 3.69(1H, d, J=13.2Hz), 3.86-3.95(2H, m), 3.89(6H, s), 4.13(1H, d, J=9.6Hz), 5.08(1H, d, J=8.4Hz), 6.90(1H, d, J=8.7Hz), 7.01(1H, s), 7.16(1H, d, J=8.7Hz), 7.58-7.63(1H, m), 7.68(1H, d, J=2.4Hz), 7.96(1H, dd, J=2.7, 8.4Hz), 8.26(1H, dd, J=1.2, 4.8Hz), 8.42(1H, d, J=2.7Hz), 9.01(1H, d, J=5.4Hz), 9.30(1H, d, J=1.5Hz) | 517 |
| B283 | (DMSO): 2.87(1H, dd, J=10.3, 12.8Hz), 3.20-3.28(1H, m), 3.50(3H, s), 3.67(1H, d, J=12.2Hz), 3.87-3.94(2H, m), 3.89(3H, s), 3.94(6H, s), 4.11(1H, d, J=10.2Hz), 5.06(1H, d, J=9.0Hz), 7.01(1H, s), 7.13(1H, d, J=8.6Hz), 7.46(1H, dd, J=2.2, 8.6Hz), 7.57(1H, d, J=2.1Hz), 8.25(1H, d, J=5.2Hz), 8.32(1H, s), 9.01(1H, d, J=5.2Hz), 9.30(1H, s) | 518 |
| B284 | (CDCl₃): 2.3-2.4(1H, m), 2.5-2.6(1H, m), 3.2-3.4(1H, m), 3.4-3.7(3H, m), 3.59(3H, s), 3.9-4.0(1H, m), 4.1-4.2(2H, m), 4.3-4.4(1H, m), 6.88(1H, dd, J=1.2, 8.4Hz), 7.01(1H, t, J=7.5Hz), 7.26(1H, t, J=8.4Hz), 7.36(1H, s), 7.63(1H, dd, J=1.5, 7.5Hz), 8.13(1H, dd, J=1.2, 5.1Hz), 8.86(1H, d, J=5.1Hz), 9.28(1H, d, J=1.2Hz) | 392 |
| B285 | (CDCl₃): 1.8-2.0(3H, m), 2.4-2.5(1H, m), 3.2-3.4(1H, m), 3.46(3H, s), 3.4-3.6(1H, m), 3.7-3.8(1H, m), 3.70(1H, d, J=13.2Hz), 3.88(1H, d, J=13.2Hz), 4.1-4.2(1H, m), 4.2-4.4(2H, m), 7.02(1H, dd, J=1.5, 7.8Hz), 7.1-7.2(1H, m), 7.2-7.3(1H, m), 7.32(1H, s), 7.6-7.7(1H, m), 8.15(1H, dd, 1.5, 5.4Hz), 8.87(1H, d, J=5.4Hz), 9.27(1H, d, J=1.5Hz) | 406 |
| C401 | (DMSO-d₆):1.5-1.7(1H, m), 1.8-2.0(2H, m), 2.0-2.1(1H, m), 2.9-3.1(1H, m), 3.1-3.2(1H, m), 3.43(3H, s), 3.6-3.8(1H, m), 3.8-4.0(2H, m), 6.96(1H, s), 7.55(2H, t, J=5.6Hz), 7.67(1H, t, J=7.8Hz), 8.03(2H, d, J=7.8Hz), 8.18(1H, d, J=5.4Hz), 8.99(1H, d, J=4.8Hz), 9.30(1H, s) | 376 |
| C501 | (CDCl₃): 3.3-3.6(3H, m), 3.58(3H, s), 3.88(1H, d, J=13.3Hz), 3.9-4.1(1H, m), 4.1-4.3(1H, m), 5.08(1H, dd, J=2.6, 9.4Hz), 7.35(1H, s), 7.50(1H, t, J=7.8Hz), 7.63(1H, t, J=7.4Hz), 8.06(1H, d, J=7.3Hz), 8.13(1H, dd, J=0.9, 5.0Hz), 8.87(1H, d, J=5.2Hz), 9.28(1H, d, J=0.8Hz) | 378 |
| C789 | (CDCl₃): 3.3-3.6(3H, m), 3.58(3H, s), 3.88(1H, d, J=13.3Hz), 3.9-4.1(1H, m), 4.1-4.3(1H, m), 5.08(1H, dd, J=2.6, 9.4Hz), 7.35(1H, s), 7.50(1H, t, J=7.8Hz), 7.63(1H, t, J=7.4Hz), 8.06(1H, d, J=7.3Hz), 8.13(1H, dd, J=0.9, 5.0Hz), 8.87(1H, d, J=5.2Hz), 9.28(1H, d, J=0.8Hz) | 378 |
| C790 | (CDCl₃): 3.3-3.6(3H, m), 3.58(3H, s), 3.88(1H, d, J=13.3Hz), 3.9-4.1(1H, m), 4.1-4.3(1H, m), 5.08(1H, dd, J=2.6, 9.4Hz), 7.35(1H, s), 7.50(1H, t, J=7.8Hz), 7.63(1H, t, J=7.4Hz), 8.06(1H, d, J=7.3Hz), 8.13(1H, dd, J=0.9, 5.0Hz), 8.87(1H, d, J=5.2Hz), 9.28(1H, d, J=0.8Hz) | 378 |
| D034 | (CDCl₃): 1.95-2.06(m, 4H), 3.13(m, 2H), 3.49(m, 1H), 3.55(s, 3H), 3.73(m, 2H), 7.33(s, 1H), 7.49(d, J=8.7Hz, 2H), 7.92(d, J=8.7Hz, 2H), 8.17(d, J=5.0Hz, 1H), 8.87(d, J=5.0Hz, 1H), 9.28(s, 1H). | 410 |

Test Example

Inhibitory Activity of the Medicament of the Present Invention Against P-GS1 Phosphorylation by Bovine Cerebral TPK1

A mixture containing 100 mM MES-sodium hydroxide (pH 6.5), 1 mM magnesium acetate, 0.5 mM EGTA, 5 mM β-mercaptoethanol, 0.02% Tween 20, 10% glycerol, 12 μg/ml P-GS1, 41.7 μM [γ-$^{32}$P] ATP (68 kBq/ml), bovine cerebral TPK1 and a compound shown in Table (a final mixture contained 1.7% DMSO deriving from a solution of a test compound prepared in the presence of 10% DMSO) was used as a reaction system. The phosphorylation was started by adding ATP, and the reaction was conducted at 25° C. for 2 hours, and then stopped by adding 21% perchloric acid on ice cooling. The reaction mixture was centrifuged at 12,000 rpm for 5 minutes and adsorbed on P81 paper (Whatmann), and then the paper was washed four times with 75 mM phosphoric acid, three times with water and once with acetone. The paper was dried, and the residual radioactivity was measured using a liquid scintillation counter. The results are shown in the table below. The test compound markedly inhibited the P-GS1 phosphorylation by TPK1. The results strongly suggest that the medicaments of the present invention inhibit the TPK1 activity, thereby suppress the A B neurotoxicity and the. PHF formation, and that the medicaments of the present invention are effective for preventive and/or therapeutic treatment of Alzheimer disease and the above-mentioned diseases.

TABLE 3

| Compound No. | IC$_{50}$ (nM) |
|---|---|
| A119 | 24 |
| A121 | 19 |
| A124 | 11 |
| A130 | 30 |
| B030 | 11 |
| B031 | 5 |
| B032 | 32 |
| B037 | 3 |
| B079 | 2.9 |
| B082 | 4.6 |
| B084 | 1.2 |
| B085 | 0.87 |
| B102 | 0.441 |
| B103 | 0.23 |
| B104 | 4.5 |
| B105 | 0.27 |
| B106 | 1.2 |
| B107 | 40 |
| B112 | 2.1 |
| B126 | 23 |
| B140 | 3.7 |
| B217 | 26.1 |
| B225 | 12 |
| B237 | 0.821 |
| B238 | 0.47 |
| B239 | 0.74 |
| B240 | 3.5 |
| B241 | 4.6 |
| B242 | 6.9 |
| B243 | 4.2 |
| B244 | 0.17 |
| B245 | 1.3 |
| B246 | 1.1 |
| B247 | 15 |
| B248 | 0.78 |
| B249 | 0.83 |
| B250 | 0.56 |
| B251 | 2.4 |
| B252 | 1 |
| B253 | 0.7 |
| B254 | 0.24 |
| B255 | 4.6 |
| B256 | 0.64 |
| B257 | 7.4 |
| B258 | 1.4 |
| B259 | 1.2 |
| B260 | 0.77 |
| B261 | 1.4 |
| B262 | 1.3 |
| B263 | 13 |
| B264 | 0.6 |
| B265 | 0.6 |
| B266 | 1.6 |
| B267 | 1.2 |
| B268 | 1.7 |
| B269 | 1.1 |
| B270 | 27 |
| B271 | 4.2 |
| B272 | 7.1 |
| B273 | 4.3 |
| B274 | 0.57 |
| B275 | 7 |
| B276 | 4.8 |
| B277 | 1.4 |

TABLE 3-continued

| Compound No. | IC$_{50}$ (nM) |
|---|---|
| B278 | 1.1 |
| B279 | 1.2 |
| B280 | 0.60 |
| B281 | 0.84 |
| B282 | 1.0 |
| B283 | 1.9 |
| B284 | 11 |
| B285 | 26 |
| C401 | 1.1 |
| C501 | 0.56 |
| C789 | 38 |
| C790 | 0.64 |
| D034 | 1.1 |

Formulation Example (1) Tablets
The ingredients below were mixed by an ordinary method and compressed by using a conventional apparatus.

| Compound of Example 1 | 30 mg |
|---|---|
| Crystalline cellulose | 60 mg |
| Corn starch | 100 mg |
| Lactose | 200 mg |
| Magnesium stearate | 4 mg |

(2) Soft Capsules
The ingredients below were mixed by an ordinary method and filled in soft capsules.

| Compound of Example 1 | 30 mg |
|---|---|
| Olive oil | 300 mg |
| Lecithin | 20 mg |

INDUSTRIAL APPLICABILITY

The compounds of the present invention have TPK1 inhibitory activity and are useful as an active ingredient of a medicament for preventive and/or therapeutic treatment of diseases caused by abnormal advance of TPK1 such as neurodegenerative diseases (e.g. Alzheimer disease) and the above-mentioned diseases.

The invention claimed is:

1. A pyrimidone derivative represented by formula (I) or a salt thereof:

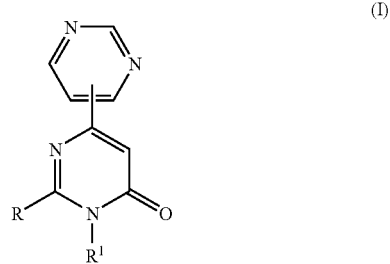

wherein R¹ represents a $C_1$-$C_{12}$ alkyl group which may be substituted;

R represents any one of groups represented by the following formulas (II) to (V):

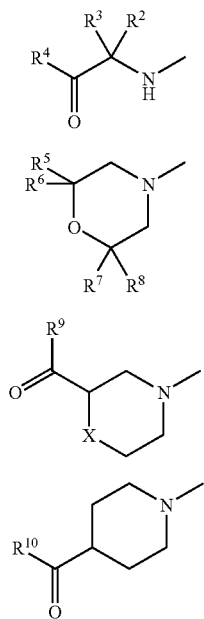

wherein R² and R³ independently represent a hydrogen atom or a $C_1$-$C_8$ alkyl group;

R⁴ represents a benzene ring which may be substituted, a naphthalene ring which may be substituted, an indan ring which may be substituted, a tetrahydronaphthalene ring which may be substituted, or an optionally substituted heterocyclic ring having 1 to 4 hetero atoms selected from the group consisting of oxygen atom, sulfur atom and nitrogen atom, and having 5 to 10 ring-constituting atoms in total;

R⁵ represents a $C_1$-$C_8$ alkyl group which may be substituted, a $C_3$-$C_8$ cycloalkyl group which may be substituted, a benzene ring which may be substituted, a naphthalene ring which may be substituted, an indan ring which may be substituted, a tetrahydronaphthalene ring which may be substituted, or an optionally substituted heterocyclic ring having 1 to 4 hetero atoms selected from the group consisting of oxygen atom, sulfur atom, and nitrogen atom, and having 5 to 10 ring-constituting atoms in total;

R⁶ represents a hydrogen atom, a $C_1$-$C_8$ alkyl group which may be substituted, a benzene ring which may be substituted;

or R⁵ and R⁶ may bind to each other to form together with the carbon to which R⁵ and R⁶ are attached an optionally substituted spiro carbocyclic ring having 3 to 11 ring-constituting atoms in total;

R⁷ and R⁸ independently represent a hydrogen atom or a $C_1$-$C_8$ alkyl group, or R⁷ and R⁸ may combine to each other to form a $C_2$-$C_6$ alkylene group;

R⁹ and R¹⁰ represent a $C_1$-$C_8$ alkyl group which may be substituted, a $C_3$-$C_8$ cycloalkyl group which may be substituted, a benzene ring which may be substituted, a naphthalene ring which may be substituted, an optionally substituted heterocyclic ring having 1 to 4 hetero atoms selected from the group consisting of oxygen atom, sulfur atom, and nitrogen atom, and having 5 to 10 ring-constituting atoms in total, or R⁹ and R¹⁰ represent —N(R¹¹)(R¹²) wherein R¹¹ represents a hydrogen atom, a $C_1$-$C_8$ alkyl group; and R¹² represents a $C_1$-$C_8$ alkyl group, a benzene ring which may be substituted, a naphthalene ring which may be substituted, or an optionally substituted heterocyclic ring having 1 to 4 hetero atoms selected from the group consisting of oxygen atom, sulfur atom, and nitrogen atom, and having 5 to 10 ring-constituting atoms in total; and X represents $CH_2$, O or $NR^{13}$ wherein R¹³ represents a hydrogen atom or a $C_1$-$C_8$ alkyl group.

2. The pyrimidone derivative or the salt thereof, according to claim 1, wherein R¹ is methyl group.

3. The pyrimidone derivative or the salt thereof, according to claim 1, wherein R is the group represented by formula (II).

4. The pyrimidone derivative or the salt thereof, according to claim 3, wherein each of R² and R³ is hydrogen atom.

5. A pyrimidone derivative which is selected from the group consisting of:
3-methyl-2-(2-oxo-2-phenylethylamino)-6-pyrimidin-4-yl-3H-pyrimidin-4-one;
3-methyl-2-(2-oxo-2-(3-fluorophenyl)ethylamino)-6-pyrimidin-4-yl-3H-pyrimidin-4-one;
3-methyl-2-(2-oxo-2-(4-fluorophenyl)ethylamino)-6-pyrimidin-4-yl-3H-pyrimidin-4-one;
3-methyl-2-(2-oxo-2-(3-chlorophenyl)ethylamino)-6-pyrimidin-4-yl-3H-pyrimidin-4-one and 3-methyl-2-(2-oxo-2-(3-methylphenyl)ethylamino)-6-pyrimidin-4-yl-3H-pyrimidin-4-one or a salt thereof.

6. The pyrimidone derivative or the salt thereof, according to claim 1, wherein R is the group represented by formula (III).

7. The pyrimidone derivative or the salt thereof, according to claim 6, wherein R⁶ is hydrogen atom.

8. The pyrimidone derivative or the salt thereof, according to claim 7, wherein each of R⁷ and R⁸ is hydrogen atom.

9. The pyrimidone derivative or the salt thereof, according to claim 7, wherein each of R⁷ and R⁸ is methyl group.

10. A pyrimidone derivative which is selected from the group consisting of:
2-[2-(4-Fluorophenyl)morpholin-4-yl]-3-methyl-6-pyrimidin-4-yl-3H-pyrimidin-4-one;
(S)-2-[2-(4-Fluorophenyl)morpholin-4-yl]-3-methyl-6-pyrimidin-4-yl-3H-pyrimidin-4-one;
2-[2-(2-Fluorophenyl)morpholin-4-yl]-3-methyl-6-pyrimidin-4-yl-3H-pyrimidin-4-one;
(S)-2-[2-(2-Fluorophenyl)morpholin-4-yl]-3-methyl-6-pyrimidin-4-yl-3H-pyrimidin-4-one;
2-[2-(4-Chlorophenyl)morpholin-4-yl]-3-methyl-6-pyrimidin-4-yl-3H-pyrimidin-4-one;
2-[2-(3-Chlorophenyl)morpholin-4-yl]-3-methyl-6-pyrimidin-4-yl-3H-pyrimidin-4-one;
2-[2-(2-Chlorophenyl)morpholin-4-yl]-3-methyl-6-pyrimidin-4-yl-3H-pyrimidin-4-one;
(S)-2-[2-(2-Chlorophenyl)morpholin-4-yl]-3-methyl-6-pyrimidin-4-yl-3H-pyrimidin-4-one;
2-[2-(4-Bromophenyl)morpholin-4-yl]-3-methyl-6-pyrimidin-4-yl-3H-pyrimidin-4-one;
(S)-2-[2-(4-Bromophenyl)morpholin-4-yl]-3-methyl-6-pyrimidin-4-yl-3H-pyrimidin-4-one;
2-[2-(3-Bromophenyl)morpholin-4-yl]-3-methyl-6-pyrimidin-4-yl-3H-pyrimidin-4-one;
(S)-2-[2-(3-Bromophenyl)morpholin-4-yl]-3-methyl-6-pyrimidin-4-yl-3H-pyrimidin-4-one;

2-[2-(2-Bromophenyl)morpholin-4-yl]-3-methyl-6-pyrimidin-4-yl-3H-pyrimidin-4-one;
2-[2-(4-Methylphenyl)morpholin-4-yl]-3-methyl-6-pyrimidin-4-yl-3H-pyrimidin-4-one;
2-[2-(3-Methylphenyl)morpholin-4-yl]-3-methyl-6-pyrimidin-4-yl-3H-pyrimidin-4-one;
2-[2-(2-Methylphenyl)morpholin-4-yl]-3-methyl-6-pyrimidin-4-yl-3H-pyrimidin-4-one;
(S)-2-[2-(2-Methylphenyl)morpholin-4-yl]-3-methyl-6-pyrimidin-4-yl-3H-pyrimidin-4-one;
2-[2-(4-Cyanophenyl)morpholin-4-yl]-3-methyl-6-pyrimidin-4-yl-3H-pyrimidin-4-one;
2-[2-(3-Cyanophenyl)morpholin-4-yl]-3-methyl-6-pyrimidin-4-yl-3H-pyrimidin-4-one;
(S)-2-[2-(3-Cyanophenyl)morpholin-4-yl]-3-methyl-6-pyrimidin-4-yl-3H-pyrimidin-4-one;
2-[2-(2-Cyanophenyl)morpholin-4-yl]-3-methyl-6-pyrimidin-4-yl-3H-pyrimidin-4-one;
2-[2-(4-Methoxyphenyl)morpholin-4-yl]-3-methyl-6-pyrimidin-4-yl-3H-pyrimidin-4-one;
(S)-2-[2-(4-Methoxyphenyl)morpholin-4-yl]-3-methyl-6-pyrimidin-4-yl-3H-pyrimidin-4-one;
2-[2-(3-Methoxyphenyl)morpholin-4-yl]-3-methyl-6-pyrimidin-4-yl-3H-pyrimidin-4-one;
(S)-2-[2-(3-Methoxyphenyl)morpholin-4-yl]-3-methyl-6-pyrimidin-4-yl-3H-pyrimidin-4-one
2-[2-(2-Methoxyphenyl)morpholin-4-yl]-3-methyl-6-pyrimidin-4-yl-3H-pyrimidin-4-one;
(S)-2-[2-(2-Methoxyphenyl)morpholin-4-yl]-3-methyl-6-pyrimidin-4-yl-3H-pyrimidin-4-one;
2-[2-(2-Ethoxyphenyl)morpholin-4-yl]-3-methyl-6-pyrimidin-4-yl-3H-pyrimidin-4-one;
2-[2-(2-Trifluoromethoxyphenyl)morpholin-4-yl]-3-methyl-6-pyrimidin-4-yl-3H-pyrimidin-4-one;
2-[2-(5-Fluoro-2-methoxyphenyl)morpholin-4-yl]-3-methyl-6-pyrimidin-4-yl-3H-pyrimidin-4-one;
2-[2-(4-Fluoro-2-methoxyphenyl)morpholin-4-yl]-3-methyl-6-pyrimidin-4-yl-3H-pyrimidin-4-one;
(S)-2-[2-(4-Fluoro-2-methoxyphenyl)morpholin-4-yl]-3-methyl-6-pyrimidin-4-yl-3H-pyrimidin-4-one;
2-[2-(2,5-Dimethoxyphenyl)morpholin-4-yl]-3-methyl-6-pyrimidin-4-yl-3H-pyrimidin-4-one;
(S)-2-[2-(2,5-Dimethoxyphenyl)morpholin-4-yl]-3-methyl-6-pyrimidin-4-yl-3H-pyrimidin-4-one;
2-[2-(2-Chloro-4,5-difluorophenyl)morpholin-4-yl]-3-methyl-6-pyrimidin-4-yl-3H-pyrimidin-4-one;
(S)-2-[2-(2-Chloro-4,5-difluorophenyl)morpholin-4-yl]-3-methyl-6-pyrimidin-4-yl-3H-pyrimidin-4-one;
2-[2-(2-Bromo-4-fluorophenyl)morpholin-4-yl]-3-methyl-6-pyrimidin-4-yl-3H-pyrimidin-4-one;
2-[2-(2,4-Difluorophenyl)morpholin-4-yl]-3-methyl-6-pyrimidin-4-yl-3H-pyrimidin-4-one;
(S)-2-[2-(2,4-Difluorophenyl)morpholin-4-yl]-3-methyl-6-pyrimidin-4-yl-3H-pyrimidin-4-one;
2-[2-(2,6-Dimethoxyphenyl)morpholin-4-yl]-3-methyl-6-pyrimidin-4-yl-3H-pyrimidin-4-one;
(S)-2-[2-(2,6-Dimethoxyphenyl)morpholin-4-yl]-3-methyl-6-pyrimidin-4-yl-3H-pyrimidin-4-one;
2-[2-(2,4-Dimethoxyphenyl)morpholin-4-yl]-3-methyl-6-pyrimidin-4-yl-3H-pyrimidin-4-one;
(S)-2-[2-(2,4-Dimethoxyphenyl)morpholin-4-yl]-3-methyl-6-pyrimidin-4-yl-3H-pyrimidin-4-one;
2-[2-(2,6-Dichlorophenyl)morpholin-4-yl]-3-methyl-6-pyrimidin-4-yl-3H-pyrimidin-4-one;
(S)-2-[2-(2,6-Dichlorophenyl)morpholin-4-yl]-3-methyl-6-pyrimidin-4-yl-3H-pyrimidin-4-one;
2-[2-(2,6-Difluorophenyl)morpholin-4-yl]-3-methyl-6-pyrimidin-4-yl-3H-pyrimidin-4-one;
(S)-2-[2-(2,6-Difluorophenyl)morpholin-4-yl]-3-methyl-6-pyrimidin-4-yl-3H-pyrimidin-4-one;
2-[2-(2-Chloro-6-fluorophenyl)morpholin-4-yl]-3-methyl-6-pyrimidin-4-yl-3H-pyrimidin-4-one;
(S)-2-[2-(2-Chloro-6-fluorophenyl)morpholin-4-yl]-3-methyl-6-pyrimidin-4-yl-3H-pyrimidin-4-one;
2-[2-(4-Fluoro-3-methoxyphenyl)morpholin-4-yl]-3-methyl-6-pyrimidin-4-yl-3H-pyrimidin-4-one;
2-[2-(5-Cyano-2-methoxyphenyl)morpholin-4-yl]-3-methyl-6-pyrimidin-4-yl-3H-pyrimidin-4-one;
(S)-2-[2-(5-Cyano-2-methoxyphenyl)morpholin-4-yl]-3-methyl-6-pyrimidin-4-yl-3H-pyrimidin-4-one;
2-[2-(4-Cyano-2-methoxyphenyl)morpholin-4-yl]-3-methyl-6-pyrimidin-4-yl-3H-pyrimidin-4-one;
(S)-2-[2-(4-Cyano-2-methoxyphenyl)morpholin-4-yl]-3-methyl-6-pyrimidin-4-yl-3H-pyrimidin-4-one;
2-[2-(2,4-Difluoro-6-methoxyphenyl)morpholin-4-yl]-3-methyl-6-pyrimidin-4-yl-3H-pyrimidin-4-one;
(S)-2-[2-(2,4-Difluoro-6-methoxyphenyl)morpholin-4-yl]-3-methyl-6-pyrimidin-4-yl-3H-pyrimidin-4-one;
2-[2-(4-(Pyrrolidin-1-yl-methyl)phenyl)morpholino-4-yl]-3-methyl-6-pyrimidin-4-yl-3H-pyrimidin-4-one;
(S)-2-[2-(4-(Pyrrolidin-1-yl-methyl)phenyl)morpholino-4-yl]-3-methyl-6-pyrimidin-4-yl-3H-pyrimidin-4-one;
2-[2-(1-Naphthyl)morpholin-4-yl]-3-methyl-6-pyrimidin-4-yl-3H-pyrimidin-4-one;
2-[2-(2-Naphthyl)morpholin-4-yl]-3-methyl-6-pyrimidin-4-yl-3H-pyrimidin-4-one;
(S)-2-[2-(2-Naphthyl)morpholin-4-yl]-3-methyl-6-pyrimidin-4-yl-3H-pyrimidin-4-one;
2-[2-(2,3-dihydrobenzofuran-7-yl)morpholin-4-yl]-3-methyl-6-pyrimidin-4-yl-3H-pyrimidin-4-one;
(S)-2-[2-(2,3-dihydrobenzofuran-7-yl)morpholin-4-yl]-3-methyl-6-pyrimidin-4-yl-3H-pyrimidin-4-one;
2-[2-(Benzofuran-2-yl)morpholin-4-yl]-3-methyl-6-pyrimidin-4-yl-3H-pyrimidin-4-one; and
(S)-2-[2-(Benzofuran-2-yl)morpholin-4-yl]-3-methyl-6-pyrimidin-4-yl-3H-pyrimidin-4-one
or a salt thereof.

11. The pyrimidone derivative or the salt thereof, according to claim 1, wherein R is the group represented by formula (IV).

12. The pyrimidone derivative or the salt thereof, according to claim 11, wherein $R^9$ is a benzene ring which may be substituted.

13. The pyrimidone derivative or the salt thereof, according to claim 11, wherein X is $CH_2$.

14. The pyrimidone derivative or the salt thereof, according to claim 11, wherein X is O.

15. A pyrimidone derivative which is selected from the group consisting of:
2-[3-(4-Fluorobenzoyl)piperidin-1-yl]-3-methyl-6-pyrimidin-4-yl-3H-pyrimidin-4-one;
2-(3-Benzoylpiperidin-1-yl)-3-methyl-6-pyrimidin-4-yl-3H-pyrimidin-4-one;
2-[3-(2-Methoxybenzoyl)piperidin-1-yl]-3-methyl-6-pyrimidin-4-yl-3H-pyrimidin-4-one;
2-[3-(4-Methoxybenzoyl)piperidin-1-yl]-3-methyl-6-pyrimidin-4-yl-3H-pyrimidin-4-one;
2-[2-(4-Fluorobenzoyl)morpholine-4-yl]-3-methyl-6-pyrimidin-4-yl-3H-pyrimidin-4-one;
2-(2-Benzoylmorpholine-4-yl)-3-methyl-6-pyrimidin-4-yl-3H-pyrimidin-4-one;
2-[2-(2-Methoxybenzoyl)morpholine-4-yl]-3-methyl-6-pyrimidin-4-yl-3H-pyrimidin-4-one; and 2-[2-(4-Methoxybenzoyl)morpholine-4-yl]-3-methyl-6-pyrimidin-4-yl-3H-pyrimidin-4-one;

or a salt thereof.

16. The pyrimidone derivative or the salt thereof, according to claim 1, wherein R is the group represented by formula (V).

17. The pyrimidone derivative or the salt thereof, according to claim 16, wherein $R^{10}$ is a benzene ring which may be substituted.

18. The pyrimidone derivative or the salt thereof, according to claim 16, wherein $R^{10}$ is a heterocyclic ring having 1 to 4 hetero atoms selected oxygen atom, sulfur atom and nitrogen atom, and having total ring-constituting atoms of 5 to 10 which may be substituted.

19. A pyrimidone derivative which is selected from the group consisting of:

2-[4-(4-Chlorobenzoyl)piperidin-1-yl]-3-methyl-6-pyrimidin-4-yl-3H-pyrimidin-4-one;

or a salt thereof.

20. A medicament composition as an active ingredient a substance selected from the group consisting of the pyrimidone derivative represented by formula (I) and a salt thereof, according to claim 1.

21. A tau protein kinase 1 inhibitor selected from the group consisting of the pyrimidone derivative represented by formula (I) and a salt thereof, according to claim 1.

22. A pyrimidone derivative represented by formula (VI) or a salt thereof:

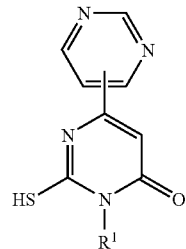

(VI)

wherein $R^1$ represents a $C_1$-$C_{12}$ alkyl group which may be substituted.

23. pyrimidone derivative represented by formula (VII) or a salt thereof:

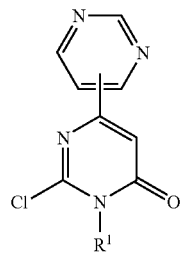

(VII)

wherein $R^1$ represents a $C_1$-$C_{12}$ alkyl group which may be substituted.

* * * * *

UNITED STATES PATENT AND TRADEMARK OFFICE
CERTIFICATE OF CORRECTION

PATENT NO. : 7,572,793 B2
APPLICATION NO. : 10/489607
DATED : August 11, 2009
INVENTOR(S) : Uehara et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1190 days.

Signed and Sealed this

Seventh Day of September, 2010

David J. Kappos
*Director of the United States Patent and Trademark Office*